(12) United States Patent
Seeberger et al.

(10) Patent No.: US 11,014,952 B2
(45) Date of Patent: May 25, 2021

(54) **STABLE HYDROLYSIS-RESISTANT SYNTHETIC POLYRIBOSYLRIBITOLPHOSPHATE DERIVATIVES AS VACCINES AGAINST *HAEMOPHILUS INFLUENZAE* TYPE B**

(71) Applicant: MAX-PLANCK-GESELLSCHAFT ZUR FÖRDERUNG DER WISSENSCHAFTEN E.V., Munich (DE)

(72) Inventors: Peter H. Seeberger, Kleinmachnow (DE); Claney Lebev Pereira, Berlin (DE)

(73) Assignees: Max-Planck-Gesellschaft zur Förderung der Wissenschaften e.V., Munich (DE); Vaxxilon AG, Reinach (CH)

( * ) Notice: Subject to any disclaimer, the term of this patent is extended or adjusted under 35 U.S.C. 154(b) by 0 days.

(21) Appl. No.: 16/320,732

(22) PCT Filed: Jul. 28, 2017

(86) PCT No.: PCT/EP2017/069254
§ 371 (c)(1),
(2) Date: Jan. 25, 2019

(87) PCT Pub. No.: WO2018/020046
PCT Pub. Date: Feb. 1, 2018

(65) Prior Publication Data
US 2019/0153015 A1    May 23, 2019

Related U.S. Application Data

(63) Continuation-in-part of application No. PCT/EP2017/062725, filed on May 26, 2017.

(30) Foreign Application Priority Data

Jul. 28, 2016 (EP) .................................... 16181659
May 26, 2017 (WO) ................ PCT/EP2017/062725

(51) Int. Cl.
| | | |
|---|---|---|
| C07H 15/04 | (2006.01) | |
| C07H 15/26 | (2006.01) | |
| A61K 39/12 | (2006.01) | |
| A61K 39/385 | (2006.01) | |
| G01N 33/569 | (2006.01) | |

(52) U.S. Cl.
CPC ............ *C07H 15/04* (2013.01); *A61K 39/12* (2013.01); *A61K 39/385* (2013.01); *C07H 15/26* (2013.01); *G01N 33/56983* (2013.01)

(58) Field of Classification Search
CPC .. C07H 15/04; C07H 15/26; G01N 33/56983; A61K 39/12; A61K 39/385
USPC ........................................................ 514/17
See application file for complete search history.

(56) References Cited

U.S. PATENT DOCUMENTS

| | | | |
|---|---|---|---|
| 6,765,091 B1 | 7/2004 | Bencomo et al. | |
| 2014/0051603 A1* | 2/2014 | Boons .................... | C07H 15/18 |
| | | | 506/19 |

FOREIGN PATENT DOCUMENTS

| | | |
|---|---|---|
| EP | 0276516 A2 | 8/1988 |
| EP | 0320942 A2 | 6/1989 |
| IN | 2989DE2013 A | 4/2015 |
| NZ | 517464 | 3/2004 |
| WO | WO 92/10936 | 7/1992 |
| WO | WO 01/16146 | 3/2001 |
| WO | WO 2016/044164 | 3/2016 |

OTHER PUBLICATIONS

Bardotti et al., "Quantitative determination of saccharide in *Haemophilus influenzae* type b glycoconjugate vaccines, alone and in combination with DPT, by use of high-performance anion-exchange chromatography with pulsed amperometric detection" Vaccine (2000) 18(19):1982-1993.
Bond et al., "Photocrosslinking of glycoconjugates using metabolically incorporated diazirine-containing sugars" Nature Protocols (2009) 4(7):1044-1063.
Bond et al. "Metabolism of Diazirine-Modified N-Acetylmannosamine Analogues to Photo-Cross-Linking Sialosides" Bioconjugate Chemistry (2011) 22(9):1811-1823.
Chong et al., "A strategy for rational design of fully synthetic glycopeptide conjugate vaccines" Infect. Immun. (1997) 65(12):4918-4925.
Fraser et al., "Mass-spectral studies of isometric d-ribofuranosylribitol disaccharides from the capsular polysaccharides of *Haemophilus influenza* type b and *Escherichia coli* K 100" Carbohydrate Research (1979) 73(1):59-65.
Nilsson et al., "Solid-Phase Synthesis of a Fragment of the Capsular Polysaccharide of *Haemophilus influenzae* Type B Using H-Phosphonate Intermediates" Journal of Carbohydrate Chemistry (1992) 11(3):265-285.
Plotkin et al, Vaccines, Table of Contents and Chapter 12 (6th edition, 2012).

(Continued)

*Primary Examiner* — Shaojia A Jiang
*Assistant Examiner* — Michael C Henry
(74) *Attorney, Agent, or Firm* — Knobbe Martens Olson & Bear LLP

(57) ABSTRACT

The present invention provides a stable synthetic saccharide of Hib polyribosylribitol-phosphate (PRP) derivative and conjugate thereof. Said saccharide, said conjugate and pharmaceutical compositions thereof are hydrolysis-resistant, long-term stable and useful for the prevention and/or treatment of diseases associated with *Haemophilus influenzae*, and more specifically of diseases associated with *Haemophilus influenzae* type b, preferably diseases selected from meningitis, pneumonia, and epiglotitis. They have general formula (I): wherein A is formula (II) or formula (III); B is formula (IV); C is formula (V); D is formula (VI); E is formula (VII); F is formula (VIII) or formula (IX).

8 Claims, 21 Drawing Sheets

(56) References Cited

OTHER PUBLICATIONS

Plotkin et al, Vaccines, Chapter 15 (6$^{th}$ edition, 2012).
Plotkin et al, Vaccines, Chapter 23 (6$^{th}$ edition, 2012).
Plotkin et al, Vaccines, Chapter 27 (6$^{th}$ edition, 2012).
Plotkin et al, Vaccines, Chapter 30 (6$^{th}$ edition, 2012).
Plotkin et al, Vaccines, Chapter 33 (6$^{th}$ edition, 2012).
Sturgess et al., "*Haemophilus influenzae* type b conjugate vaccine stability: catalytic depolymerization of PRP in the presence of aluminum hydroxide" Vaccine (1999) 17(9-10):1169-1178.
Verez-Bencomo et al., "A Synthetic Conjugate Polysaccharide Vaccine Against *Haemophilus influenzae* Type b" Science (2004) 305(5683):522-525.
International Search Report and Written Opinion dated Sep. 1, 2017 for PCT Application No. PCT/EP2017/069254, filed Jul. 28, 2017.
International Preliminary Report on Patentability completed Nov. 9, 2018 for PCT Application No. PCT/EP2017/069254, filed Jul. 28, 2017.

* cited by examiner

Figure 5
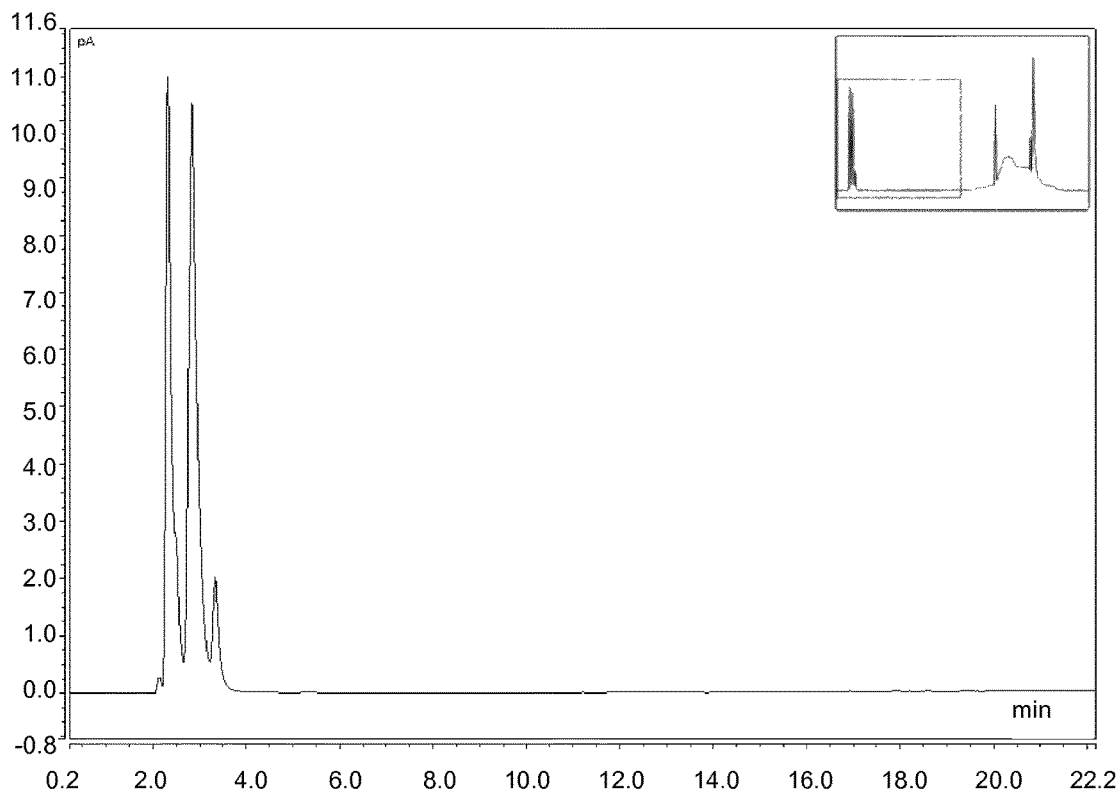
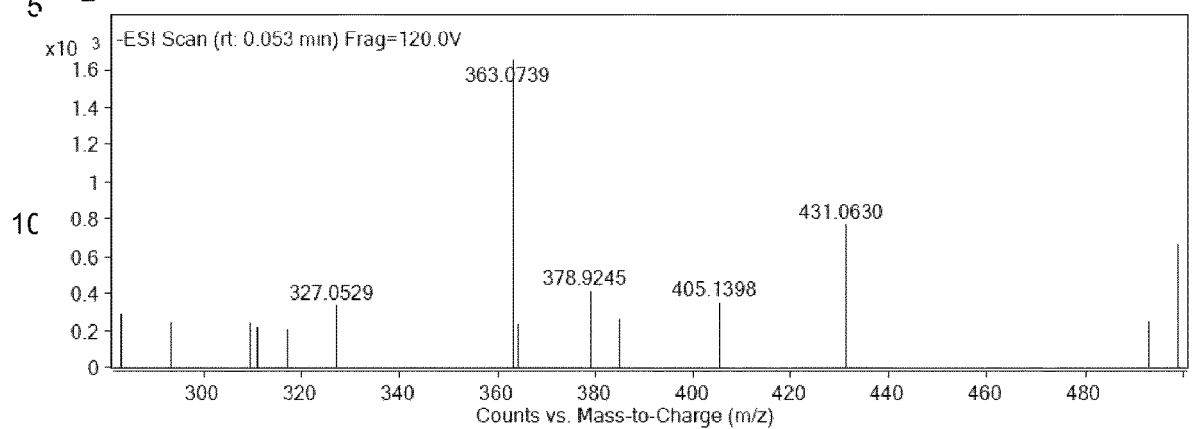
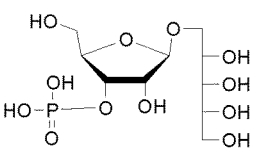
Chemical Formula: $C_{10}H_{21}O_{12}P$
Exact Mass: 364.0771
Molecular Weight: 364.2398
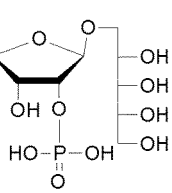
Chemical Formula: $C_{10}H_{21}O_{12}P$
Exact Mass: 364.0771
Molecular Weight: 364.2398

A: 2–8°C after 7 d in Alhydrogel®

B: 2–8°C after 7 d in Al₃PO₄

C: 2–8°C after 7 d in H₂O

D: control: 16

E: control: 8

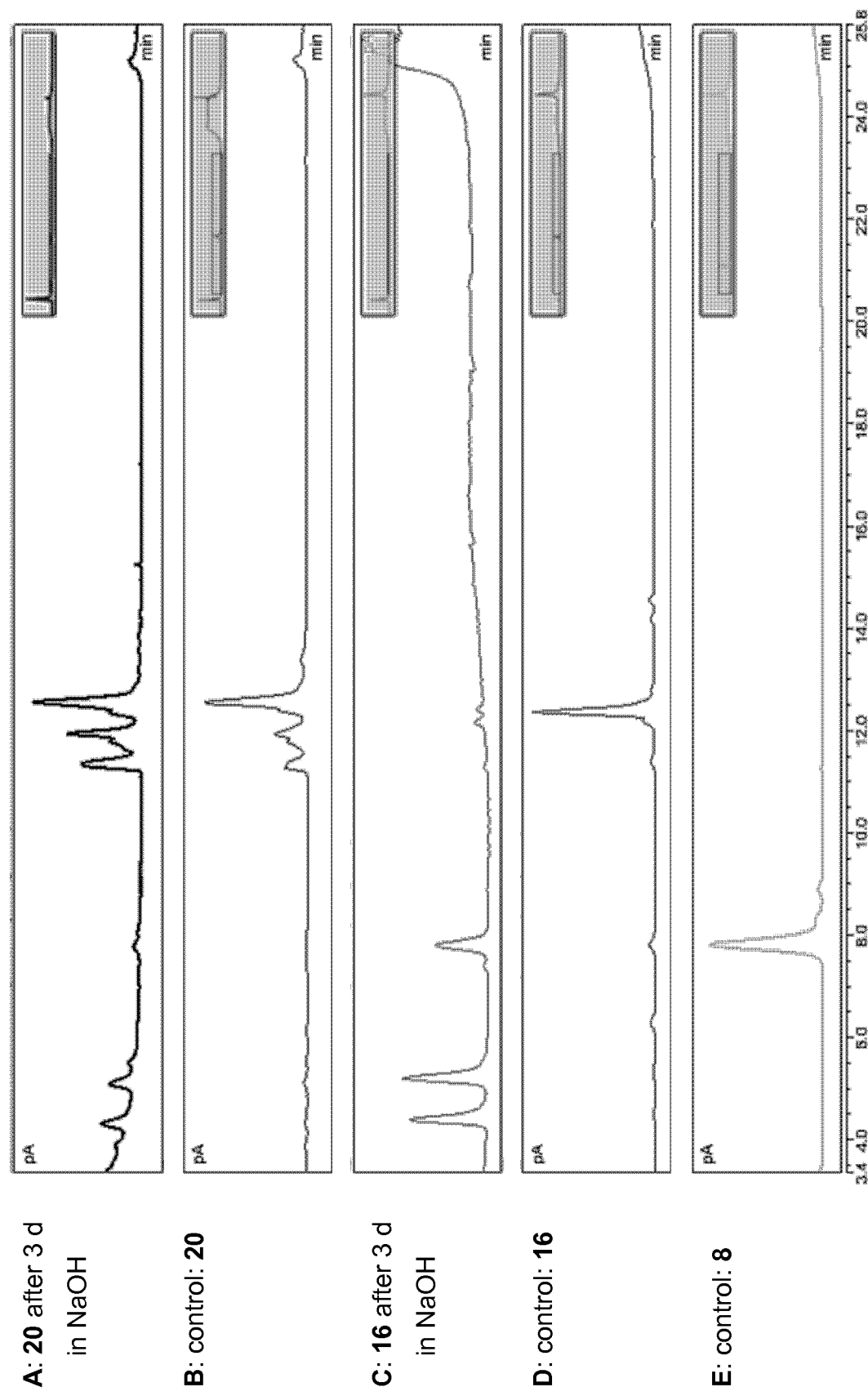

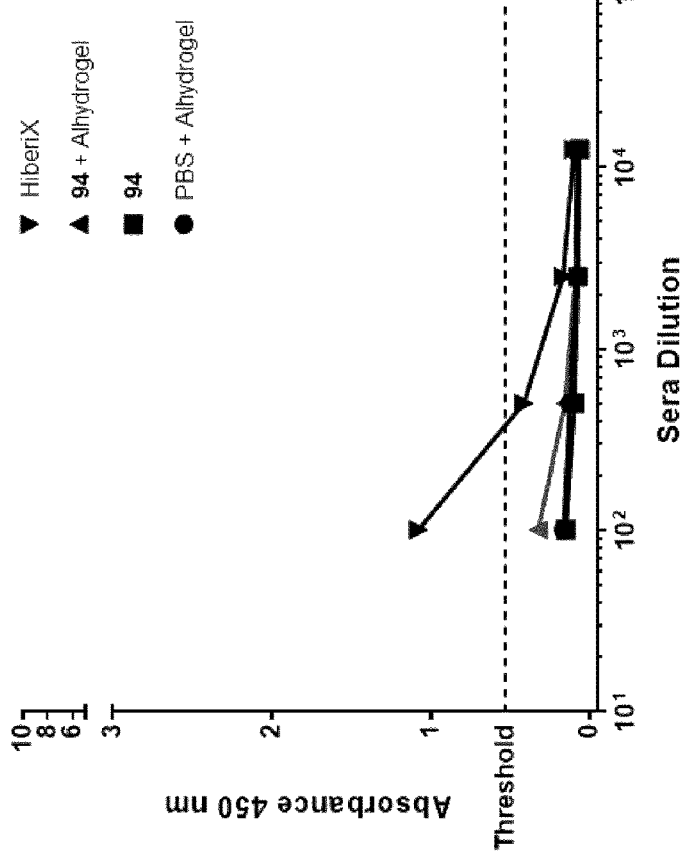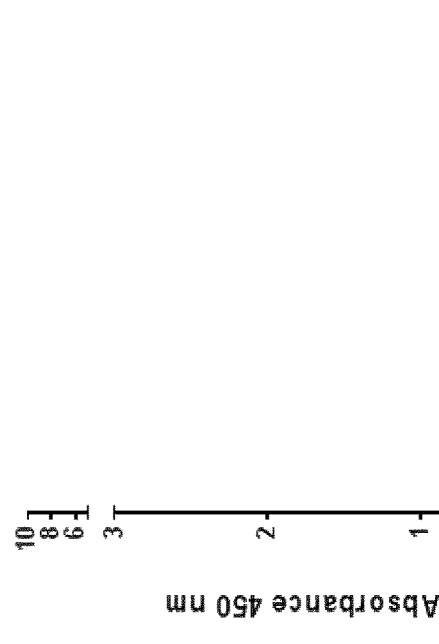
Figure 19

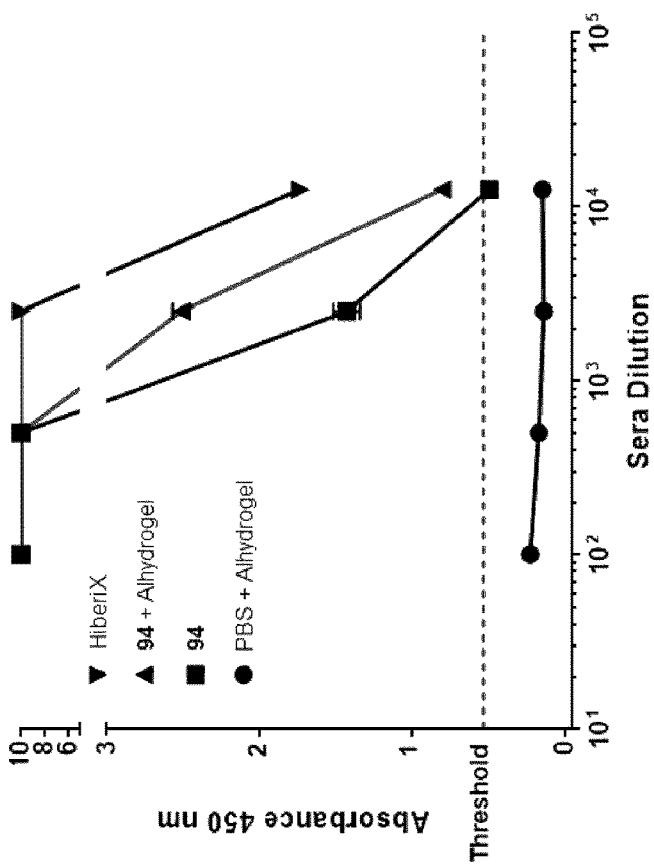
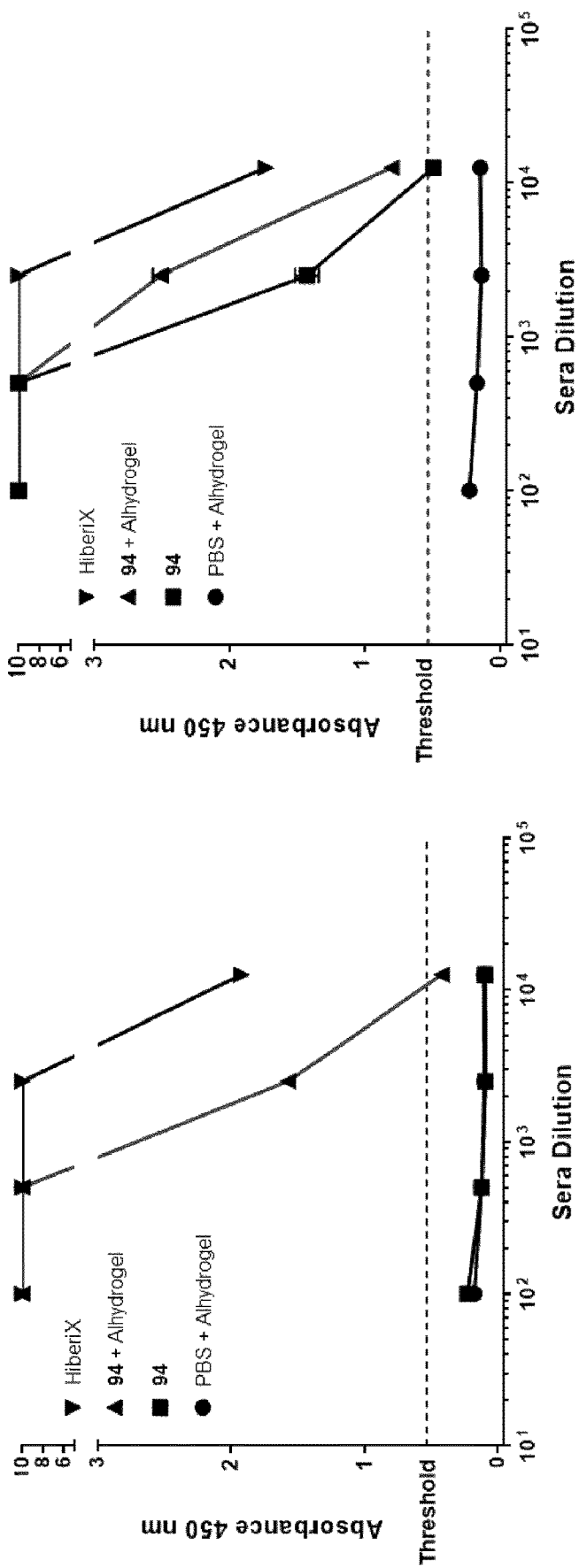
Figure 19 continued

STABLE HYDROLYSIS-RESISTANT SYNTHETIC POLYRIBOSYLRIBITOLPHOSPHATE DERIVATIVES AS VACCINES AGAINST *HAEMOPHILUS INFLUENZAE* TYPE B

FIELD OF THE INVENTION

The present invention provides a stable synthetic saccharide of Hib polyribosylribitolphosphate (PRP) derivative and conjugate thereof. Said saccharide, said conjugate and pharmaceutical compositions thereof are hydrolysis-resistant, long-term stable and useful for the prevention and/or treatment of diseases associated with *Haemophilus influenzae*, and more specifically of diseases associated with *Haemophilus influenzae* type b.

BACKGROUND OF THE INVENTION

*Haemophilus influenzae* type b (Hib) is a serious human health problem worldwide, being responsible of a variety of diseases including meningitis, pneumonia, epiglotitis, and other diseases of the respiratory tract especially in children under the age of 5. 30% of the survivors of the diseases present sequels ranging from auditive problems to mental retardation.

Purified capsular polysaccharide of *Haemophilus influenzae* is able to induce protective immunity in adults. However, the immune response in children is very poor and practically absent in infants under 2 years old. The capsular polysaccharide isolated from the Hib bacteria presents a ribosylribitolphosphate repeating unit:

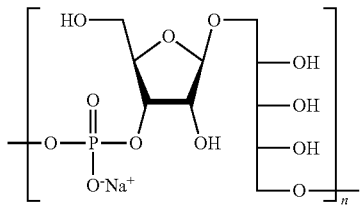

A

A variety of vaccines for prevention of Hib infection were developed and are consisting of synthetic polyribosylribitolphosphate (PRP) or mixtures of synthetic PRP of different lengths conjugated to carrier protein (WO 9210936 A1, EP 0276516 A2, EP 0320942 A2, WO 0116146 A1). Several vaccines have recently been licensed in the USA and elsewhere for pediatric use.

The synthesis of Hib oligosaccharides was reported to be a useful alternative to costly and cumbersome isolation of Hib PRP from bacteria (IN 2013/DEL/02989, U.S. Pat. No. 6,765,091, WO2016044164 A1 and EP 0320942A). In *Journal of Carbohydrate Chemistry* 1992, 11, 265 a solid phase synthesis of Hib oligosaccharides is described. The acetylated and methylated Hib disaccharides were investigated by mass-spectrometry in *Carbohydrate Research* 1979, 73, 59.

As mentioned above, polyribosylribitolphosphate (PRP) is the active ingredient in a variety of vaccines that have proven successful in preventing disease caused by *Haemophilus influenzae* type b (Hib).

Long-term stability of the Hib vaccine is required to maintain the immunogenicity of said vaccine and this can be a challenge for Hib-conjugate vaccines given the potential susceptibility of the phosphodiester bond in the PRP polymer to hydrolytic cleavage. Usually, metabolization of the capsular polysaccharide of vaccine reduces the immunogenicity of the vaccine. It is known that aluminum oxide used as adjuvant accelerates the hydrolysis of PRP and depolymerization of PRP causes instability of the Hib vaccine and reduced immunogenicity of Hib vaccine (Vaccine 19, 1999, p 1169-1178).

With the consequence that commercially available licensed Hib vaccines need to be stored at 2° C.-8° C. and are usually stable at these conditions for only 24-36 months. Moreover, liquid Hib vaccine formulations are prone to being damaged by freezing which is assumed to be caused by the aluminum salt present in the liquid formulation. Sensitivity towards freeze damaging impedes the storage and transport of liquid Hib vaccines which have to be cooled since the use of ice has to be avoided to prevent freezing.

It is also reported that the purified natural polysaccharide component of the bacterial cell wall contained in commercially available vaccines may be responsible for inhibition of b receptors leading to increased bronchoconstriction. Furthermore, it is well-known that the Hib vaccines increase the risk of seizure symptom in infants under 3 years old. Thus, new Hib vaccine having enhanced immunogenicity by administering a smaller amount of dose and reduced side effects is requested.

It is the objective of the present invention to provide a synthetic saccharide of Hib polyribosylribitolphosphate (PRP) derivative and conjugate thereof should be metabolic stable, hydrolysis-resistant and shelf-stable in liquid formulations. Said saccharide, said conjugate and pharmaceutical compositions thereof have enhanced immunogenicity and thus should be particularly useful for the prevention and/or treatment of diseases associated with *Haemophilus influenzae*, and more specifically of diseases associated with *Haemophilus influenzae* type b.

The objective of the present invention is solved by the teaching of the independent claims. Further advantageous features, aspects and details of the invention are evident from the dependent claims, the description, the figures, and the examples of the present application.

DESCRIPTION OF THE INVENTION

It is the objective of the present invention to provide saccharide of general formula (I)

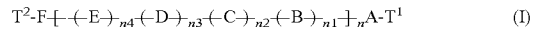
(I)

wherein
A is

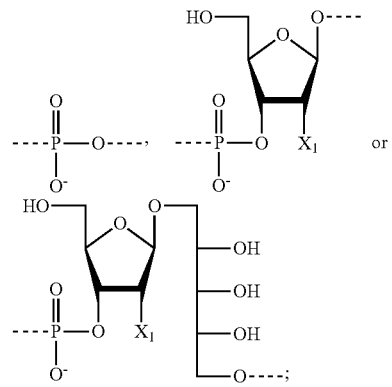

B is

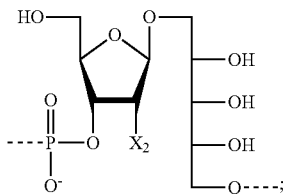

C is

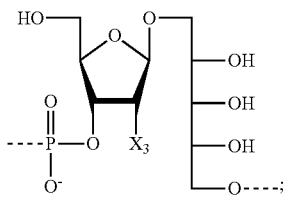

D is

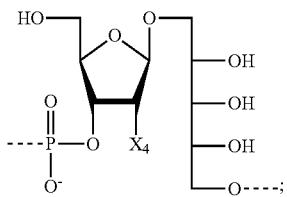

E is

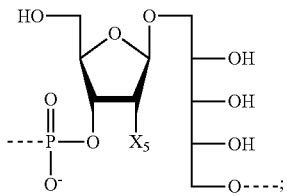

F is

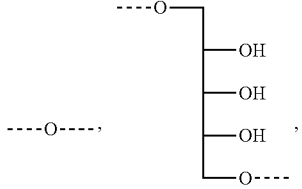

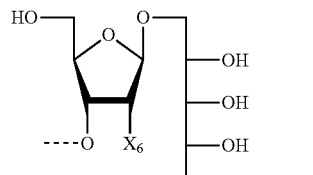

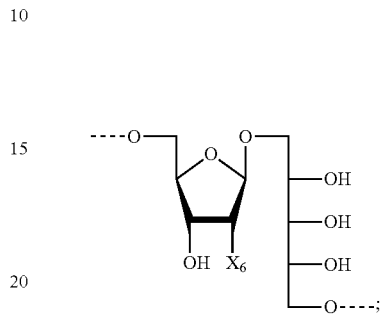

$T^1$ and $T^2$ represent —H, -L-$NH_2$ or -L-COOH; wherein if $T^1$ is -L-$NH_2$ or -L-COOH, then $T^2$ is —H and if $T^1$ is —H, then $T^2$ is -L-$NH_2$ or -L-COOH, or wherein one of $T^1$ and $T^2$ represents —H and the other one of $T^1$ and $T^2$ represents -L-$NH_2$ or -L-COOH;

$X_1$, $X_2$, $X_3$, $X_4$, $X_5$, and $X_6$ represent independently of each other —H, —OH, —F, —Cl, —$CH_3$, —$C_2H_5$, —CN, —$OCH_3$, —$OC_2H_5$, —$OCH(CH_3)_2$, —$OCH_2F$, —$OCF_3$, —OCO—$N(CH_3)_2$, —O—$C_2H_4$—O—$CH_3$, —O—$CH_2$—$CF_3$ and at least one of $X_1$, $X_2$, $X_3$, $X_4$, $X_5$, and $X_6$ is not —OH; preferred at least 50% of $X_1$, $X_2$, $X_3$, $X_4$, $X_5$, and $X_6$ are not —OH; more preferred at least two of $X_1$, $X_2$, $X_3$, $X_4$, $X_5$, and $X_6$ are not —OH;

most preferred all of $X_1$, $X_2$, $X_3$, $X_4$, $X_5$, and $X_6$ are not —OH;

n is an integer selected from 1, 2, 3, or 4;

n1, n2, n3 and n4 are independently of each other selected from 0 and 1; and n1+n2+n3+n4≥1;

under the proviso that if n1+n2+n3+n4=1 and if n=1 and if A is

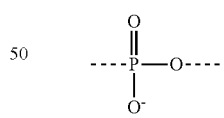

than

F is

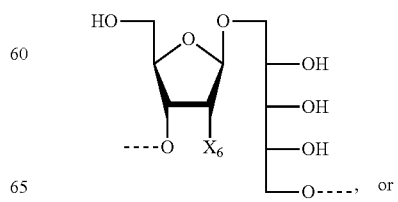

-continued

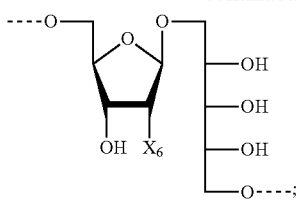

and
under the proviso that if n1+n2+n3+n4=1 and if n=1 and if F is

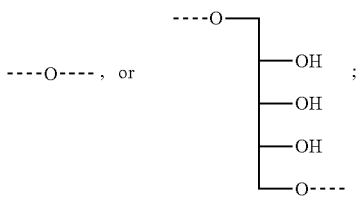

than
A is

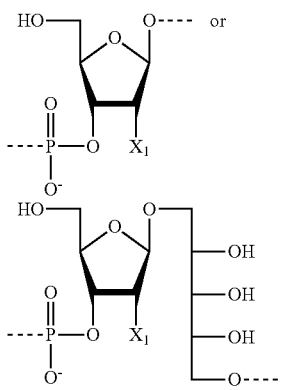

and
L is selected from: -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-, wherein -L$^a$- is selected from: —(CH$_2$)$_a$—, —(CF$_2$)$_a$—, —(CH$_2$—CH$_2$—O)$_a$—C$_2$H$_4$—, —(CH$_2$—CH$_2$—)—H$_2$—O)$_a$—CH$_2$—, (CR$^{10}$R$^{11}$)$_a$—,

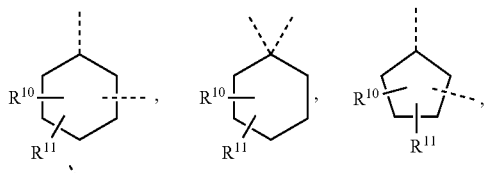

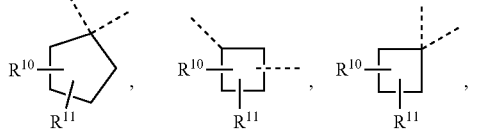

-continued

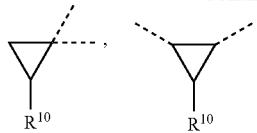

-L$^b$- and -L$^c$- are independently of each other selected from: —O—, —S—, —NH—C(O)—NH—, —NH—C(S)—NH—, —NH—C(O)—, —C(O)—NH—, —S—S—, —NH—C(O)—O—, —NR$^9$—, —NR$^{18}$—, —SO$_2$—, —OP(O)(OH)—O—,

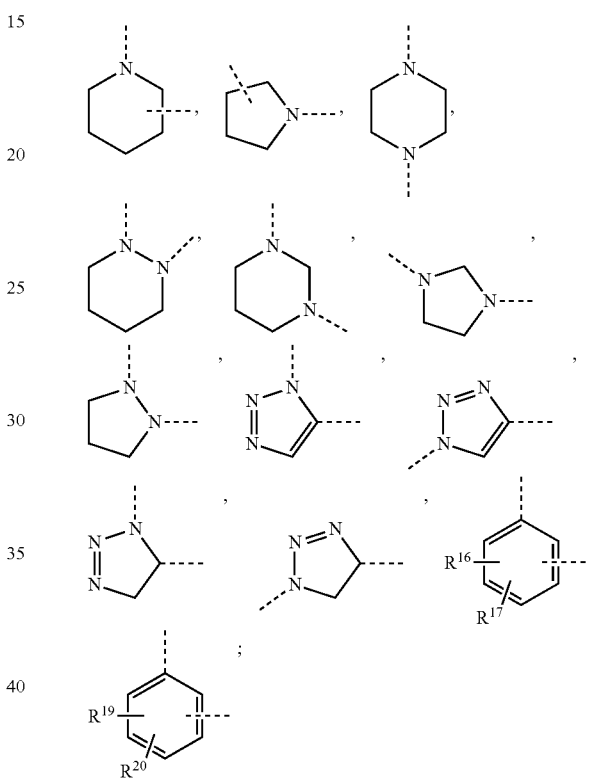

-L$^d$- represents —(CH$_2$)$_d$—, —(CF$_2$)$_d$—, —(CR$^{12}$R$^{13}$)$_d$—, —(CH$_2$—CH$_2$—O)$_d$—C$_2$H$_4$—, —(CH$_2$—CH$_2$—O)$_d$—CH$_2$—,

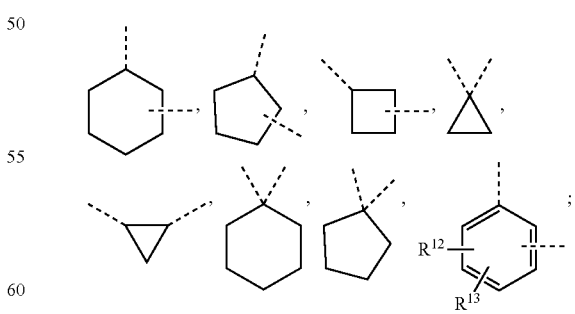

-L$^e$- is selected from: —(CH$_2$)$_{e1}$—, —(CF$_2$)$_{e1}$—, —C$_2$H$_4$—(—CH$_2$—CH$_2$)$_{e2}$—, —CH$_2$—(—CH$_2$—CH$_2$)$_{e2}$—, —(CH$_2$)$_{e1}$—O—(CH$_2$)$_{e2}$—, —(CH$_2$)$_{e1}$—S—(CH$_2$)$_{e2}$—, —(CR$^{14}$R$^{15}$)$_{e1}$—, —(CR$^{14}$R$^{15}$)$_{e1}$—O—(CR$^{21}$R$^{22}$)$_{e2}$—, —(CR$^{14}$R$^{15}$)$_{e1}$—S—(CR$^{21}$R$^{22}$)$_{e2}$—,

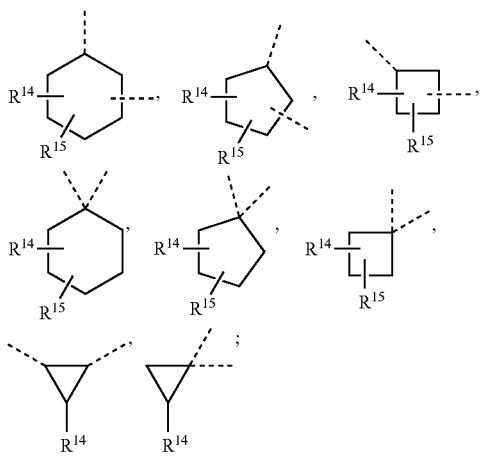

$R^9$ and $R^{18}$ are independently of each other selected from: —$CH_3$, —$C_2H_5$, —$C_3H_7$, and —$C(O)CH_3$;

$R^{10}$, $R^1$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —$C(O)$—$NH_2$, —$SCH_3$, —$SC_2H_5$, —$NHC(O)CH_3$, —$N(CH_3)_2$, and —$N(C_2H_5)_2$;

a, d, e1 and e2 are independently of each other an integer selected from 1, 2, 3, 4, 5, 6, 7, 8, 9, and 10;

and enantiomers, diastereomers, mixtures of enantiomers, mixtures of diastereomers, anomers, hydrates, solvates of the above mentioned compounds and pharmaceutically acceptable salts thereof.

The smallest saccharides claimed by formula (I) are disaccharides so that the disclaimer under the proviso that if n1+n2+n3+n4=1 and if n=1 and if A is

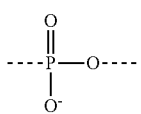

than

F is

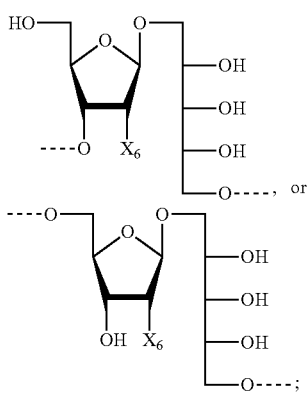

and under the proviso that if n1+n2+n3+n4=1 and if n=1 and if

F is

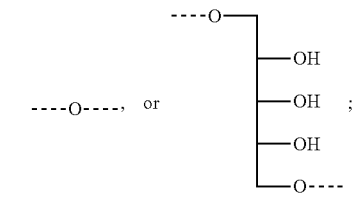

than

A is

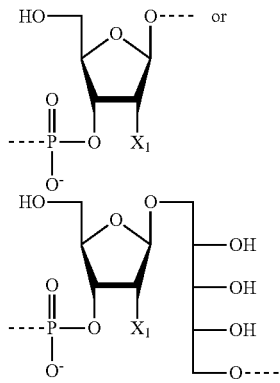

could be replaced by the condition that "saccharide of general formula (I) is at least a disaccharide".

Alternatively the afore-mentioned disclaimer could be replaced by the condition that if n1+n2+n3+n4=1 than n≠1 (n different from 1) and if n=1 than n1+n2+n3+n≠1 (n1+n2+n3+n4 different from 1).

Thus, alternatively preferred is the saccharide of general formula (I)

$$T^2\text{-F}\{[(\text{-E-})_{n4}(\text{-D-})_{n3}(\text{-C-})_{n2}(\text{-B-})_{n1}]_n\}\text{A-T}^1 \quad (I)$$

wherein

A is

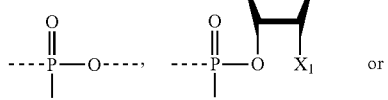
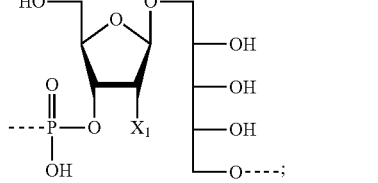

B is

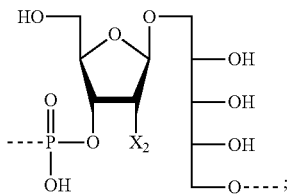

C is

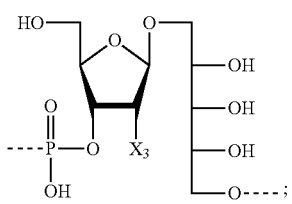

D is

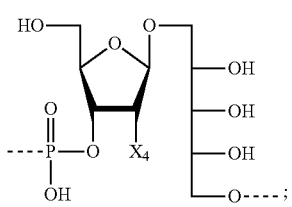

E is

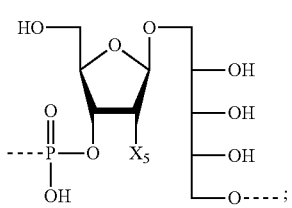

F is

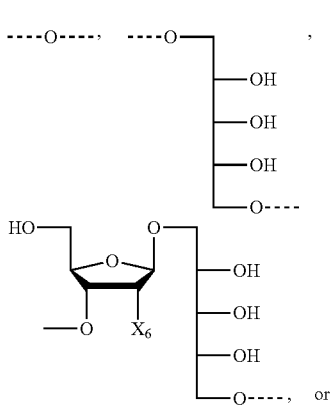

or

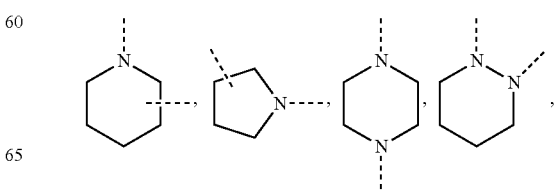

$T^1$ and $T^2$ represent —H, -L-NH$_2$ or -L-COOH; wherein if $T^1$ is -L-NH$_2$ or -L-COOH, then $T^2$ is —H and if $T^1$ is —H, then $T^2$ is -L-NH$_2$ or -L-COOH, or wherein one of $T^1$ and $T^2$ represents —H and the other one of $T^1$ and $T^2$ represents -L-NH$_2$ or -L-COOH;

$X_1$, $X_2$, $X_3$, $X_4$, $X_5$, and $X_6$ represent independently of each other —H, —OH, —F, —Cl, —CH$_3$, —C$_2$H$_5$, —CN, —OCH$_3$, —OC$_2$H$_5$, —OCH(CH$_3$)$_2$, —OCH$_2$F, —OCF$_3$, —OCO—N(CH$_3$)$_2$, —O—C$_2$H$_4$—O—CH$_3$, —O—CH$_2$—CF$_3$ and at least one of $X_1$, $X_2$, $X_3$, $X_4$, $X_5$, and $X_6$ is not —OH; preferred at least 50% of $X_1$, $X_2$, $X_3$, $X_4$, $X_5$, and $X_6$ are not —OH; more preferred at 80% of $X_1$, $X_2$, $X_3$, $X_4$, $X_5$, and $X_6$ are not —OH; most preferred all of $X_1$, $X_2$, $X_3$, $X_4$, $X_5$, and $X_6$ are not —OH;

n is an integer selected from 1, 2, 3, or 4;

n1, n2, n3 and n4 are independently of each other selected from 0 and 1; and n1+n2+n3+n4≥2;

L is selected from: -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-, wherein -L$^a$- is selected from: —(CH$_2$)$_a$—, —(CF$_2$)$_a$—, —(CH$_2$—CH$_2$—O)$_a$C$_2$H$_4$—, - CH$_2$—CH$_2$—O)$_a$—CH$_2$—, —(CR$^{10}$R$^{11}$)$_a$—,

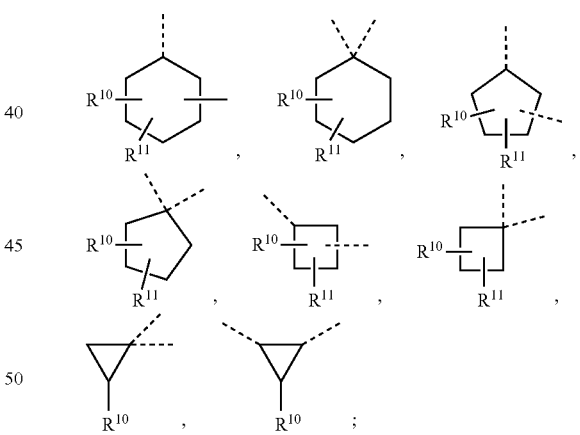

-L$^b$- and -L$^c$- are independently of each other selected from: —O—, —S—, —NH—C(O)—NH—, —NH—C(S)—NH—, —NH—C(O)—, —C(O)—NH—, —S—S—, —NH—C(O)—O—, —NR$^9$—, —NR$^{18}$—, —SO$_2$—, -continued

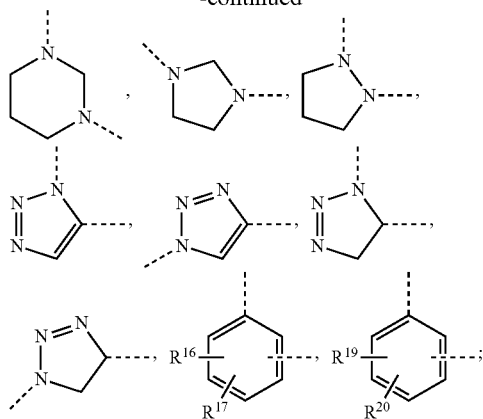

-L$^d$- represents —$(CH_2)_d$—, —$(CF_2)_d$—, —$(CR^{12}R^{13})_d$—, —$(CH_2—CH_2—O)_d—C_2H_4$—, —$(CH_2—CH_2—O)_d—CH_2$—,

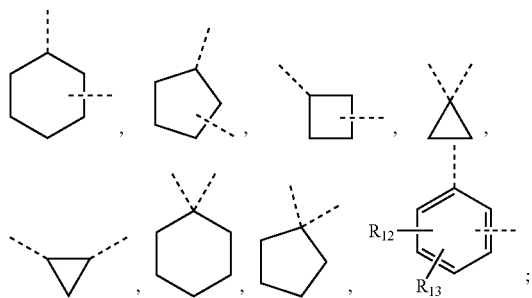

-L$^e$- is selected from: —$(CH_2)_{e1}$—, —$(CF_2)_{e1}$—, —$C_2H_4$—$(—CH_2—CH_2)_{e2}$—, —$CH_2—(—CH_2—CH_2)_{e2}$—, —$(CH_2)_{e1}$—$O(CH_2)_{e2}$—, —$(CH_2)_{e1}$—$S$—$(CH_2)_{e2}$—, —$(CR^{14}R^{15})_{e1}$—, —$(CR^{14}R^{15})_{e1}$—$O$—$(CR^{21}R^{22})_{e2}$—, —$(CR^{14}R^{15})_{e1}$—$S$—$(CR^{21}R^{22})_{e2}$—,

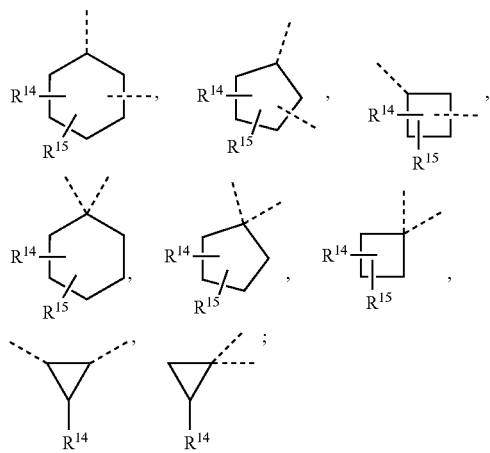

$R^9$ and $R^{18}$ are independently of each other selected from: —$CH_3$, —$C_2H_5$, —$C_3H_7$, and —$C(O)CH_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —$C(O)$—$NH_2$, —$SCH_3$, —$SC_2H_5$, —$NHC(O)CH_3$, —$N(CH_3)_2$, and —$N(C_2H_5)_2$;

a, d, e1 and e2 are independently of each other an integer selected from 1, 2, 3, 4, 5, 6, 7, 8, 9, and 10;

and enantiomers, diastereomers, mixtures of enantiomers, mixtures of diastereomers, anomers, hydrates, solvates of the above mentioned compounds and pharmaceutically acceptable salts thereof.

More preferably $X_1$, $X_2$, $X_3$, $X_4$, $X_5$, and $X_6$ represent independently of each other —H, —F, —$CH_3$, —$C_2H_5$, —CN, —$OCH_3$, —$OC_2H_5$, —$OCH(CH_3)_2$, —$OCH_2F$, —$OCF_3$, —$OCO$—$N(CH_3)_2$, —$O$—$C_2H_4$—$O$—$CH_3$, —$O$—$CH_2$—$CF_3$, and still more preferably —H, —F, —$CH_3$, —CN, —$OCH_3$, —$OC_2H_5$, —$OCH_2F$, —$OCF_3$, —$OCO$—$N(CH_3)_2$.

The saccharides of formula (I) are at least disaccharides, while at least trisaccharides are preferred and more preferred is that the saccharide of general formula (I) is at least a tetrasaccharide.

The saccharides of the present invention bear basic and/or acidic groups and they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, $NH_4OH$, trialkylamine, triethylamine, tetraalkylammonium hydroxide, lysine or arginine and the like. Salts may be prepared in a conventional manner using methods well known in the art, for example by treatment of a solution of the saccharide of the general formula (I) with a solution of base, selected out of the group mentioned above.

Most preferably, phosphate groups of the saccharide of the general formula (I) build salts or zwitterionic form with sodium or triethylammonium cations.

Preferred are salts with an inorganic cation and more preferred are salts with an inorganic cation which has a single positive charge such as $Li^+$, $Na^+$, and $K^+$. Most preferred are $Na^+$ salts.

It was surprisingly found that the saccharides of general formula (I) are stable in basic aqueous media as well as suspensions containing aluminum phosphate or aluminum hydroxide, such as the commonly used adjuvant Alhydrogel. While natural Hib PRP hydrolyzes within one day in basic aqueous media or in the presence of aluminum salts, the saccharides of general formula (I) as well as conjugates thereof are stable over several days even at elevated temperatures. The increased stability is particularly advantageous for their use in vaccines against *Haemophilus influ-* enzae. Thus the saccharides of general formula (I) as well as conjugates thereof are particularly useful for shelf-stable liquid vaccines against *Haemophilus influenzae*, which can be stored at ambient temperature and which are not prone to being damaged by freezing which may occur for instance during transport.

Surprisingly, it was also found that the saccharides of general formula (I) conjugated to an immunogenic carrier are able to provide a protective immune response against *Haemophilus influenzae* bacteria in a human and/or animal host. Additionally, the saccharides of general formula (I) conjugated to an immunogenic carrier are able to elicit substantial IgM and IgG responses in rabbits that are comparable in terms of kinetics and IgG production to the corresponding commercially available Hib PRP conjugate vaccines. Antibodies elicited by the saccharides of general formula (I) conjugated to an immunogenic carrier are cross-reacting with the natural Hib PRP, thus indicating the ability of these antibodies to bind to *Haemophilus influenzae* bacteria and to confer protection against *Haemophilus influenzae* infections.

Preferred is a saccharide of the formula (II-1)

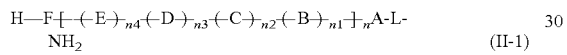
(II-1)

wherein

A is

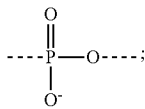

F is

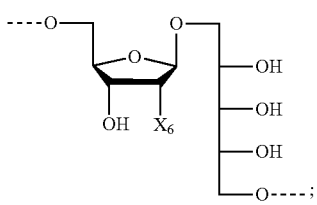

B, C, D, E, L, n1, n2, n3 and n4 have the meanings as defined above;
n is 1 or 2; and
$X_2$-$X_6$ are —H, —F, or —OCH$_3$;
and enantiomers, diastereomers, mixtures of enantiomers, mixtures of diastereomers, anomers, hydrates, solvates of the above mentioned compounds and pharmaceutically acceptable salts thereof.

Also preferred is a saccharide of the formula (II-2)

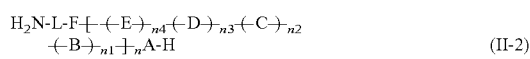
(II-2)

wherein

A is

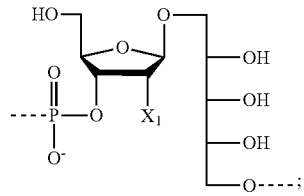

F is

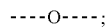

B, C, D, E, L, n1, n2, n3 and n4 have the meanings as defined above;
n is 1 or 2; and
$X_1$-$X_5$ are —H, —F, or —OCH$_3$;
and enantiomers, diastereomers, mixtures of enantiomers, mixtures of diastereomers, anomers, hydrates, solvates of the above mentioned compounds and pharmaceutically acceptable salts thereof.

Also preferred is a saccharide of the formula (II-3)

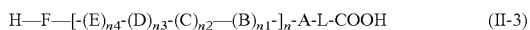
(II-3)

wherein

A is

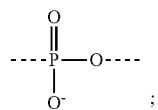

F is

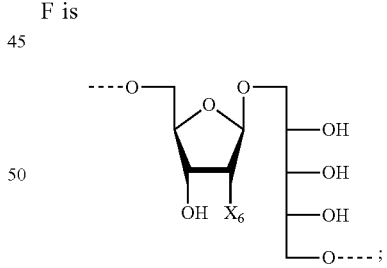

B, C, D, E, L, n1, n2, n3 and n4 have the meanings as defined above;
n is 1 or 2; and
$X_2$-$X_6$ are —H, —F, or —OCH$_3$;
and enantiomers, diastereomers, mixtures of enantiomers, mixtures of diastereomers, anomers, hydrates, solvates of the above mentioned compounds and pharmaceutically acceptable salts thereof.

Also preferred is a saccharide of the formula (II-4)

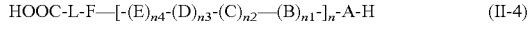
(II-4)

wherein
A is

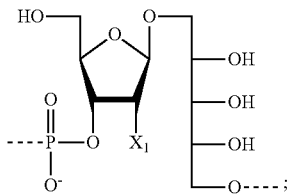

F is

----O----;

B, C, D, E, L, n1, n2, n3 and n4 have the meanings as defined above;
n is 1 or 2; and
$X_1$-$X_5$ are —H, —F, or —OCH$_3$;
and enantiomers, diastereomers, mixtures of enantiomers, mixtures of diastereomers, anomers, hydrates, solvates of the above mentioned compounds and pharmaceutically acceptable salts thereof.

Further preferred is saccharide of the formula (III-1)

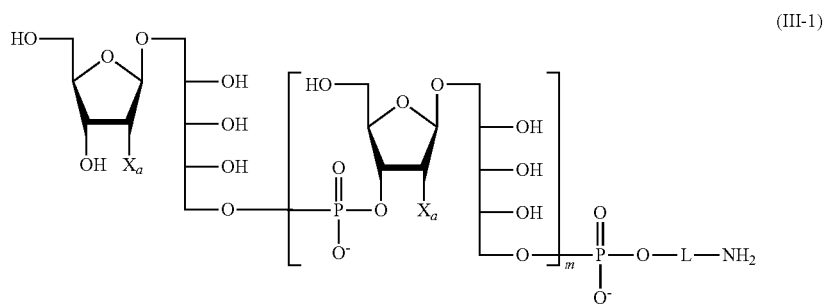

(III-1)

wherein
L has the meaning as defined above;
m is an integer selected from 1 to 9; and
Xa is —H, —F or —OCH$_3$.

Yet further preferred is saccharide of the formula (III-2)

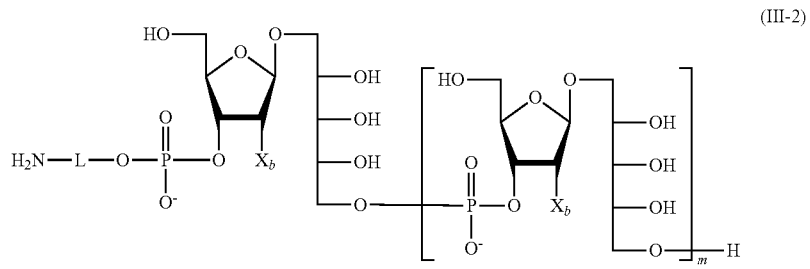

(III-2)

wherein
L has the meaning as defined above;
m is an integer selected from 1 to 9; and
$X_b$ is —H, —F or —OCH$_3$.

More preferred is a saccharide of the formula (IV-1)

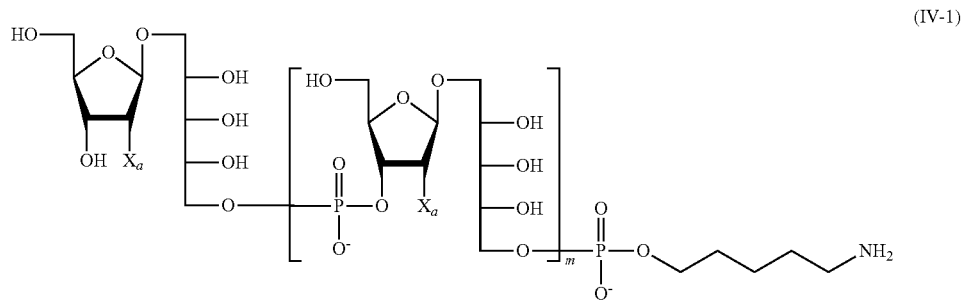

(IV-1)

wherein
m is an integer selected from 1 to 9; and
$X_a$ is —H, —F or —OCH$_3$.
Still more preferred is a saccharide of the formula (IV-2)
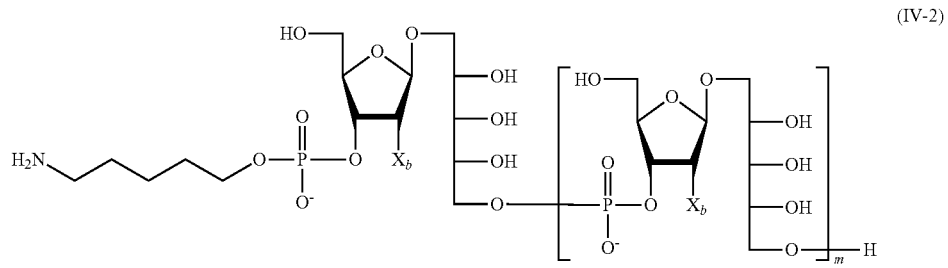
(IV-2)
wherein
m is an integer selected from 1 to 9; and
Xb is —H, —F or —OCH$_3$.
Most preferred is a saccharide selected from the group consisting of:
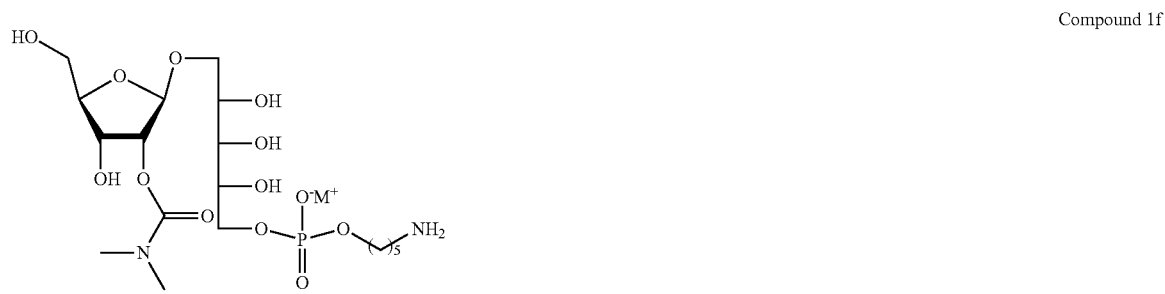
Compound 1f
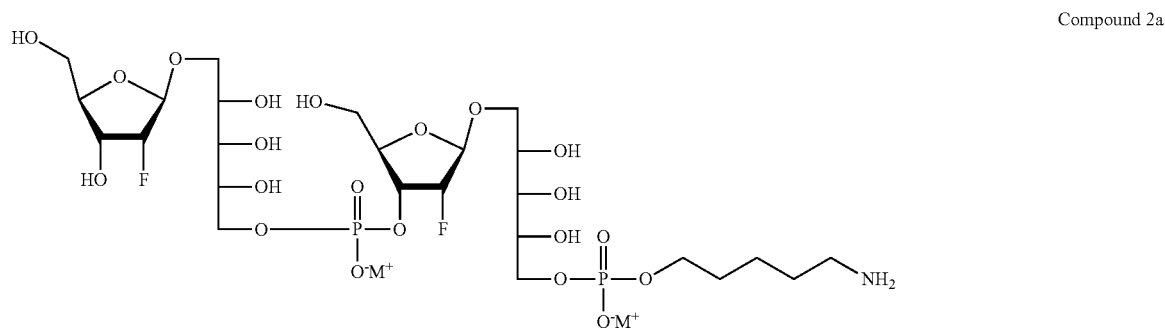
Compound 2a
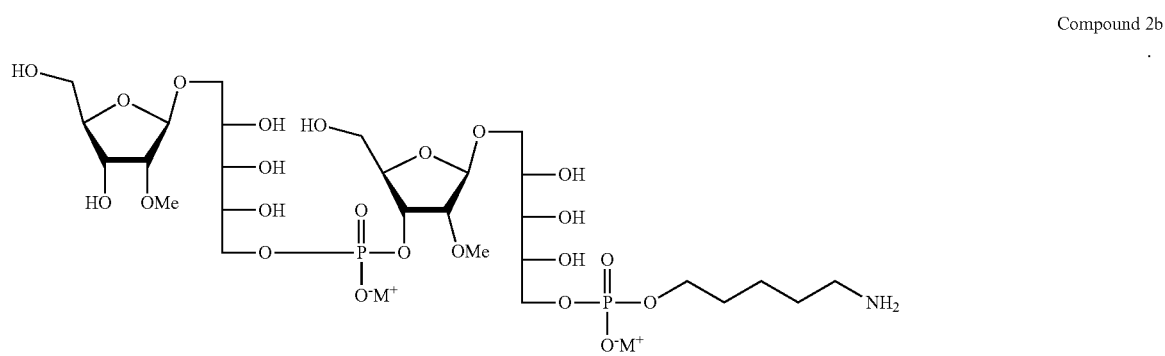
Compound 2b -continued
Compound 2b′
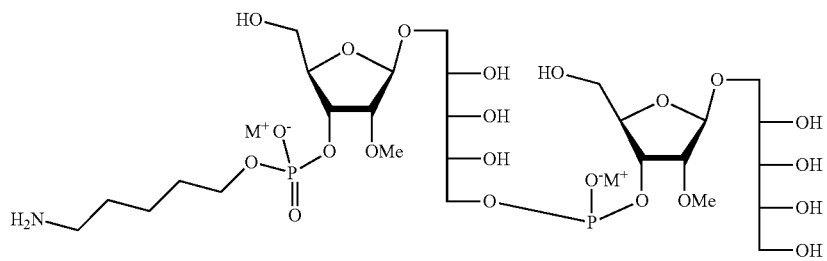
Compound 2c
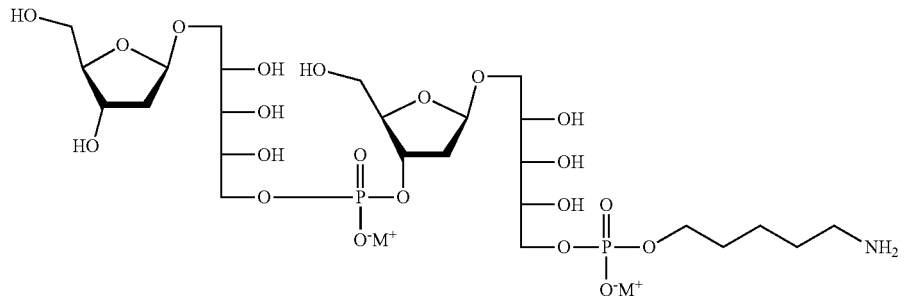
Compound 2f
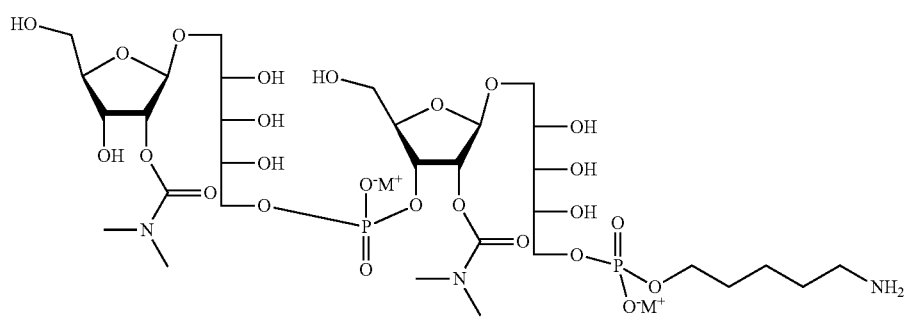
Compound 4a
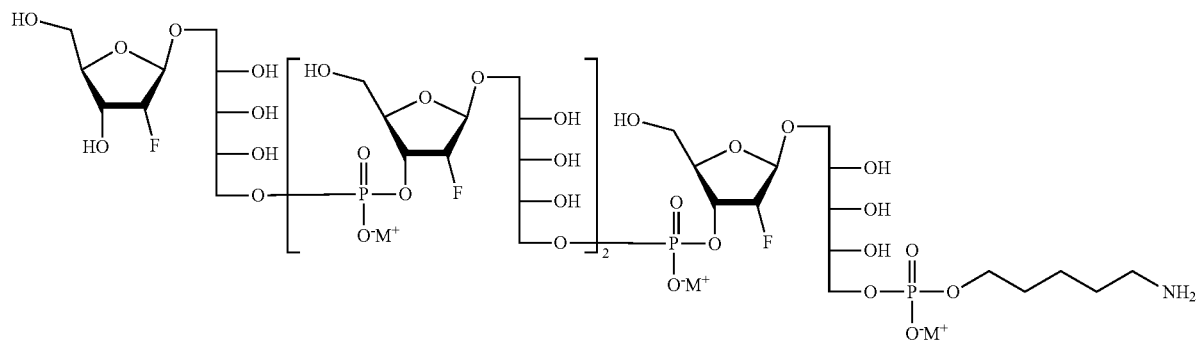
Compound 4b
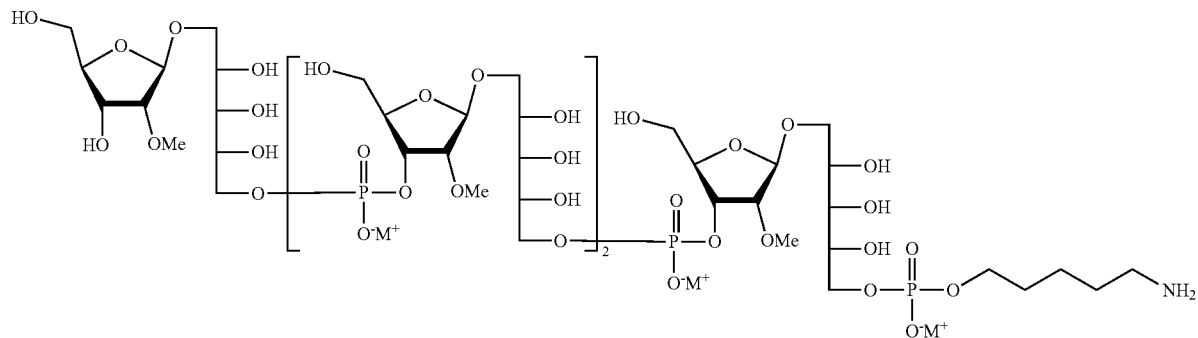

Compound 4c
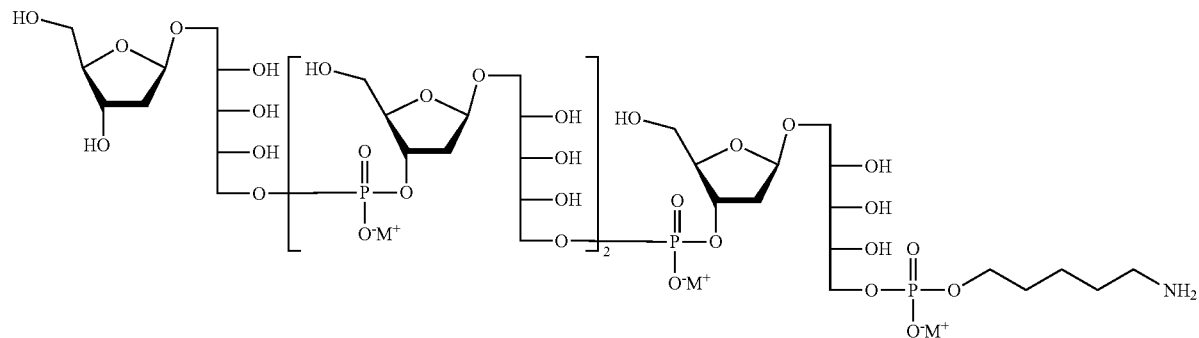
Compound 4d
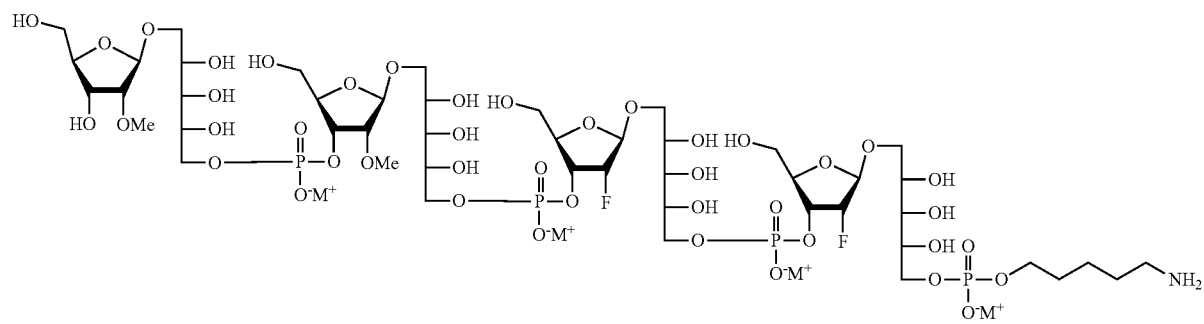
Compound 4e
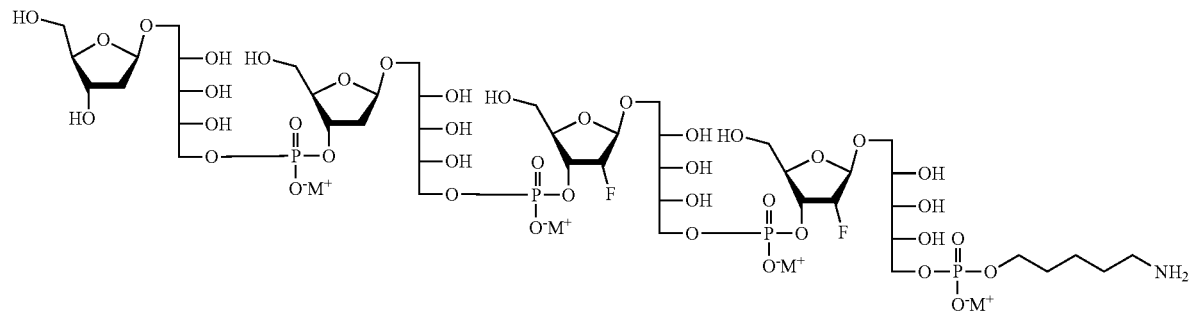
Compound 4f
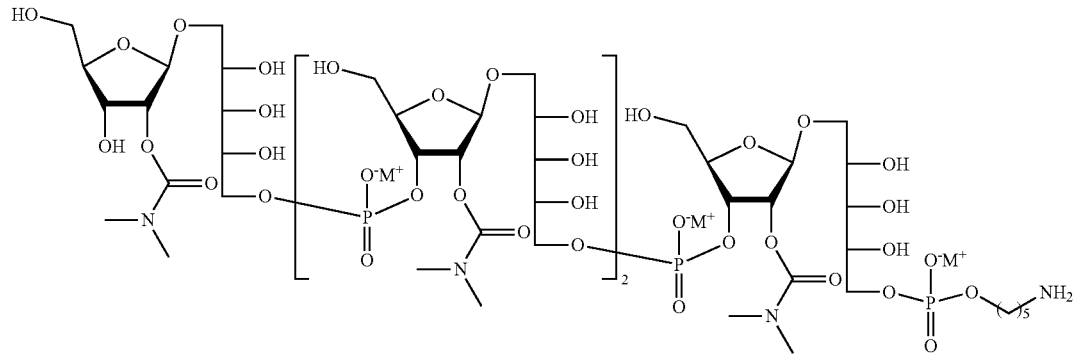

Compound 6a
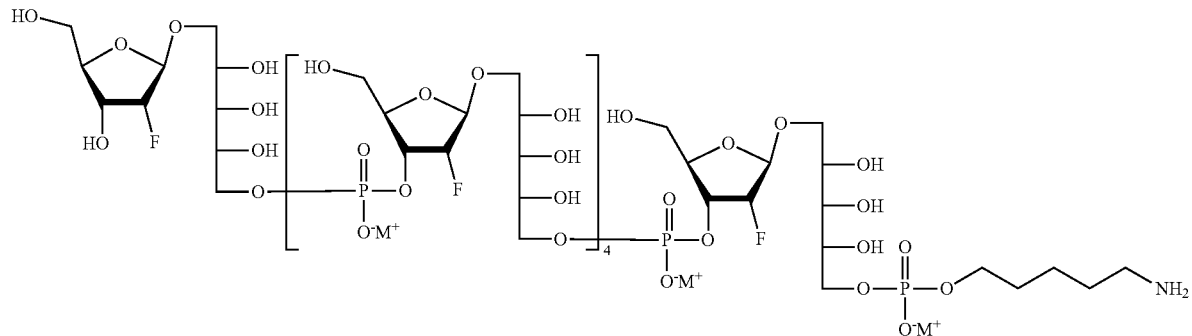
Compound 6b
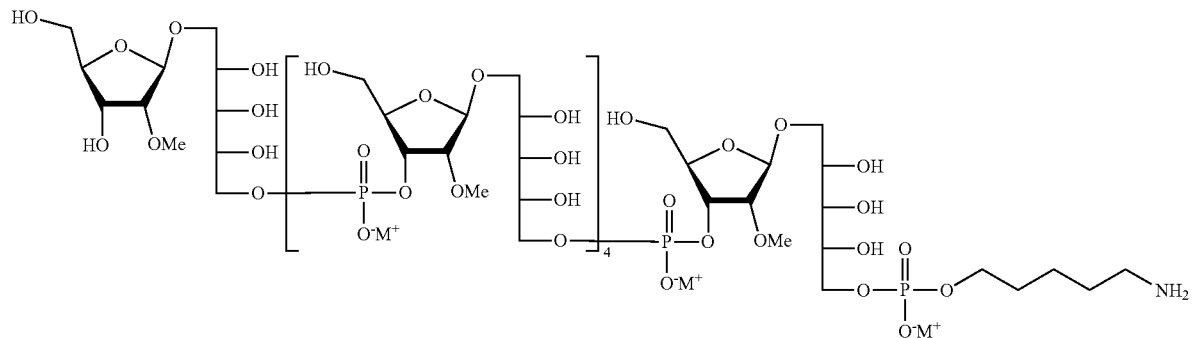
Compound 6c
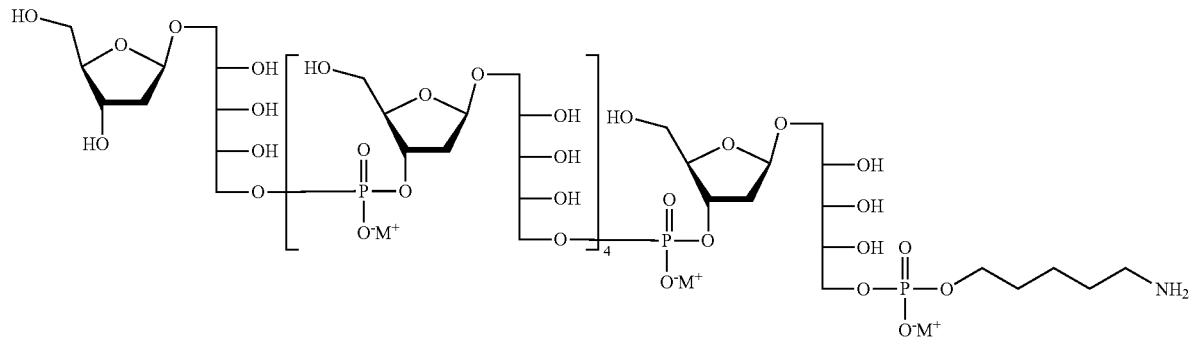
Compound 6f
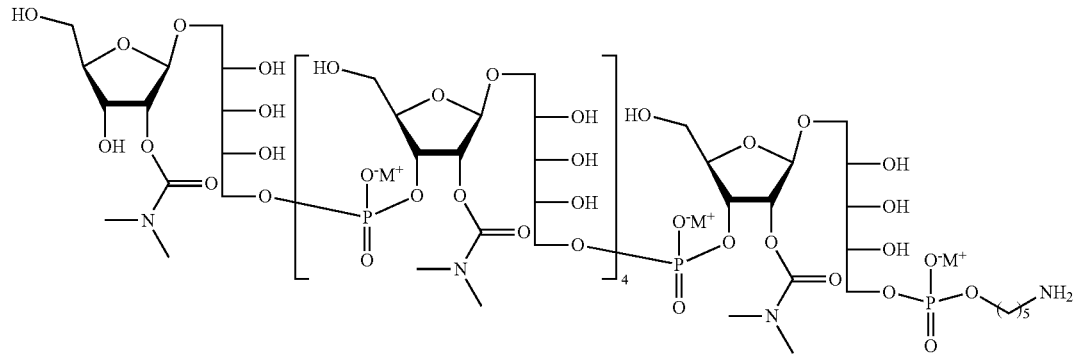

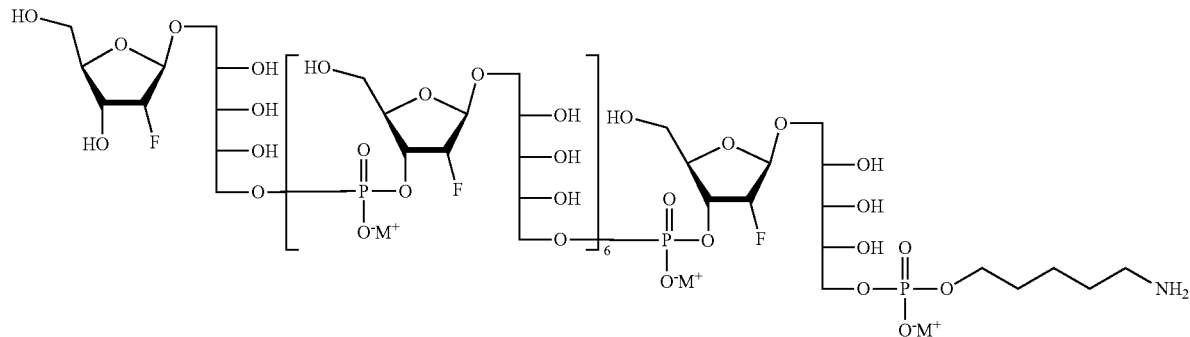

Compound 8a

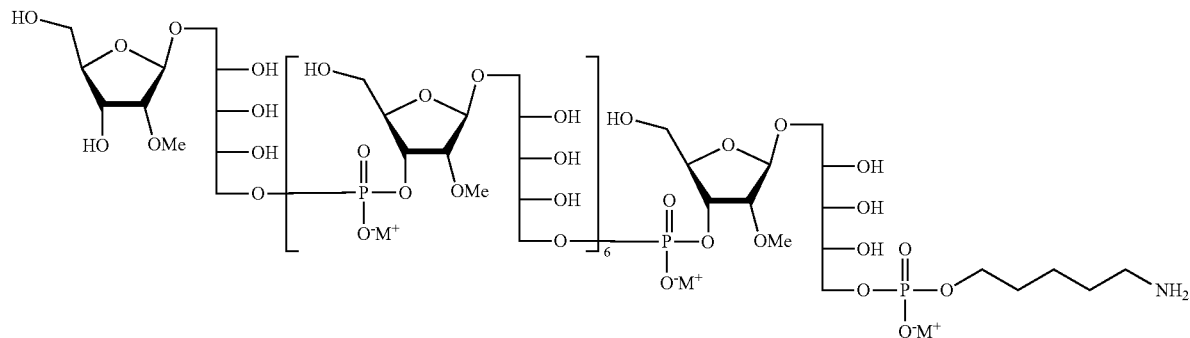

Compound 8b

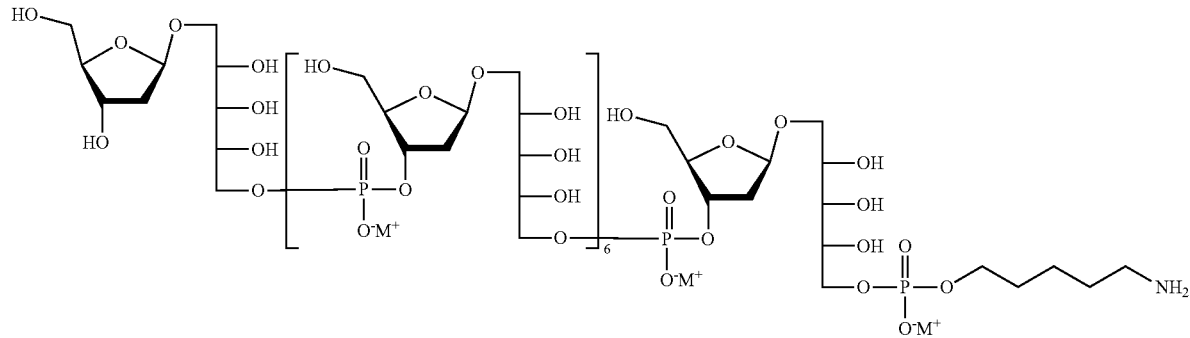

Compound 8c

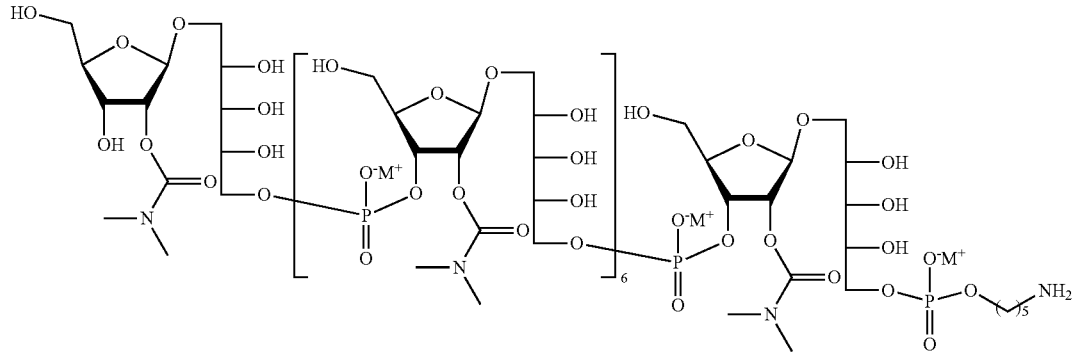

Compound 8f

Synthetic Approach
1. Stepwise Synthesis of the Inventive Saccharide.

Disaccharide repeating units having ribosylribitol backbone protected by appropriate protecting groups A1*-3-A1*-5, B1*-1-B1*-6, C*1-3, half repeating units having ribose or ribitol back bone A1*-1, A1*-2, C1*-1, C1*-2, and terminal units comprising a linker L, or T1*-T3*can be applied for various synthetic routes of the inventive saccharide. A1*-1-A1*-5, B1*-1-B1*-6, C1*-1-C1*-3 and T1*-T3*have the following structures:

27
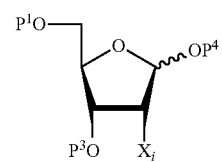
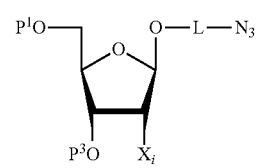
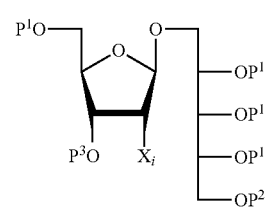
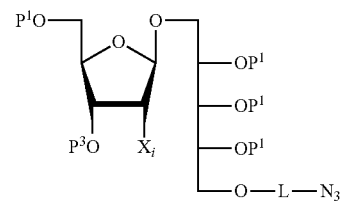
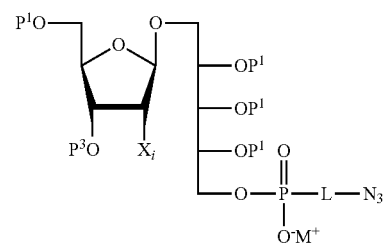
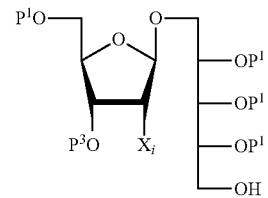
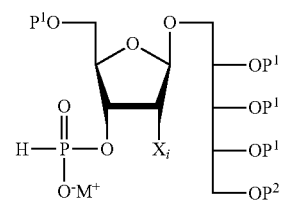
28
-continued
A1*-1
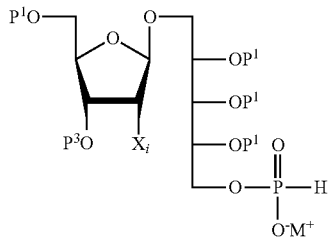
B1*-3
A1*-2
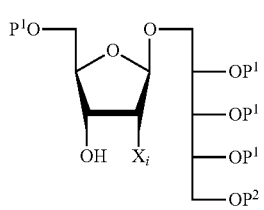
B1*-4
A1*-3
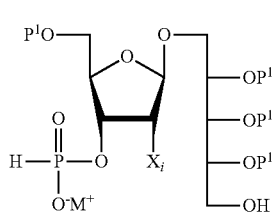
B1*-5
A1*-4
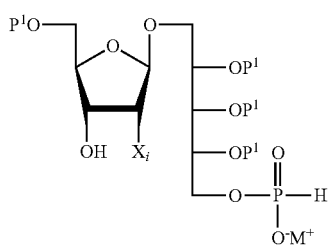
B1*-6
A1*-5
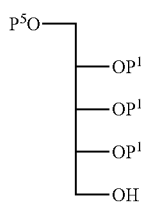
C1*-1
B1*-1
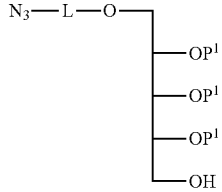
C1*-2
B1*-2
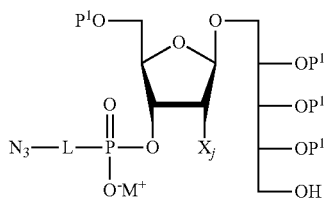
C1*-3
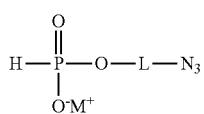
T1*

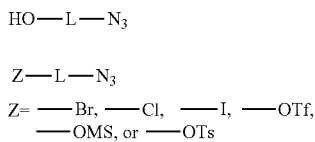

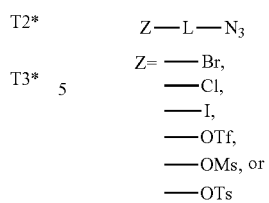

wherein $X_i$ and $X_j$ represent independently of each other $X_1$, $X_2$, $X_3$, $X_4$, $X_5$ or $X_6$;

$P^1$, $P^2$, $P^3$, $P^4$ and $P^5$ represent protecting groups that when bound to —O— cannot be identical to $X_i$ and/or $X_j$;

L has the meaning as defined above; and $M^+$ represents $Na^+$, $K^+$, $NH_4^+$, $H^+$ or $Et_3NH^+$.

A person skilled in the art may envision, that the protecting groups $P^1$ to $P^5$ employed in the synthesis of the inventive saccharides of the general formulae (I), (II-1), (II-2), (III-1), (III-2), (IV-1) and (IV-2) as well as conjugates with immunogenic carriers thereof cannot be identical to $X_i$ and/or $X_j$, when bound to an oxygen atom.

Some of useful synthetic routes are available by the combinations of the above-mentioned building blocks.

In an embodiment of the present invention, the following building blocks A1*-3, B1*-1 and T1*or T3*may be used for the synthesis of the inventive saccharide (Scheme 1).

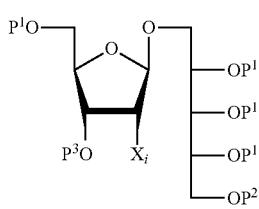

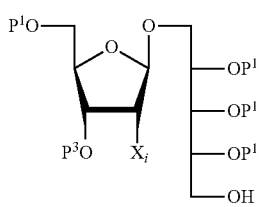

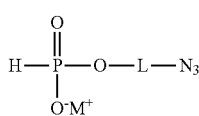

As starting building block A1*-3 may be used.
The synthetic method A comprising the following steps:
i) Providing a starting building block A1*-3

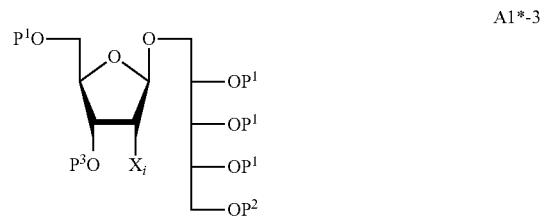

wherein $X_i$ represents $X_1$, $X_2$, $X_3$, $X_4$, $X_5$ or $X_6$; $P^1$, $P^2$ and $P^3$ are protecting groups that when bound to —O— are not identical to $X_i$;

ii) Removing $P^3$ group from A1*-3;
iii) Introducing hydrogen phosphonate group at C-3 position of a ribose of a resulting compound after step ii);
iv) Coupling an building block B1*-1 with a resulting compound after step iii)

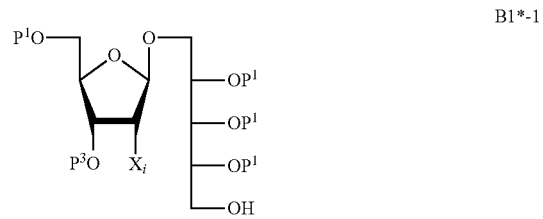

wherein $X_i$ represents $X_1$, $X_2$, $X_3$, $X_4$, $X_5$ or $X_6$; $P^1$ and $P^3$ are protecting groups that when bound to —O— are not identical to $X_i$;

v) Optionally repeating the steps i)-iv) for t times by using a resulting compound after the step iv) instead of the starting building block A1*-3 in the step i), wherein t is an integer 0 to 20;
vi) Removing $P^2$ protecting group from a resulting compound after step v);
vii) Coupling the compound T1*with a resulting compound after step vi);
viii) Removing $P^1$ and $P^3$ protecting groups and transforming an azido group to an amine group for obtaining the compound of the formula (I).

In the above-mentioned synthetic method A, the compound T3*also can be used instead of T1*in the step vii). In the step viii), removing $P^1$ and $P^3$ protecting groups and transforming an azido group to an amine group can be performed stepwise, but preferred at the same time under the same reaction condition.

When the half repeating unit A1*-1 is used as starting building block instead of the starting building block A1*-3 in the abovementioned synthetic method A, then after step v), the following steps vi') and vii') may be performed instead of the steps vi)-viii):

vi') Coupling a resulting compound after step v) with T2*;
vii') Removing $P^1$ and $P^3$ protecting groups and transforming an azido group to an amine group for obtaining the compound of the formula (I).

The half repeating unit C1*-1 can be used as termination building block after the step v) in the abovementioned synthetic method A and then the following steps vi")-xi") may be performed instead of the steps vi)-viii):

vi") Removing $P^3$ protecting group from a resulting compound after step v);
vii") Introducing hydrogen phosphonate group at C-3 position of a ribose of a resulting compound after step vi');
viii") Coupling a resulting compound after step vii") with C1*-1;

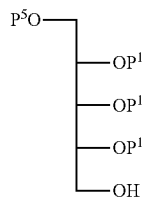

C1*-1 wherein $P^1$ and $P^5$ are protecting groups;

ix") Removing $P^2$ protecting group from a resulting compound after the step viii");
x") Coupling the compound T1* with a resulting compound after step ix");
xi") Removing $P^1$ and $P^5$ protecting groups and transforming an azido group to an amine group for obtaining the compound of the formula (I).

In step iii) and vii") of synthetic method A, a phosphoramidite group can also be introduced instead of a hydrogen phosphonate group at C-3 position of a ribose of a resulting compound after step ii) or step vi"). T1* is then replaced by bis(diisopropylamino)benzyloxyphosphine and HO-L-$N_3$.

In another embodiment of the present invention, the following building blocks A1*-4 or A1*-5, and B1*-1 may be used for the synthesis of the inventive saccharide (Scheme 2).

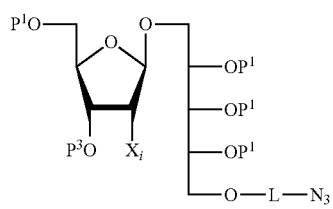

A1*-4

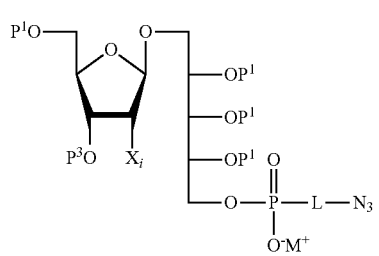

A1*-5

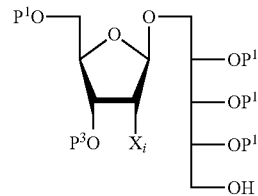

B1*-1

As starting building block A1*-4 or A1*-5 may be used.
The synthetic method B comprising the following steps:

i) Providing a starting building block A1*-4 or A1*-5

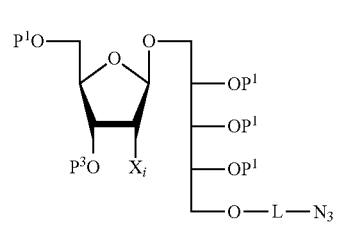

A1*-4 wherein L is a linker and has the same meaning as defined above;
$X_i$ represents $X_1$, $X_2$, $X_3$, $X_4$, $X_5$ or $X_6$; $P^1$ and $P^3$ are protecting groups that when bound to —O— are not identical to $X_i$;

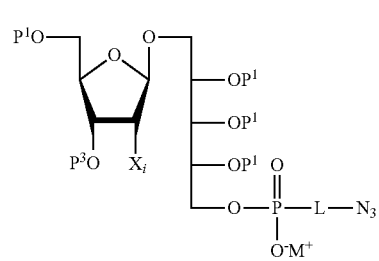

A1*-5 wherein L is a linker and has the same meaning as defined above;
$X_i$ represents $X_1$, $X_2$, $X_3$, $X_4$, $X_5$ or $X_6$; $P^1$ and $P^3$ are protecting groups that when bound to —O— are not identical to $X_i$;

ii) Removing $P^3$ group from A1*-4 or A1*-5
iii) Introducing hydrogen phosphonate group at C-3 position of a ribose of a resulting compound after step ii);
iv) Coupling an building block B1*-1 with a resulting compound after step iii)

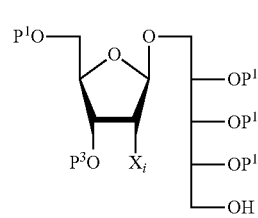

B1*-1 wherein $X_i$ represents $X_1$, $X_2$, $X_3$, $X_4$, $X_5$ or $X_6$; $P^1$ and $P^3$ are protecting groups that when bound to —O— are not identical to $X_i$;

v) Optionally repeat the steps i)-iv) for t times by using a resulting compound after the step iv) instead of the starting building block A1*-4 or A1*-5 in the step i), wherein t is an integer 0 to 20;

vi) Removing $P^1$ and $P^3$ protecting groups and transforming an azido group to an amine group for obtaining the compound of the formula (I).

In the step vi), removing $P^1$ and $P^3$ protecting groups and transforming an azido group to an amine group can be performed stepwise, but preferred at the same time under the same reaction condition.

The half repeating unit C1*-1 can be used as termination building block after the step v) in the abovementioned synthetic method B and then the following steps vi")-ix") may be performed instead of the step vi):

vi") Removing $P^3$ protecting group from a resulting compound after step v);

vii") Introducing hydrogen phosphonate group at C-3 position of a ribose of a resulting compound after step vi");

viii") Coupling a resulting compound after step vii") with C1*-1;

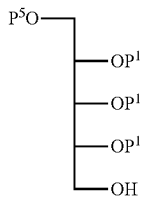

C1*-1 wherein $P^1$ and $P^5$ are protecting groups;

ix") Removing $P^1$ and $P^5$ protecting groups and transforming an azido group to an amine group for obtaining the compound of the formula (I).

In step iii) and vii") of synthetic method B, a phosphoramidite group can also be introduced instead of a hydrogen phosphonate group at C-3 position of a ribose of a resulting compound after step ii) or step vi"). Starting building block A1*-5 is then replaced by A1*-5' or A1*-5".

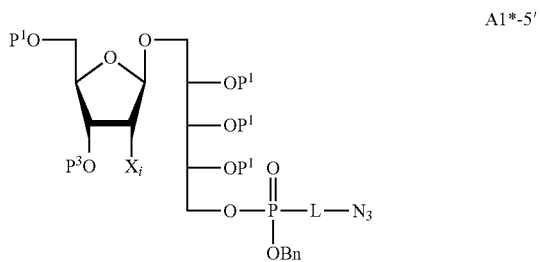

A1*-5'

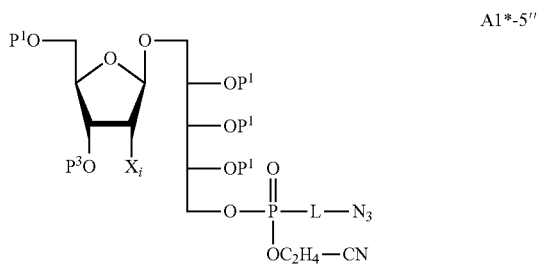

A1*-5"

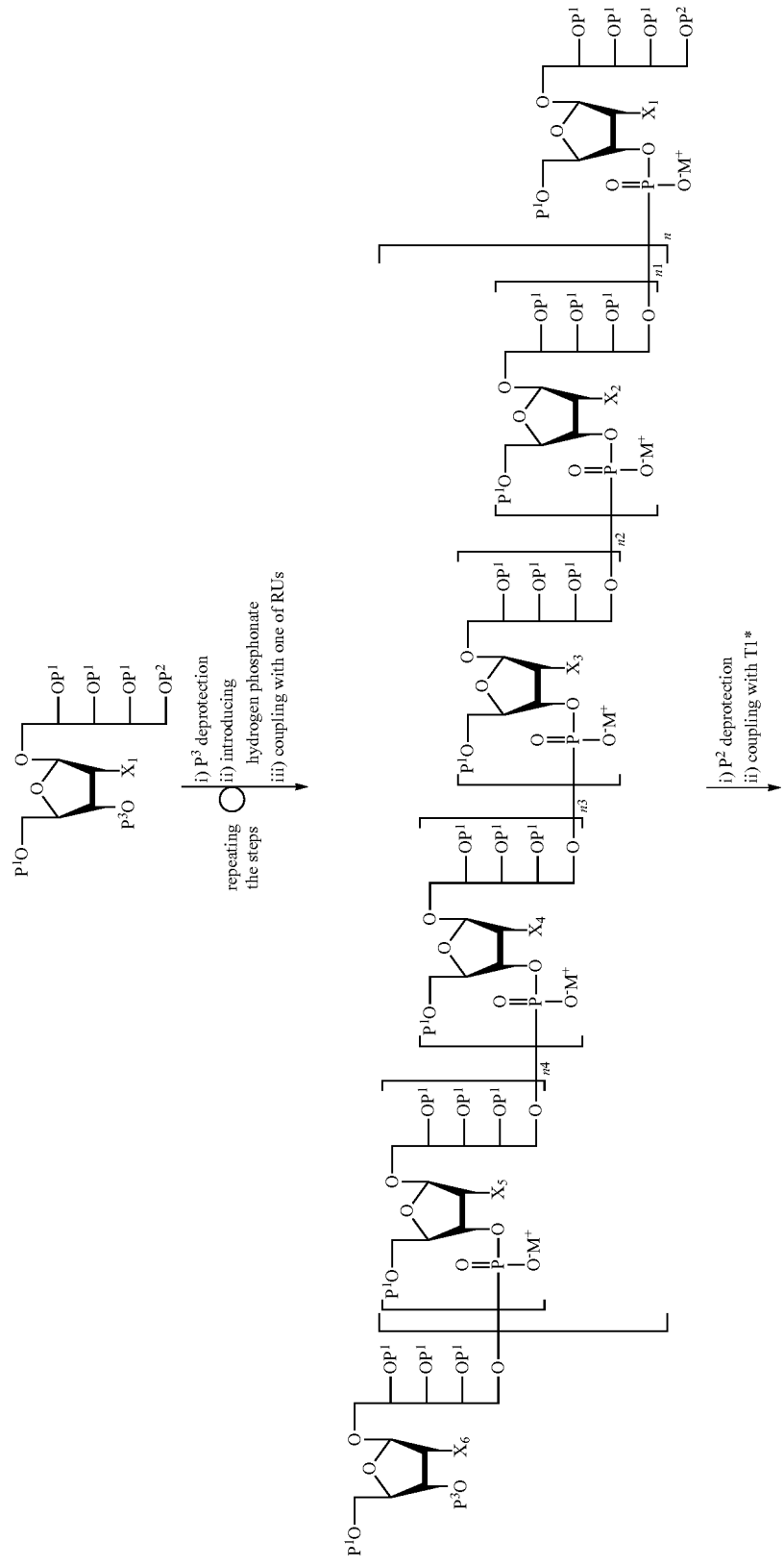

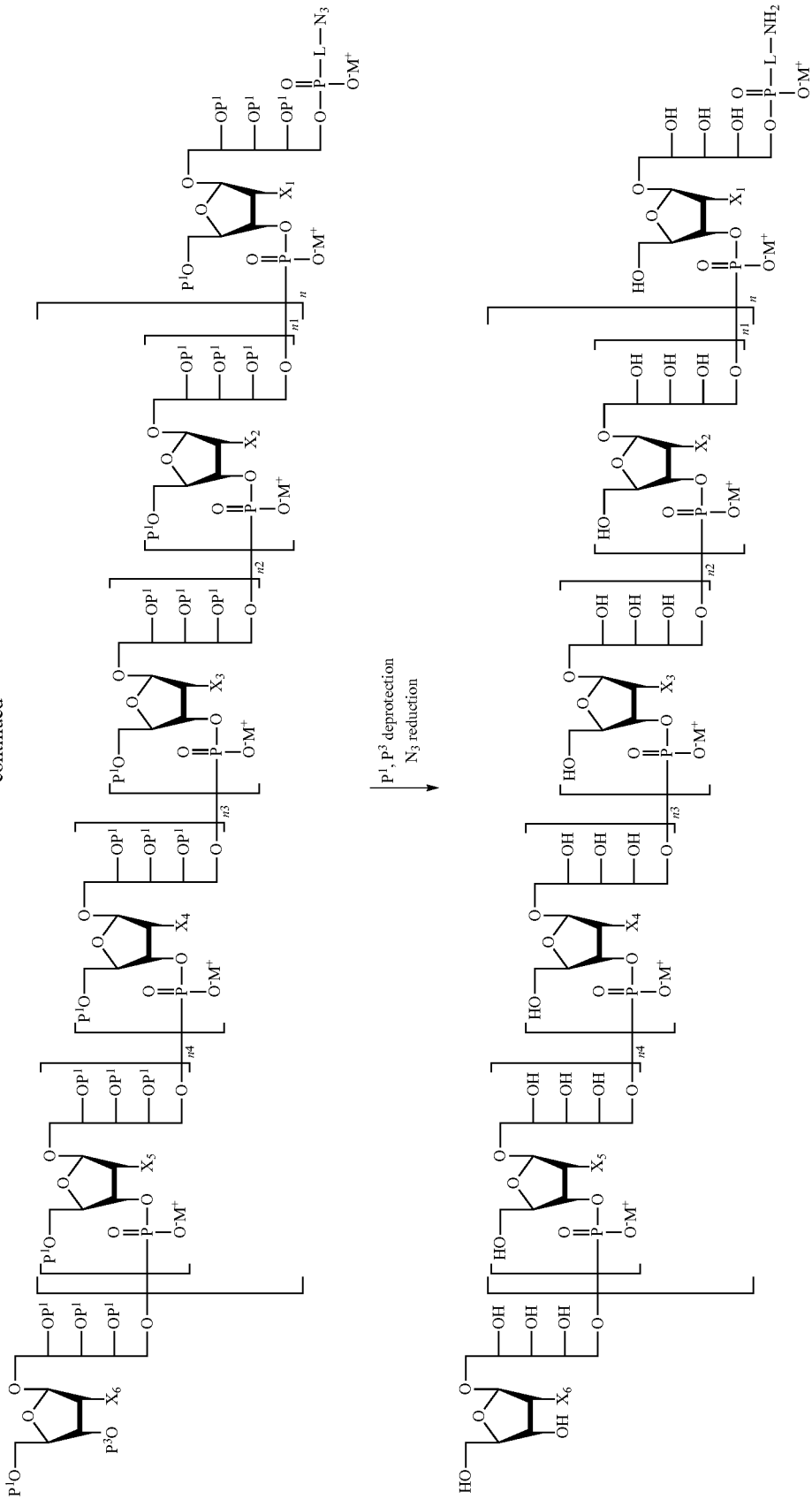

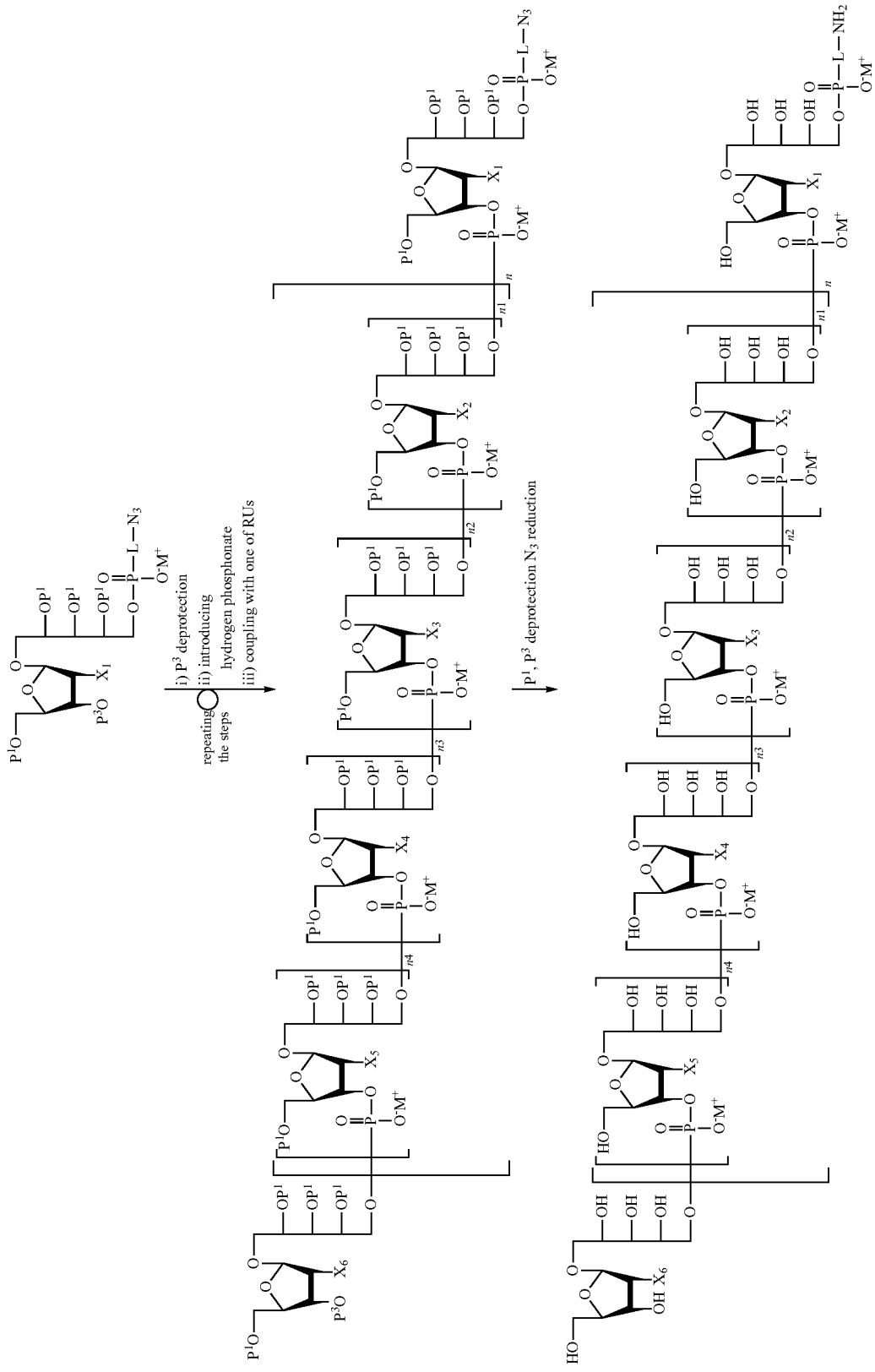

In an embodiment of the present invention, the following building blocks A1*-3, B1*-1 and T1* or T3* may be used for the synthesis of the inventive saccharide (Scheme 1).

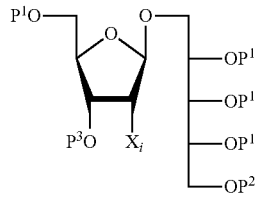

A1*-3'

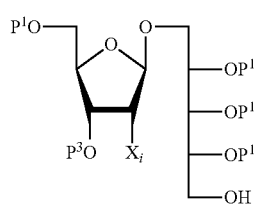

B1*-1

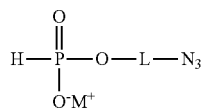

T1*

Z—L—N$_3$

Z = —Br, —Cl, —I,
—OTf, —OMs, or
—OTs

T3*

As starting building block A1*-3 may be used.

The synthetic method C comprising the following steps:
i) Providing a starting building block A1*-3

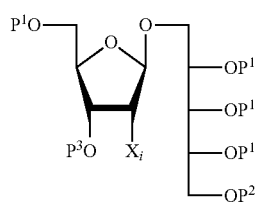

A1*-3 wherein $X_i$ represents $X_1$, $X_2$, $X_3$, $X_4$, $X_5$ or $X_6$; $P^1$, $P^2$ and $P^3$ are protecting groups that when bound to —O— are not identical to $X_i$;

ii) Removing $P^3$ group from A1*-3;
iii) Introducing hydrogen phosphonate group at C-3 position of a ribose of a resulting compound after step ii);
iv) Coupling an building block B1*-1 with a resulting compound after step iii)

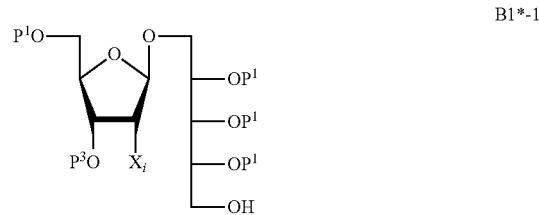

B1*-1 wherein $X_i$ represents $X_1$, $X_2$, $X_3$, $X_4$, $X_5$ or $X_6$; $P^1$ and $P^3$ are protecting groups that when bound to —O— are not identical to $X_i$;

v) Optionally repeating the steps i)-iv) for t times by using a resulting compound after the step iv) instead of the starting building block A1*-3 in the step i), wherein t is an integer 0 to 20;
vi) Removing $P^3$ protecting group from a resulting compound after step v);
vii) Coupling the compound T1* or T3* with a resulting compound after step vi);
viii) Removing $P^1$ and $P^2$ protecting groups and transforming an azido group to an amine group for obtaining the compound of the formula (I).

In the step viii), removing $P^1$ and $P^3$ protecting groups and transforming an azido group to an amine group can be performed stepwise, but preferred at the same time under the same reaction condition.

The half repeating unit A1*-1 can be used as a starting building block

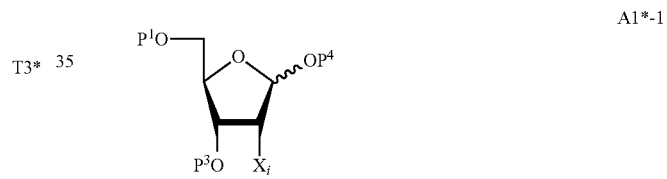

A1*-1 instead of A1*-3 in the step i) in the abovementioned synthetic method C and then a step for removing $P^4$ protecting group is added into the step viii).

The half repeating unit C1*-1 can be used as termination building block after the step v) in the abovementioned synthetic method C and then the following steps vi")-xi") may be performed instead of the steps vi)-viii):
vi") Removing $P^3$ protecting group from a resulting compound after step v);
vii") Introducing hydrogen phosphonate group at C-3 position of a ribose of a resulting compound after step vi");
viii") Coupling a resulting compound after step vii") with C1*-1;

C1*-1 wherein $P^1$ and $P^5$ are protecting groups;

ix") Removing $P^5$ protecting group from a resulting compound after the step viii");

x") Coupling the compound T1*or T3*with a resulting compound after step ix");

xi") Removing $P^1$ protecting groups and transforming an azido group to an amine group for obtaining the compound of the formula (I).

In step iii) and vii") of synthetic method C, a phosphoramidite group can also be introduced instead of a hydrogen phosphonate group at C-3 position of a ribose of a resulting compound after step ii) or step vi"). T1*is then replaced by bis(diisopropylamino)benzyloxyphosphine and HO-L-$N_3$.

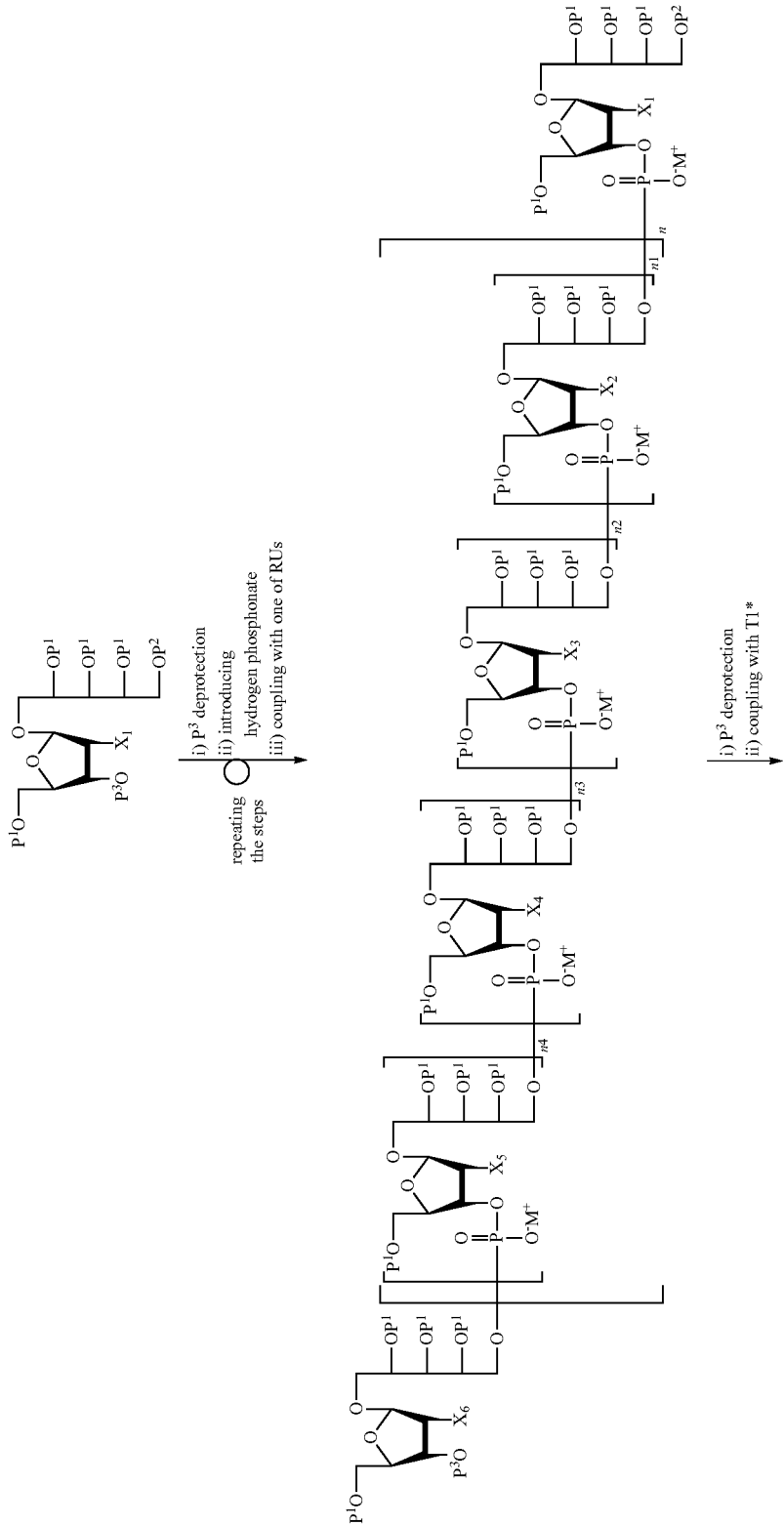

-continued
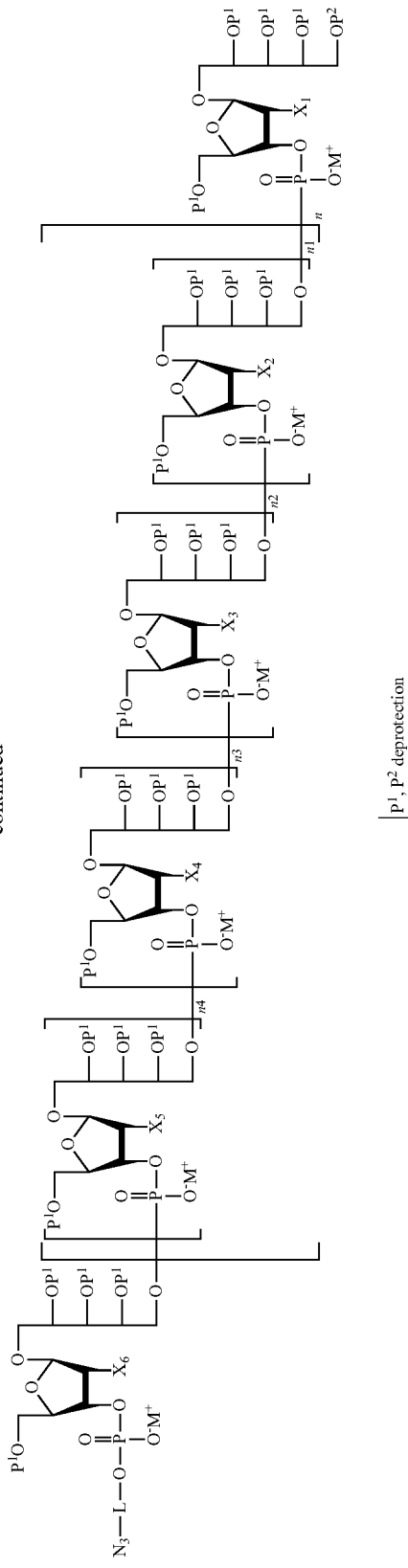 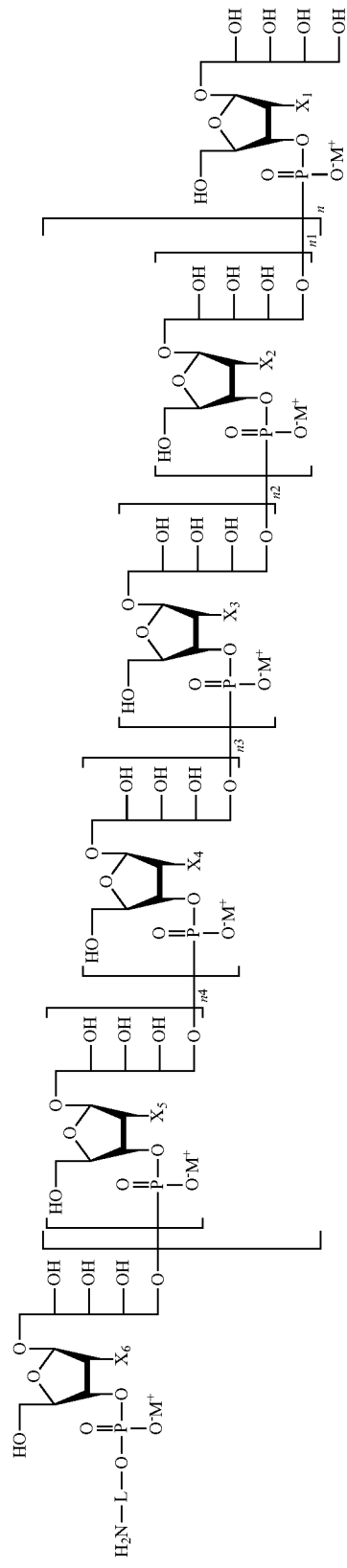

In another embodiment of the present invention, the following building blocks A1*-3 B1*-1, and C1*-2 or C1*-3 may be used for the synthesis of the inventive saccharide.

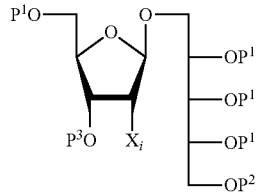

A1*-3

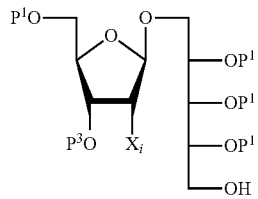

B1*-1

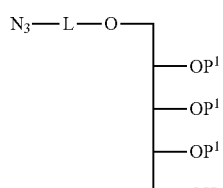

C1*-2

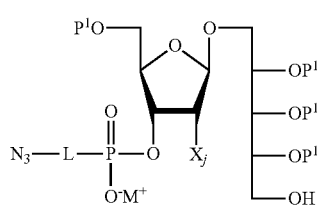

C1*-3

As starting building block A1*-3 may be used.
The synthetic method D comprising the following steps:
i) Providing a starting building block A1*-3

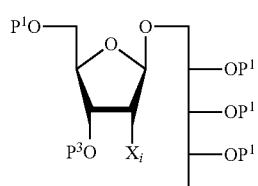

A1*-3 wherein L is a linker and has the same meaning as defined above;
$X_i$ represents $X_1, X_2, X_3, X_4, X_5$ or $X_6$; $P^1$, $P^2$ and $P^3$ are protecting groups that when bound to —O— are not identical to $X_i$;
ii) Removing $P^3$ group from A1*-3;
iii) Introducing hydrogen phosphonate group at C-3 position of a ribose of a resulting compound after step ii);

iv) Coupling an building block B1*-1 with a resulting compound after step iii)

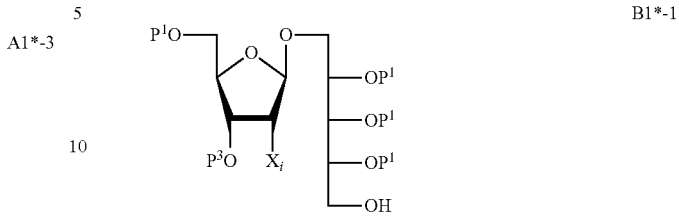

B1*-1 wherein $X_i$ represents $X_1, X_2, X_3, X_4, X_5$ or $X_6$; $P^1$ and $P^3$ are protecting groups that when bound to —O— are not identical to $X_i$;

v) Optionally repeat the steps i)-iv) for t times by using a resulting compound after the step iv) instead of the starting building block A1*-3 in the step i), wherein t is an integer 0 to 20;

vi) Removing $P^3$ group from a resulting compound after the step v);

vii) Coupling a building block C1*-2 or C1*-3 with a resulting compound after the step vi)

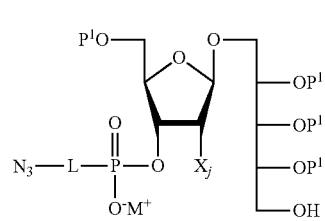

C1*-2 wherein $P^1$ is protecting group;

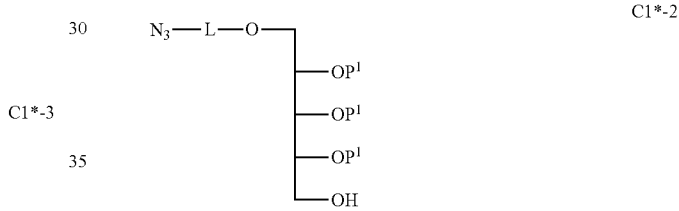

C1*-3 wherein $X_j$ represents $X_1, X_2, X_3, X_4, X_5$ or $X_6$; $P^1$ is protecting group that when bound to —O— is not identical to $X_j$;

viii) Removing $P^1$ and $P^2$ protecting groups and transforming an azido group to an amine group for obtaining the compound of the formula (I).

In the step viii), removing $P^1$ and $P^2$ protecting groups and transforming an azido group to an amine group can be performed stepwise, but preferred at the same time under the same reaction condition.

In step iii), a phosphoramidite group can also be introduced instead of a hydrogen phosphonate group at C-3 position of a ribose of a resulting compound after step ii). Starting building block C1*-3 is then replaced by C1*-3' or C1*-3".

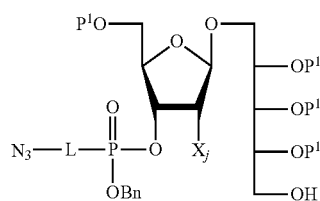
C1*-3'
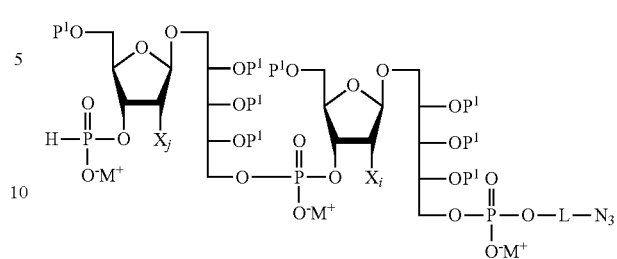
A2*-4
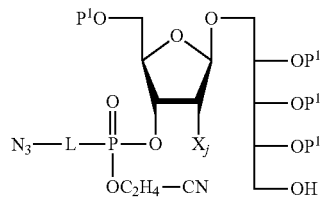
C1*-3''
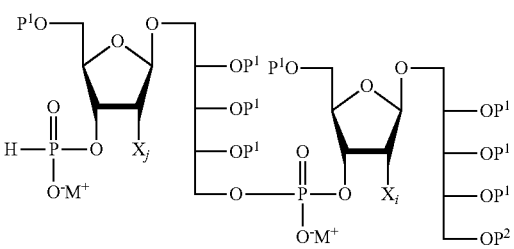
B2*-1
In one embodiment of the present invention, the following building blocks consisting of two repeating units are useful for synthesis of the inventive saccharide by [2+2] synthetic approach:
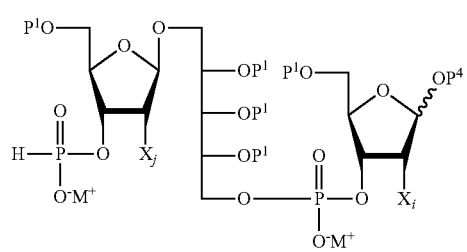
A2*-1
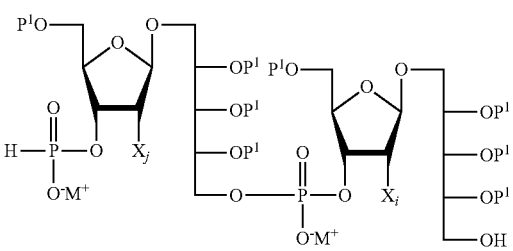
B2*-2
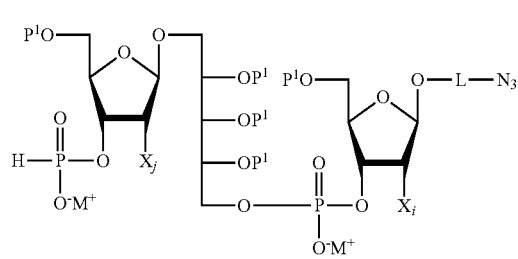
A2*-2
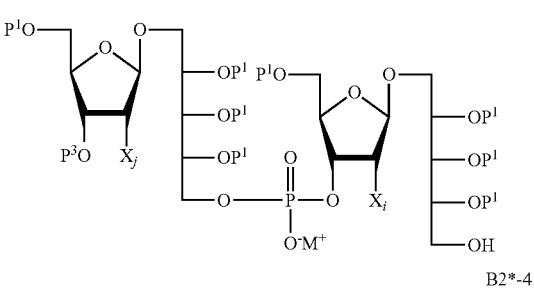
B2*-3
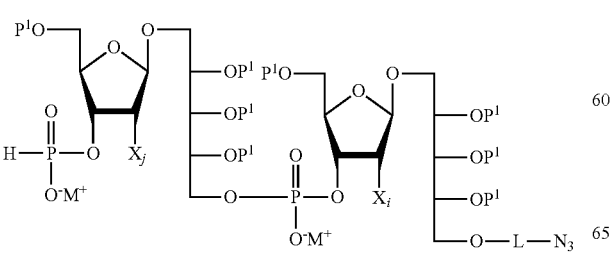
A2*-3
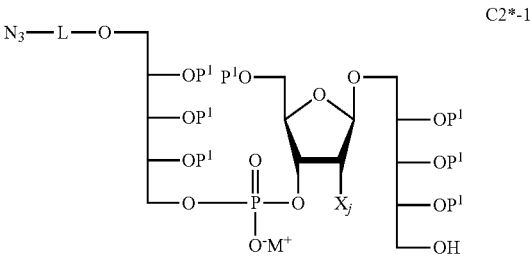
B2*-4
C2*-1

-continued

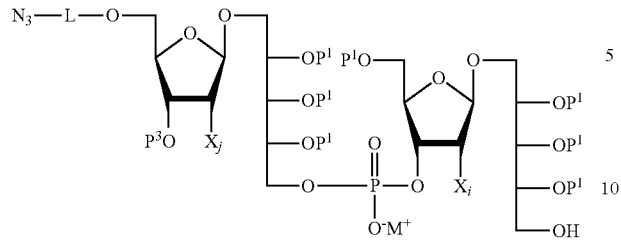
C2*-2

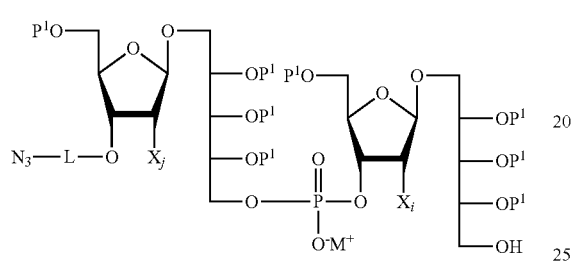
C2*-3

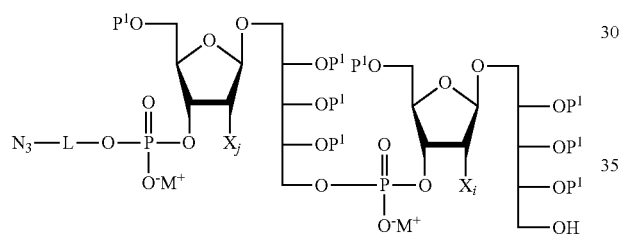
C2*-4

A synthetic method E-1 comprises the following steps (Scheme 4):

i) Providing a starting building block selected from A2*-2, A2*-3, or A2*-4

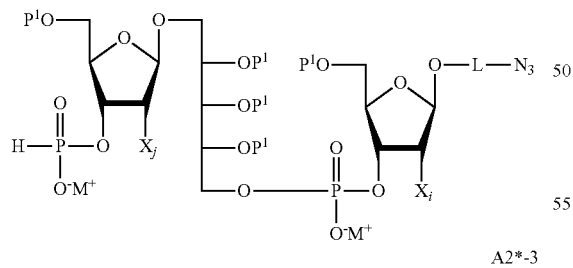
A2*-2

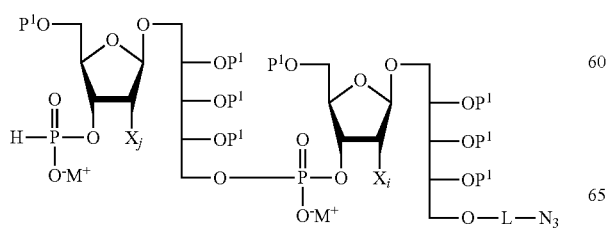
A2*-3

-continued

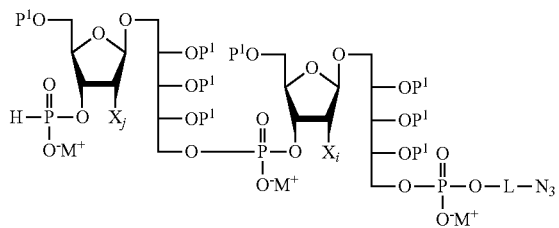
A2*-4 wherein L is a linker and has the same meaning as defined above;

$X_i$ and $X_j$ represents independently of each other $X_1$, $X_2$, $X_3$, $X_4$, $X_5$ or $X_6$;

$P^1$ represents protecting group that when bound to —O— is not identical to $X_i$ and $X_j$; and ii) Coupling a building block B2*-3 with the starting building block selected from A2*-2, A2*-3, or A2*-4

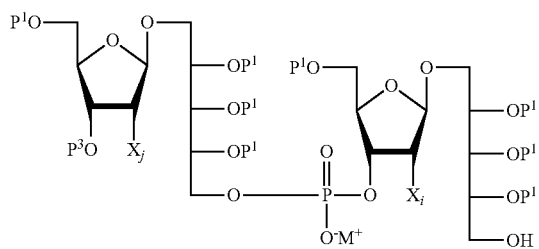
B2*-3 wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

iii) Removing $P^3$ group from a resulting compound after the step ii);

iv) Introducing hydrogen phosphonate at C-3 position of ribose of a resulting compound after the step iii);

v) Optionally repeat the steps i)-iv) for t times by using a resulting compound after the step iv) instead of the starting building block in the step i), wherein t is an integer 0 to 10;

vi) Removing $P^1$ and $P^3$ protecting groups from a resulting compound after step v) and transforming an azido group to an amine group for obtaining the compound of the formula (I).

In the step vi), removing $P^1$ and $P^3$ protecting groups and transforming an azido group to an amine group can be performed stepwise, but preferred at the same time under the same reaction condition.

After the step v) of the synthetic method E-1, a further building block B2*-4 may be alternatively coupled with the resulting compound after the step v). In this case, the synthetic method E-1 comprises the following steps instead of the step vi):

vi') coupling a building block B2*-4 with a resulting compound after the step v);

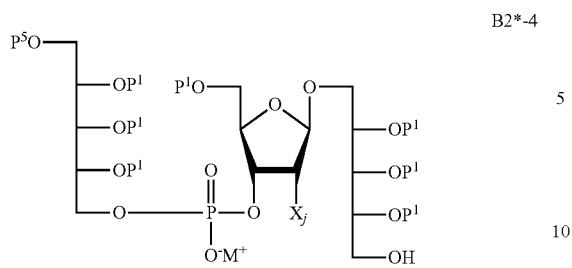
B2*-4
wherein $X_j$ represents $X_1$, $X_2$, $X_3$, $X_4$, $X_5$ or $X_6$; $P^1$ and $P^5$ are protecting groups that when bound to —O— are not identical to $X_j$;
vii') Removing $P^1$ and $P^5$ protecting groups from a resulting compound after the step vi') and transforming an azido group to an amine group for obtaining the compound of the formula (I).

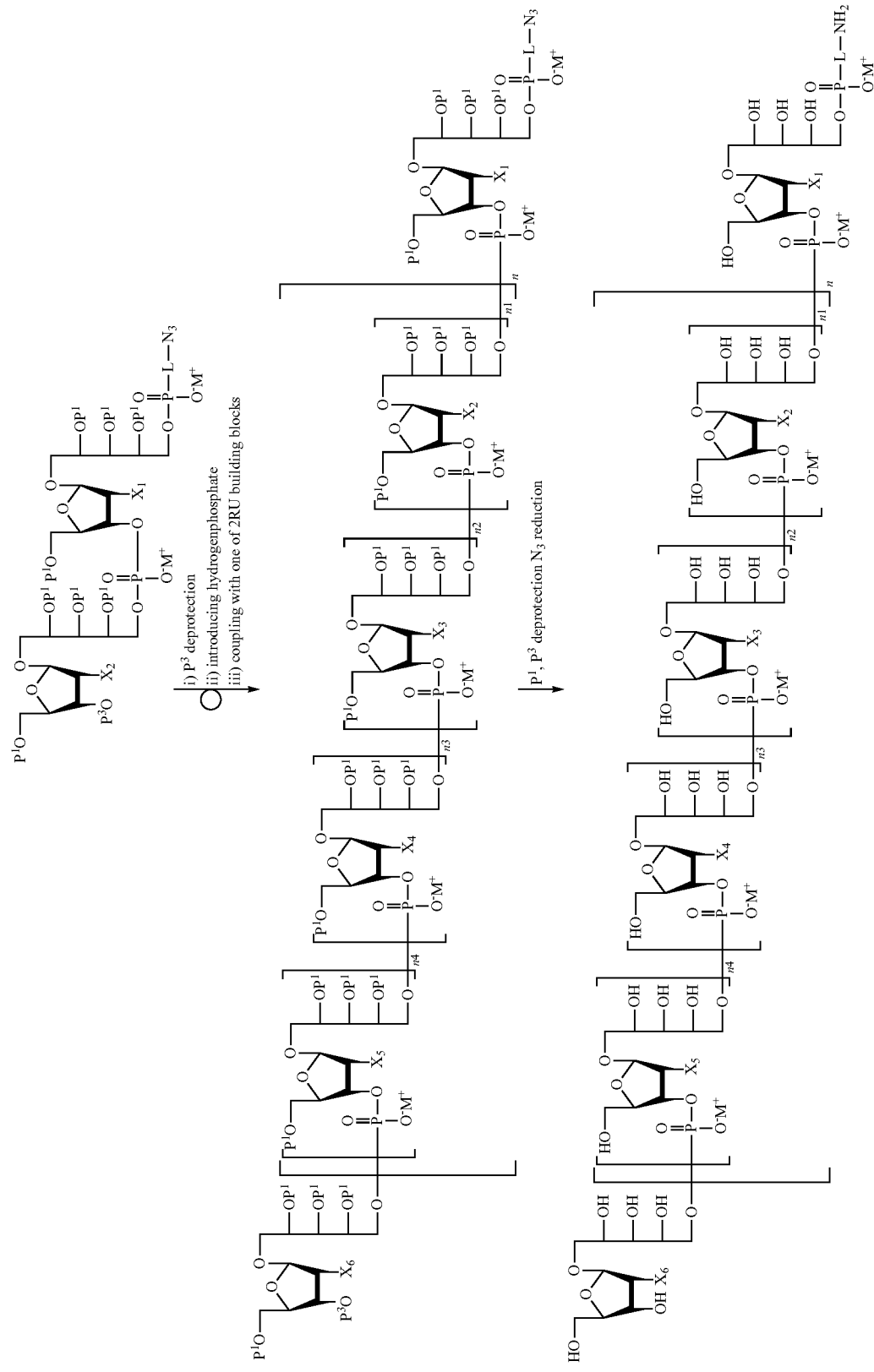

Of course, B2*-3 or B2*-4 can be used as a starting building block. In this case, an alternative synthetic method E-2 comprises the following steps:
i) Providing a starting building block selected from B2*-3, or B2*-4

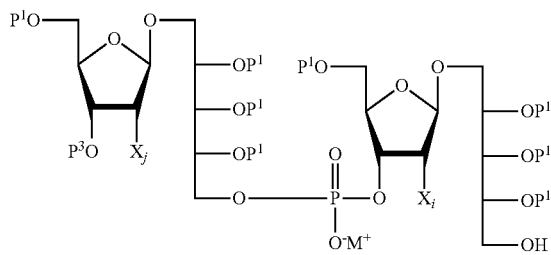

B2*-3 wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

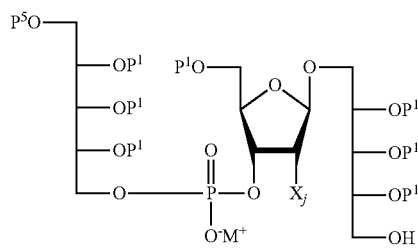

B2*-4 wherein $X_j$ represents $X_1$, $X_2$, $X_3$, $X_4$, $X_5$ or $X_6$; $P^1$ and $P^5$ are protecting groups that when bound to —O— are not identical to $X_j$;

ii) Coupling a building block B2*-1 with the starting building block selected from B2*-3, or B2*-4

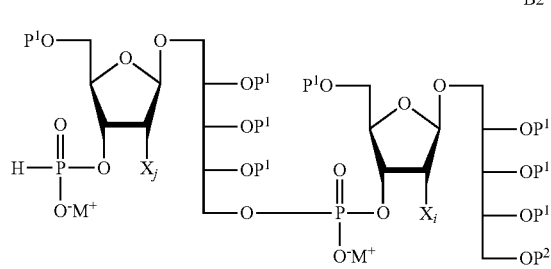

B2*-1 wherein $X_i$ and $X_j$ represents independently of each other $X_1$, $X_2$, $X_3$, $X_4$, $X_5$ or $X_6$; $P^1$ and $P^2$ are protecting groups that when bound to —O— are not identical to $X_i$ and $X_j$;

iii) Removing $P^2$ protecting group from a resulting compound after the step ii);

iv) Optionally repeat the steps i)-iii) for t times by using a resulting compound after the step iii) instead of the starting building block in the step i), wherein t is an integer 0 to 10;

v) Coupling a resulting compound after the step iv) with a building block selected from A2*-2, A2*-3, or A2*-4

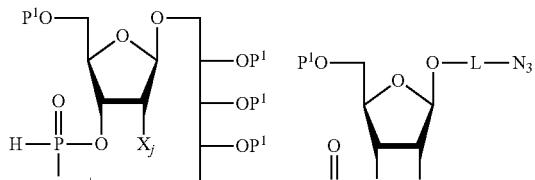

A2*-2

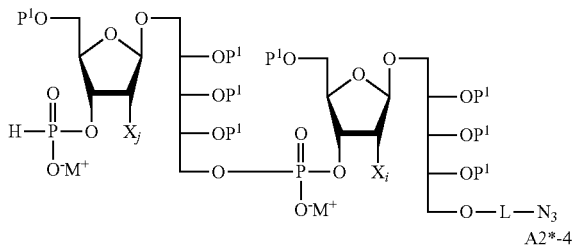

A2*-3

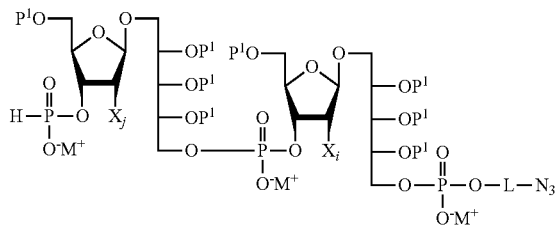

A2*-4 wherein L is a linker and has the same meaning as defined above;

$X_i$ and $X_j$ represents independently of each other $X_1$, $X_2$, $X_3$, $X_4$, $X_5$ or $X_6$; $P^1$ represents protecting group that when bound to —O— is not identical to $X_i$ and/or $X_j$;

vi) Removing $P^1$, $P^3$ and $P^5$ protecting groups from a resulting compound after step v) and transforming an azido group to an amine group for obtaining the compound of the formula (I).

In the step vi), removing $P^1$, $P^3$ and $P^5$ protecting groups and transforming an azido group to an amine group can be performed stepwise, but preferred at the same time under the same reaction condition.

An alternative synthetic method E-3 differs from synthetic method E-1 in that phosphoramidite is employed instead of phosphonate chemistry. Thus, synthetic method E-3 comprises the following steps:
i) Providing a starting building block selected from A2*-2", A2*-3", or A2*-4"

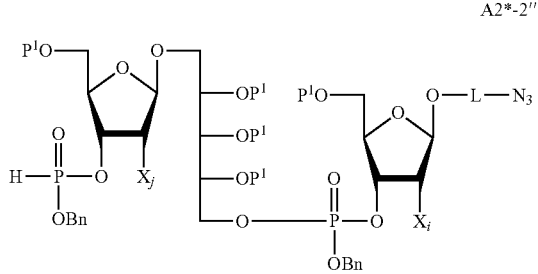

A2*-2"

-continued

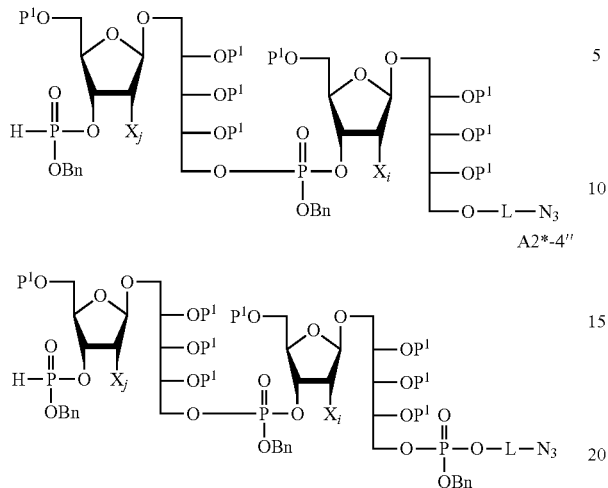

wherein L is a linker and has the same meaning as defined above;

$X_i$ and $X_j$ represents independently of each other $X_1$, $X_2$, $X_3$, $X_4$, $X_5$ or $X_6$;

$P^1$ represents protecting group that when bound to —O— is not identical to $X_i$ and X; and ii) Coupling a building block B2*-3" with the starting building block selected from A2*-2", A2*-3", or A2*-4"

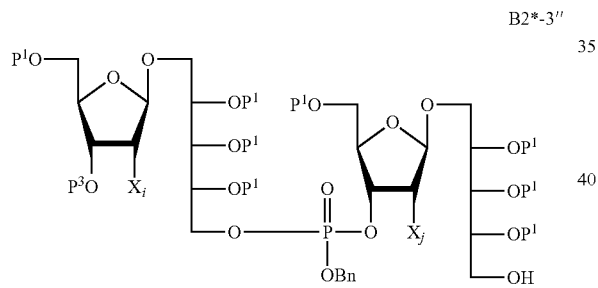

wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

iii) Removing $P^3$ group from a resulting compound after the step ii);

iv) Introducing phosphoramidite group at C-3 position of ribose of a resulting compound after the step iii);

v) Optionally repeat the steps i)-iv) for t times by using a resulting compound after the step iv) instead of the starting building block in the step i), wherein t is an integer 0 to 10;

vi) Removing $P^1$ and $P^3$ protecting groups from a resulting compound after step v) and transforming an azido group to an amine group for obtaining the compound of the formula (I).

In the step vi), removing $P^1$ and $P^3$ protecting groups and transforming an azido group to an amine group can be performed stepwise, but preferred at the same time under the same reaction condition.

After the step v) of the synthetic method E-3, a further building block B2*-4" may be alternatively coupled with the resulting compound after the step v). In this case, the synthetic method E-3 comprises the following steps instead of the step vi):

vi') coupling a building block B2*-4" with a resulting compound after the step v);

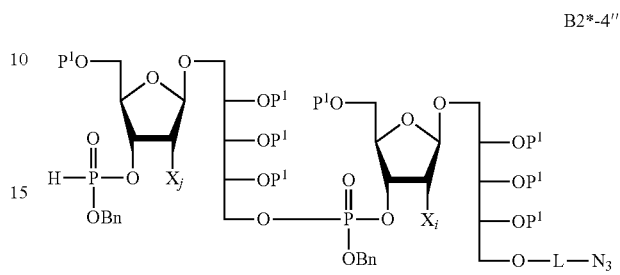

wherein $X_j$ represents $X_1$, $X_2$, $X_3$, $X_4$, $X_5$ or $X_6$; $P^1$ and $P^5$ are protecting groups that when bound to —O— are not identical to $X_j$;

vii') Removing $P^1$ and $P^5$ protecting groups from a resulting compound after the step vi') and transforming an azido group to an amine group for obtaining the compound of the formula (I).

A synthetic method F-1 comprises the following steps (Scheme 5):

i) Providing a starting building block selected from A2*-1 or B2*-1

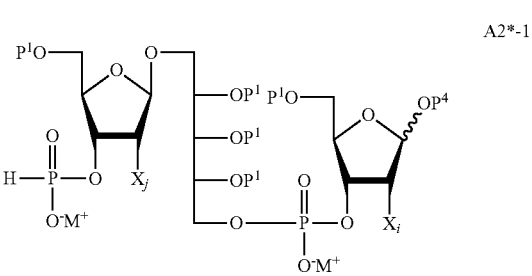

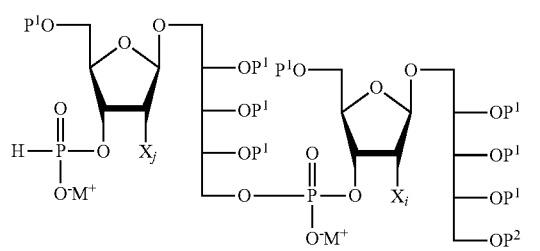

wherein $X_i$ and $X_j$ represents independently of each other $X_1$, $X_2$, $X_3$, $X_4$, $X_5$ or $X_6$; $P^1$, $P^2$ and $P^4$ represent protecting group that when bound to —O— are not identical to $X_i$ and $X_j$;

ii) Coupling a building block B2*-3 with the starting building block selected from A2*-1 or B2*-1

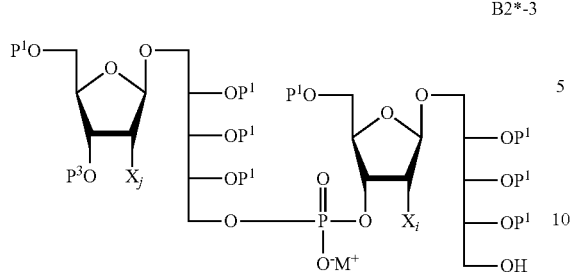

B2*-3

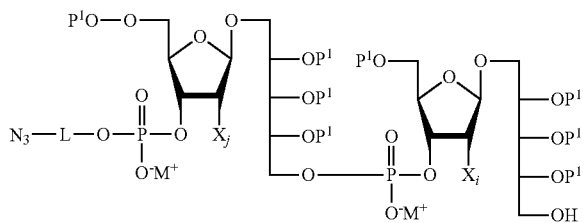

C2*-4 wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

iii) Removing $P^3$ group from a resulting compound after the step ii);

iv) Introducing hydrogen phosphonate at C-3 position of ribose of a resulting compound after the step iii);

v) Optionally repeat the steps i)-iv) for t times by using a resulting compound after the step iii) instead of the starting building block in the step i), wherein t is an integer 0 to 10;

vi) Coupling a building block selected from C2*-1, C2*-2, C2*-3 or C2*-4 wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

vii) Removing $P^1$, $P^2$, $P^3$ and $P^4$ protecting groups from a resulting compound after step vi) and transforming an azido group to an amine group for obtaining the compound of the formula (I).

In the step vii), removing $P^1$ $P^2$, $P^3$ and $P^4$ protecting groups and transforming an azido group to an amine group can be performed stepwise, but preferred at the same time under the same reaction condition.

Of course, C2*-1, C2*-2, C2*-3, or C2*-4 can be used as a starting building block. In this case, an alternative synthetic method F-2 comprises the following steps:

i) Providing a starting building block selected from C2*-1, C2*-2, C2*-3, or C2*—

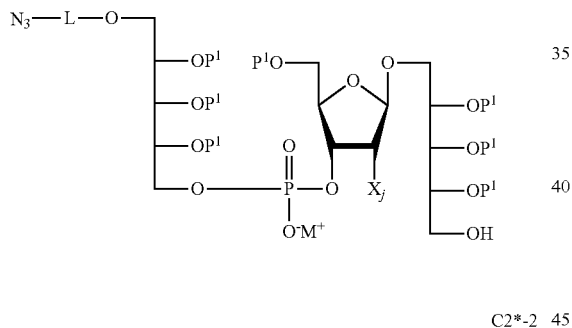

C2*-1

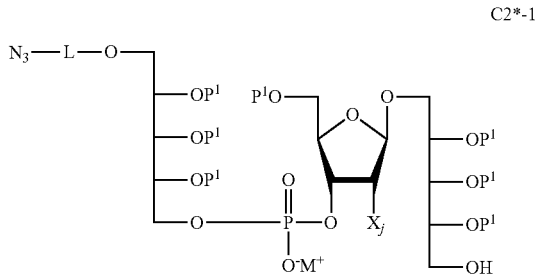

C2*-1

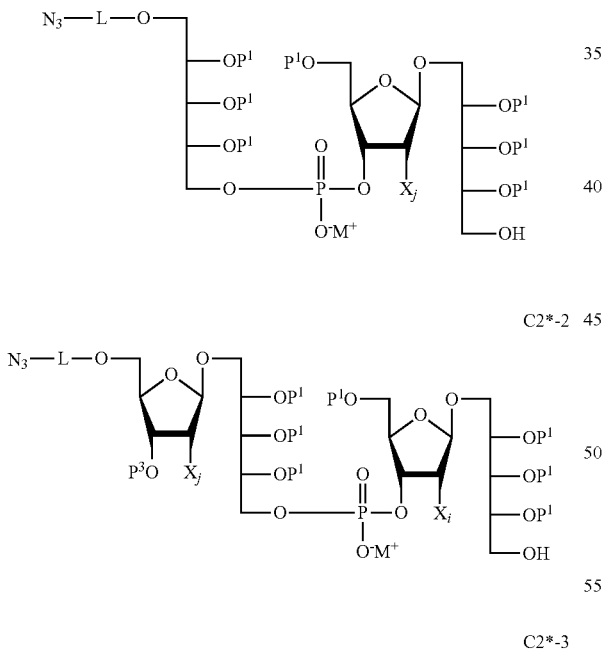

C2*-2

C2*-3

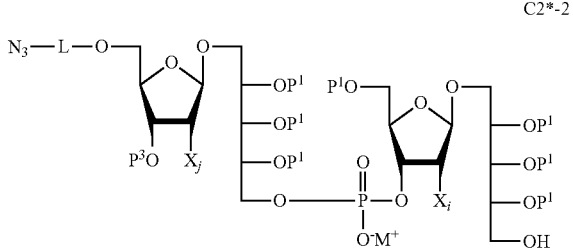

C2*-2

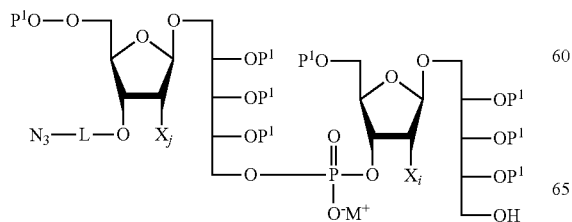

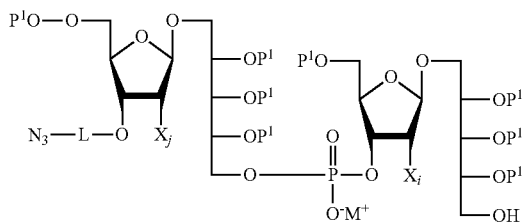

C2*-3

-continued

C2*-4

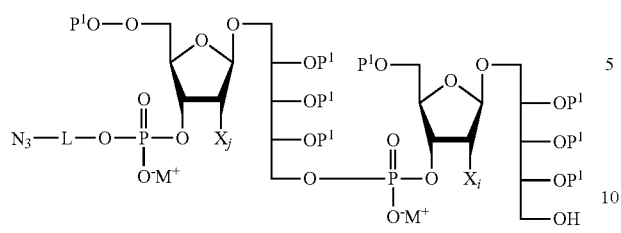

wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

ii) Coupling a building block B2*-1 with the starting building block selected from C2*-1, C2*-2, C2*-3, or C2*-4

B2*-1

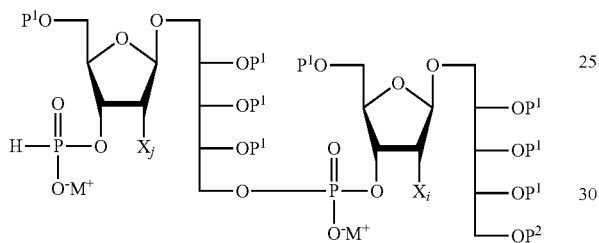

wherein $X_i$ and $X_j$ represents independently of each other $X_1$, $X_2$, $X_3$, $X_4$, $X_5$ or $X_6$; $P^1$ and $P^2$ are protecting groups that when bound to —O— are not identical to $X_i$ and $X_j$;

iii) Removing $P^2$ protecting group from a resulting compound after the step ii);

iv) Optionally repeat the steps i)-iii) for t times by using a resulting compound after the step iii) instead of the starting building block in the step i), wherein t is an integer 0 to 10;

v) Coupling a starting building block selected from A2*-1 or B2*-1

A2*-1

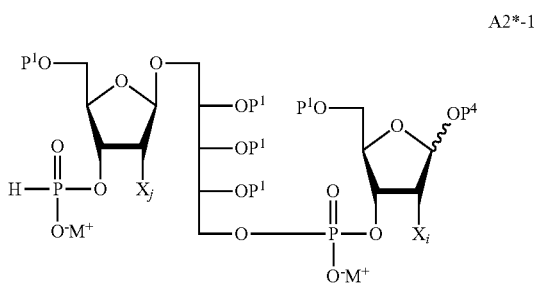

B2*-1

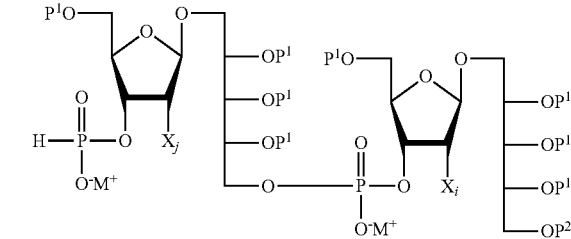

wherein $X_i$ and $X_j$ represents independently of each other $X_1$, $X_2$, $X_3$, $X_4$, $X_5$ or $X_6$; $P^1$, $P^2$ and $P^4$ represent protecting group that when bound to —O— are not identical to $X_i$ and $X_j$;

vi) Removing $P^1$, $P^2$, $P^3$ and $P^4$ protecting groups from a resulting compound after step v) and transforming an azido group to an amine group for obtaining the compound of the formula (I).

In the step vi), removing $P^1$, $P^2$, $P^3$ and $P^4$ protecting groups and transforming an azido group to an amine group can be performed stepwise, but preferred at the same time under the same reaction condition.

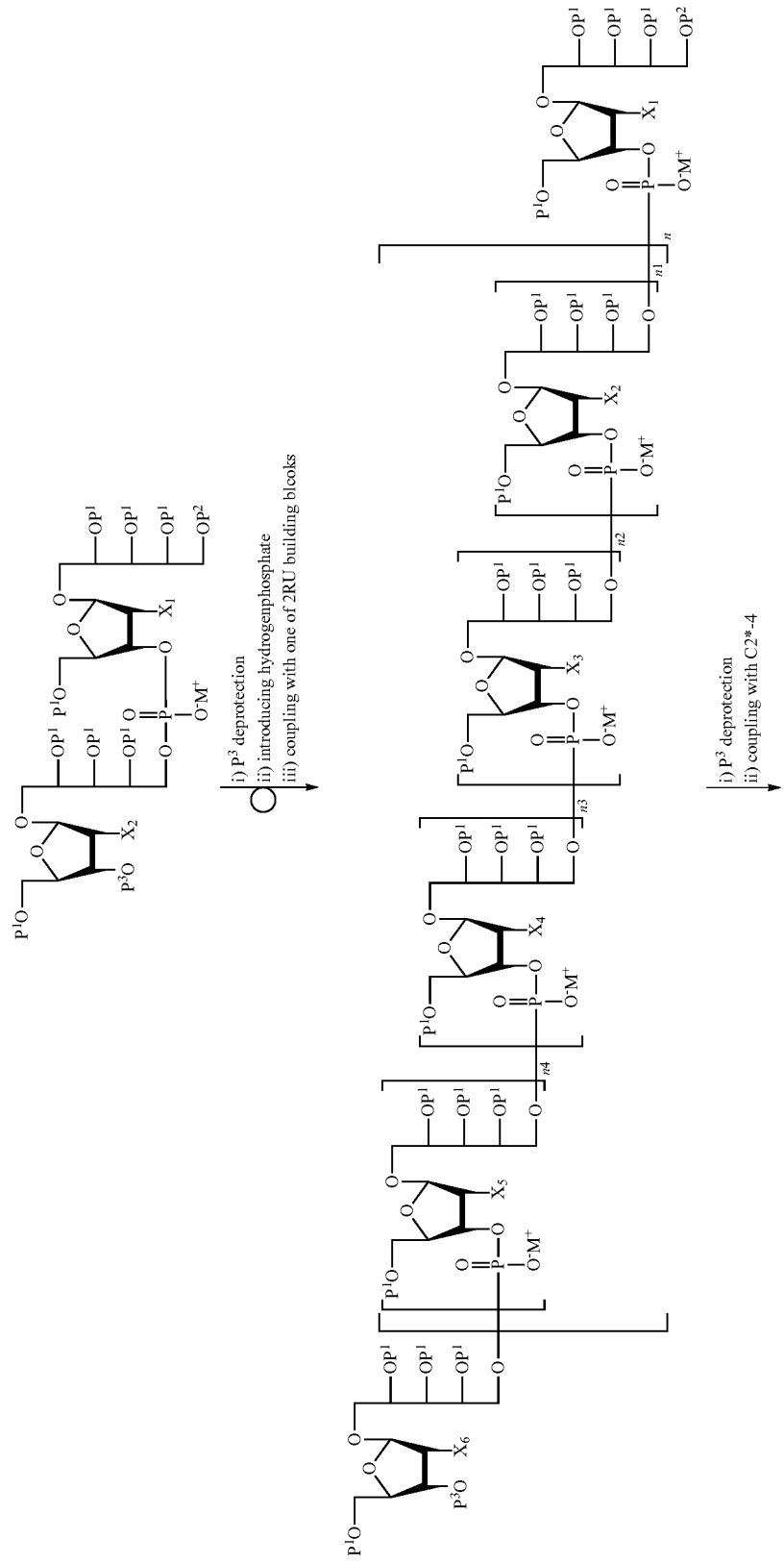
Scheme 5. Synthesis of the Hib capsular oligosaccharide derivatives by method F-1

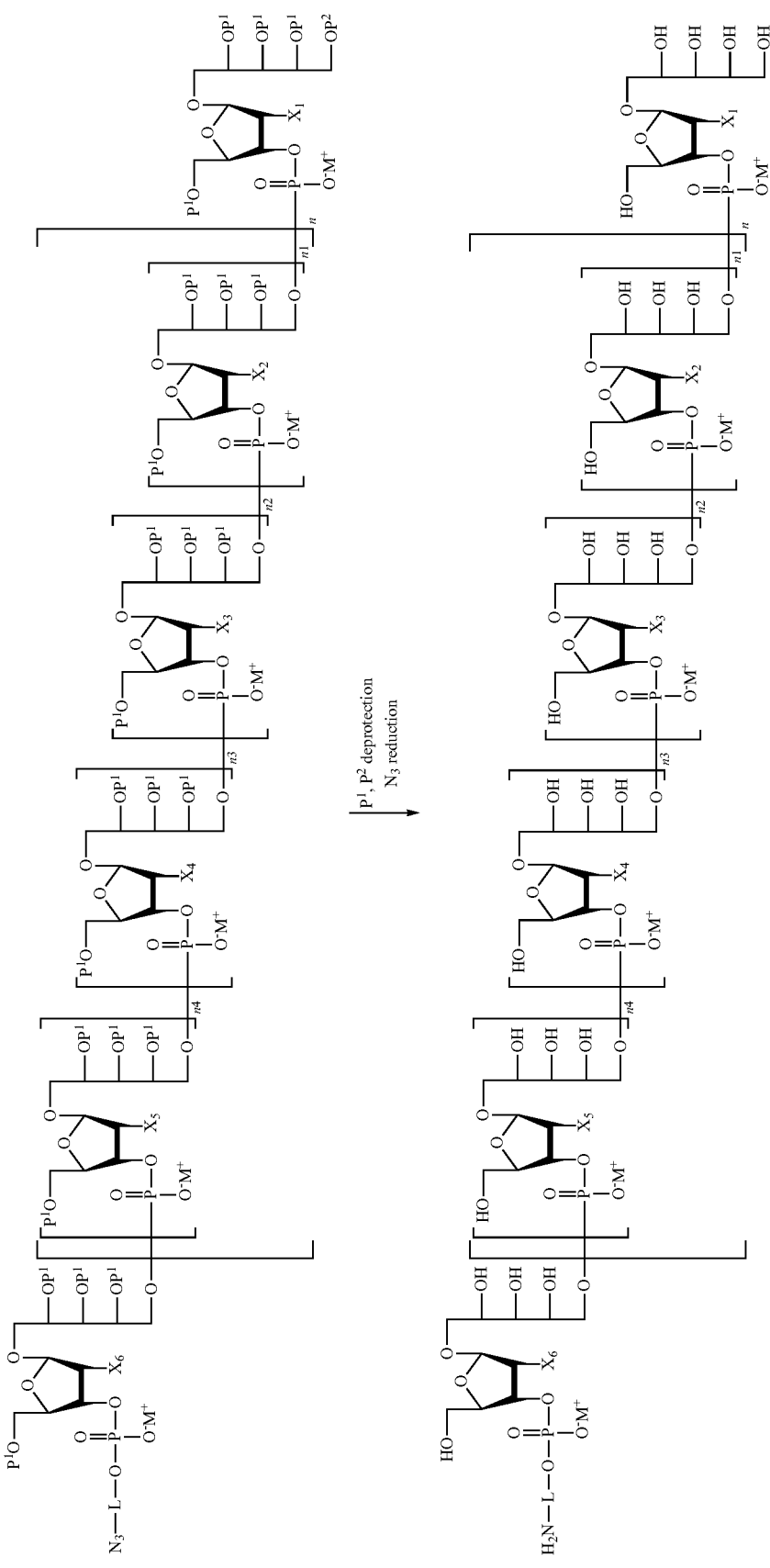

Further, the following building blocks consisting of two repeating units are useful for synthesis of the inventive saccharide by [2+2] synthetic approach:
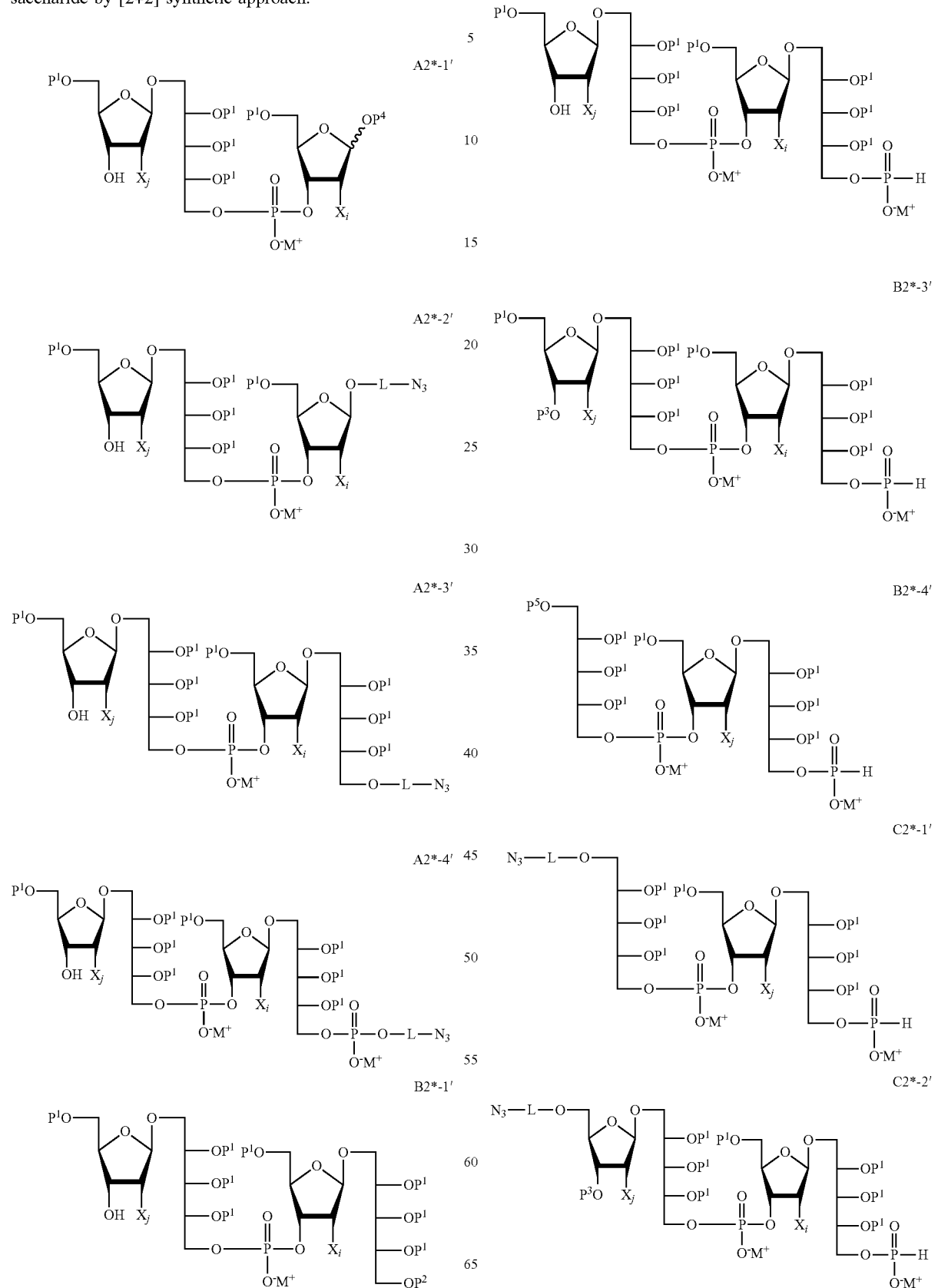

C2*-3'

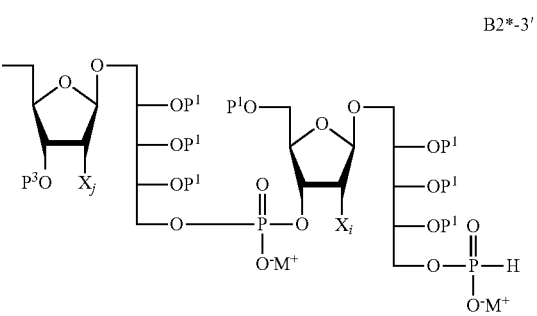

C2*-4'

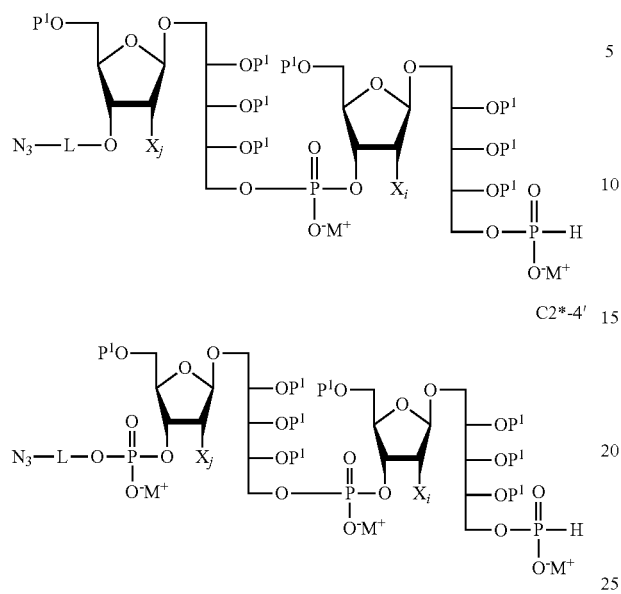

A synthetic method G-1 comprises the following steps:
i) Providing a starting building block selected from A2*-2', A2*-3', or A2*-4'

A2*-2'

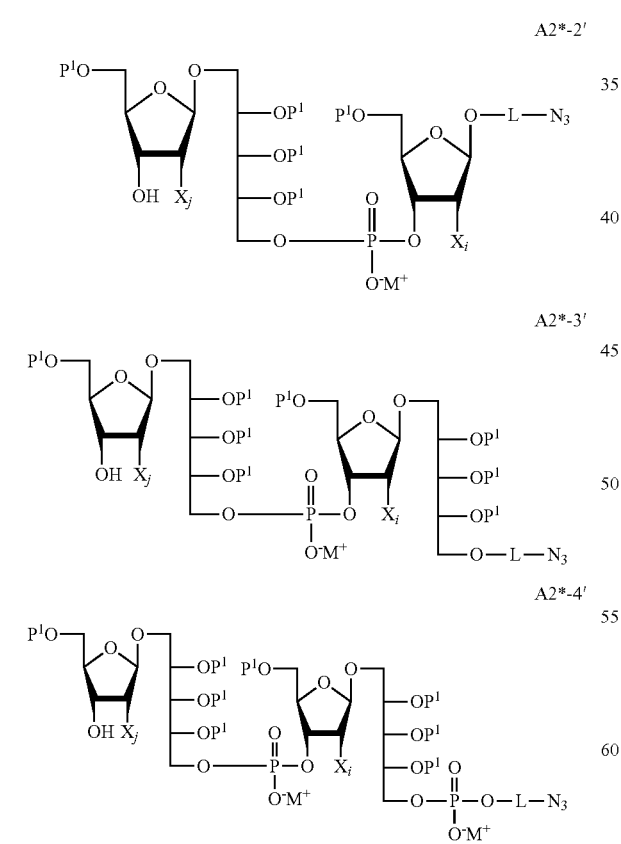

wherein L is a linker and has the same meaning as defined above;

$X_i$ and $X_j$ represents independently of each other $X_1$, $X_2$, $X_3$, $X_4$, $X_5$ or $X_6$; $P^1$ represents protecting group that when bound to —O— is not identical to $X_i$ and $X_j$;

ii) Coupling a building block B2*-3" with the starting building block selected from A2*-2', A2*-3', or A2*-4'

B2*-3'

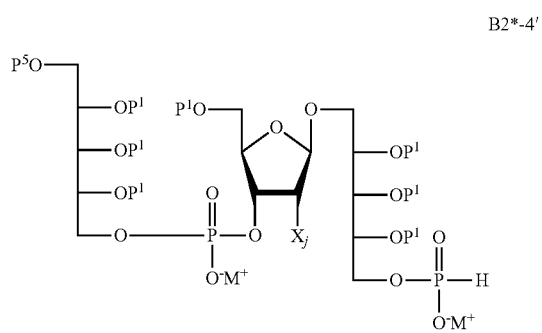

wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

iii) Removing $P^3$ group from a resulting compound after the step ii);
iv) Optionally repeat the steps i)-iii) for t times by using a resulting compound after the step iii) instead of the starting building block in the step i), wherein t is an integer 0 to 10;
v) Removing $P^1$ and $P^3$ protecting groups from a resulting compound after step iv) and transforming an azido group to an amine group for obtaining the compound of the formula (I).

In the step v), removing $P^1$ and $P^3$ protecting groups and transforming an azido group to an amine group can be performed stepwise, but preferred at the same time under the same reaction condition.

After the step iv) of the synthetic method G-1, a further building block B2*-4' may be alternatively coupled with the resulting compound after the step v). In this case, the synthetic method G-1 comprises the following steps instead of the step vi):
v') Coupling a building block B2*-4' with a resulting compound after the step vi);

B2*-4' wherein $X_j$ represents $X_1$, $X_2$, $X_3$, $X_4$, $X_5$ or $X_6$; $P^1$ and $P^5$ are protecting groups that when bound to —O— are not identical to $X_j$;
vi') Removing $P^1$ and $P^5$ protecting groups from a resulting compound after the step v') and transforming an azido group to an amine group for obtaining the compound of the formula (I).

Of course, B2*-3' or B2*-4' can be used as a starting building block. In this case, an alternative synthetic method G-2 comprises the following steps:

i) Providing a starting building block selected from B2*-3', or B2*-4'

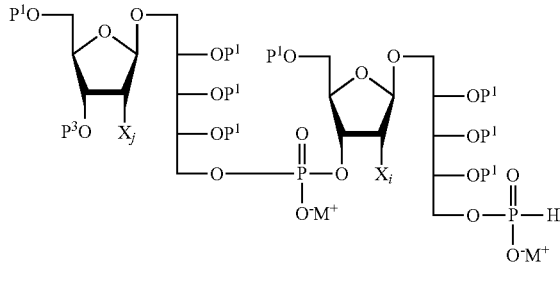

wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

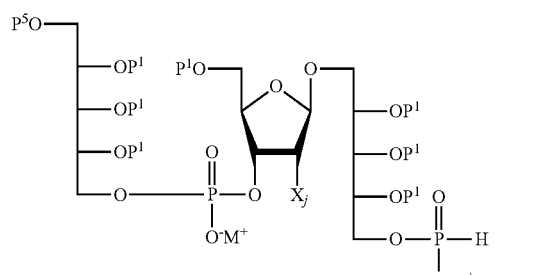

wherein $X_j$ represents $X_1$, $X_2$, $X_3$, $X_4$, $X_5$ or $X_6$; $P^1$ and $P^5$ are protecting groups that when bound to —O— are not identical to $X_j$;

ii) Coupling a building block B2*-1' with the starting building block selected from B2*-3, or B2*-4

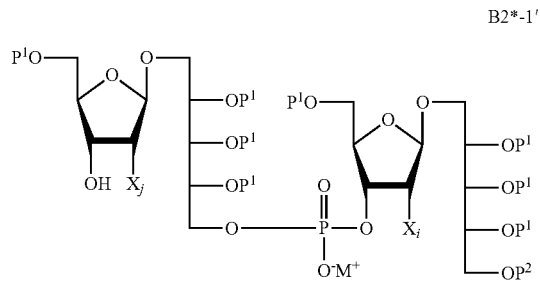

wherein $X_i$ and $X_j$ represents independently of each other $X_1$, $X_2$, $X_3$, $X_4$, $X_5$ or $X_6$; $P^1$ and $P^2$ are protecting groups that when bound to —O— are not identical to $X_i$ and $X_j$;

iii) Removing $P^2$ protecting group from a resulting compound after the step ii);

iv) Introducing hydrogen phosphonate at C-5 position of ribitol of a resulting compound after the step iii);

v) Optionally repeat the steps i)-iv) for t times by using a resulting compound after the step iv) instead of the starting building block in the step i), wherein t is an integer 0 to 10;

vi) Coupling a resulting compound after the step v) with a building block selected from A2*-2', A2*-3', or A2*-4'

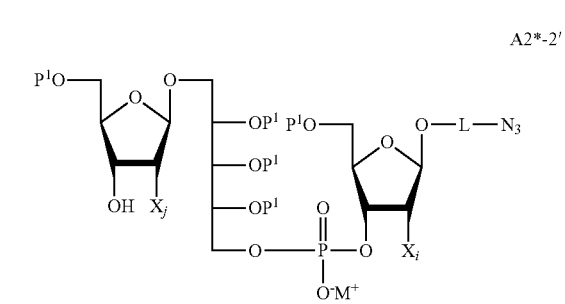

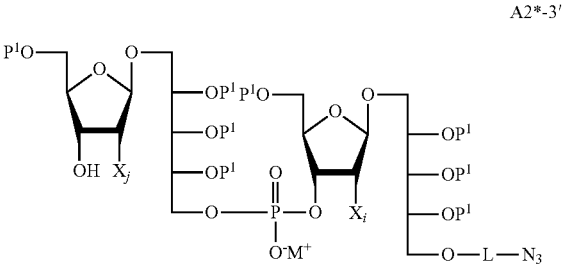

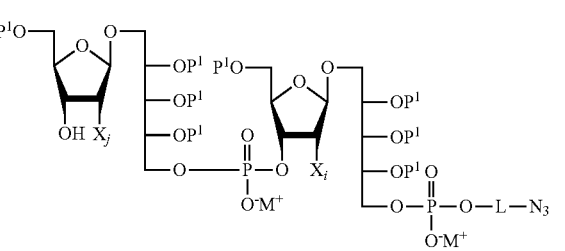

wherein L is a linker and has the same meaning as defined above;

$X_i$ and $X_j$ represents independently of each other $X_1$, $X_2$, $X_3$, $X_4$, $X_5$ or $X_6$; $P^1$ represents protecting group that when bound to —O— is not identical to $X_i$ and $X_j$;

vii) Removing $P^1$, $P^3$ and $P^5$ protecting groups from a resulting compound after step vi) and transforming an azido group to an amine group for obtaining the compound of the formula (I).

In the step vii), removing $P^1$, $P^3$ and $P^5$ protecting groups and transforming an azido group to an amine group can be performed stepwise, but preferred at the same time under the same reaction condition.

A synthetic method H-1 comprises the following steps:

i) Providing a starting building block selected from A2*-1' or B2*-1'

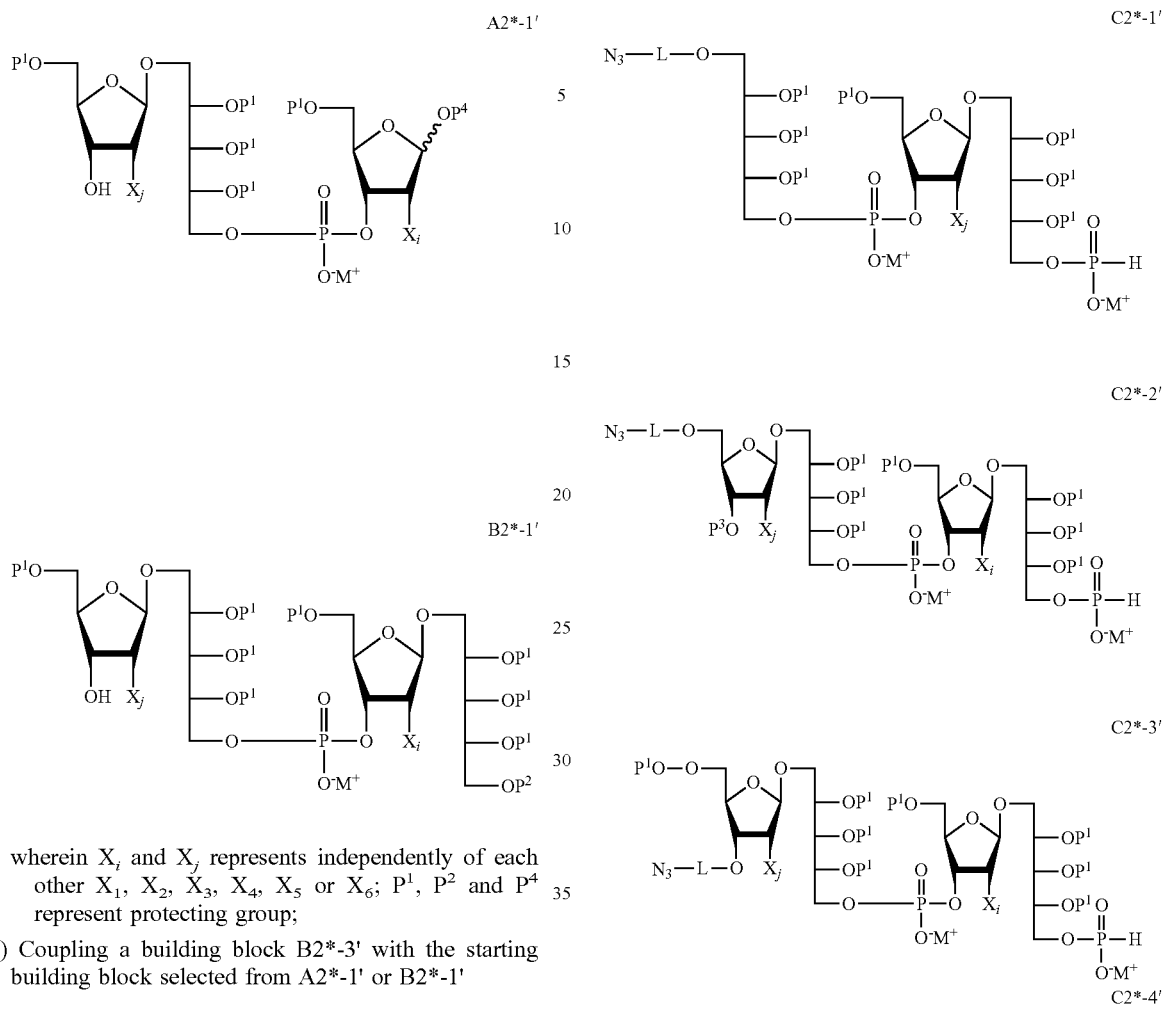

A2*-1′

B2*-1′ wherein $X_i$ and $X_j$ represents independently of each other $X_1$, $X_2$, $X_3$, $X_4$, $X_5$ or $X_6$; $P^1$, $P^2$ and $P^4$ represent protecting group;

ii) Coupling a building block B2*-3′ with the starting building block selected from A2*-1′ or B2*-1′

B2*-3′

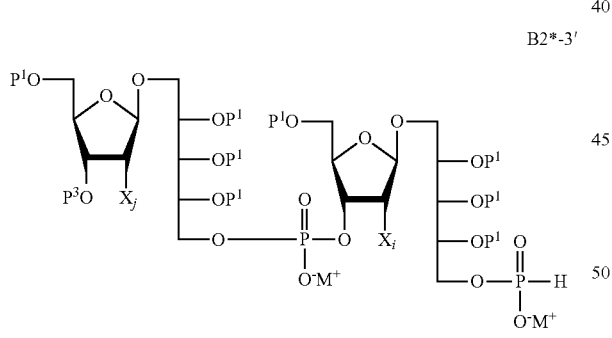

wherein $X_i$ and $X_j$ represents independently of each other $X_1$, $X_2$, $X_3$, $X_4$, $X_5$ or $X_6$; $P^1$ and $P^3$ are protecting groups;

iii) Removing $P^3$ group from a resulting compound after the step ii);

iv) Optionally repeat the steps i)-iii) for t times by using a resulting compound after the step iii) instead of the starting building block in the step i), wherein t is an integer 0 to 10;

v) Coupling a resulting compound after the step iv) with a building block selected from C2*-1′, C2*-2′, C2*-3′, or C2*-4′

C2*-1′

C2*-2′

C2*-3′

C2*-4′ wherein $X_i$ and $X_j$ represents independently of each other $X_1$, $X_2$, $X_3$, $X_4$, $X_5$ or $X_6$; $P^1$ and $P^3$ are protecting groups;

vi) Removing $P^1$, $P^2$, $P^3$ and $P^4$ protecting groups from a resulting compound after step v) and transforming an azido group to an amine group for obtaining the compound of the formula (I).

In the step vi), removing $P^1$ $P^2$, $P^3$ and $P^4$ protecting groups and transforming an azido group to an amine group can be performed stepwise, but preferred at the same time under the same reaction condition.

Of course, C2*-1′, C2*-2′, C2*-3′, or C2*-4′ can be used as a starting building block. In this case, an alternative synthetic method H-2 comprises the following steps:

i) Providing a starting building block selected from C2*-1′, C2*-2′, C2*-3′, or C2*-4′

C2*-1'

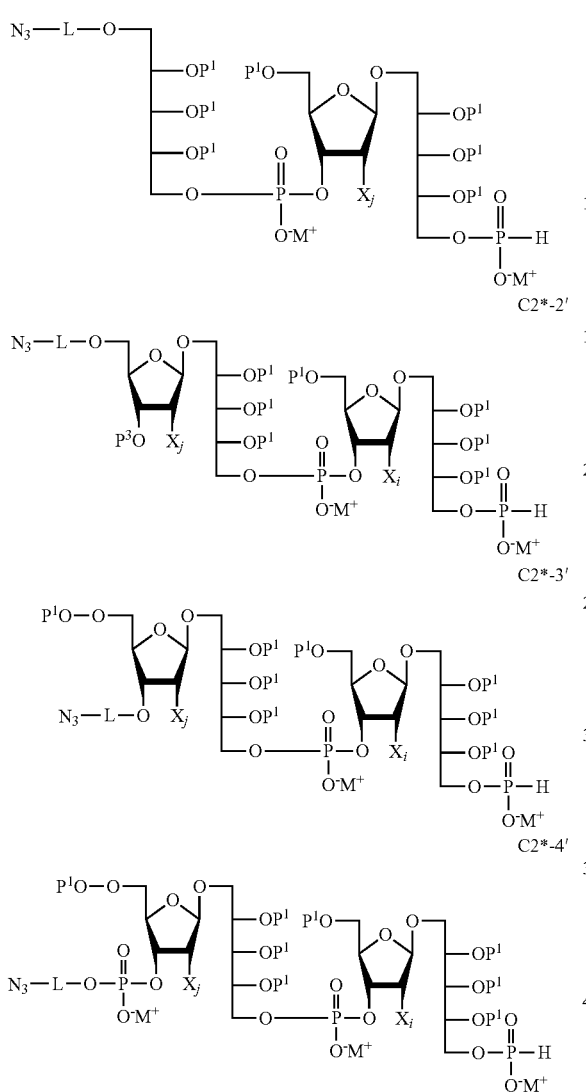

C2*-2'

C2*-3'

C2*-4' wherein $X_i$ and $X_j$ represents independently of each other $X_1$, $X_2$, $X_3$, $X_4$, $X_5$ or $X_6$; $P^1$ and $P^3$ are protecting groups that when bound to —O— are not identical to $X_i$ and $X_j$;

ii) Coupling a building block B2*-1' with the starting building block selected from C2*-1', C2*-2', C2*-3', or C2*-4'

B2*-1'

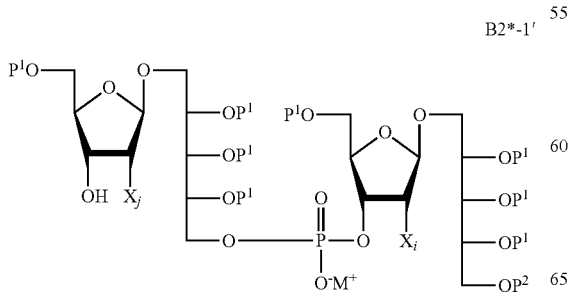

wherein $X_i$ and $X_j$ represents independently of each other $X_1$, $X_2$, $X_3$, $X_4$, $X_5$ or $X_6$; $P^1$ and $P^2$ are protecting groups that when bound to —O— are not identical to $X_i$ and $X_j$;

iii) Removing $P^2$ protecting group from a resulting compound after the step ii);

iv) Introducing hydrogen phosphonate at C-5 position of ribitol of a resulting compound after the step iii);

v) Optionally repeat the steps i)-iv) for t times by using a resulting compound after the step iii) instead of the starting building block in the step i), wherein t is an integer 0 to 10;

vi) Coupling a resulting compound after the step v) with a building block selected from A2*-1' or B2*-1'

A2*-1'

B2*-1'

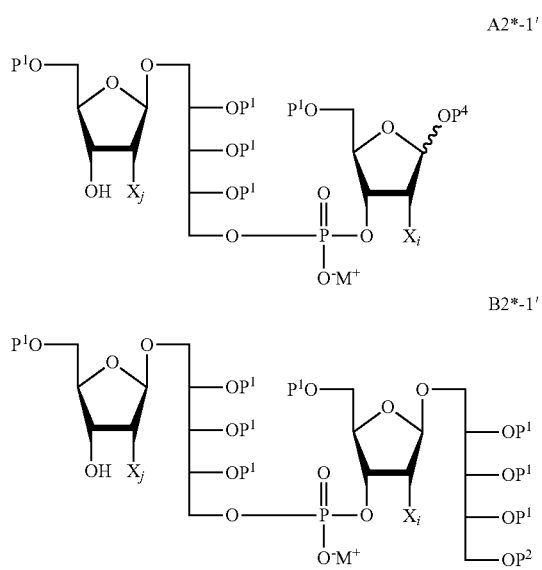

wherein $X_i$ and $X_j$ represents independently of each other $X_1$, $X_2$, $X_3$, $X_4$, $X_5$ or $X_6$; $P^1$, $P^2$ and $P^4$ represent protecting group that when bound to —O— are not identical to $X_i$ and $X_j$;

vii) Removing $P^1$, $P^2$, $P^3$ and $P^4$ protecting groups from a resulting compound after step vi) and transforming an azido group to an amine group for obtaining the compound of the formula (I).

In the step vii), removing $P^1$, $P^2$, $P^3$ and $P^4$ protecting groups and transforming an azido group to an amine group can be performed stepwise, but preferred at the same time under the same reaction condition.

A synthetic method J-1 comprises the following steps:
i) Providing starting building block B2*-1"

B2*-1"

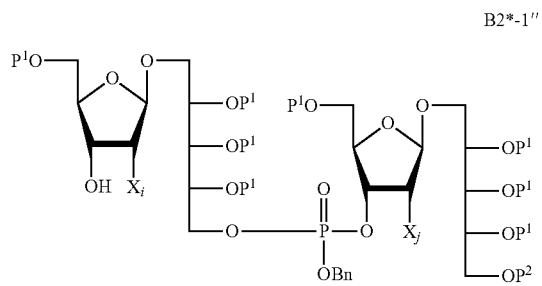

wherein $X_i$ and $X_j$ represent independently of each other $X_1$, $X_2$, $X_3$, $X_4$, $X_5$ or $X_6$; $P^1$, $P^2$ and $P^3$ represent protecting groups that when bound to —O— are not identical to $X_i$ and $X_j$;

ii) Introducing phosphoramidite group at C-3 position of a ribose of starting block B2*-1";

iii) Coupling building block B2*-3" with the resulting compound after step ii);

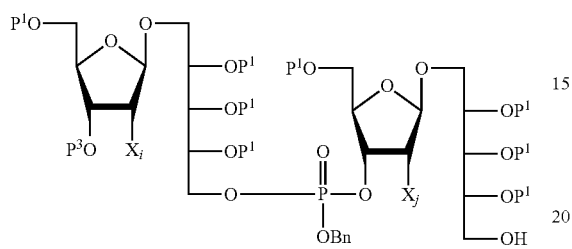

B2*-3"

wherein $X_i$ and $X_j$ represent independently of each other $X_1$, $X_2$, $X_3$, $X_4$, $X_5$ or $X_6$; $P^1$ and $P^3$ are protecting groups that when bound to —O— are not identical to $X_i$ and $X_j$;

iv) Removing $P^3$ group from a resulting compound after the step iii);

v) Optionally repeat the steps i)-iv) for t times by using a resulting compound after the step iv) instead of the building block B2*-3" in the step iii), wherein t is an integer 0 to 10;

vi) Coupling a compound HO-L-N$_3$ with a resulting compound after step v);

vii) Removing $P^1$, $P^2$, and $P^3$ protecting groups and transforming an azido group to an amine group for obtaining the compound of the formula (I).

In the step vii), removing $P^1$ $P^2$, and $P^3$ protecting groups and transforming an azido group to an amine group can be performed stepwise, or at the same time under the same reaction condition.

A synthetic method J-2 comprises the following steps:

i) Providing starting building block B2*-1'"

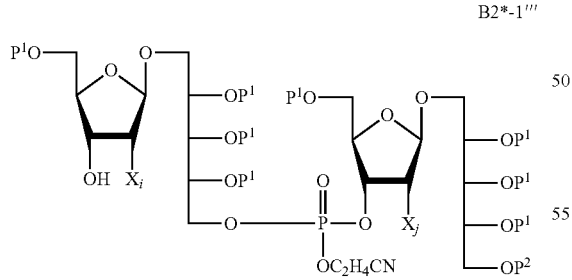

B2*-1'"

wherein $X_i$ and $X_j$ represent independently of each other $X_1$, $X_2$, $X_3$, $X_4$, $X_5$ or $X_6$; $P^1$, $P^2$ and $P^3$ represent protecting groups that when bound to —O— are not identical to $X_i$ and $X_j$;

ii) Introducing phosphoramidite group at C-3 position of a ribose of starting block B2*-1'";

iii) Coupling building block B2*-3'" with the resulting compound after step ii);

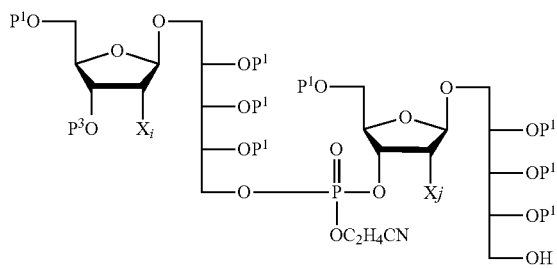

B2*-3'"

wherein $X_i$ and $X_j$ represent independently of each other $X_1$, $X_2$, $X_3$, $X_4$, $X_5$ or $X_6$; $P^1$ and $P^3$ are protecting groups that when bound to —O— are not identical to $X_i$ and $X_j$;

iv) Removing $P^3$ group from a resulting compound after the step iii);

v) Optionally repeat the steps i)-iv) for t times by using a resulting compound after the step iv) instead of the building block B2*-3'" in the step iii), wherein t is an integer 0 to 10;

vi) Coupling a compound HO-L-N$_3$ with a resulting compound after step v);

vii) Removing $P^1$, $P^2$, and $P^3$ protecting groups and transforming an azido group to an amine group for obtaining the compound of the formula (I).

In the step vii), removing $P^1$ $P^2$, and $P^3$ protecting groups and transforming an azido group to an amine group can be performed stepwise, or at the same time under the same reaction condition.

Furthermore, Hib capsular oligosaccharide derivatives of the present invention can be synthesized by polycondensation method I. The following building blocks are suitable for the polycondensation method I:

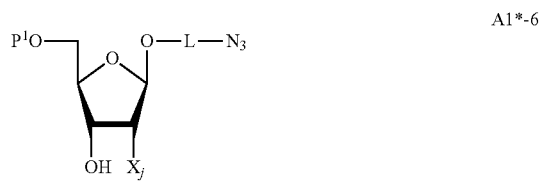

A1*-6

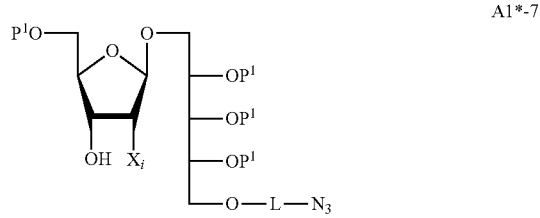

A1*-7

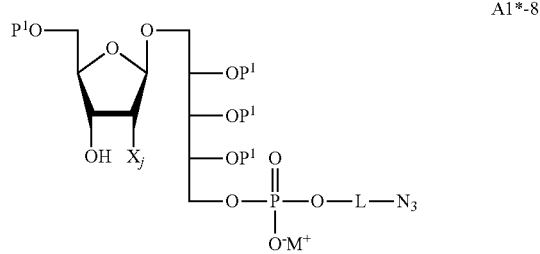

A1*-8

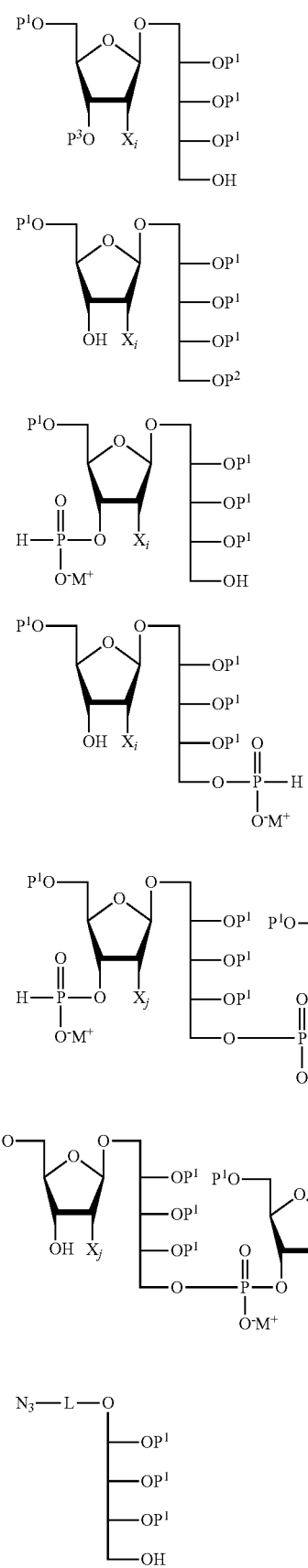
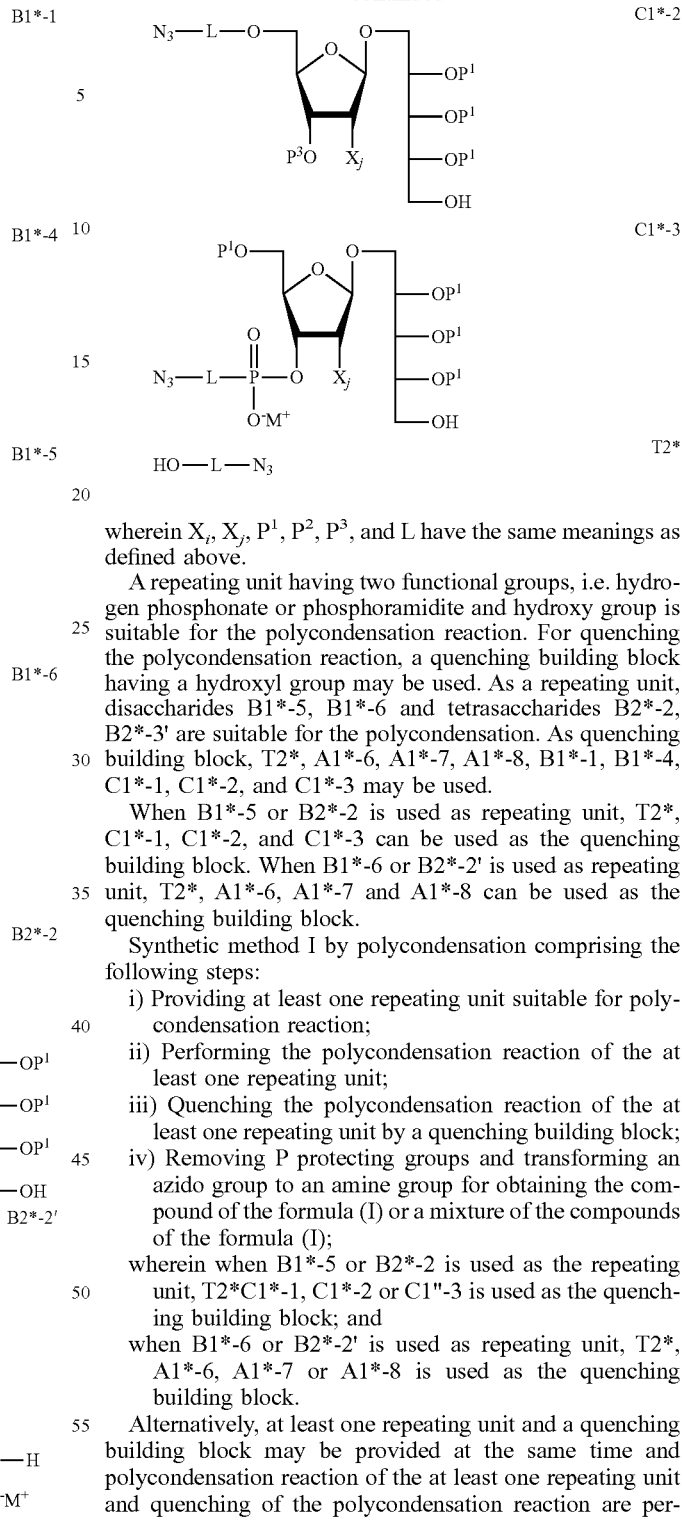

wherein $X_i$, $X_j$, $P^1$, $P^2$, $P^3$, and L have the same meanings as defined above.

A repeating unit having two functional groups, i.e. hydrogen phosphonate or phosphoramidite and hydroxy group is suitable for the polycondensation reaction. For quenching the polycondensation reaction, a quenching building block having a hydroxyl group may be used. As a repeating unit, disaccharides B1*-5, B1*-6 and tetrasaccharides B2*-2, B2*-3' are suitable for the polycondensation. As quenching building block, T2*, A1*-6, A1*-7, A1*-8, B1*-1, B1*-4, C1*-1, C1*-2, and C1*-3 may be used.

When B1*-5 or B2*-2 is used as repeating unit, T2*, C1*-1, C1*-2, and C1*-3 can be used as the quenching building block. When B1*-6 or B2*-2' is used as repeating unit, T2*, A1*-6, A1*-7 and A1*-8 can be used as the quenching building block.

Synthetic method I by polycondensation comprising the following steps:
  i) Providing at least one repeating unit suitable for polycondensation reaction;
  ii) Performing the polycondensation reaction of the at least one repeating unit;
  iii) Quenching the polycondensation reaction of the at least one repeating unit by a quenching building block;
  iv) Removing P protecting groups and transforming an azido group to an amine group for obtaining the compound of the formula (I) or a mixture of the compounds of the formula (I);
  wherein when B1*-5 or B2*-2 is used as the repeating unit, T2*C1*-1, C1*-2 or C1"-3 is used as the quenching building block; and
  when B1*-6 or B2*-2' is used as repeating unit, T2*, A1*-6, A1*-7 or A1*-8 is used as the quenching building block.

Alternatively, at least one repeating unit and a quenching building block may be provided at the same time and polycondensation reaction of the at least one repeating unit and quenching of the polycondensation reaction are performed automatically in an one-pot system.

A molar ratio between sum of at least one repeating unit and a quenching building block plays a critical role for length and diversity of oligosaccharide(s).

At least one repeating unit and a quenching building are provided in the range of a molar ratio between the repeating unit and quenching building block of 20:1 to 1:1, preferred 20:1 to 3:1, more preferred 15:1 to 4:1, most preferred 10:1 to 5:1.

Thus, an embodiment of the present invention is intermediate compound for synthesis of the saccharide of the formula (I) is selected from the group consisting of:
A1*-2, A1*-3, A1*-4, A1*-5, A1*-5', A1*-5", A1*-6, A1*-7, A1*-8, B1*-1, B1*-2, B1*-3, B1*-4, B1*-5, B1*-6, C1*-2, C1*-3, C1*-3', C1*-3"A2*-1, A2*-2, A2*-3, A2*-4, B2*-1, B2*-2, B2*-3, B2*-4, C2*-1, C2*-2, C2*-3, C2*-4, A2*-1', A2*-2', A2*-3', A2*-4', A2*-2", A2*-3", A2*-4", B2*-1', B2*-1", B2*-1"', B2*-2', B2*-3', B2*-3", B2*-3"', B2*-4', C2*-1', C2*-2', C2*-3' and C2*-4':
A1*-2
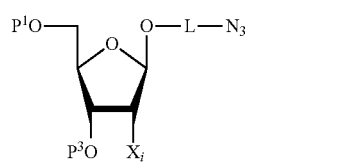
A1*-3
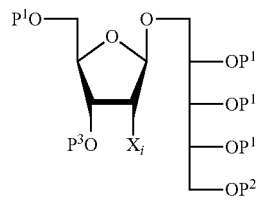
A1*-4
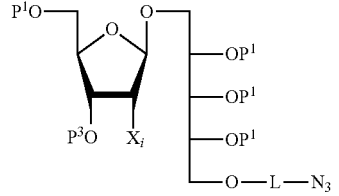
A1*-5
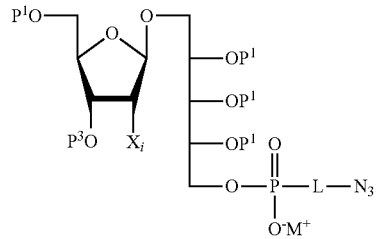
A1*-5'
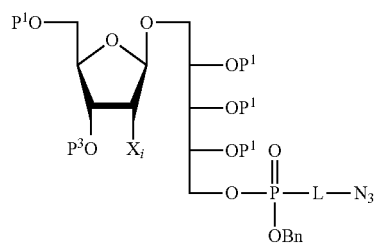
A1*-6
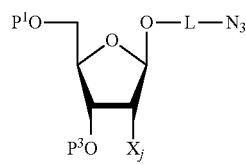
A1*-5"
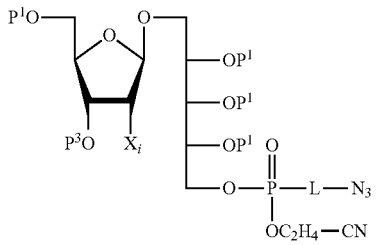
A1*-7
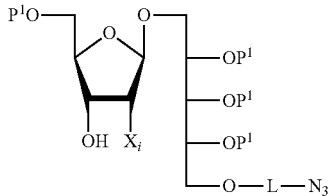
A1*-8
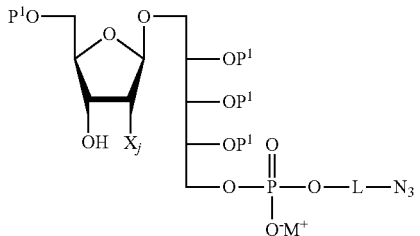
B1*-1
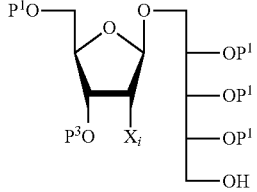
B1*-2
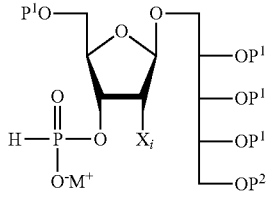
B1*-3
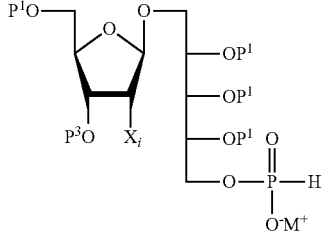
B1*-4
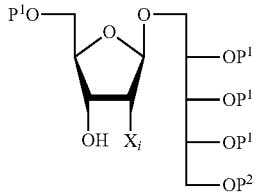

87
-continued
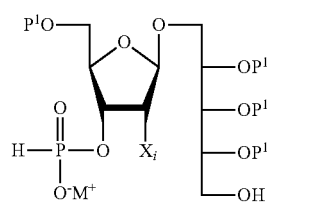
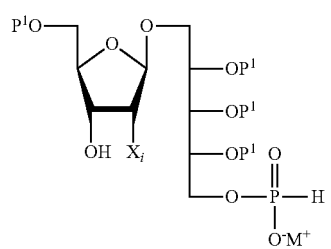
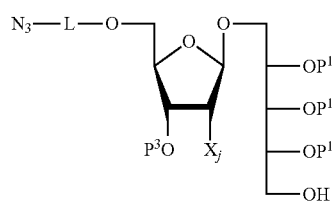
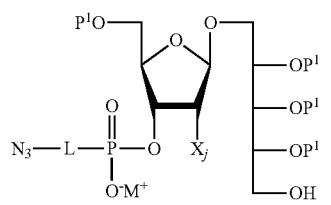
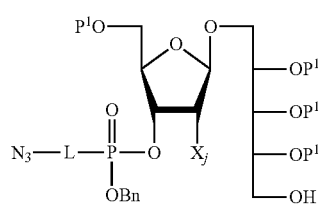
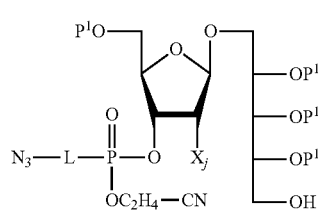
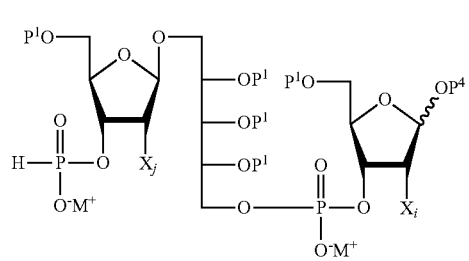
88
-continued
B1*-5
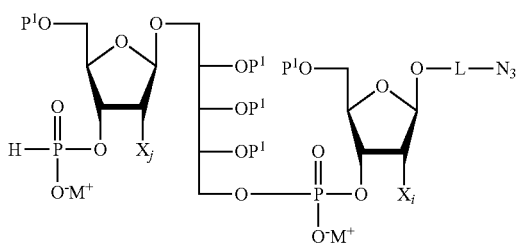
B1*-6
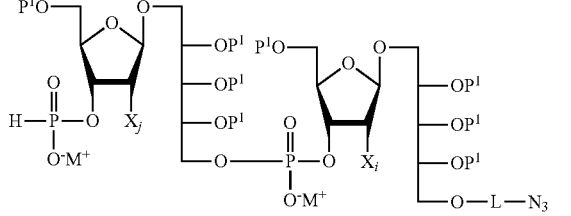
C1*-2
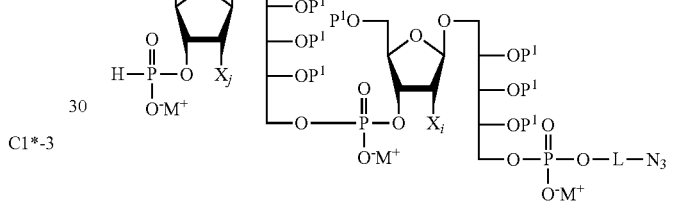
C1*-3
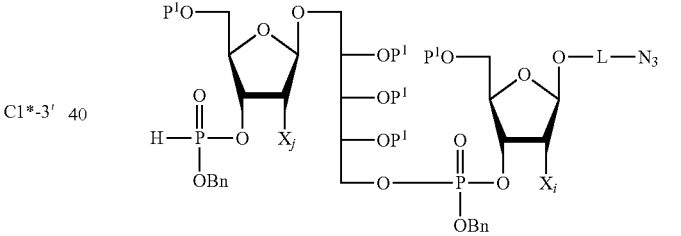
C1*-3'
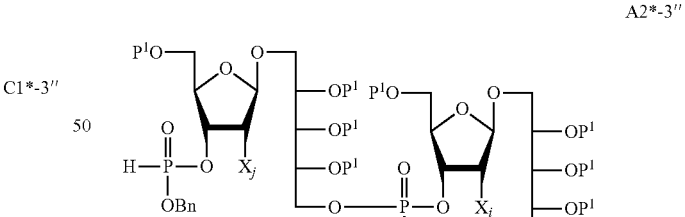
C1*-3''
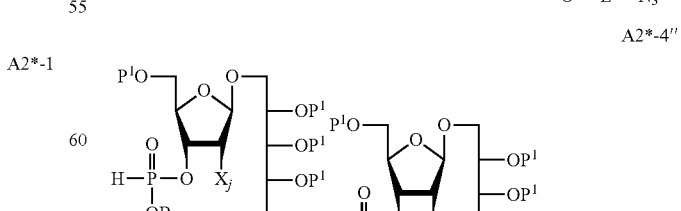
A2*-1
A2*-2
A2*-3
A2*-4
A2*-2''
A2*-3''
A2*-4''
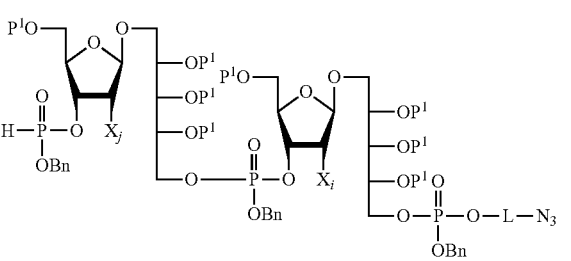

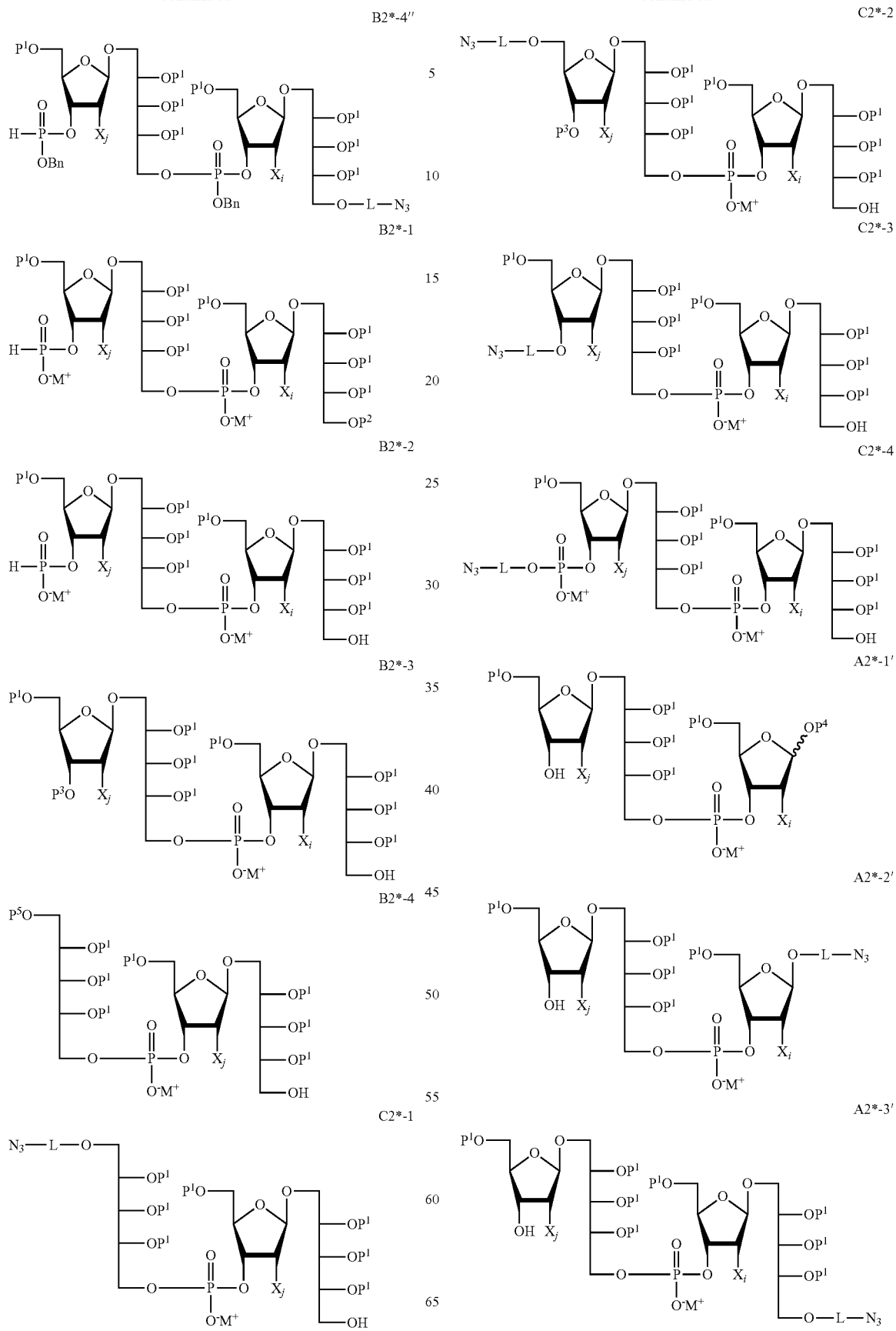

-continued
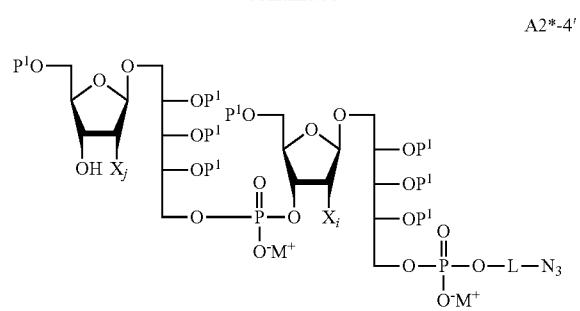
A2*-4'
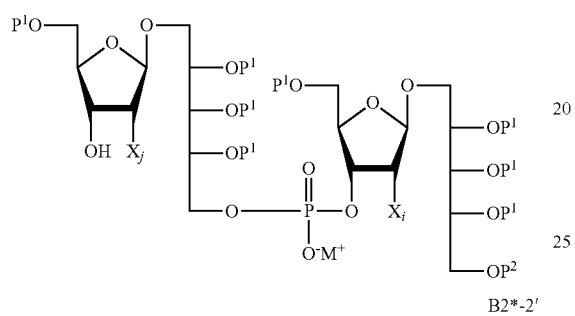
B2*-1'
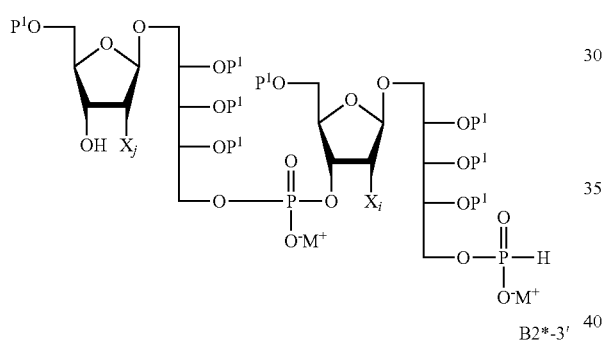
B2*-2'
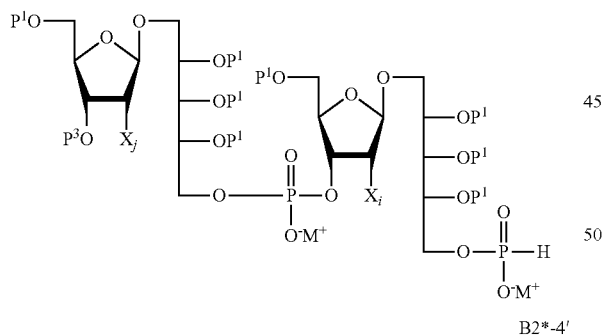
B2*-3'
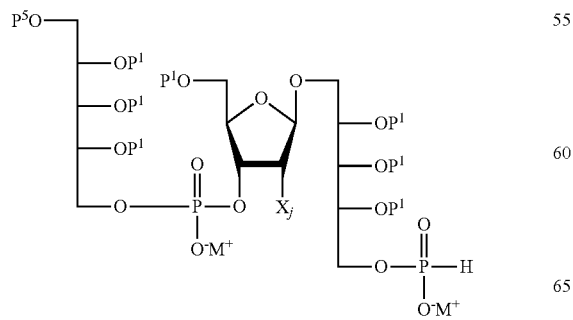
B2*-4'
-continued
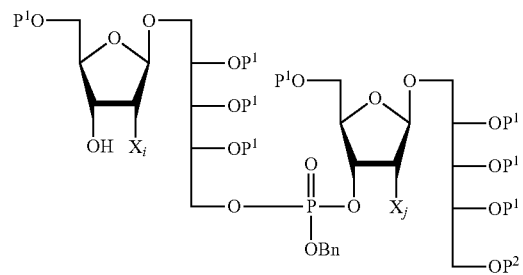
B2*-1''
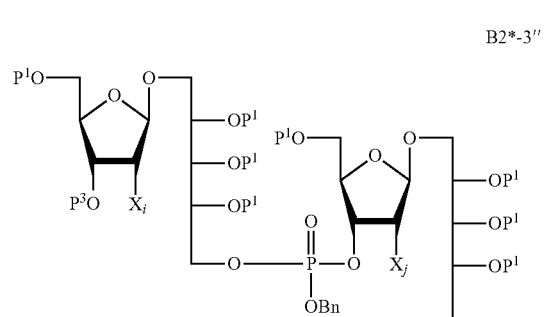
B2*-3''
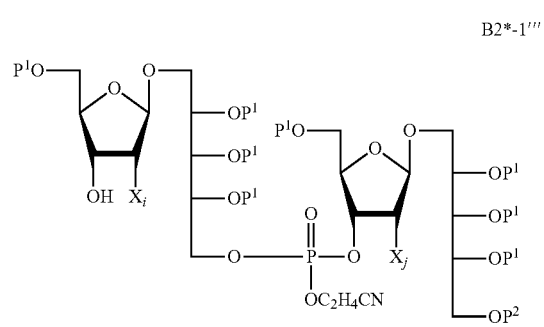
B2*-1'''
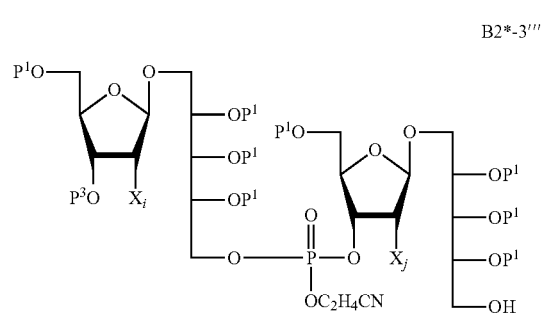
B2*-3'''
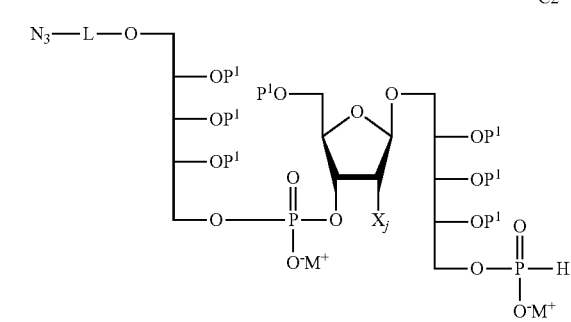
C2*-1'

-continued

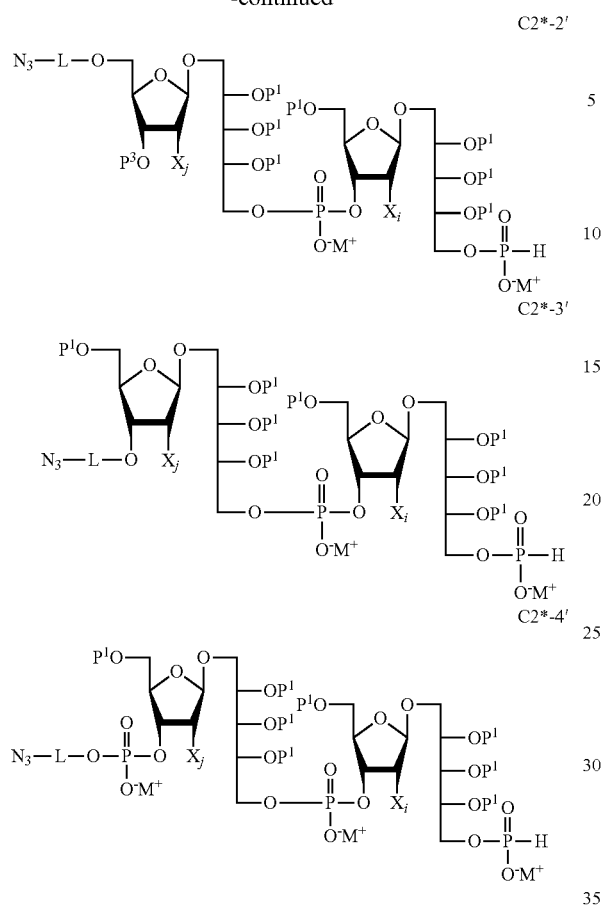

wherein P¹, P², P³, P⁴, and P⁵ represent protecting groups that when bound to —O— are not identical to $X_i$ and $X_j$;
$X_i$ and $X_j$ represent independently of each other —H, —OH, —F, —CH₃, —C₂H₅, —CN, —OCH₃, —OC₂H₅, —OCH(CH₃)₂, —OCH₂F, —OCF₃, —OCO—N(CH₃)₂, —O—C₂H₄—O—CH₃, —O—CH₂—CF₃, wherein
if only one group $X_i$ or $X_j$ is present, $X_i$ or $X_j$ cannot be —OH;
if both groups $X_i$ and $X_j$ are present, $X_i$ and $X_j$ cannot be simultaneously —OH,
L has the meaning defined above; and
M⁺ represents Na⁺, K⁺, NH₄⁺, or HNEt₃⁺:

Alternatively, an embodiment of the present invention is intermediate compound for synthesis of the saccharide of the formula (I) is selected from the group consisting of: A1*-4, A1*-5, A1*-6, A1*-7, A1*-8, B1*-1, B1*-2, B1*-3, B1*-4, B1*-5, B1*-6, C1*-2, C1*-3, A2*-1, A2*-2, A2*-3, A2*-4, B2*-1, B2*-2, B2*-3, B2*-4, C2*-1, C2*-2, C2*-3, C2*-4, A2*-1', A2*-2', A2*-3', A2*-4', B2*-1', B2*-2', B2*-3', B2*-4', B2*-1''', B2*-3''', C2*-1', C2*-2', C2*-3' and C2*-4':

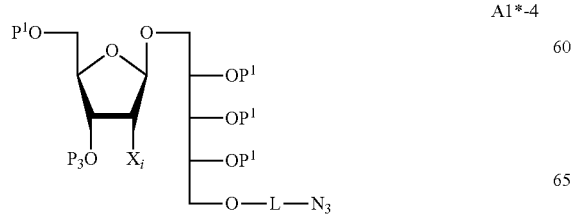

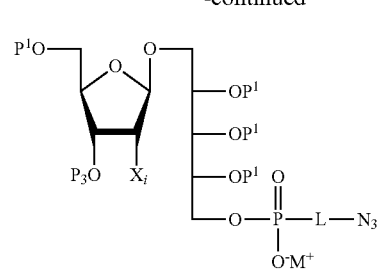

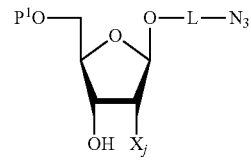

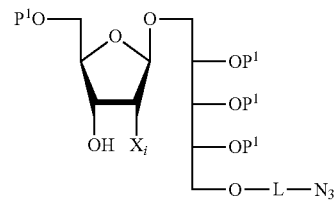

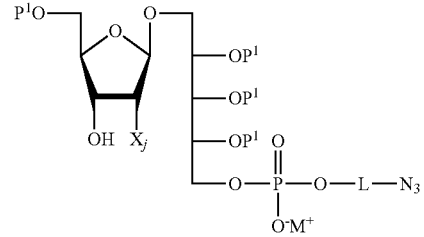

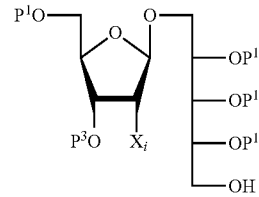

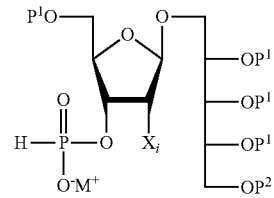

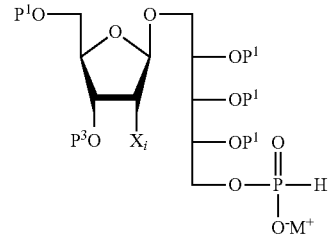

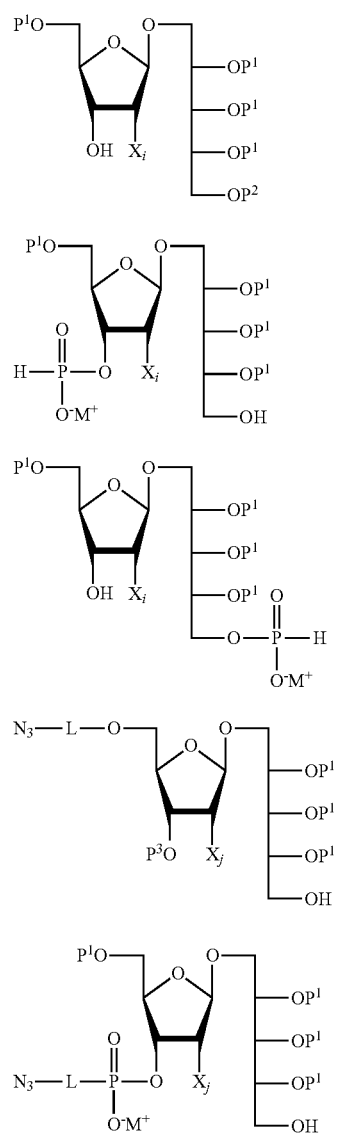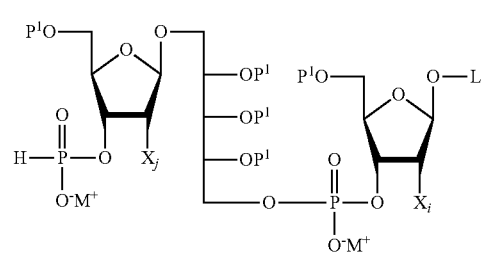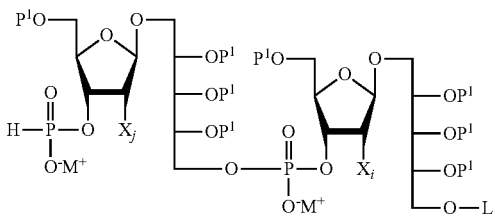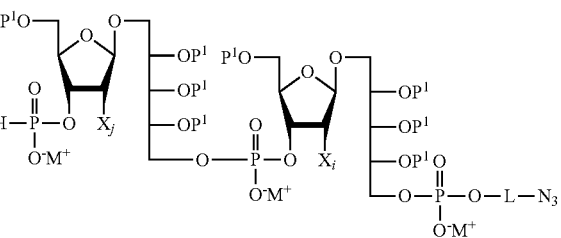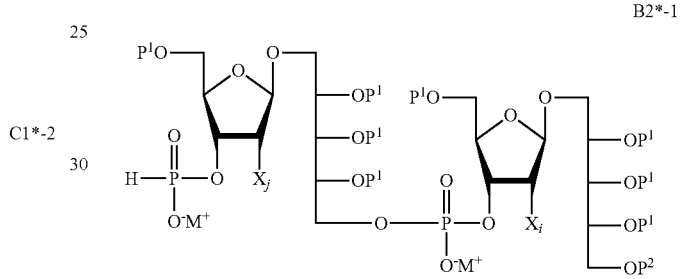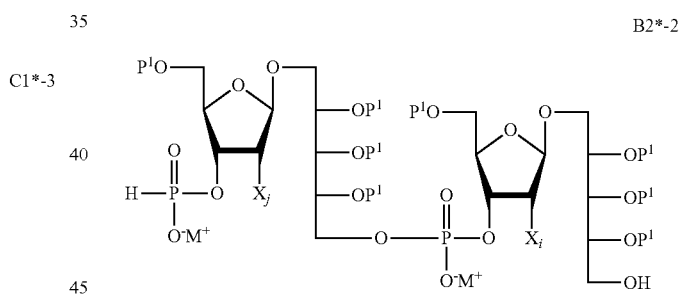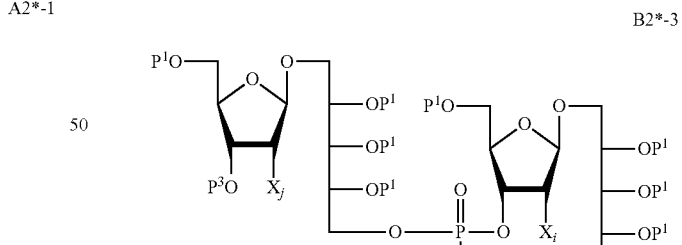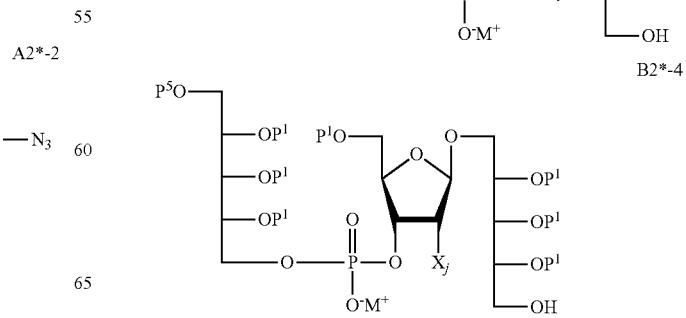

97
-continued
C2*-1
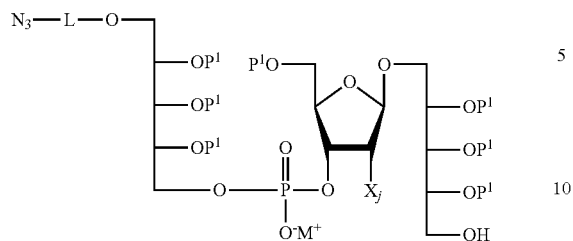
C2*-2
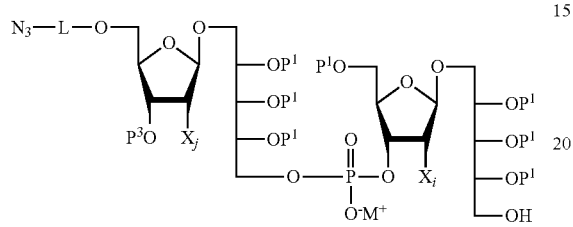
C2*-3
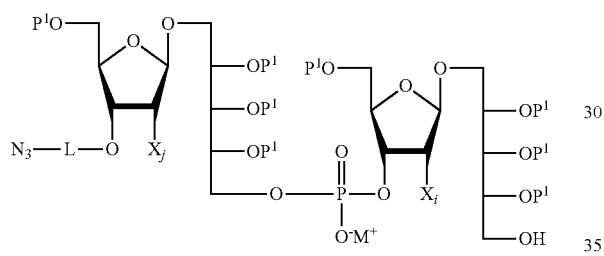
C2*-4
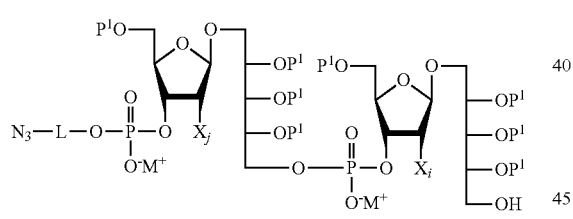
A2*-1'
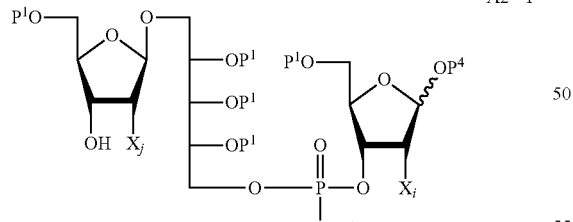
A2*-2'
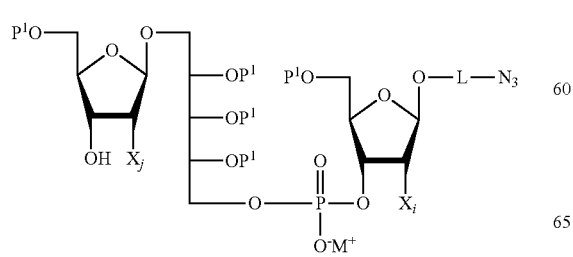
98
-continued
A2*-3'
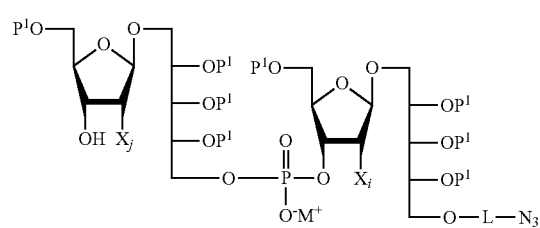
A2*-4'
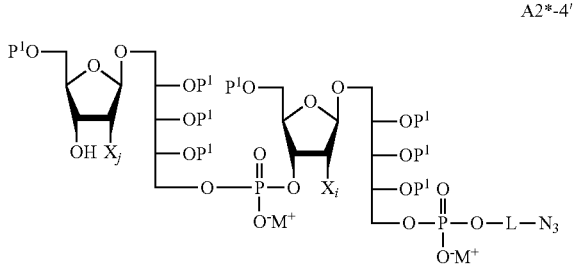
B2*-1'
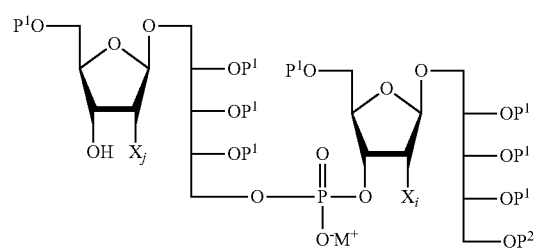
B2*-2'
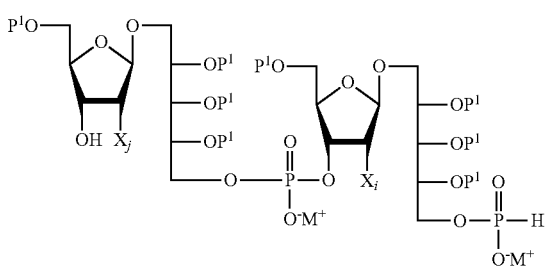
B2*-3'
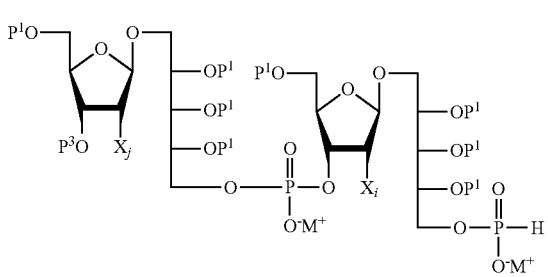

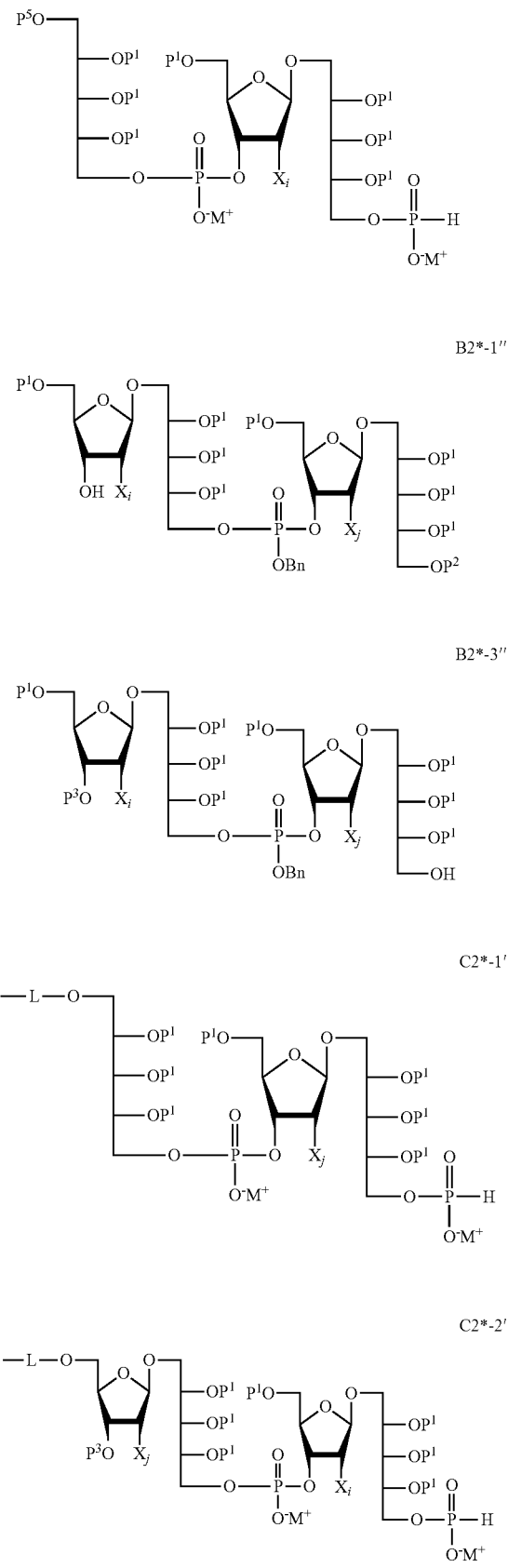

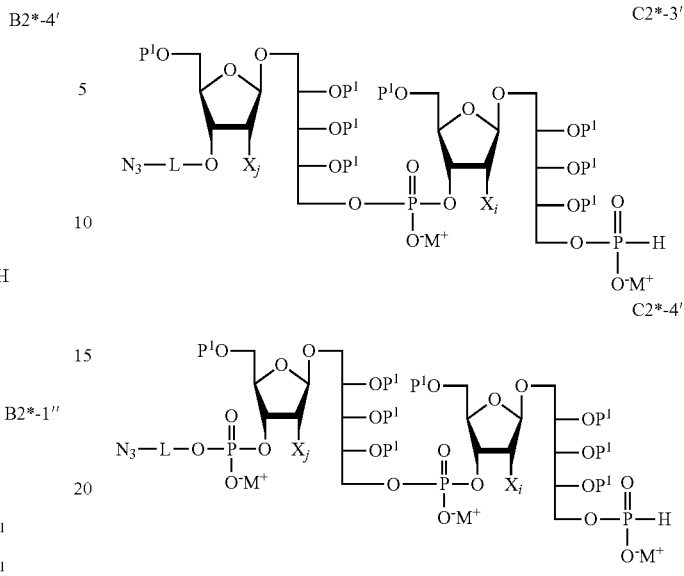

wherein $P^1$, $P^2$, $P^3$, $P^4$, and $P^5$ represent protecting groups; $X_i$ and $X_j$ represent independently of each other —H, —OH, —F, —CH$_3$, —C$_2$H$_5$, —CN, —OCH$_3$, —OC$_2$H$_5$, —OCH(CH$_3$)$_2$, —OCH$_2$F, —OCF$_3$, —OCO—N(CH$_3$)$_2$, —O—C$_2$H$_4$—O—CH$_3$, —O—CH$_2$—CF$_3$, wherein if only one group $X_i$ or $X_j$ is present, $X_i$ or $X_j$ cannot be —OH;

if both groups $X_i$ and $X_j$ are present, $X_i$ and $X_j$ cannot be simultaneously —OH, L has the meaning defined above; and $M^+$ represents Na$^+$, K$^+$, NH$_4^+$, or HNEt$_3^+$:

The term "protecting groups" as used herein refers to commonly used protection groups in organic synthesis, preferably for hydroxyl groups.

More specifically, $P^1$, $P^2$, $P^3$, $P^4$, $P^5$ and $P^6$ preferably are suitable protecting groups for hydroxyl groups, more preferably different suitable protecting groups for hydroxyl groups capable of being removed subsequently one after another by a suitable sequence of deprotection reactions. Therefore protecting groups $P^1$, $P^2$, $P^3$, $P^4$, $P^5$ and $P^6$ for hydroxyl groups may be selected from the group consisting of or comprising: acetyl, benzyl, benzoyl, p-methoxybenzyl, p-methoxyphenyl, para-bromobenzyl, o-nitrophenyl, p-nitrophenyl, allyl, methyl, isopropyl, levulinyl, dimethoxytrityl(DMTr), trityl, 2-naphthylmethyl (Nap), pivaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl.

More specifically, in a preferred embodiment of the present invention $P^1$, $P^5$ and $P^6$ may be benzyl or p-methoxybenzyl, $P^2$ may be allyl, dimethoxytrityl (DMTr), 2-naphthylmethyl (Nap) or trityl, $P^3$ may be levulinyl (Lev) or 2-naphthylmethyl (Nap), $P^4$ may be methyl or acetyl.

In a particularly preferred embodiment, $P^1$ may be benzyl, $P^2$ may be 2-naphthylmethyl and $P^3$ may be levulinyl.

Removing a DMTr group as $P^2$ protecting group by treatment with trichloroacetic acid leads to a primary alcohol at C-5 position of ribitol, which is coupled with a hydrogen phosphonate or phosphoramidite at C-3 position of ribose of a partner building block. iCleavage of a levulinyl group as $P^3$ protecting group by treatment with hydrazine acetate leads to a secondary alcohol at the C-3 position of ribose, which also reacts with hydrogen phosphonate or phosphoramidite at C-5 position of a ribitol of partner building block.

Deprotection of a benzyl group as $P^1$ protecting group is carried out preferred by Pd-catalyzed hydrogenation reaction. The same reaction condition may apply to the transformation of an azido group to an amine group.

For introducing a hydrogen phosphonate group at C-3 position of ribose or at C-5 position of ribitol of a building block or a resulting compound after deprotection of $P^3$ or $P^2$ protecting group, a hydroxyl group at C-3 position of ribose or at C-5 position of ribitol is preferred reacted with trichlorophosphine and triethylamine in the presence of imidazole.

For introducing a phosphoramidite group at C-3 position of ribose or at C-5 position of ribitol of a building block or a resulting compound after deprotection of $P^3$ or $P^2$ protecting group, a hydroxyl group at C-3 position of ribose or at C-5 position of ribitol is preferred reacted with bis(diisopropylamino)-benzyloxyphosphine in the presence of diisopropylammonium tetrazolide.

Pivaloyl chloride is used as a coupling or condensation reagent for coupling a pair of building block. As described above, for the coupling reaction, one coupling partner has a hydroxyl group and the other coupling partner has hydrogen phosphonate group.

For the polycondensation reaction, a building block has two functional groups, i.e. hydroxyl group and hydrogen phosphonate group.

Linker

Therefore the present invention is related to a saccharide of any of the general formulae (I), (II-1), (II-2), (II-3), (II-4), (III-1), (III-2), (IV-1) and (IV-2) containing a —O-L-$NH_2$ group which is suitable for conjugation with an immunogenic carrier through the nitrogen atom of the —O-L-$NH_2$ group. The present invention is also related to a saccharide of any of the general formulae containing a —O-L-COOH group which is suitable for conjugation with an immunogenic carrier through the carboxylic acid of the —O-L-COOH group. The linker L may be any non-immunogenic moiety as defined above. Thus the linker L although being part of the saccharide of any of the general formulae (I), (II-1), (II-2), (II-3), (II-4), (III-1), (III-2), (IV-1) and (IV-2) as well as of any conjugate of a saccharide of any of the general formulae (I), (II-1), (II-2), (III-1), (III-2), (IV-1) and (IV-2) with an immunogenic carrier does not affect the immunogenic properties of the saccharide of any of the general formulae (I), (II-1), (II-2), (II-3), (II-4), (III-1), (III-2), (IV-1) and (IV-2) as well as of any conjugate of the saccharide of any of the general formulae (I), (II-1), (II-2), (II-3), (II-4), (III-1), (III-2), (IV-1) and (IV-2) with an immunogenic carrier.

Any bifunctional linker of the formula HO-L-$NH_2$ or HO-L-COOH can be used in the inventive saccharides of any of the general formulae (I), (II-1), (II-2), (II-3), (II-4), (III-1) and (III-2) as well as their conjugates with an immunogenic carrier. In one embodiment of the present invention the saccharide of any of the general formulae (I), (II-1), (II-2), (II-3), (II-4), (III-1), and (III-2) the Linker -L- is selected from: -$L^a$-, -$L^a$-$L^e$-, -$L^a$-$L^b$-$L^e$-, -$L^a$-$L^d$-$L^e$-; wherein
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—, or —O—P(O)(OH)—O—;
-$L^d$- is selected from —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;

and o, q, p1 and p2 are independently of each other an integer selected from 1, 2, 3, 4, 5, and 6.

Thus, the present invention is also directed to a saccharide of general formula (I)

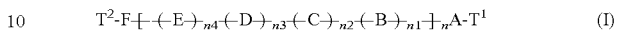  (I)

wherein

A is

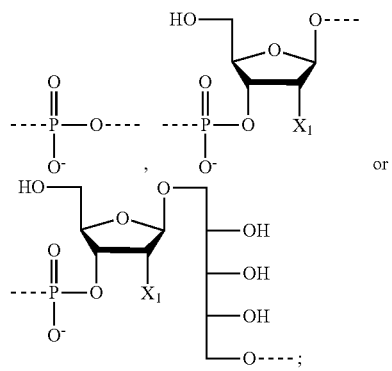

B is

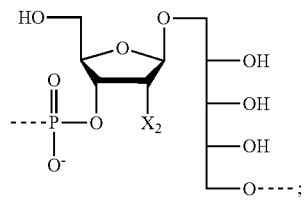

C is

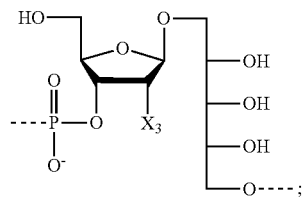

D is

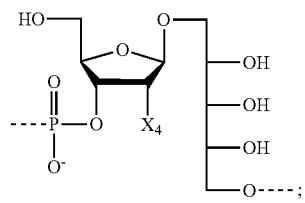

E is

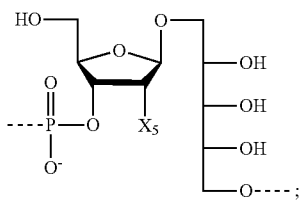

F is

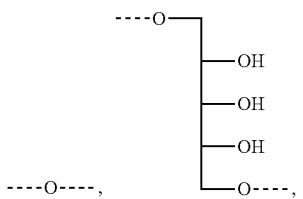

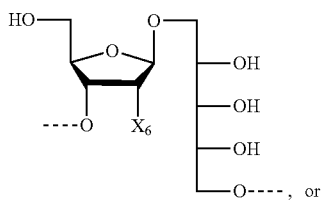

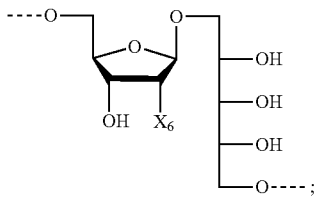

$T^1$ and $T^2$ represent —H, -L-NH$_2$; wherein if $T^1$ is -L-NH$_2$, then $T^2$ is —H and if $T^1$ is —H, then $T^2$ is -L-NH$_2$ or -L-COOH;

$X_1$, $X_2$, $X_3$, $X_4$, $X_5$, and $X_6$ represent independently of each other —H, —OH, —F, —CH$_3$, —C$_2$H$_5$, —CN, —OCH$_3$, —OC$_2$H$_5$, —OCH(CH$_3$)$_2$, —OCH$_2$F, —OCF$_3$, —OCO—N(CH$_3$)$_2$, —O—C$_2$H$_4$—O—CH$_3$, —O—CH$_2$—CF$_3$, and at least two of $X_1$, $X_2$, $X_3$, $X_4$, $X_5$, and $X_6$ are not —OH;

n is an integer selected from 1, 2, 3, or 4;

n1, n2, n3 and n4 are independently of each other selected from 0 and 1 and n1+n2+n3+n4≥1;

under the proviso that if n1+n2+n3+n4=1 and if n=1 and if A is

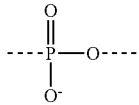

than
F is

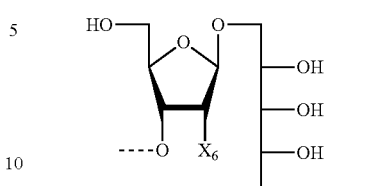

and
under the proviso that if n1+n2+n3+n4=1 and if n=1 and if F is

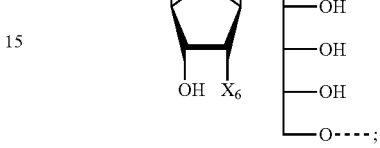

than
A is

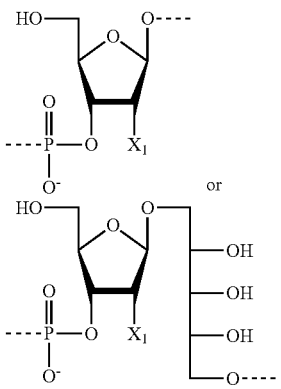

L is a linker and L is selected from: -L$^a$-, -L$^a$-L$^e$-, -L$^a$-L$^b$-L$^e$-, -L$^a$-L$^d$-L$^e$-;

wherein -L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;

-L$^b$- represents —O—, or —O—P(O)(OH)—O—;

-L$^d$- is selected from —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;

and o, q, p1 and p2 are independently of each other an integer selected from 1, 2, 3, 4, 5, and 6;

and enantiomers, diastereomers, mixtures of enantiomers, mixtures of diastereomers, anomers, hydrates, solvates of the above mentioned compounds and pharmaceutically acceptable salts thereof.

It is also preferred that the inventive saccharide of any of the general formulae (I), (II-1), (II-2), (II-3), (II-4), (III-1), and (III-2) has a linker -L- which is $-L^a-L^e-$; and wherein
$-L^a-$ is selected from: $-(CH_2)_o-$, $-(CH_2-CH_2-O)_o-C_2H_4-$, $-(CH_2-CH_2-O)_o-CH_2-$;
$-L^e-$ is selected from: $-C_2H_4-(O-CH_2-CH_2)_{p1}-$, $-CH_2-(O-CH_2-CH_2)_{p1}-$, $-(CH_2)_{p1}-$, and $-(CH_2)_{p1}-O-(CH_2)_{p2}-$; and
o, p1, p2, are independently of each other an integer selected from 1, 2, 3, 4, 5, and 6.

In one embodiment the saccharide of any of the general formulae (I), (II-1), (II-2), (II-3), (II-4), (III-1), and (III-2) the Linker -L- is $-L^a-$, wherein
$-L^a-$ represents: $-(CH_2)_{o1}-$, $-(CH_2-CH_2-O)_{o2}-C_2H_4-$, $-(CH_2-CH_2-O)_{o2}-CH_2-$;
o1 is an integer selected from 2, 3, 4, 5 and 6;
o2 is an integer selected from 1, 2, 3, 4, 5 and 6.

Glycoconjugates

Another aspect of the present invention refers to a saccharide of any of the general formulae (I), (II-1), (II-2), (II-3), (II-4), (III-1), (III-2), (IV-1) and (IV-2) conjugated with an immunogenic carrier through the nitrogen atom of the $-O-L-NH_2$ group. Said saccharide is also defined as a glycoconjugate obtained by reacting a saccharide of any of the general formulae (I), (II-1), (II-2), (II-3), (II-4), (III-1), (III-2), (IV-1) and (IV-2) with an immunogenic carrier. Thus said saccharide of any of the general formulae (I), (II-1), (II-2), (II-3), (II-4), (III-1), (III-2), (IV-1) and (IV-2) conjugated with an immunogenic carrier through the nitrogen atom of the $-O-L-NH_2$ group and said glycoconjugate obtained by reacting a saccharide of any of the general formulae (I), (II-1), (II-2), (II-3), (II-4), (III-1), (III-2), (IV-1) and (IV-2) with an immunogenic carrier have the same meaning.

Said glycoconjugate proved to be efficient as a vaccine for immunization against diseases associated with bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formulae (I), (II-1), (II-2), (II-3), (II-4), (III-1), (III-2), (IV-1) and (IV-2) are conjugated to an immunogenic carrier to provide glycoconjugates, which present increased immunogenicity in comparison with the saccharides.

Saccharide-protein conjugate consisting of at least one synthetic saccharide of the general formula (I) and an immunogenic carrier to which the at least one saccharide (I) is covalently bound.

In this context the term "immunogenic carrier" is defined as a structure, which is conjugated to the saccharide to form a glycoconjugate that presents an increased immunity in comparison with the saccharide per se. Thus, the conjugation of the saccharides of the general formulae (I), (II-1), (II-2), (II-3), (II-4), (III-1), (III-2), (IV-1) and (IV-2) to the immunogenic carrier has as effect the stimulation of the immune response against the saccharide of the general formulae (I), (II-1), (II-2), (II-3), (II-4), (III-1), (III-2), (IV-1) and (IV-2) without inducing an immune response against the said immunogenic carrier.

Preferred immunogenic carriers are carrier proteins. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid.

An embodiment of the present invention is saccharide (I) covalently linked to an immunogenic carrier through the nitrogen atom of the $-O-L-NH_2$-group. -L- of the $-O-L-NH_2$-group is the linkage to the immunogenic carrier in form of a covalent bond (oxygen atom of $O-L-NH_2$-group directly or indirectly linked to the immunogenic carrier) or in form of the -L-NH—, wherein the nitrogen atom is linked directly or indirectly to the carrier protein Directly linked means to a functional group or side chain of the immunogenic carrier and indirectly linked refers to a linkage through an additional functional group with which the immunogenic carrier and/or the nitrogen of the $-O-L-NH_2$-group.

If a carrier protein is used as immunogenic carrier, for the coupling of saccharide to a carrier protein, chemical activation of the saccharide and sometimes of the protein is necessary. The choice of the conjugation method to saccharide to proteins is restricted due to the pH and temperature sensitivity of the proteins, and their limited solubility in most organic solvents. The procedure has to be performed under mild conditions in order to prevent denaturation of the protein and degradation of the saccharide. As such, conjugation reactions are carried out in buffers at or near neutral pH. To date, numerous protocols have been reported for the covalent attachment of carbohydrates to protein. The following linking methods can be used for linking synthetic saccharide (I) to the carrier protein:

Reductive amination is the one of the most popular glycoconjugation methods for the binding of free oligosaccharides via the reducing-end to the ε-amino group of the lysine residues in proteins. In the present invention the amino group of synthetic saccharide (I) can be further functionalized with an aldehyde function, e.g. using glutaraldehyde, and glycoconjugation between synthetic saccharide functionalized with aldehyde and a carrier protein having lysine residues can be formed by reductive amination.

Maleimide-Thiol conjugation as the irreversible reaction of maleimide with thiols to afford stable linkages has also been employed frequently for the preparation of glycoconjugates. For example, maleimide can be prepared from a synthetic saccharide (I) bearing an amine linker at the reducing-end. The saccharide-maleimide construct can then react with thiol side-chains in cysteines of a carrier protein, resulting in the stable glycoconjugate. Inversely, a carrier protein can be activated with maleimide and a synthetic saccharide (I) can be further funtionalized with a thiol function.

A glycoconjugation method using squarate ester can be applied. At first, a squaric acid amide ester of synthetic saccharide (I) can be prepared by the coupling of amine group with squarate ester. The squaric acid amide ester of synthetic saccharide (I) can be further coupled with the ε-amino group of the lysine residues of a carrier protein and squaric acid diamides are formed.

Activated esters including di(N-succinimidyl) adipate, di(N-succinimidyl) glutarate (DSG), N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), 2-pyridyldithiol-tetraoxatetradecane-N-hydroxysuccinimide (PEG-4-SPDP) can be applied. (see FIG. 1). Preferred, di(N-succinimidyl) adipate can be used for the preparation of glycoconjugate.

Zero-length cross linking method with carbodiimides, most of all EDC (1-Ethyl-3-(3-dimethylaminopropyl)carbodiimide) can be used. N-substituted carbodiimides can react with carboxylic acids of a carrier protein to form highly reactive, O-acylisourea derivatives. This active species then can react with a primary amine of synthetic saccharide (I) to form an amide bond.

As further conjugation method click chemistry can be used. Click chemistry is the [3+2] cycloaddition of alkyne and azide. Preferably, strain-promoted azide-alkyne cycloaddition (SPAAC) can be applied for the glycoconjugation. Strained alkynes such as cyclooctyne are advantageous for a bioconjungation due to the non-toxic reaction condition. A carrier protein can be simply labelled with an azide-containing amino acid and conjugated with synthetic saccharide (I) functionalized with an alkyne. Inversely, synthetic saccharide (I) functionalized with an azide can be conjugated with a carrier protein labeled with an alkyne.

Native chemical ligation (NCL) can be used for gylcoconjugation. To apply this method to glycoconjugation, synthetic saccharide (I) should be further functionalized with a thioester, for example, benzylthioester, ethylthioester, or phenylthioester. In the native chemical ligation the thiolate group of an N-terminal cysteine residue of a carrier protein attacks the thioester of functionalized synthetic saccharide (I). This reversible transthioesterification step is chemoselective and regioselective and leads to form a thioester intermediate and this intermediate rearranges by an intramolecular S,N-acyl shift that results in the formation of a native amide bond at the ligation site. Consequently the synthetic saccharide (I) and a carrier protein are conjugated with an amide bond.

Traceless Staudinger ligation can be also used for glycoconjugation. In this reaction, the phosphine bears a thioester electrophile; after reaction with an azide, the products are an amide and the leaving phosphine oxide. The Staudinger ligation has been demonstrated to be ideal for labeling azide-bearing proteins both in vitro, on living cells, and in living animals, due to the demonstrated non-toxicity of both azides and phosphines at relevant concentrations. For glycoconjugating applications, synthetic saccharide (I) is functionalized with thioester bearing phosphine and azide group is introduced into a carrier protein of interest in several ways for subsequent phosphine probe introduction. Usually, azidohomoalanine can be incorporated in place of methionine of a protein. A carrier protein modified with azidohomoalanine can be effectively and specifically conjugated with synthetic saccharide (I) by the Staudinger ligation.

Photo-cross-linking is an important chemical method in the filed of molecular biology. Recently, much attention has been devoted to the application of this method to the identification of ligand-binding regions. Photo-cross-linking methods can be applied for glycoconjugation. Photoaffinity labeling requires functional groups that can be activated photochemically to generate highly reactive intermediates, usually nitrenes or carbenes. As functional groups, benzophenone, arylazide, aryl-, or alkyldiazirine are applied. Recently, alkyl- or aryldiazirine is preferred used for photoaffinity labeling (M. R. Bond et al. *Nature Protocols* 2009, 4(7), 1044-1063; M. R. Bond et al. *Bioconjugate Chemistry* 2011, 22 (9), 1811-1823). For conjugation of synthetic saccharide (I) with a carrier protein, synthetic saccharide (I) can be functionalized with an alkyl- or aryldiazirine, for example, 3-trifluoromethyl-3-phenyldiazirine. After UV-irridation an reactive carbene is produced from synthetic saccharide (I) functionalized with aryldiazirine and this carbene coupled with a carrier protein by a C—C covalent bond.

It is especially preferred that the saccharide of the general formula (I) and/or preferably saccharides 2a, 2b, 2c, 4a, 4b, 4c, 4d, 4e, 6a, 6b, 6c, 8a, 8b and 8c are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines (e.g. Prevnar) for diseases such as pneumococcal bacterial infections.

Preferably, di(N-succinimidyl) adipate is first attached to a synthetic saccharide (I) having a primary amino group. Activated saccharide (I) is subsequently condensed with a carrier protein such as $CRM_{197}$, to afford the glycoconjugate. Also, the use of the related disuccinimidyl glutarate can be applied (FIG. 2 (A)).

Said saccharide conjugated with a carrier protein has preferably a purity of ≥95%, preferably ≥96%, more preferably ≥97%, still more preferably ≥98%, and most preferably ≥99%.

Another aspect of the present invention relates to the use of the inventive saccharides and their glycoconjugates as drugs, i.e. as pharmaceutically active agents applicable in medicine.

It was found that the saccharides of general formulae (I), (II-1), (II-2), (II-3), (II-4), (III-1), (III-2), (IV-1) and (IV-2) and said glycoconjugate obtained by reacting the saccharides of general formulae (I), (II-1), (II-2), (III-1), (III-2), (IV-1) and (IV-2) with an immunogenic carrier are suitable for pharmaceutically active agent in medicine. Said saccharides and said glycoconjugates are suitable to elicit an immune response in an animal, and therefore are useful raising a protective immune response in a human and/or animal host.

Preferred, said saccharides and said glycoconjugates are useful for prevention and/or treatment of diseases associated with *Haemophilus influenzae* type b, preferably diseases selected from meningitis, pneumonia, and epiglotitis.

Surprisingly, it was found that the novel conjugates of the present invention are also suitable to raise an immune response in human and/or animal host and therefore, are suitable for protection against diseases associated with *Haemophilus influenzae* type b. Thus, the inventive conjugates disclosed herein are useful for prevention or treatment of diseases associated with *Haemophilus influenzae* type b. Such diseases include, but are not restricted to meningitis, pneumonia, epiglotitis, and other diseases of the respiratory tract. Moreover, it was found that the treatment of an animal with the novel conjugate of the current invention lead to the formation of immunoglobuline IgG-isotypes, which prove the development of memory B-cells in the living organism. The presence of memory B-cells demonstrates immunological memory. Thus, it has been shown that the conjugates of the current invention are capable to induce a long term protection in an animal against *Haemophilus influenzae* type b.

Therefore, conjugates according to the present invention are suitable for the use as a pharmaceutically active agent applicable in medicine, especially for use in vaccination against diseases caused or associated with *Haemophilus influenzae* type b.

Vaccine Composition

One aspect of the present invention relates to pharmaceutical compositions, especially vaccine compositions containing at least one saccharide of any one of general formulae (I), (II-1), (II-2), (II-3), (II-4), (III-1), (III-2) (IV-1), and (IV-2), pharmaceutically acceptable salts thereof, glycoconjugate thereof, together with at least one pharmaceutically acceptable adjuvant, carrier, cryoprotectant, lyoprotectant, excipient and/or diluent.

Thus the inventive syntheses for the synthetic saccharides of the general formula (I) may further comprise step B)
B) preparing a salt of a saccharide of the general formula (I) or preparing a lyophilisate of a saccharide of the general formula (I) or of the salt of a synthetic saccharide of the general formula (I).

In a preferred embodiment, the inventive syntheses for the saccharide of the formula (I) may further comprise step B)
B) preparing a salt of a saccharide of the general formula (I) or preparing a lyophilisate of a saccharide of the formula (I) or of the salt of a saccharide of the formula (I).

Pharmaceutical compositions according to the present invention comprise the at least one saccharide of any one of general formulae (I), (II-1), (II-2), (II-3), (II-4), (III-1), (III-2), (IV-1) and (IV-2) pharmaceutically acceptable salts thereof. Especially the saccharides 2a, 2b, 2c, 4a, 4b, 4c, 4d, 4e, 6a, 6b, 6c, 8a, 8b and 8c obtained according to the total chemical synthesis disclosed herein are used in these vaccines. The saccharides of general formulae (I), (II-1), (II-2), (II-3), (II-4), (III-1), (III-2), (IV-1) and (IV-2) as well as the saccharides 2a, 2b, 2c, 4a, 4b, 4c, 4d, 4e, 6a, 6b, 6c, 8a, 8b and 8c obtained by the total chemical synthesis disclosed herein have a purity of at least 95%, more preferably of at least 96%, still more preferably of at least 97%, still more preferably of at least 98%, and most preferably of at least 99%.

The saccharides of the present invention as well as the pharmaceutical compositions containing at least one saccharide of any one of general formulae (I), (II-1), (II-2), (II-3), (II-4), (III-1), (III-2), (IV-1) and (IV-2) and especially the vaccines containing at least one inventive saccharide, especially saccharides 2a, 2b, 2c, 4a, 4b, 4c, 4d, 4e, 6a, 6b, 6c, 8a, 8b and 8c are highly useful for use as a vaccine in immunization against diseases caused or associated with by *Haemophilus influenzae* type b, preferably meningitis, pneumonia, and epiglotitis.

According to the present invention saccharides 2a, 2b, 2c, 4a, 4b, 4c, 4d, 4e, 6a, 6b, 6c, 8a, 8b and 8c as well as any other inventive saccharide disclosed herein is useful for the manufacture of said pharmaceutical composition for use as vaccine for immunization against above-mentioned diseases.

The vaccine may be prepared in the form of a suspension or may be lyophilized. The suspension form may be stored frozen. In the lyophilized form, it is preferable to add one or more stabilizers. Vaccination can be performed at any age. The vaccine many be administered subcutaneously, by spray, by injection, orally, intraocularly, intratracheally or nasally. The amount of vaccine of the invention to be administered a human or animal and the regime of administration can be determined in accordance with standard techniques well known to those of ordinary skill in the pharmaceutical and veterinary arts taking into consideration such factors as the particular antigen, the adjuvant (if present), the age, sex, weight, species and condition of the particular animal or patient, and the route of administration.

A method of inducing immune response against *Haemophilus influenzae* type b in a subject comprises administering of the saccharide of the present invention, a mixture thereof, the conjugation thereof or pharmaceutical composition thereof. A method of treating or preventing diseases caused or associated with by *Haemophilus influenzae* type b, preferably meningitis, pneumonia, and epiglotitis in a subject comprises administering of at least one synthetic saccharide of the present invention or a mixture thereof, the conjugation thereof or the composition or vaccine thereof.

In the present invention, the amount of the saccharide of any one of the formulae (I), (II-1), (II-2), (II-3), (II-4), (III-1), (III-2), (IV-1) and (IV-2) to provide an efficacious dose for vaccination against *Haemophilus influenzae* type b can be from between 0.02 µg to about 10 µg per kg body weight. The saccharide of any one of the formulae (I), (II-1), (II-2), (II-3), (II-4), (III-1), (III-2), (IV-1) and (IV-2) optionally conjugated to an immunogenic carrier, preferred carrier protein such as $CRM_{197}$ can be administered as a single dose or in a series (i.e., with a "booster" or "boosters"). For example, a child could receive a single dose early in life, then be administered a booster dose up to ten years later, as is currently recommended for other vaccines to prevent childhood diseases.

Intravenous and parenteral administration is preferred. Such compositions may be in admixture with a suitable carrier, diluent, or excipient such as sterile water, physiological saline, glucose or the like. The compositions or the saccharides of any one of the formulae (I), (II-1), (II-2), (II-3), (II-4), (III-1), (III-2), (IV-1) and (IV-2) according to the present invention optionally conjugated to an immunogenic carrier can also be lyophilized.

Lyophilized saccharides of the invention will ultimately be reconstituted with a liquid component to give material suitable for administration to a patient. The reconstitution will typically take place at the point of use. Thus a saccharide of the invention and an oil-in-water emulsion adjuvant or a buffer solution of an adjuvant may be kept separately in a packaged or distributed vaccine kit, ready for final formulation at the time of use. In a kit containing two containers, one will include liquid for reconstitution and the second container includes lyophilized material. For stability reasons, the lyophilized component of the invention may include a stabilizer such as lactose, sucrose and/or mannitol, as well as mixtures thereof. Using a sucrose/mannitol mixture can speed up the drying process. A lyophilized component may also include sodium chloride. Soluble components in the lyophilized material will be retained in the composition after reconstitution, and so final liquid vaccines may thus contain lactose and/or sucrose.

Formulation of the vaccines of the present invention can be accomplished using methods known by the art. Obviously, the choice of suitable carriers and other additives will depend on the exact route of administration and the nature of the particular dosage form.

The vaccine compositions of the present invention may contain one or more adjuvants. As defined herein, an "adjuvant" is a substance that serves to enhance the immunogenicity of a saccharide of any one of the formulae (I), (II-1), (II-2), (II-3), (II-4), (III-1), (III-2), (IV-1) and (IV-2) according to the present invention optionally conjugated to an immunogenic carrier. An immune adjuvant may enhance an immune response to an antigen that is weakly immunogenic when administered alone, e.g., inducing no or weak antibody titers or cell-mediated immune response. Further an adjuvant may increase antibody titers to the antigen, and/or lowers the dose of the antigen effective to achieve an immune response in the individual. Thus, adjuvants are often given to boost the immune response and are well known to the skilled person. Suitable adjuvants to enhance effectiveness include, by way of example and not limitation, aluminum adjuvants (e.g., aluminum salts such as aluminum hydroxide, aluminum phosphate, aluminum sulfate or combinations thereof), Freund's Adjuvant (Complete or Incomplete), BAY R1005 (N-(2-Deoxy-2-L-leucylamino-β-D-glucopyranosyl)-N-octadecyldodecanoylamide hydroacetate), DC-chol (dimethylaminoethane)-carbamoyl cholesterol, PCPP (poly[di(carboxylatophenoxy) phosphazene]), monophoshoryl lipid A, CpG oligonucleotides, QS-21 (*Quillaja saponaria* saponin immunologic adjuvant), cholera toxin and formyl methionyl peptide.

Alternative adjuvants include oil-in-water emulsion formulations for example MF59 as described in PCT Publ. No. WO 90/14837, SAF-1 (Syntex Adjuvant Formulation threonyl-MDP (0.05-1%) in an emulsion vehicle [5% squalane, 2.5% Pluronic® L121, 0.2% Polysorbate 80 and phosphate buffered saline (pH 7.4)], and one or more bacterial cell wall components from the group consisting of monophosphorylipid A (MPL), trehalose dimycolate (TDM), and cell wall skeleton (CWS), saponin adjuvants, such as Stimulon™ (Cambridge Bioscience, Worcester, Mass.) may be used or particles generated thereof. Various oil-in-water emulsion adjuvants are known, and they typically include at least one oil and at least one surfactant, with the oil(s) and surfactant(s) being biodegradable (metabolisable) and biocompatible. Squalane, the saturated analog to squalene, is preferred oil. Other preferred oils are the tocopherols. Mixtures of oils can be used. Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens); copolymers of ethylene oxide (EO), propylene oxide (PO), and/or butylene oxide (BO); octoxynols, which can vary in the number of repeating ethoxy (oxy-1,2-ethanediyl) groups, such as octoxynol-9 (Triton X-100, or toctylphenoxypolyethoxyethanol); phospholipids such as phosphatidylcholine (lecithin); polyoxyethylene fatty ethers derived from lauryl, cetyl, stearyl and oleyl alcohols (known as Brij surfactants). Preferred surfactants for including in the emulsion are Tween 80 (polyoxyethylene sorbitan monooleate), Span 85 (sorbitan trioleate), lecithin and Triton X-100.

Further adjuvants may be cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF).

The compositions can contain auxiliary substances such as wetting or emulsifying agents, pH buffering agents, gelling or viscosity enhancing additives, preservatives, flavoring agents, colors, and the like, depending upon the route of administration and the preparation desired. Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

A composition may include a temperature protective agent. Examples include glycerin, propylene glycol, and/or polyethylene glycol (PEG).

The vaccine compositions of the present invention may further comprises at least one of diphtheria antigen, tetanus antigen, pertussis antigen, hepatitis B antigen, inactivated polio vaccine and inactivated rotavirus vaccine.

The term "diphtheria antigen" as used herein is preferably a diphtheria toxoid. The diphtheria toxoid is the formaldehyde-inactivated toxin of *Corynebacterium diphtheriae*, used as an active immunizing agent against diphtheria. The preparation of diphtheria toxoids is well documented (e.g. Plotkin et al, Vaccines, 6$^{th}$ edition, 2012, Chapter 12). Any suitable diphtheria toxoid may be used. The concentration of diphtheria toxoid is generally between 5 and 100 Lf(Limit of Floculation)/mL. A preferred concentration is between 10 and 50 Lf/mL. A more preferred concentration is between 20 and 40 Lf/mL. Most preferably, the concentration is about 30 Lf/mL.

The term "tetanus antigen" as used herein is preferably a tetanus toxoid. The tetanus toxid is well-known for a person skilled in the art (e.g. Plotkin et al, Vaccines, 6$^{th}$ edition, 2012, Chapter 33). Any suitable tetanus toxoid may be used. The concentration of tentaus toxoid is generally between 1 and 50 Lf/mL. A preferred concentration is between 2 and 9 Lf/mL. A more preferred concentration is between 5 and 8 Lf/mL. Most preferably, the concentration is about 6.5 Lf/mL.

The term "pertussis antigen" as used herein may be cellular (e.g. whole cell) or acellular. The preparation of both types of antigen is well documented (e.g. Plotkin et al, Vaccines, 6$^{th}$ edition, 2012, Chapter 23). For cellular pertussis antigens, the concentration of pertussis antigens is generally between 5 and 50 OU/mL. A preferred concentration is between 10 and 40 OU/mL. A more preferred concentration is between 25 and 35 OU/mL. Most preferably, the concentration is about 30 OU/mL. Where acellular antigens are used, it is preferred to use pertussis holotoxin (PT) and filamentous haemagglutinin (FHA), more preferably combined with pertactin (also known as PRN or 69 kDa antigen) and optionally, agglutinogens (also known as fimbriae) 2 and 3. PT is a toxic protein and, when present in the pertusssis antigen, it is preferably detoxified. Detoxification may be by chemical and/or genetic means. A preferred detoxified mutant is the 9K/129G doulb mutant.

The term "hepatitis B antigen" as used herein may be hepatitis B surface antigen. The preparation of hepatitis B surface antigen is well documented (e.g. Plotkin et al, Vaccines, 6$^{th}$ edition, 2012, Chapter 15).

The term "inactivated polio vaccine (IPV)" as used herein, preferably consists of inactivated (killed) poliovirus strains of all three poliovirus types I-3. In the present invention virus inactivation refers to elimination of the infectious ability of a virus. In the two method of inactivation (chemical and physical), most commonly used chemicals are formaldehyde and betapropiolactone. The preparation of diphtheria toxoids is well documented (e.g. Plotkin et al, Vaccines, $6^{th}$ edition, 2012, Chapter 27).

The term "inactivated rotavirus vaccine" as used herein, preferably may be the bovine(UK strain)/human reassortant vaccine, the human neonatal RV3 strain or the bovine/human neonatal 116E strain. In the present invention virus inactivation refers to elimination of the infectious ability of a virus. In the two method of inactivation (chemical and physical), most commonly used chemicals are formaldehyde and betapropiolactone. The preparation of inactivated rotavirus vaccine is well documented (e.g. Plotkin et al, Vaccines, $6^{th}$ edition, 2012, Chapter 30).

Compositions of the invention are conveniently provided as liquid preparations, e.g., isotonic aqueous solutions, suspensions, emulsions or viscous compositions that may be buffered to a selected pH. Pharmaceutically acceptable carriers for liquid formulations may be aqueous or nonaqueous solutions, suspensions, emulsions or oils. Examples of non-aqueous solvents are propylene glycol, polyethylene glycol, and injectable organic esters such as ethyl oleate. Aqueous carriers include water, alcoholic solutions, emulsions or suspensions, including saline and buffered media. The pH of a composition after reconstitution is preferably between 6 and 8, and more preferably between 6.5 and 7.5 (e.g. about 7). Compositions of the invention may be maintained by the use of a buffer e.g. a Tris buffer, acetate, glutamate, lactate, maleate, tartrate, phosphate, citrate, carbonate, glycinate, histidine, glycine, succinate and triethanolamine buffer. Thus compositions of the invention will preferably include a buffer. The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to sorbitol and glycerol.

In a preferred embodiment of the invention, the vaccine composition is formulated as a sterile liquid, pyrogenfree, phosphate-buffered physiological saline, with or without a preservative.

A pharmaceutically acceptable preservative can be employed to increase the shelf life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

The composition of the invention can be formulated as single dose vials, multidose vials or as pre-filled syringes.

Another aspect of the present invention relates to pharmaceutical formulations and pharmaceutical compositions containing at least one saccharide of any one of the general formulae (I), (II-1), (II-2), (II-3), (II-4), (III-1), (III-2), (IV-1) and (IV-2) optionally conjugated with an immunogenic carrier or the vaccine as an active ingredient, together with at least one pharmaceutically acceptable adjuvant, carrier, excipient, solvent and/or diluents.

Further preferred, the pharmaceutical composition is formulated in the form of a lyophilisate or liquid buffer solution.

The vaccine or pharmaceutical composition can also be administered in form of its pharmaceutically active salt optionally using substantially nontoxic pharmaceutically acceptable carrier, excipients, adjuvants or diluents. The vaccine or pharmaceutical composition of the present invention is prepared in a conventional solid or liquid carrier or diluents and a conventional pharmaceutically-made adjuvant at suitable dosage level in a known way. The preferred preparations and formulations are in administrable form which is suitable for oral application. These administrable forms, for example, include pills, tablets, film tablets, coated tablets, capsules, powders and deposits. Other than oral administrable forms are also possible. The inventive vaccine or pharmaceutical composition may be administered by any appropriate means, including but not limited to inhalation, injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrically, intracutaneously, intravaginally, intravasally, intranasally, intrabuccally, percutaneously, sublingually, or any other means available within the pharmaceutical arts.

The vaccine or pharmaceutical composition of the present invention, containing at least one saccharide of any of general formulae (I), (II-1), (II-2), (II-3), (II-4), (III-1), (III-2), (IV-1) and (IV-2), preferred the saccharides 2a, 2b, 2c, 4a, 4b, 4c, 4d, 4e, 6a, 6b, 6c, 8a, 8b and 8c or pharmaceutically acceptable salt thereof as an active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active ingredient may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent of the tetrasaccharide.

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the vaccine or pharmaceutical composition of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidifies.

Also included are solid form preparations which are intended to be converted, shortly before use, to liquid form preparations for either oral or parenteral administration. Such liquid forms include solutions, suspensions and emulsions.

The inventive vaccine or pharmaceutical composition containing at least one saccharide of any of general formulae (I), (II-1), (II-2), (II-3), (II-4), (III-1), (III-2), (IV-1) and (IV-2), preferably the saccharides 1f, 2a, 2b, 2b', 2c, 2f, 4a, 4b, 4c, 4d, 4e, 4f, 6a, 6b, 6c, 6f, 8a, 8b, 8c and 8f may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refer to the active ingredients dispersed or solubilized in a hydrophilic semi-solid matrix.

Powders for constitution refer to powder blends containing the active ingredients and suitable diluents which can be suspended in water or juices.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.01 to 10% by weight of the composition, preferably from about 0.05 to 6% by weight, more preferably from about 0.1 to about 4% by weight of the composition, and most preferably from about 0.1 to about 1%.

Techniques for the formulation and administration of the vaccine of the present invention may be found in "Remington's Pharmaceutical Sciences" Mack Publishing Co., Easton Pa. A suitable vaccine composition comprising at least one saccharide of any one of the general formulae (I), (II-1), (II-2), (II-3), (II-4), (III-1), (III-2), (IV-1) and (IV-2), preferably the saccharides 1f, 2a, 2b, 2b', 2c, 2f, 4a, 4b, 4c, 4d, 4e, 4f, 6a, 6b, 6c, 6f, 8a, 8b, 8c and 8f and/or pharmaceutically acceptable salts thereof may be a solution of such saccharide(s) in a suitable liquid pharmaceutical carrier or any other formulation such as tablets, pills, film tablets, coated tablets, dragees, capsules, powders and deposits, gels, syrups, slurries, suspensions, emulsions, and the like.

A therapeutically effective dosage of the saccharide of any one of general formulae (I), (II-1), (II-2), (II-3), (II-4), (III-1), (III-2), (IV-1) and (IV-2), preferably the saccharides 1f, 2a, 2b, 2b', 2c, 2f, 4a, 4b, 4c, 4d, 4e, 4f, 6a, 6b, 6c, 6f, 8a, 8b, 8c and 8f refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

The mentioned vaccine formulation displays an extraordinary stability at room temperature due to the modular constitution of the compounds of the present invention, wherein said vaccine formulation may be maintained at a temperature of at least 25° C. for a period of at least 3 months prior to reconstitution. The temperature-stability of the herein described vaccine formulations constitutes a particular advantage of the present invention over the vaccines directed against *Haemophilus influenzae* type b, which were described up to present.

In a preferred embodiment of the invention the said period is comprises 6 months or at least 12 months.

Antibody

The present invention refers also to an antibody against at least one synthetic saccharide of general formulae (I), (II-1), (II-2), (II-3), (II-4), (III-1), (III-2), (IV-1), and (IV-2). The antibody is produced by the monoclonal hybridoma. The antibody is for diagnostics, prophylaxis, and treatment of pneumonia, meningitis, otitis media, bacteremia and acute exacerbation of chronic bronchitis, sinusitis, arthritis and conjunctivitis. Another embodiment of the present invention is use of the antibody for manufacture of medicaments or devices for diagnosis, prophylaxis, and treatment of meningitis, pneumonia, and epiglotitis caused by *Haemophilus influenzae* type b.

The term "antibody" as used herein encompasses polyclonal and monoclonal antibody preparations, as well as preparations including hybrid antibodies, F(ab')$_2$ fragments, F(ab) molecules, single domain antibodies and functional fragments thereof which exhibit immunological binding properties of the parent antibody molecule. The antibody according to the invention may be polyclonal or monoclonal.

The saccharide of any one of general formulae (I), (II-1), (II-2), (II-3), (II-4), (III-1), (III-2), (IV-1), and (IV-2), preferably the saccharides 1f, 2a, 2b, 2b', 2c, 2f, 4a, 4b, 4c, 4d, 4e, 4f, 6a, 6b, 6c, 6f, 8a, 8b, 8c and 8f or the antibody thereof can be used for preparing a pharmaceutical composition especially vaccines for the treatment or prevention of diseases caused by *Haemophilus influenzae* type b. The saccharide of the present invention or the antibody thereof can be used for the treatment or prevention of a disease caused by *Haemophilus influenzae* type b.

Further the present invention refers to the use of at least one saccharide of general formulae (I), (II-1), (II-2), (II-3), (II-4), (III-1), (III-2), (IV-1), and (IV-2) preferably the saccharides 1f, 2a, 2b, 2b', 2c, 2f, 4a, 4b, 4c, 4d, 4e, 4f, 6a, 6b, 6c, 6f, 8a, 8b, 8c and 8f according to the invention or at least one antibody against at least one saccharide of the present invention in immunological assays for diagnostics of meningitis, pneumonia, and epiglotitis caused by *Haemophilus influenzae* type b.

Such assays comprise, for instance, microarray and ELISA useful for diagnosis of diseases caused by *Haemophilus influenzae* type b. Therefore another aspect of the present invention refers to the use of any one of saccharides of formulae (I), (II-1), (II-2), (II-3), (II-4), (III-1), (III-2), (IV-1), and (IV-2) preferably the saccharides 1f, 2a, 2b, 2b', 2c, 2f, 4a, 4b, 4c, 4d, 4e, 4f, 6a, 6b, 6c, 6f, 8a, 8b, 8c and 8f for diagnosis of diseases caused by *Haemophilus influenzae* type b.

Any one of saccharides of general formulae (I), (II-1), (II-2), (II-3), (II-4), (III-1), (III-2), (IV-1), and (IV-2) preferably the saccharides 1f, 2a, 2b, 2b', 2c, 2f, 4a, 4b, 4c, 4d, 4e, 4f, 6a, 6b, 6c, 6f, 8a, 8b, 8c and 8f or a mixture of such saccharides could be immobilized on a microarray surface or any other surface and used for an in vitro method of detecting *Haemophilus influenzae* type b. A method of identifying *Haemophilus influenzae* type b comprises the use of at least one saccharide of the present invention. Furthermore, the synthetic saccharide of general formulae (I), (II-1), (II-2), (II-3), (II-4), (III-1), (III-2), (IV-1), and (IV-2) preferably the saccharides 1f, 2a, 2b, 2b', 2c, 2f, 4a, 4b, 4c, 4d, 4e, 4f, 6a, 6b, 6c, 6f, 8a, 8b, 8c and 8f or a mixture of such saccharides can be used as an analytical standard for immuno-assays.

Diagnostic Devices

Another aspect of the present invention is related to a solid support comprising at least one saccharide of general formula (I), preferred saccharides of the formulae (I-1), (II-2), (II-3), (II-4), more preferred saccharide of the formulae (III-1), (III-2), (IV-1), and (IV-2), preferably the saccharides 1f, 2a, 2b, 2b', 2c, 2f, 4a, 4b, 4c, 4d, 4e, 4f, 6a, 6b, 6c, 6f, 8a, 8b, 8c and 8f.

This solid support is preferable a part of a diagnostic device. The solid support and the diagnostic device are used for diagnosis of meningitis, pneumonia, and epiglotitis caused by *Haemophilus influenzae* type b, wherein the at least one saccharide of general formula (I) is immobilized on said solid support by preferably covalent bonding.

The other embodiment of the present invention is the diagnostic device wherein the solid support is selected from the group comprising a glass slide, glass plate, a microtitre plate, microspheres, or beads.

The even other embodiment of the present invention is the diagnostic device wherein the at least one saccharide of general formula (I) is covalently bound using a linking molecule.

Moreover, the present invention shows that the saccharide according to formula (I) can be used in immunological assays for meningitis, pneumonia, and epiglotitis caused by *Haemophilus influenzae* type b.

Such assays comprise, for instance, microarray and ELISA useful for diagnosis of meningitis, pneumonia, and epiglotitis caused by *Haemophilus influenzae* type b.

Therefore another aspect of the present invention refers to the use of a saccharide of formula (I) for diagnosis of meningitis, pneumonia, and epiglotitis caused by *Haemophilus influenzae* type b.

Saccharide (I) according to the invention is immobilized on a solid support by covalent bonding. At least one synthetic saccharide (I) unbound or immobilized on a solid support is used for diagnosis of meningitis, pneumonia, and epiglotitis caused by *Haemophilus influenzae* type b.

Use of saccharide (I) for the diagnosis of meningitis, pneumonia, and epiglotitis caused by *Haemophilus influenzae* type b is based on the detection of the presence of antibodies specific for at least one saccharide of general formula (I). Thus, a diagnostic device comprising at least one saccharide of general formula (I) is used for diagnosis of meningitis, pneumonia, and epiglotitis caused by *Haemophilus influenzae* type b.

It is further preferred that a saccharide of formula (I) used for meningitis, pneumonia, and epiglotitis caused by *Haemophilus influenzae* type b is substantially pure, having a purity of ≥95%, preferably ≥96%, more preferably ≥97%, still more preferably ≥98%, and most preferably ≥99%.

There are different possibilities for the choice of an assay system in which a saccharide of formula (I) is used for diagnosis of meningitis, pneumonia, and epiglotitis caused by *Haemophilus influenzae* type b. An assay conducted for diagnostic purposes according to the invention may be an immune assay like a solid-phase enzyme immunoassay (EIA), an enzyme linked immunosorbent assay (ELISA), especially an "indirect" ELISA or a radioimmune assay (RIA). For the use of a saccharide of formula (I) in such assays it could be necessary to immobilize the saccharide of formula (I) on a solid support.

Thus other embodiment of the present invention is solid support on which at least one saccharide (I) is immobilized by covalent attachment through a linker or spacer. Even other embodiment of the invention is saccharide immobilized by covalent bonding on the solid support directly or indirectly through the nitrogen atom of the —O-L-NH$_2$ group (FIG. 2 (B)).

Therefore a saccharide of formula (I) may be immobilized on a solid support, particularly for diagnostic applications. One preferred embodiment of the present invention is a saccharide of general formula (I) immobilized on a solid support by covalent bonding. One particularly preferred embodiment of the present invention is a saccharide of general formula (I) immobilized on a solid support by direct or indirect covalent bonding. Thereby direct covalent bonding is especially preferred.

Further preferred the solid support is selected from the group comprising or consisting of: a glass slide, a microtitre plate, test tubes, microspheres, nanoparticle or beads.

It is particularly preferred that the solid support is a glass slide or a microtitre plate. A microtitre plate or microplate or microwell plate is a flat plate with multiple "wells" used as small test tubes. Typically a microtitre plate having 6, 24, 96, 384 or even 1536 sample wells can be used. Microplates are produced from many different materials, like polycarbonate for microtitre plate used for PCR. The most common is polystyrene as used for most optical detection microplates. It can be colored white by the addition of titanium dioxide for optical absorbance or luminescence detection or black by the addition of carbon for fluorescent biological assays.

"Direct covalent bonding" as used herein refers to immobilization of a compound of general formula (I) by reacting a functional group of the saccharide of general formula (I) with a functional group of the material the solid support is made from. It is preferred that the functional group of the saccharide of general formula (I) is amine as defined above in —O-L-NH$_2$. Possible reactive, functional groups of the solid support may be: phenyl, amino groups, hydroxyl groups, thiols, carbonyls, carboxyls, vinyls, halides such as fluorides, chlorides, bromides and iodides, maleimides; succinimide esters.

"Indirect covalent bonding" as used herein refers to immobilization of a saccharide of general formula (I) on a solid support wherein the saccharide of general formula (I) is covalently linked to a second compound which mediates the immobilization to the solid support. It is preferred that this second compound is a protein which does not cause an immune reaction. It is important that the second compound itself is most probably not bound by any antibody present in the blood or serum of a patient to avoid false positive results. Further the second compound should be able to be immobilized on the solid carrier, by covalent or non-covalent bonding. It is preferred that this second compound is selected from the group comprising or consisting of bovine serum albumin (BSA), human serum albumin (HAS), gelatin or casein. The immobilization using indirect covalent bonding therefore refers preferably to covalent bonding of a saccharide of general formula (I) to a protein as a second compound (eg using the free amino groups of a protein) and subsequently binding of the protein to the solid support by covalent bonding or non covalent interaction between the solid support and the protein. Possible non-covalent interactions are: hydrogen bonds, ionic bonds, van der Waals forces, and hydrophobic interactions. Many polymers, such as polystyrene and polypropylene are hydrophobic in nature. Nevertheless there are also manufacturers which supply solid support having specialized surfaces optimized for different adhesion conditions.

However, immobilization, especially using indirect covalent bonding, may also occur by strong adhesion. Thus, an effective immobilization according to the present invention may be realized not only by chemical bonding, but also unbound by immobilization related to physisorption. As key feature for physisorption acts the phenomenon that the force for adhesion is caused by van der Waals force. The term "unbonded" refers to a bonding other than covalent bonding.

Chemisorption as immobilization form according to the present invention uses chemical bonds between solid support and a saccharide of formula (I). Such bond may be covalent, but may also be ionic.

In a preferred embodiment of the present invention immobilization of a saccharide of the formula (I) on a solid support is realized by direct covalent bonding namely a chemical reaction between these two reactants, preferably by a substitution reaction. In a more preferred embodiment of the present invention the solid support is modified with a functional group which is capable of leaving the solid support upon reaction with the compound of the present invention. Such functional group may be bound directly to a composing molecule of the solid support or may be bound to a linker which is directly bound to the composing molecule of the solid support. Thus, in a more preferred embodiment of the present invention the solid support is modified to bearing a suitable leaving group. Suitable leaving groups may be halides such as chlorides, bromides and iodides; hydroxides, oximes, maleimides, succinimide, alcohols and esters. Such leaving group may be or may be incorporated in maleimide; α-iodoacetyl; α-bromoacetyl; N-hydroxysuccinimide ester (NHS) and 2-pyridyldithiols. In yet more preferred embodiment the leaving group on the solid support is capable of reacting with amines, alcohols and thiols, preferably upon proton exchange. In most preferred embodiment of the present invention the solid support is functionalized with a succinimidyl hydroxide functional group, more preferably N-succinimidyl hydroxide, which will leave the solid support upon reaction with a compound of the present invention as N-hydroxysuccinimide.

Modification of the solid support by introduction of a suitable leaving group is preferably carried out by reaction of an unmodified carrier with a reactive bifunctional molecule, preferably a bifunctional molecule with a molecular bridge or spacer arm between the two functional groups. In a preferred embodiment of the present invention functional groups willingly reacting with the solid support comprise sulfosuccinimide esters and succinimides.

One further preferred aspect of the bifunctional linking molecules is the ability of providing the functional group meant to bind with a saccharide of the formula (I) is an appropriate distance to the solid carrier. Such an appropriate distance is provided by a molecular bridge or spacer arm of suitable length. Such a molecular bridge or spacer arm may have a length preferably from 3 Å ($10^{-10}$ m) to 10 nm, more preferably from 5 Å to 50 Å, and most preferably from 6 Å to 30 Å.

Suitable reactive bifunctional molecules for modification of the solid support comprise N-(γ-maleimidobutyryloxy) sulfosuccinimide ester (sulfo-GMBO), succinimidyl (4-iodoacetyl) aminobenzoate (sulfo-SIAN), succinimidyl-3-(bromoacetamido)propionate (SBAP), disuccinimidyl glutarat (DSG), 2-pyridyldithiol-tetraoxatetradecane-N-hydroxysuccinimide (PEG-4-SPDP).

There are also solid supports commercially available made from polymers with reactive functional introduced for covalent bonding. One example are microplates named CovaLink™ NH by Thermo scientific which allow covalent binding through a secondary amine group.

Another aspect of the present invention is the use of the diagnostic device comprising at least one synthetic saccharide of general formula (I) immobilized on a solid support by covalent bonding for diagnosis of meningitis, pneumonia, and epiglotitis caused by *Haemophilus influenzae* type b.

Kit

One embodiment of the present invention relates to a kit comprising at least one saccharide of general formula (I) immobilized on a solid support by covalent bonding or the saccharide of general formula (I) for immobilization on a solid support. The at least one saccharide of general formula (I) may be used as a marker in said assays. Another embodiment of the present invention relates to a kit comprising at least one antibody against a saccharide of any one of general formulae (I), (II-1), (II-2), (II-3), (II-4), (III-1), (III-2), (IV-1) and (IV-2).

A kit in molecular biology or in medical diagnostics is a package which includes all necessary ingredients for performing a certain method or singular step. Standard chemicals as present in any standard molecular biology or medical laboratory are normally not included. Nevertheless some of these standard chemicals may be indispensable to carry out the diagnosis or the immobilization properly. It is understood that all ingredients are provided in quantities that allow for a proper execution of the desired reactions for the majority of scientific, diagnostic and industrial applications.

Often, but not always, these ingredients are provided in already prepared solutions ready- or close to ready-for-use. There may be also combinations of different ingredients already added together. A further advantage is that such kits use to be verified. Therefore the operator doesn't have to prove again the viability of the diagnostic method and can save on at least some control experiments. Therefore kits are a very popular tool in laboratories in research, diagnostics and industry.

Such a kit according to the invention shall include at least the following components:
A) solid support on which at least one saccharide of general formulae (I), (II-1), (II-2), (II-3), (II-4), (III-1), (III-2), (IV-1) and (IV-2) is immobilized
B) at least one antibody, like detection antibody
C) a standard solution or a kit according to the invention shall include at least the following components:
A') solid support on which at least one antibody against a saccharide of general formulae (I), (II-1), (II-2), (II-3), (II-4), (III-1), (III-2), (IV-1) and (IV-2) is immobilized
B) at least one further antibody, like detection antibody
C) a standard solution The following components may also be included in such kits:
D) blocking solution
E) wash solution
F) sample buffer An antibody in the kit may be a specific antibody which can be used as a capture antibody. But preferably it is at least an enzyme-linked secondary antibody used as detection antibody that binds specifically to antibody's Fc region. For quantitative determinations, the optical density (OD) or fluorescence of the sample is compared to a standard curve, which is typically a serial dilution of a known-concentration solution of the target molecule (a standard solution). A blocking solution may be a solution of a non-reacting protein, such as bovine serum albumin or casein, which is added to block any plastic surface in the well that remains uncoated by the antigen. Washing solutions are used to remove unbound components. A sample buffer may be used to dilute the sample of the patient (blood, serum, urine) so that the concentration of the target molecule is in the range which can normally be detected by the test system used.

If the kit shall be allowed for the immobilization of a saccharide of general formulae (I), (II-1), (II-2), (II-3), (II-4), (III-1), (III-2), (IV-1) and (IV-2) on a solid support, the kit should include at least:
A) At least one saccharide of any one of general formulae (I), (II-1), (II-2), (II-3), (II-4), (III-1), (III-2), (IV-1) and (IV-2), or an antibody against at least one synthetic saccharide of general formula (I), (II-1), (II-2), (II-3), (II-4), (III-1), (III-2), (IV-1) and (IV-2)
B) A solid support, like a microtiter plate or microarray slide Thereby the solid support may be modified, for example the solid support may be functionalized with a linker molecule as described above.

The following components may also be included in such kits:
C) blocking solution
D) wash solution
E) reaction buffer

DESCRIPTION OF FIGURES

FIG. 5: (A) HPLC chromatogram and (B) ESI mass spectrum of fragmented Hib CPS after treatment with 0.1 M sodium hydroxide solution for 20 hours.

FIG. 13: HPLC chromatogram of (A) compound 30 after treatment with after treatment with 0.1 M sodium hydroxide solution for 3 days; (C) compound 16 after treatment with after treatment with 0.1 M sodium hydroxide solution for 3 days, HPLC chromatograms of untreated compounds 30, 16 and 8 are shown in (B), (D) and (E).

FIG. 19: ELISA study: Binding of IgG antibodies from rabbits (n=4) immunized with unadjuvanted conjugate 94 (■), with conjugate 94 adjuvanted with Alhydrogel (▲), with PBS/Alhydrogel (●) and with HiberiX® (▼) to commercial ADi plates precoated with native Hib PRP antigen after 0 days (A—negative control), 14 days (B), 21 days (C) and 35 days (D). Sera were diluted 5-fold with 1% BSA-PBS. Diluted sera (100 µL) were added per well of the microtiter plate which was coated with 1 µg of Hib-PRP polysaccharide, detected with a HRP conjugated goat anti-rabbit secondary antibody diluted to 1:10000 and developed using TMB. Absorbance was measured at 450 nm and the data were plotted using the graphpad prism software.

Figure 1:
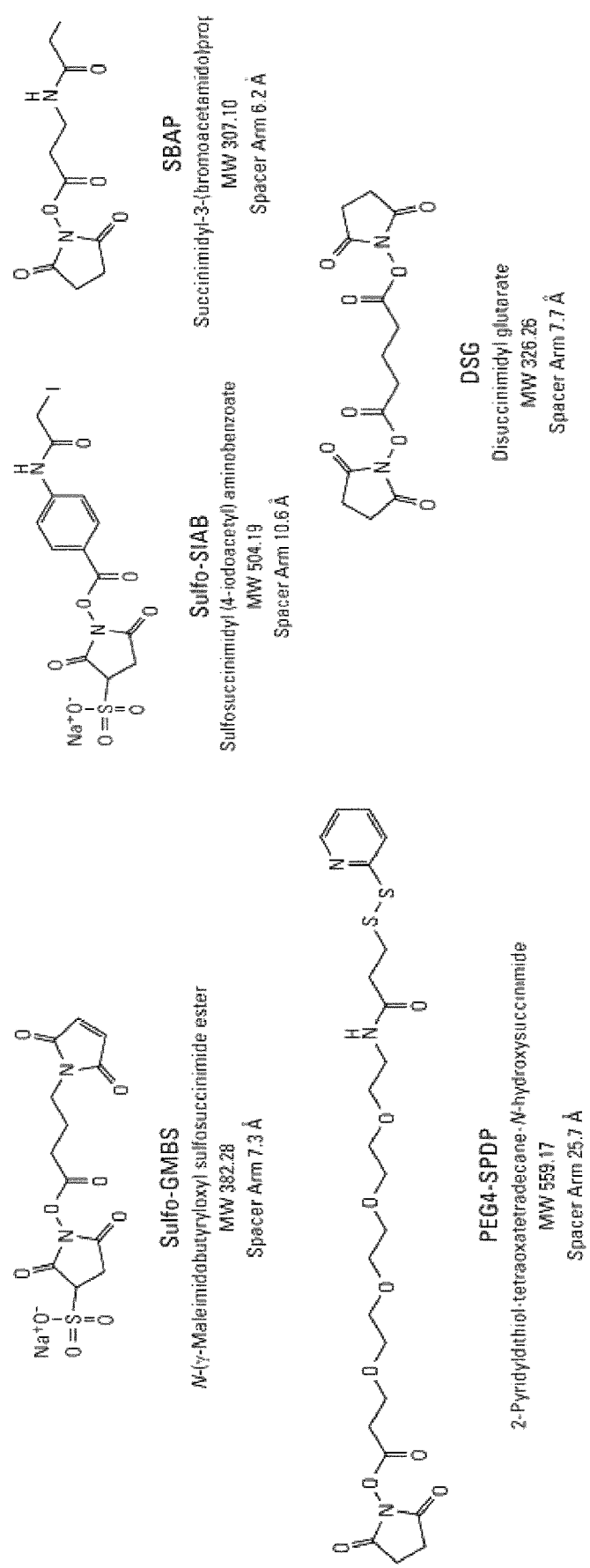
FIG. 1: Commercially available interconnecting molecules according to the present invention.
Figure 2:
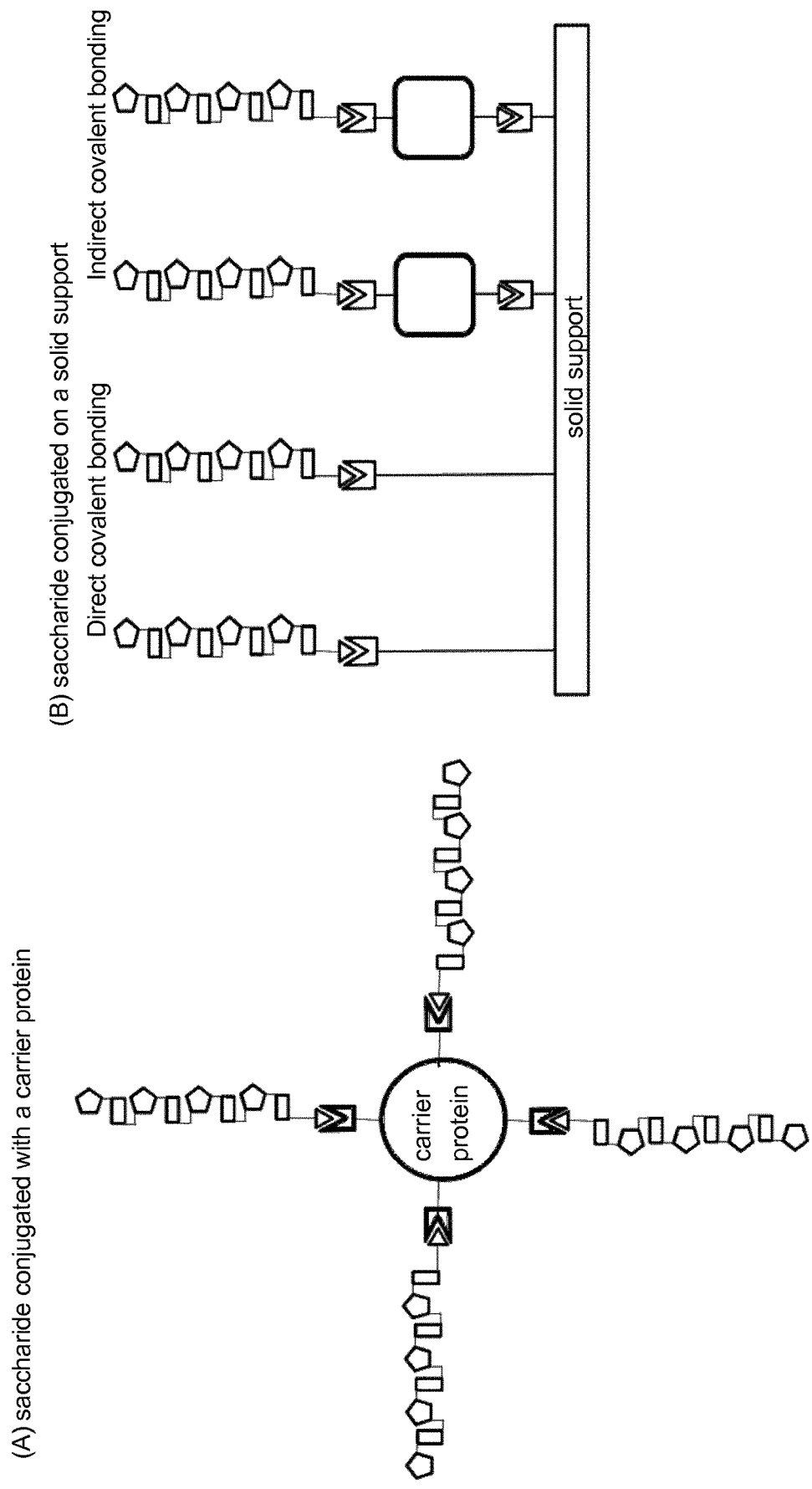
FIG. 2: (A) saccharide conjugated with a carrier protein; (B) saccharide conjugated on a solid support.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Chemical Synthesis
Abbreviations:
TLC: thin layer chromatography, EtOAc: ethyl acetate, DCM: dichloromethane, RBF: round bottom flask, ACN: acetonitrile, AcOH: acetic acid, TBAF: tetrabutylammonium fluoride, BnBr: benzyl bromide, DMAP: dimethylaminopyridine, PTFE: polytetrafluoroethylene, AIBN: azobisisobutyronitrile, THF: tetrahydrofuran, NAP: 2-naphthylmethyl, Lev: levulinyl.
General Information for Chemical Synthesis
Commercial reagents were used without further purification except where noted. Solvents were dried and redistilled prior to use in the usual way. All reactions were performed in oven-dried glassware under an inert atmosphere unless noted otherwise. Analytical thin layer chromatography (TLC) was performed on Kieselgel 60 F254 aluminium plates precoated with a 0.25 mm thickness of silica gel. The TLC plates were visualized with UV light and by staining with Hanessian solution (ceric sulfate and ammonium molybdate in aqueous sulfuric acid) or sulfuric acid-ethanol solution. Column chromatography was performed on Fluka Kieselgel 60 (230-400 mesh). Optical rotations (OR) were measured with a Schmidt & Haensch UniPol L1000 polarimeter at a concentration (c) expressed in g/100 mL. $^1$H and $^{13}$C NMR spectra were measured with a Varian 400-MR or Varian 600 spectrometer with Me$_4$Si as the internal standard. NMR chemical shifts ($\delta$) were recorded in ppm and coupling constants (J) were reported in Hz. High-resolution mass spectra (HRMS) were recorded with an Agilent 6210 ESI-TOF mass spectrometer.

General Procedure A) Disilyloxy Deprotection

TBAF (0.21 mL, 0.21 mmol) and AcOH (7 µL, 0.11 mmol) were added to a stirred solution of starting material (0.073 mmol) in THF (1.5 mL) at room temperature in a 10 mL RBF (oven dried) under argon atmosphere. Reaction mixture was stirred at room temperature for 4 h. Reaction was monitored by TLC. After complete consumption of starting material reaction mixture was diluted with DCM (10 mL) and concentrated under vacuum to obtain the crude product. The crude product was by automated flash chromatography using EtOAc in n-hexane (20-60%) as the eluent. Concentration of solvent from test tubes containing product (based on TLC) in vacuum resulted in a colourless oil.

General Procedure B) Benzylation Using Bu$_2$SnO

Ag$_2$O (0.116 g, 0.5 mmol) and BnBr (8 µL, 0.07 mmol) were added to a stirred solution of starting material (0.063 mmol) in DCM (1 mL) at room temperature in a 10 mL RBF (oven dried) under argon atmosphere. Reaction mixture was kept for stirring at room temperature for 6 h. Reaction was monitored by TLC. After complete consumption of starting material reaction mixture was diluted with DCM (30 mL) and filtered through celite pad and the filtrate was concentrated under vacuum to obtain the crude product. The crude product was purified by automated flash chromatography using EtOAc in n-hexane (0-50%) as the eluent. Concentration of solvent from test tubes containing the product (based on TLC) in vacuum resulted in the colourless oil.

Bu$_2$SnO (2.42 g, 9.73 mmol) was added to a clear solution of the diol starting material (4.6 g, 6.48 mmol) in toluene (50 mL) at room temperature under argon atmosphere equipped with a stir bar and stirring of 1400 rpm. Then the reaction mixture was kept under reflux at 130° C. for 6 h. After 6 h, solvent were removed under vacuum and the reaction was azeotropic dried with toluene (5×10 mL dry toluene). After complete removal of solvents acetal was dried under vacuum for 20 min. Acetal was removed from vacuum in presence of argon and dissolved in DMF (50 mL). To this solution BnBr (1.16 mL, 9.73 mmol) and TBAI (4.78 g, 12.96 mmol) were added and the reaction mixture was kept for stirring at 100° C. for 20 h. Reaction was monitored by TLC (40% EtOAc in n-hexane). After 20 h, reaction mixture was diluted with EtOAc (50 mL) and water (20 mL). The aqueous layer was separated and washed with EtOAc (2×30 mL). The combined organic layers were dried over Na$_2$SO$_4$ (~2 g), filtered, and the filtrate was concentrated under vacuum to obtain the crude product. The crude product was purified by column chromatography on silica gel using EtOAc in n-hexane (gradient, 0 to 30%) as the eluent. Concentration of solvent from test tubes resulted in the colourless oil (3.8 g, 73%).

General Procedure C) Protection with Lev

To a solution of the hydroxyl compound (0.195 mmol) in DCM (3 mL) in a 25 mL RBF under argon atmosphere was added levulinic acid (0.3 mmol, 30 µL), N-(3-Dimethylaminopropyl)-N'-ethylcarbodiimide hydrochloride (0.3 mmol, 58 mg) and DMAP (0.2 mmol, 24 mg). The resulting reaction mixture was stirred at room temperature for 2 h. The reaction was monitored by TLC. After complete consumption of the starting material, the reaction mixture was diluted with DCM (10 mL) and washed with brine (5 mL). The aqueous layer was extracted with DCM (2×5 mL). The organic layer was dried over Na$_2$SO$_4$ (0.2 g), filtered, and the filtrate was concentrated under vacuum to obtain the crude product. The crude product was purified by automated flash chromatography using EtOAc in n-hexane (0-50%) as the eluent. Concentration of solvent from test tubes containing the products (based on TLC) in vacuum resulted in a white oil.

General Procedure D) NAP Deprotection

To a solution of the NAP protected compound (0.048 mmol) in dichloromethane:H$_2$O (1.8:0.2 mL) in a 10 mL RBF (oven dried) under argon atmosphere was added 2.3-dichloro-5,6-dicyano-1,4-benzoquinone (14 mg, 0.058 mmol) at 0° C. The reaction mixture was stirred at room temperature for 1.5 h. Reaction was monitored by TLC. Reaction was diluted with DCM (10 mL) and extracted with NaHCO$_3$ aq. sat. solution (5 mL) and brine (5 mL). The organic layer was dried over Na$_2$SO$_4$ (0.2 g), filtered, and the filtrate was concentrated under vacuum for 15 min to obtain the crude product. The crude product was purified by automated flash chromatography using EtOAc in n-hexane (0-80%) as the eluent. Concentration of solvent from test tubes containing the products (based on TLC) in vacuum resulted in a white oil.

General Procedure E) Phosphate Coupling: Phosphoramidite Method

To a solution of 3-OH compound (0.054 mmol) in DCM (1.2 mL) in a 25 mL RBF (oven dried) under argon atmosphere was added bis(diisopropylamino)-benzyloxyphosphine (0.108 mmol) and diisopropylammonium tetrazolide (0.081 mmol) and the solution stirred at room temperature for 1.5 h. Reaction was monitored by TLC. Reaction mixture was diluted with DCM (10 mL) and quenched with NaHCO$_3$ aq. sat. solution (5 mL). The aqueous layer was extracted with DCM (2×5 mL). The combined organic layer was washed with brine (5 mL), dried over Na$_2$SO$_4$ (0.5 g), filtered, and the filtrate was concentrated under vacuum to obtain the crude product. The crude product was purified on silica gel column chromatography (column 2×10 cm) using EtOAc in n-hexane (0-30%) and 2% triethylamine as the eluent. Concentration of solvent from test tubes containing product (based on TLC) in vacuum resulted in a yellow oil. The product was transferred to a smaller RBF (10 mL) using toluene (5 mL) and evaporation of the solvent under vacuum for 20 min resulted in a white oil. The product was left in high vacuum for 10 min flushed with argon and used immediately for the next step. To a solution of the phosphoramidite (0.054 mmol) in DCM (1.2 mL) in a 10 mL RBF (oven dried) under argon atmosphere was added 5-OH compound (0.036 mmol) and tetrazole 0.45 M solution in ACN (0.24 mL, 0.108 mmol) and the solution stirred at room temperature for 2 h. Then, t-butyl peroxide 5.0-6.0 M solution in decane (0.015 mL, 0.072 mmol) was added at room temperature and the reaction mixture stirred for 1 h. Reaction mixture was diluted with DCM (10 mL) and quenched with NaHCO$_3$ aq. sat. solution (5 mL). The aqueous layer was extracted with DCM (2×5 mL). The combined organic layer was washed with brine (5 mL), dried over Na$_2$SO$_4$ (0.3 g), filtered, and the filtrate was concentrated under vacuum at 35° C. bath temperature of rotary evaporator for 15 min to obtain the crude product. The crude product was purified by automated flash chromatography using EtOAc in n-hexane (0-80%). Concentration of solvent from test tubes containing the product (based on TLC) in vacuum resulted in a colorless oil.

General Procedure F) Phosphate Coupling with Linker: Phosphoramidite Method (One Pot Procedure)

To a solution of the hydroxyl compound (0.016 mmol) in DCM (1.0 mL) in a 10 mL RBF (oven dried) under argon atmosphere was added bis(diisopropylamino)-benzyloxy-phosphine (0.032 mmol) and diisopropylammonium tetrazolide (0.024 mmol) and the solution stirred at room temperature for 1.5 h. Then, linker (0.097 mmol) and tetrazole 0.45 M solution in ACN (0.11 mL, 0.049 mmol) and the solution stirred at room temperature for 2 h. Reaction was monitored by TLC. Then, t-butyl peroxide 5.0-6.0 M solution in decane (0.006 mL, 0.032 mmol) was added at room temperature and the reaction mixture stirred for 1 h. Reaction was monitored by TLC. Reaction mixture was diluted with DCM (5 mL) and quenched with NaHCO$_3$ aq. sat. solution (3 mL). The aqueous layer was extracted with DCM (2×3 mL). The combined organic layer was washed with brine (3 mL), dried over Na$_2$SO$_4$ (0.2 g), filtered, and the filtrate was concentrated under vacuum to obtain the crude product. The crude product was purified by automated flash chromatography using EtOAc in n-hexane (0-80%). Concentration of solvent from test tubes containing the product (based on TLC) in vacuum resulted in a colorless oil.

The following linkers were employed in the synthesis:

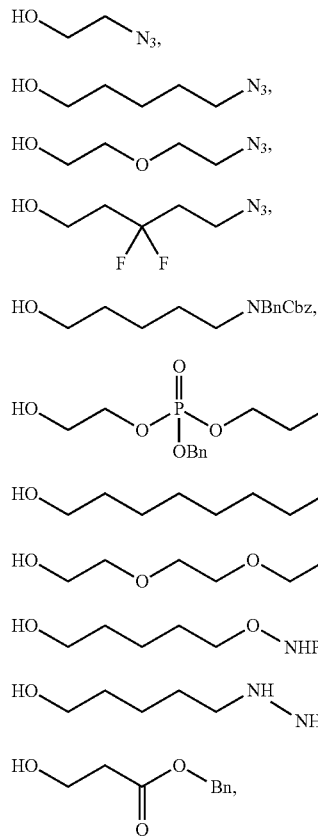

-continued

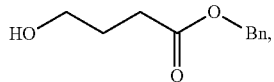
31

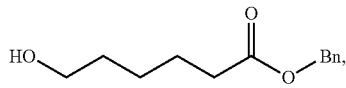
3m

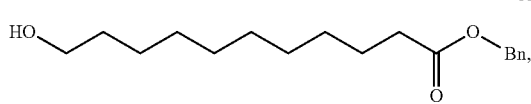
3n

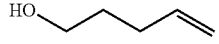
3o

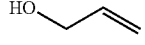
3p

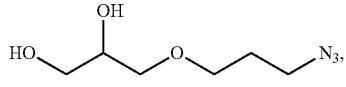
3q

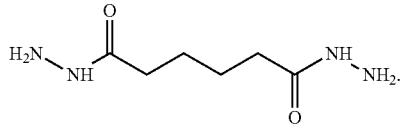
3r

General Procedure G) Lev Deprotection

To a solution of the Lev protected compound (0.060 mmol) in DCM (2 mL), a solution of hydrazine hydrate (0.267 mmol, 13 µL) dissolved in acetic acid (0.08 mL) and pyridine (0.12 mL) was added. The resulting reaction mixture was stirred at room temperature for 2 h. The reaction was quenched by the addition of acetone (0.5 mL) and the solvent removed under vacuum to obtain the crude product. The crude product was purified by automated flash chromatography using EtOAc in n-hexane (0-80%) as the eluent. Concentration of solvent from test tubes containing the products (based on TLC) in vacuum resulted in a white oil.

General Procedure H) Hydrogenation

To a solution of the protected compound (20 mg) in a EtOAc:MeOH:H$_2$O:AcOH (1.0:0.5:0.25:0.125, 1.825 mL) in a 10 mL round bottom flask equipped with a stir bar was added palladium on carbon (20 mg). Using a balloon, the solution was flushed with hydrogen for 2 minutes and stirred at room temperature under hydrogen pressure for 40 h. Reaction was filtered through PTFE filter (0.45 µM) and the flask washed using H$_2$O:MeOH solution (1:1, 5 mL). The filtrate was concentrated under vacuum to obtain the crude product. The crude product was purified on SepPak C18 ec (small) using 100% H$_2$O, H$_2$O:MeOH (1:1) and 100% MeOH as the eluent. Concentration of solvent from the vial containing the main product in lyophilizer overnight resulted in a white solid.

Example A. Glycosylation

Example A-1. Compound 4

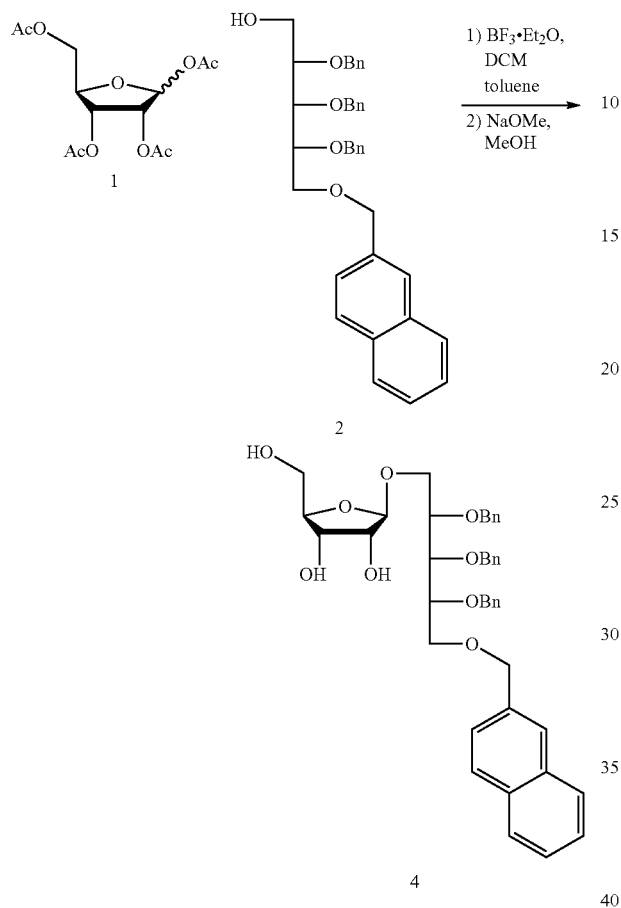

2,3,4-Tri-O-benzyl-5-O-(2-naphthalenylmethyl)-1-O-D-ribitol 2 (40 g, 71.08 mmol) was coevaporated with anhydrous toluene and dried in vacuum. A solution of 2 in anhydrous DCM (320 mL) under argon atmosphere and stirring was cooled to 0° C. and BF$_3$.Et$_2$O (19.3 mL, 156.38 mmol) added dropwise. After 5 min, a solution of 1,2,3,5-tetra-O-acetyl-β-D-ribofuranose 1 (15.08 g, 47.38 mmol) in toluene (480 mL) was added over 45 minutes. The reaction mixture was warmed to room temperature and stirred for 2 h. Reaction was monitored by TLC. Reaction mixture was quenched by addition of triethylamine (50 mL) and diluted with DCM (200 mL). The reaction mixture was washed with NaHCO$_3$ aq. sat. solution (200 mL) and the aqueous layer extracted with DCM (2×150 mL). The combined organic layers were washed with NaCl aq. sat. solution (100 mL) and dried over Na$_2$SO$_4$ (~20 g), filtered, and the filtrate was concentrated under vacuum to obtain the crude product. The crude product 4 was purified on silica gel column chromatography using EtOAc in n-hexane (20-30%) as the eluent. Concentration of solvent from test tubes containing product in vacuum resulted in the yellow oil. The product (31.05 g, 37.82 mmol) was then redissolved in methanol (70 mL) in a 250 mL RBF (oven dried) under argon atmosphere and sodium methoxide 25% wt solution in methanol (4.09 mL, 18.91 mmol) was added. The solution was stirred at room temperature for 4 h. Reaction was monitored by TLC. Reaction mixture was neutralized (pH 7) by addition of Amberlite IR-120H (500 mg), filtered and the solvent evaporated under vacuum to obtain the crude product. The crude product was purified on silica gel column chromatography using EtOAc in n-hexane (50-100%) as the eluent. Concentration of solvent from test tubes containing product 4 in vacuum resulted in the yellow oil (11.46 g, 35% over 2 steps). HRMS (ESI$^+$) Calcd for C$_{42}$H$_{46}$O$_9$Na$^+$[M+Na]$^+$ 717.3040, found 717.3057.

Example A-2. Compound 5

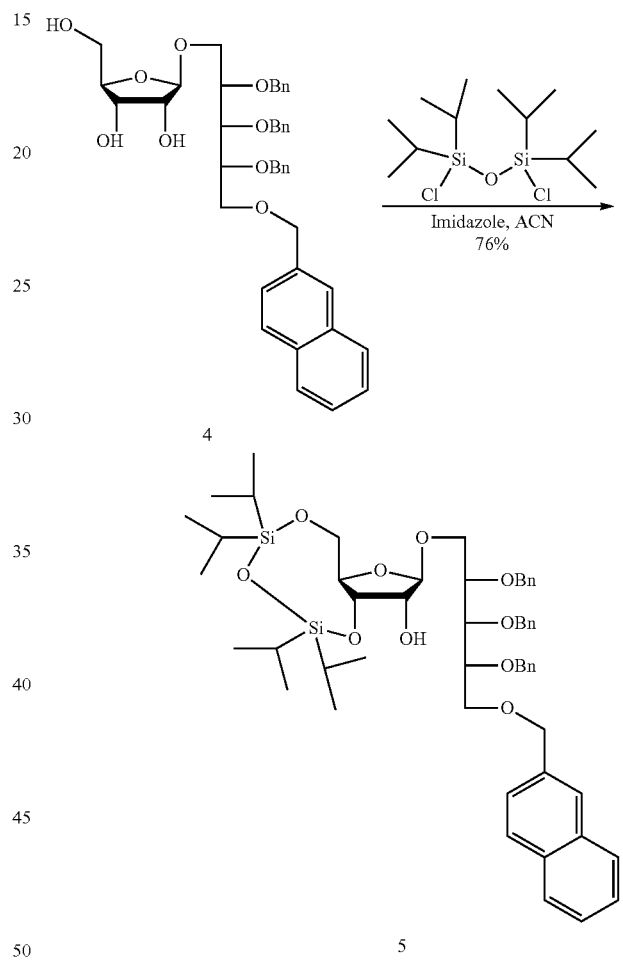

1,3-Dichloro-1,1,3,3-tetraisopropyldisiloxane (8.2 g, 11.79 mmol) was added dropwise to a solution of triol 4 (3.53 g, 11.2 mmol) and imidazole (3.05 mg, 44.8 mmol) in acetonitrile (70 mL) in a 100 mL RBF (oven dried) under argon atmosphere. Reaction was monitored by TLC. After stirring at room temperature for 10 min, reaction mixture was quenched by addition of water (10 mL) and diluted with DCM (50 mL) and water (20 mL). The aqueous layer was separated and washed with DCM (2×30 mL). The combined organic layers were dried over Na$_2$SO$_4$ (~2 g), filtered, and the filtrate was concentrated under vacuum to obtain the crude product. The crude product was purified by automated flash chromatography using EtOAc in n-hexane (0-30%) as the eluent. Concentration of solvent from test tubes containing product 5 in vacuum resulted in a colourless oil (8.4 g, 76%). HRMS (ESI+) Calcd for $C_{54}H_{72}N_2O_{10}Si_2Na^+$ [M+Na]+ 959.4562, found 959.4590.

Example B. 2'-Methoxypolyribosylribitolphosphate

Example B-1. Compound 6

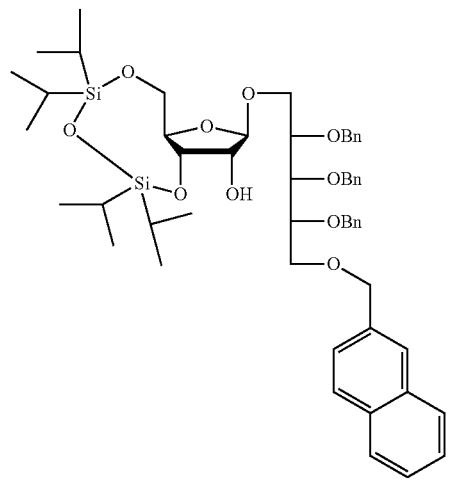

5

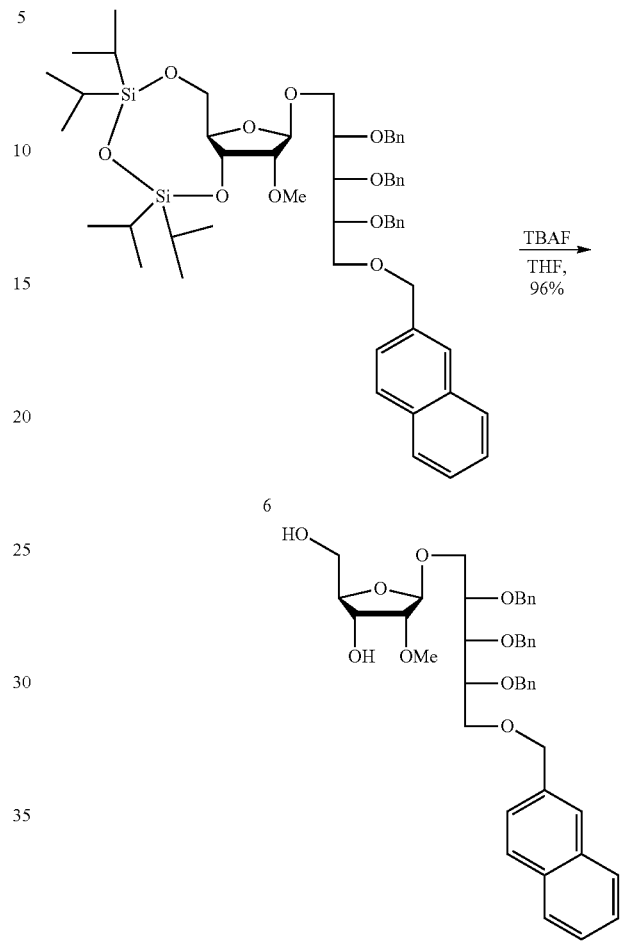

6

Ag$_2$O (6 g, 26.0 mmol) was added to a stirred solution of the alcohol 5 (3.5 g, 3.73 mmol) in MeI (6 mL) at room temperature in a 25 mL RBF (oven dried) under argon atmosphere. Reaction mixture was stirred for 2.5 days. Reaction was monitored by TLC. After complete consumption of starting material reaction mixture was diluted with DCM (50 mL) and filtered through Celite® pad and the filtrate was concentrated under vacuum to obtain the crude product. The crude product was purified on silica gel column chromatography using EtOAc in n-hexane (0-20%) as the eluent. Concentration of solvent from test tubes containing product in vacuum resulted in the colourless oil 6 (3.0 g, 85%). HRMS (ESI+) Calcd for $C_{55}H_{74}N_2O_{10}Si_2Na^+$ [M+Na]+ 973.4718, found 973.4738.

Example B-2. Compound 7

According to general procedure A) the silylated compound 6 was converted to diol product 7 (4.6 g, 96%). HRMS (ESI+) Calcd for $C_{43}H_{48}O_9Na^+$ [M+Na]+ 731.3196, found 731.3217.

Example B-3. Compound 8

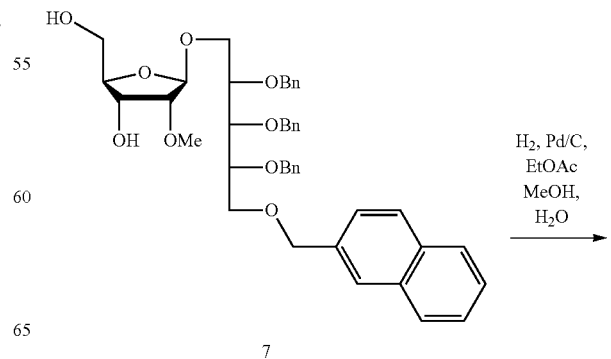

7

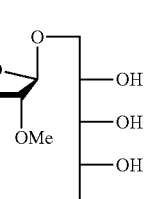

8

According to general procedure H), the monomer 7 was converted to the deprotected monomer 8 (5 mg, 67%). HRMS (ESI+) Calcd for $C_{11}H_{22}O_9Na^+$ [M+Na]+ 321.1162, found 321.1187.

Example B-4. Compound 9

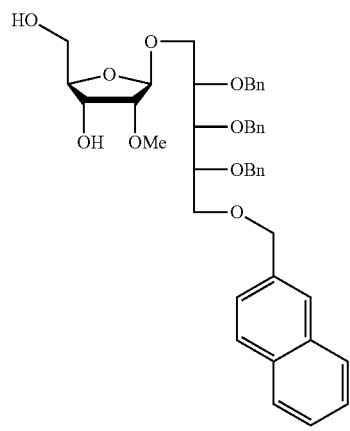

7

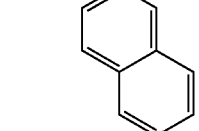

9

Benzyl bromide (77 mg, 0.45 mmol) and sodium hydride (16 mg, 0.672 mmol) were added to a stirred solution of the diol 7 (80 mg, 0.112 mmol) in THF:DMF (1.5:0.2, 1.7 mL) solution under argon atmosphere at 0° C. The reaction was warmed to room temperature and stirred overnight. The reaction mixture was quenched with ice cold water (1 mL) and extracted with EtOAc (3×10 mL). The combined organic layers were dried over $Na_2SO_4$ (~0.5 g), filtered, and the filtrate was concentrated under vacuum to obtain the crude product. The crude product was purified by flash chromatography using EtOAc in n-hexane (0-50%) as the eluent. Concentration of solvent from test tubes containing product 9 in vacuum resulted in a colourless oil (75 mg, 75%). HRMS (ESI+) Calcd for $C_{57}H_{60}O_9Na^+$ [M+Na]+ 911.4135, found 911.4162.

Example B-5. Compound 10

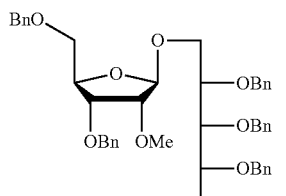

9

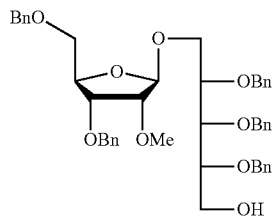

10

According to general procedure D), the NAP protected intermediate 9 was converted to the 5-hydroxyl compound 10 (189 mg, 89%). HRMS (ESI+) Calcd for $C_{46}H_{52}O_9Na^+$ [M+Na]+ 771.3509, found 771.3521.

Example B-6. Compound 11

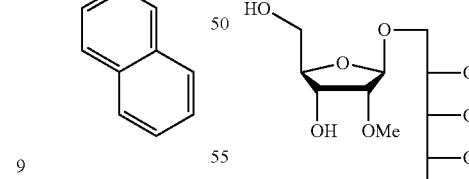

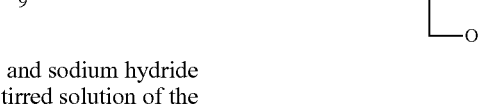

7

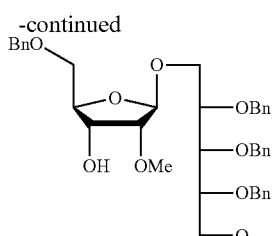

According to general procedure B) the diol 7 was converted to the benzylated product 11 (3.8 g, 73%). HRMS (ESI$^+$) Calcd for $C_{50}H_{54}O_9Na^+$[M+Na]$^+$ 821.3666, found 821.3672.

Example B-7. Compound 12

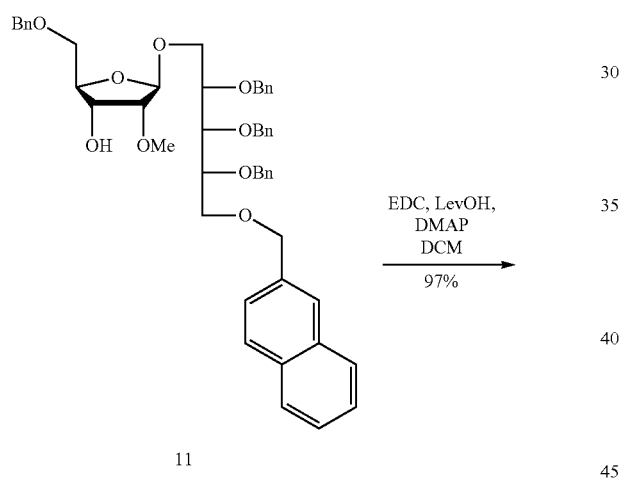

12

According to general procedure C), the 3-hydroxyl intermediate 11 was converted to the Lev protected compound 12 (1.75 g, 97%). HRMS (ESI$^+$) Calcd for $C_{55}H_{60}O_{11}Na^+$[M+Na]$^+$ 919.4033, found 919.4062.

Example B-8. Compound 13

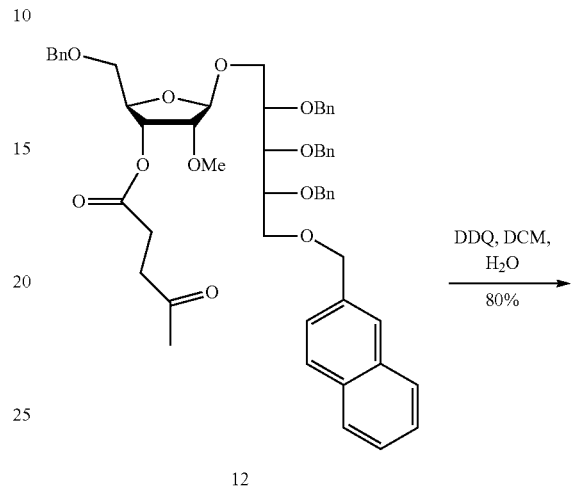

13

According to general procedure D), the NAP protected intermediate 12 was converted to the 5-hydroxyl compound 13 (1.23 g, 80%). HRMS (ESI$^+$) Calcd for $C_{44}H_{52}O_{11}Na^+$ [M+Na]$^+$ 779.3407, found 779.3431.

Example B-9. Compound 15

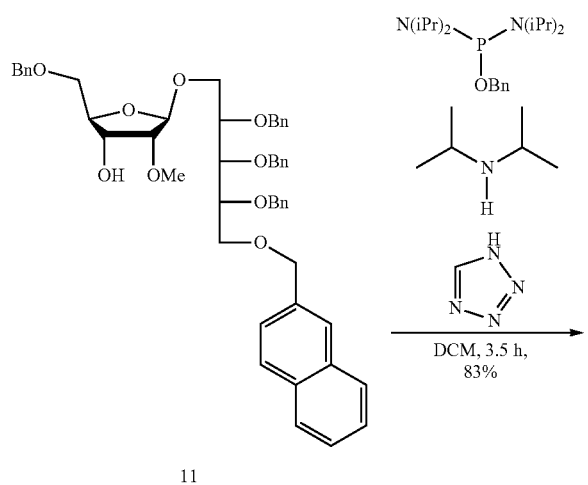

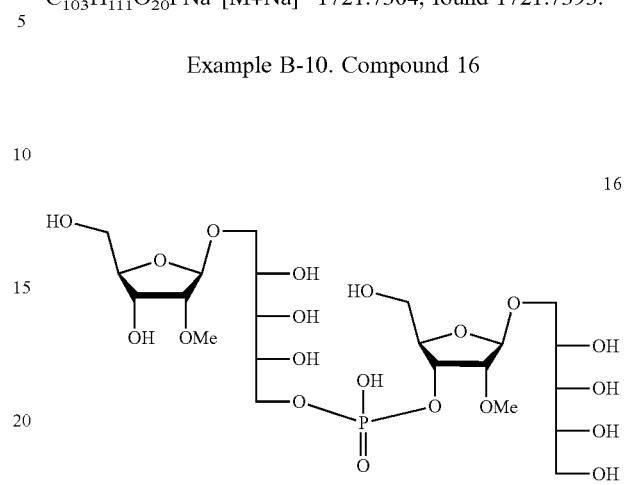

According to general procedure E), the 3-hydroxyl compound 11 and the 5-hydroxyl compound 10 were converted to dimer 15 (60 mg, 95%). HRMS (ESI$^+$) Calcd for $C_{103}H_{111}O_{20}PNa^+$ [M+Na]$^+$ 1721.7304, found 1721.7393.

Example B-10. Compound 16

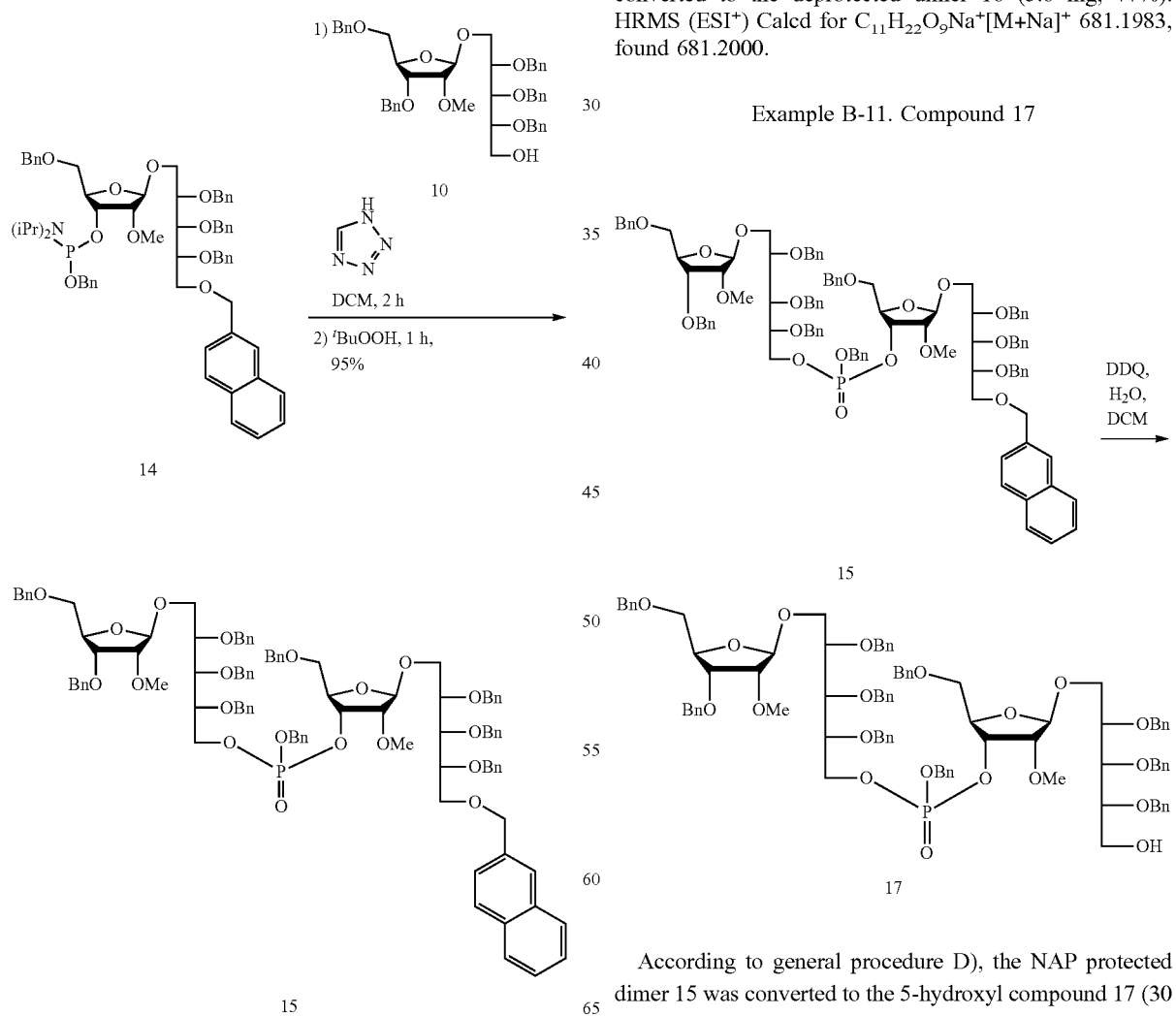

According to general procedure H), the dimer 15 was converted to the deprotected dimer 16 (5.6 mg, 77%). HRMS (ESI$^+$) Calcd for $C_{11}H_{22}O_9Na^+$ [M+Na]$^+$ 681.1983, found 681.2000.

Example B-11. Compound 17

According to general procedure D), the NAP protected dimer 15 was converted to the 5-hydroxyl compound 17 (30 mg, 60%). HRMS (ESI$^+$) Calcd for $C_{92}H_{103}O_{20}Na^+$ [M+Na]$^+$ 1581.6678, found 1581.6734.

Example B-12. Compound 18

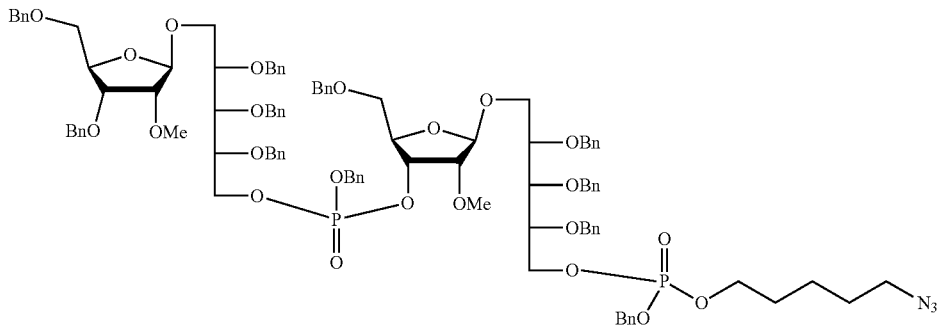

According to general procedure E), the dimer 17 was coupled to the linker 5-azido-pentanol to give dimer 18 (6 mg, 42%). HRMS (ESI$^+$) Calcd for $C_{104}H_{119}N_3O_{23}P_2Na^+$ [M+Na]$^+$ 1863.7641, found 1863.7709.

Example B-13. Compound 19

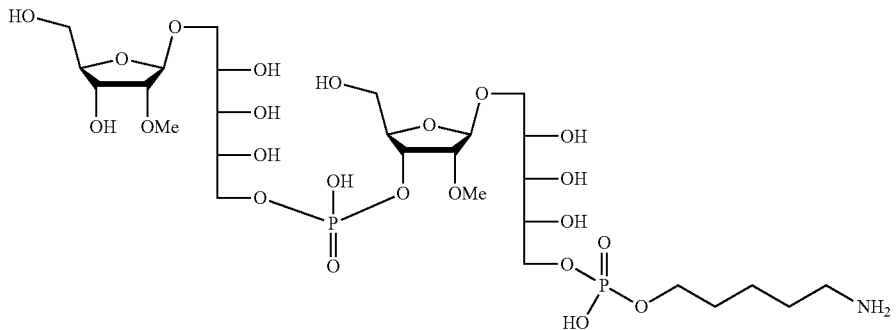

According to general procedure H), the dimer 18 was converted to the deprotected dimer 19 (1.2 mg, 55%). HRMS (ESI$^+$) Calcd for $C_{27}H_{50}O_{23}P_2Na^+$[M+Na]$^+$ 846.2538, found 846.2540.

Example B-14. Compound 20

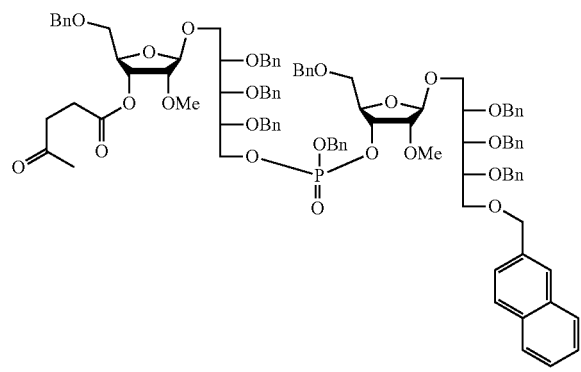

According to general procedure E), the 3-hydroxyl compound 11 and the 5-hydroxyl compound 13 were converted to dimer 20 (1.5 g, 76%). HRMS (ESI$^+$) Calcd for $C_{101}H_{111}O_{22}PNa^+$[M+Na]$^+$ 1729.7202, found 1729.7240.

Example B-15. Compound 21

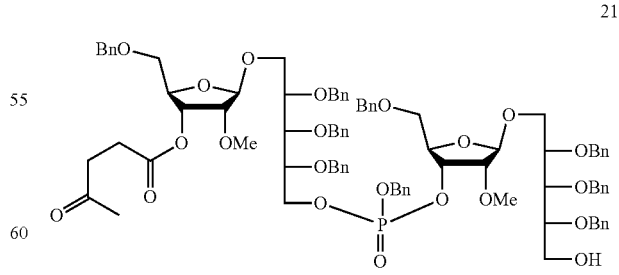

According to general procedure D), the NAP protected intermediate 20 was converted to the 5-hydroxyl compound 21 (386 mg, 63%). HRMS (ESI$^+$) Calcd for $C_{90}H_{103}O_{22}PNa^+$[M+Na]$^+$ 1589.6576, found 1589.6613.

Example B-16. Compound 22
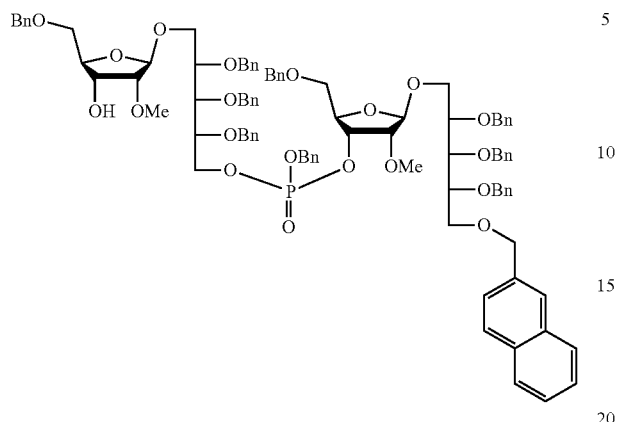
According to general procedure G), the dimer 20 was converted to 3-hydroxyl dimer 22 (473 mg, 74%). HRMS (ESI$^+$) Calcd for $C_{96}H_{105}O_{20}PNa^+[M+Na]^+$ 1631.6835, found 1631.6873.
Example B-17. Compound 23
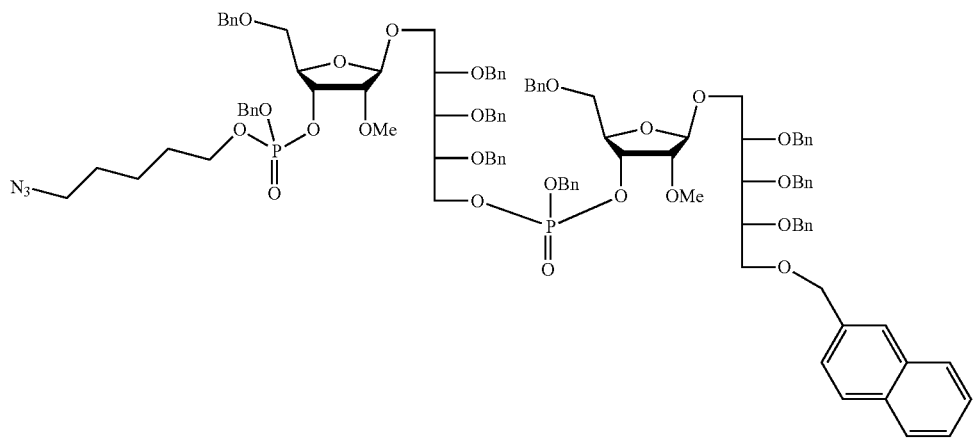
According to general procedure E), the 3-hydroxyl dimer 22 was coupled to the linker 5-azido-pentanol to give dimer 23 (3 mg, 30%). HRMS (ESI$^+$) Calcd for $C_{108}H_{121}N_3O_{23}P_2Na^+[M+Na]^+$ 1912.7764, found 1912.7781.
Example B-18. Compound 24
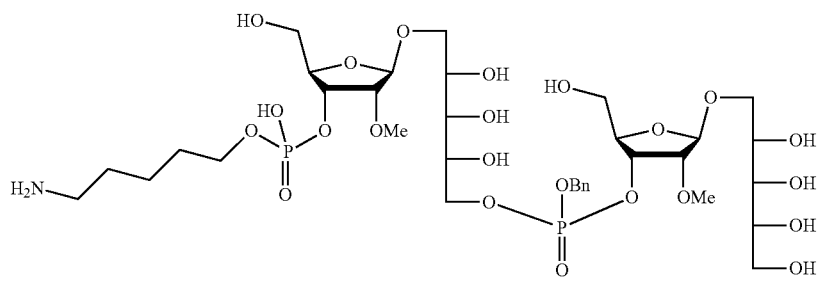

According to general procedure H), the dimer 23 was converted to the deprotected dimer 24 (1.1 mg, 76%). HRMS (ESI+) Calcd for $C_{27}H_{50}O_{23}P_2Na^+$ [M+Na]+ 846.2538, found 846.2540.

Example B-19. Compound 25

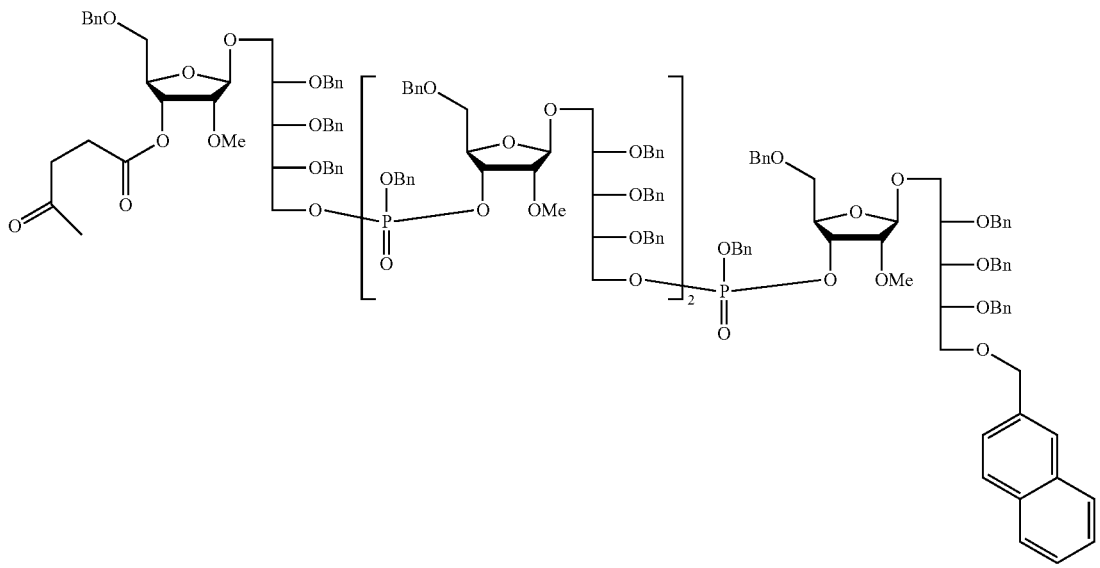

According to general procedure E), the 3-hydroxyl dimer 22 and the 5-hydroxyl dimer 21 were converted to tetramer 25 (367 mg, 86%). HRMS (ESI+) Calcd for $C_{193}H_{213}O_{44}P_3Na^+$ [M+Na]+ 3350.3540, found 3350.3531.

Example B-20. Compound 26

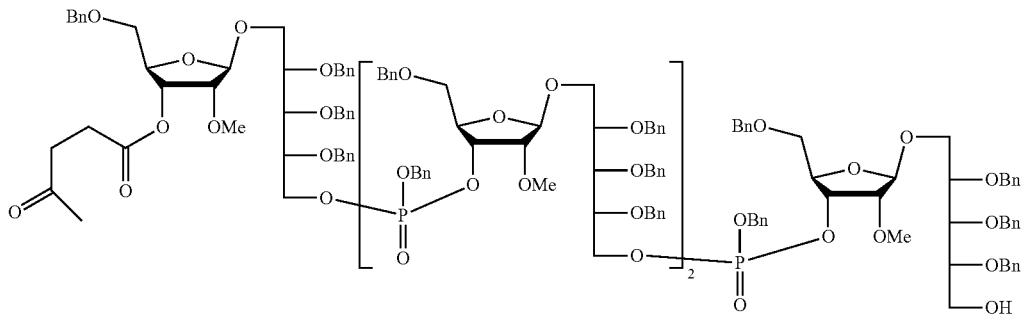

According to general procedure D), the NAP protected tetramer 25 was converted to the 5-hydroxyl tetramer 26 (125 mg, 75%). HRMS (ESI+) Calcd for $C_{182}H_{205}O_{44}P_3Na^+$ [M+Na]+ 3210.2914, found 3210.2911.

Example B-21. Compound 27
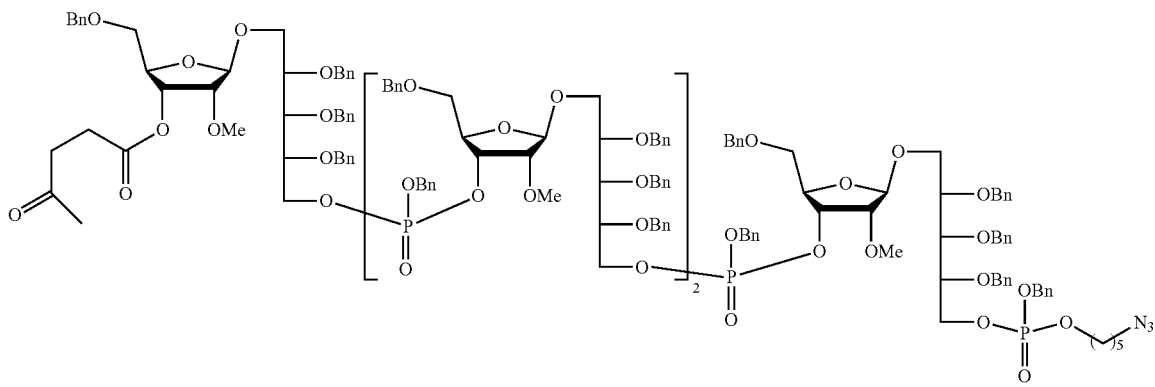
According to general procedure E), the tetramer 26 was coupled to the linker 5-azido-pentanol to give tetramer 27 (35 mg, 77%). HRMS (ESI$^+$) Calcd for $C_{194}H_{221}N_3O_{47}P_4Na^+$ [M+Na]$^+$ 3491.3844, found 3492.3787.
Example B-22. Compound 28
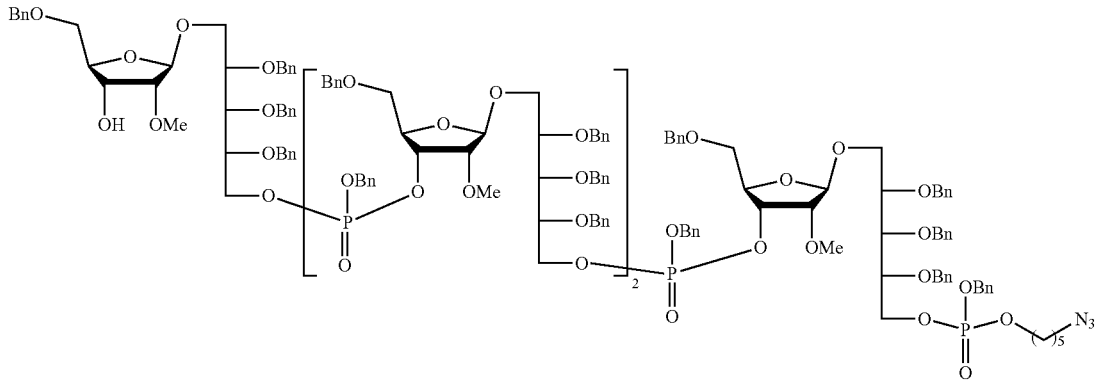
According to general procedure G), the tetramer 27 was converted to 3-hydroxyl tetramer 28 (30 mg, 90%). HRMS (ESI$^+$) Calcd for $C_{189}H_{215}N_3O_{45}P_4Na^+$ [M+Na]$^+$ 3393.3476, found 3393.3543.
Example B-23. Compound 29
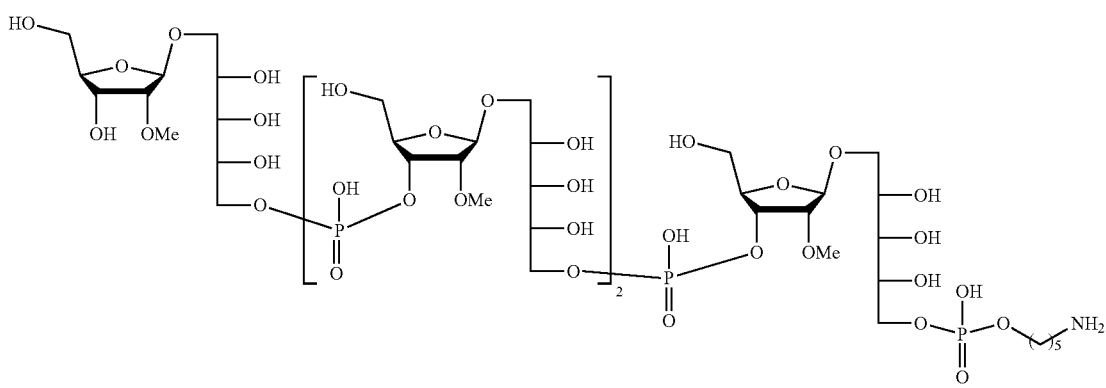

According to general procedure H), the tetramer 28 was converted to the deprotected tetramer 29 (10 mg, 73%). HRMS (ESI$^+$) Calcd for $C_{49}H_{97}NO_{45}P_4Na^+[M+Na]^+$ 1566.4181, found 1566.4174.

Example B-24. Compound 30

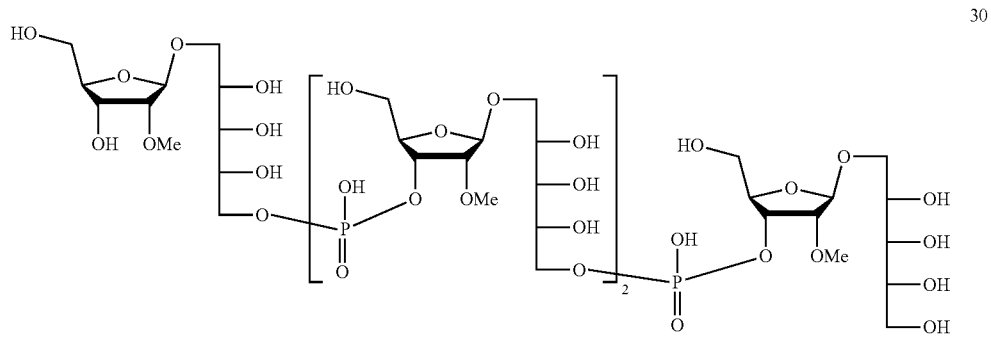

Tetramer 30 is prepared in two steps from tetramer 26 according to general procedure G) and general procedure H).

Example B-25. Compound 31

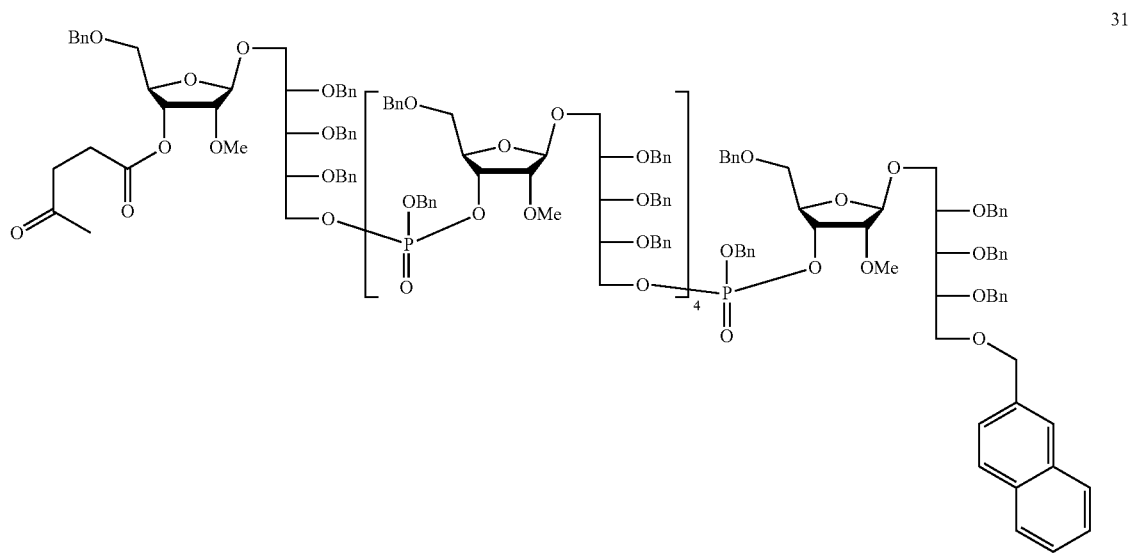

According to general procedure E), the 3-hydroxyl dimer 22 and the 5-hydroxyl tetramer 26 were converted to hexamer 31 (85 mg, 85%). HRMS (ESI$^+$) Calcd for $C_{285}H_{315}O_{66}P_5Na^+[M/2+Na]^+$ 2496.9888, found 2496.0271.

Example B-26. Compound 32

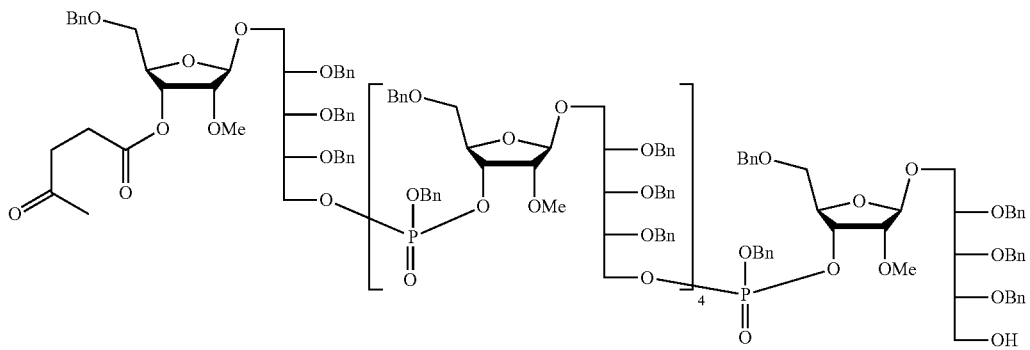

32

According to general procedure D), the NAP protected hexamer 31 was converted to the 5-hydroxyl hexamer 32 (50 mg, 65%). HRMS (ESI$^+$) Calcd for $C_{274}H_{307}O_{66}P_5Na^+$[M/2+Na]$^+$2426.9677, found 2426.9977.

Example B-27. Compound 33

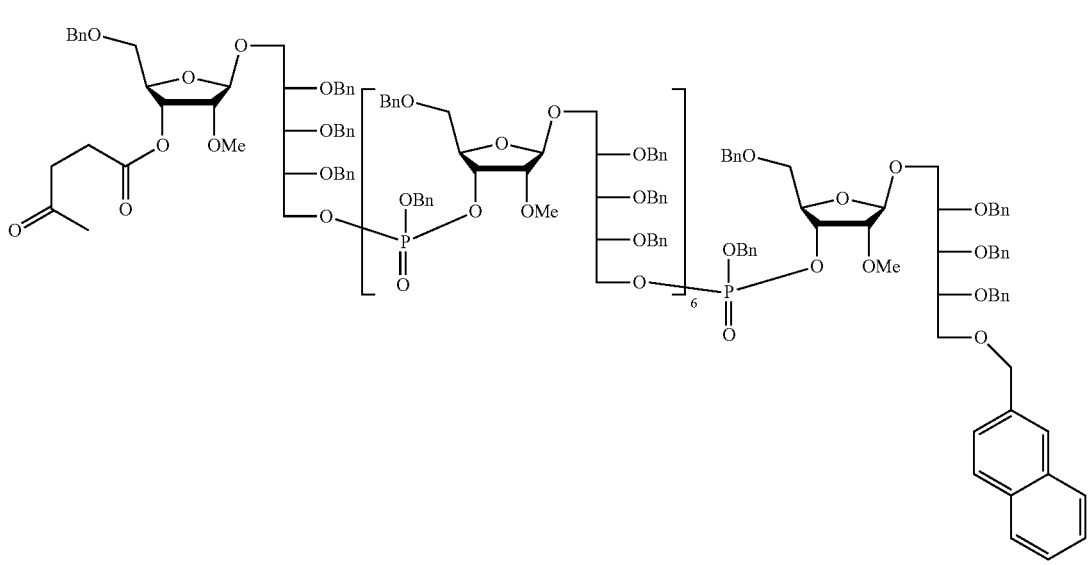

33

According to general procedure E), the 3-hydroxyl dimer 22 and the 5-hydroxyl hexamer 32 were converted to octamer 33 (50 mg, 77%). $^1$H NMR (400 MHz, Chloroform-d) δ 7.86-7.62 (m, 4H), 7.51-7.35 (m, 3H), 7.37-7.06 (m, 195H), 5.10 (t, J=5.5 Hz, 1H), 5.03 (dt, J=7.6, 4.2 Hz, 7H), 4.97-4.77 (m, 22H), 4.69-4.37 (m, 60H), 4.36-4.14 (m, 23H), 3.98-3.55 (m, 47H), 3.53-3.36 (m, 13H), 3.34-3.21 (m, 24H), 2.72 (t, J=6.5 Hz, 2H), 2.65-2.54 (m, 2H), 2.16 (s, 3H).

Example B-28. Compound 34

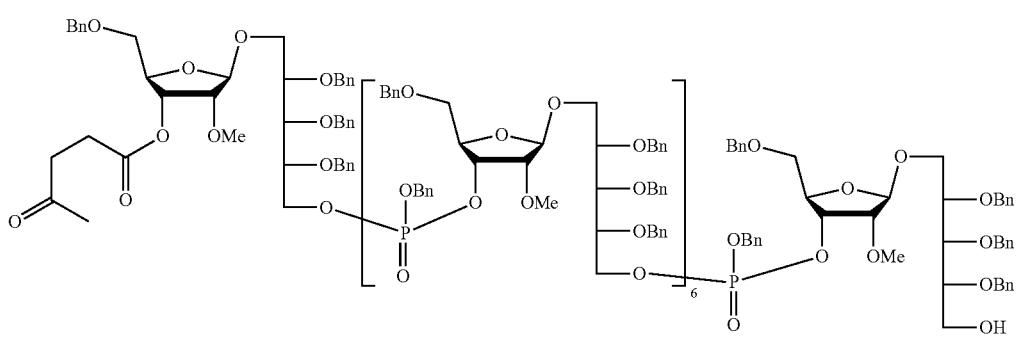

According to general procedure D), the NAP protected octamer 33 was converted to the 5-hydroxyl octamer 34 (35 mg, 73%). $^1$H NMR (400 MHz, Chloroform-d) δ 7.43-7.07 (m, 195H), 5.10 (t, J=5.4 Hz, 1H), 5.08-4.78 (m, 29H), 4.70-4.45 (m, 51H), 4.45-4.15 (m, 38H), 3.95-3.54 (m, 50H), 3.54-3.36 (m, 16H), 3.36-3.25 (m, 24H), 2.72 (t, J=6.5 Hz, 2H), 2.65-2.56 (m, 2H), 2.16 (s, 3H).

Example B-29. Compound 35—Phosphonate Chemistry

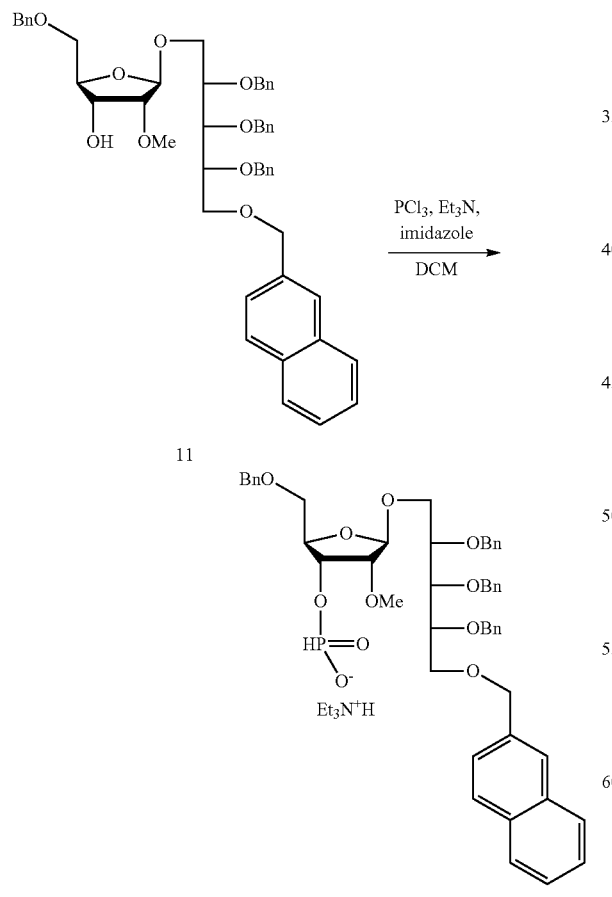

To a solution of 3-hydroxyl compound 11 (10 mg) and imidazole (5.96 mg, 0.087 mmol) in DCM (2 mL) in a 10 mL RBF (oven dried) under argon atmosphere was added PCl$_3$ (4.37 μL, 0.050 mmol) and triethylamine (12.28 μL, 0.087 mmol) at 0° C. After 5 min, the reaction mixture was warmed to room temperature and stirred for 1 h. Reaction was monitored by TLC. The reaction was diluted with DCM (5 mL), quenched by the addition of NaHCO$_3$ aq. sat. solution (5 mL) and triethylammonium buffer solution (5 mL). The aqueous layer was extracted with DCM (2×10 mL), the combined organic layers were washed with brine (5 mL). The organic layer was dried over Na$_2$SO$_4$ (0.25 g), filtered, and the filtrate was concentrated under vacuum to obtain the crude product. The crude product was purified on silica gel column chromatography using 10% MeOH in DCM as the eluent. Concentration of solvent from test tubes containing product 35 (based on TLC) in vacuum resulted in the yellow oil (10 mg, 83%). HRMS (ESI$^+$) Calcd for C$_{56}$H$_{71}$NO$_{11}$SP$^+$[M+H]$^+$ 964.4765, found 964.4759.

Example B-30. Compound 36

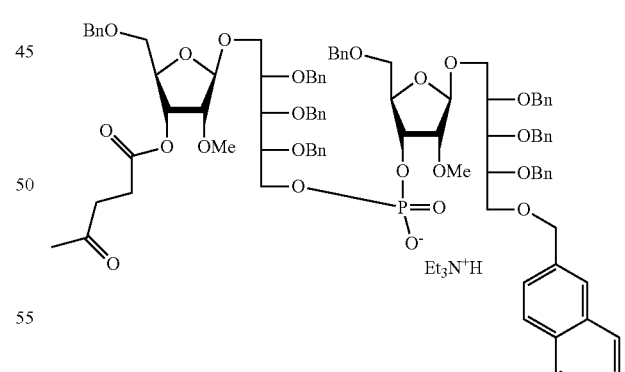

H-phosphonate 35 (10 mg, 0.010 mmol) and compound 13 (7.85 mg, 0.010 mmol) were dissolved in 1n pyridine (1 mL). Trimethylacetyl chloride (3.83 μL, 0.031 mmol) was then slowly added. The reaction mixture was stirred for 1 h at room temperature. A solution of iodine (2.6 mg, 0.010 mmol) in pyridine-water (96:4, v/v; 67 μL) was added and the reaction was further stirred for 30 min at room temperature. The reaction mixture was diluted with CH$_2$Cl$_2$ (5 mL), washed with aq. sat. Na$_2$S$_2$O$_3$ (5 mL) and then with 1.0 M TEAB solution (5 mL). The combined organic layers were dried over Na$_2$SO$_4$ filtered, and concentrated in vacuum. The residue was purified by flash chromatography (DCM/MeOH, 10:1, v/v) to yield 36 (5.5 g, 29%) as colorless oil. HRMS (ESI$^+$) Calcd for C$_{94}$H$_{104}$O$_{22}$P$^+$[M]$^-$ 1615.6762, found 1615.7056.

Example C. 2'-Deoxypolyribosylribitolphosphate

Example C-1. Compound 37

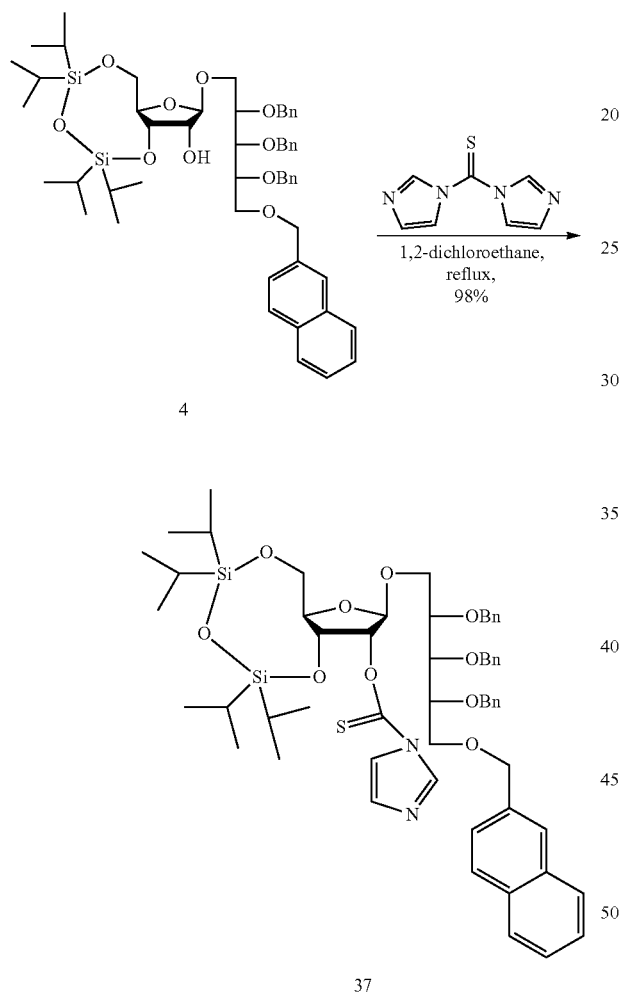

Example C-2. Compound 38

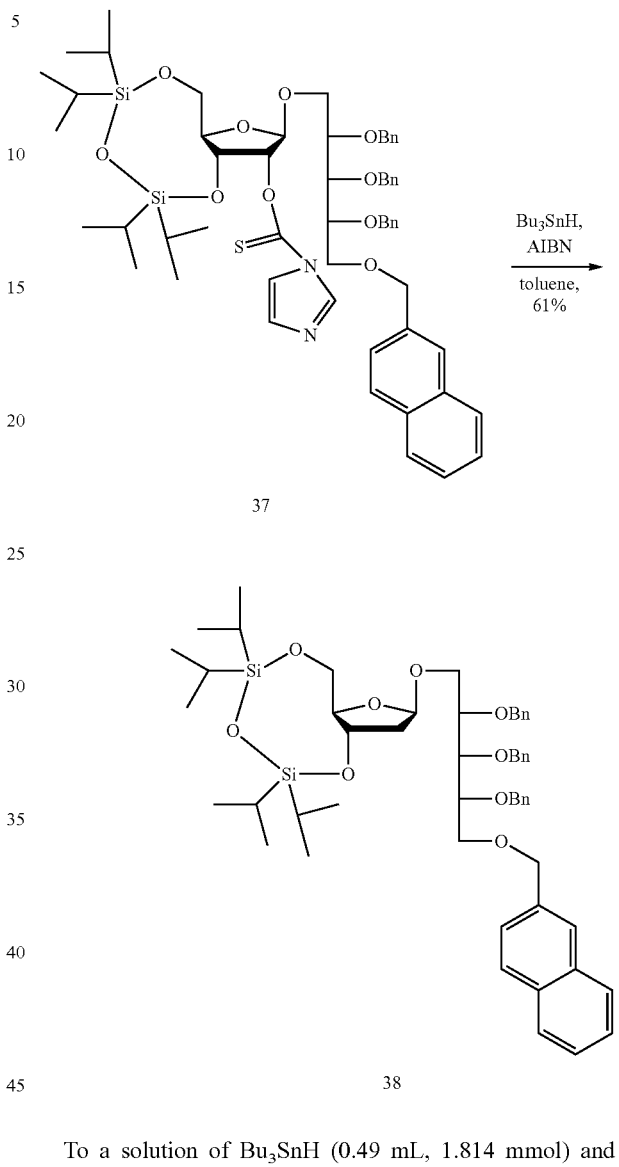

To a solution of the alcohol 4 (860 mg, 0.92 mmol) in 1,2-dichloroethane (5 mL) in a 25 mL RBF (oven dried) under argon atmosphere was added thiocarbonyldiimidazole (327 mg, 1.83 mmol). The solution was stirred at 60° C. for 64 h. Reaction was monitored by TLC. The solvent was evaporated under vacuum to obtain the crude product. The crude product was purified by flash column chromatography using EtOAc in n-hexane (0-30%) as the eluent. Concentration of solvent from test tubes containing the product 37 (based on TLC) in vacuum resulted in a white oil (950 mg, 98%). HRMS (ESI$^+$) Calcd for C$_{58}$H$_{74}$N$_2$O$_{10}$SSi$_2$Na$^+$[M+Na]$^+$1069.4500, found 1069.4525.

To a solution of Bu$_3$SnH (0.49 mL, 1.814 mmol) and AIBN (0.2 M in toluene, 0.46 mL, 0.091 mmol) in toluene (20 mL) in a 100 mL RBF (oven dried) under argon atmosphere at 60° C. was added dropwise a solution of the thiocarbamate 37 (950 mg, 0.907 mmol) in toluene (20 mL). The reaction mixture was stirred for 2 h. Reaction was monitored by TLC. Reaction mixture was diluted was quenched with NaHCO$_3$ aq. sat. solution (10 mL). The aqueous layer was extracted with ethyl acetate (2×20 mL). The combined organic layer was washed with brine (10 mL), dried over Na$_2$SO$_4$ (0.5 g), filtered, and the filtrate was concentrated under vacuum to obtain the crude product. The crude product was purified by automated flash chromatography using EtOAc in n-hexane (0-50%). Concentration of solvent from test tubes containing the product 38 (based on TLC) in vacuum resulted in a colorless oil (510 mg, 61%). HRMS (ESI$^+$) Calcd for C$_{58}$H$_{72}$O$_9$Si$_2$Na$^+$[M+Na]$^+$ 943.4613, found 943.4640.

Example C-2. Compound 39

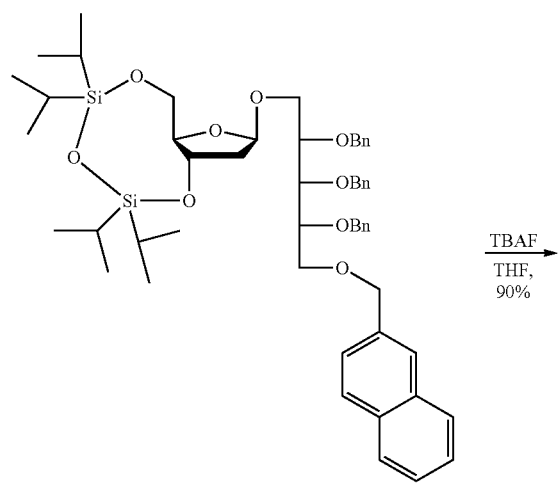

38

According to general procedure A) the silylated compound 38 was converted to diol product 39 (330 mg, 90%). HRMS (ESI$^+$) Calcd for $C_{42}H_{46}O_8Na^+$[M+Na]$^+$701.3090, found 701.3117.

Example C-3. Compound 40

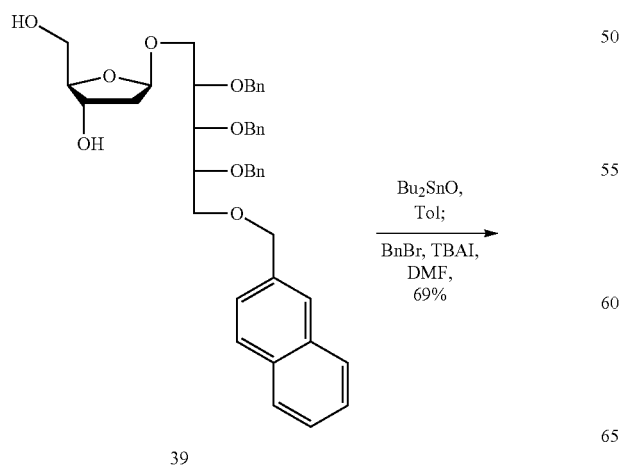

39

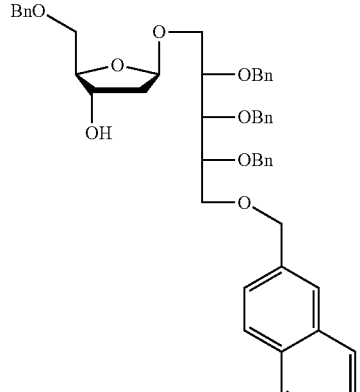

40

According to general procedure B) the diol 39 was converted to the benzylated product 40 (260 mg, 69%). HRMS (ESI$^+$) Calcd for $C_{49}H_{52}O_8Na^+$[M+Na]$^+$791.3560, found 791.3565.

Example C-4. Compound 41

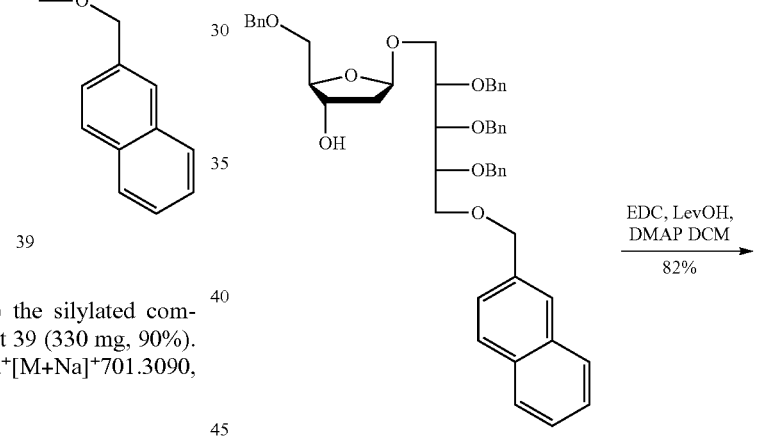

41

According to general procedure C), the 3-hydroxyl intermediate 40 was converted to the Lev protected compound 41

(135 mg, 82%). HRMS (ESI$^+$) Calcd for $C_{54}H_{58}O_{10}Na^+$[M+Na]$^+$889.3928, found 889.3928.

Example C-5. Compound 42

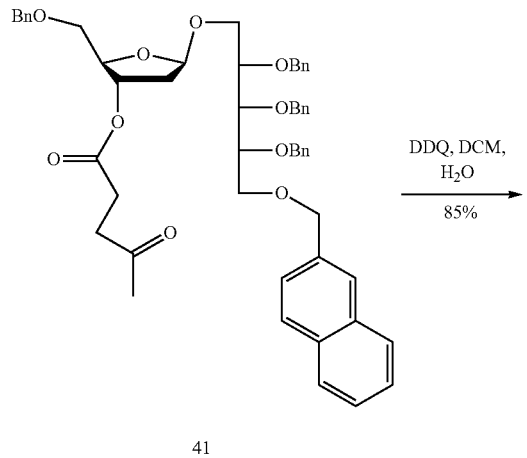

41

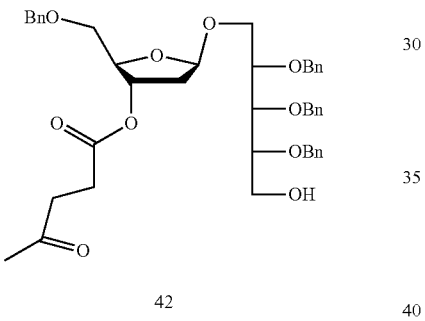

42

According to general procedure D), the NAP protected intermediate 41 was converted to the 5-hydroxyl compound 42 (95 mg, 85%). HRMS (ESI$^+$) Calcd for $C_{43}H_{50}O_{10}Na^+$ [M+Na]$^+$749.3302, found 749.3325.

Example C-6. Compound 44

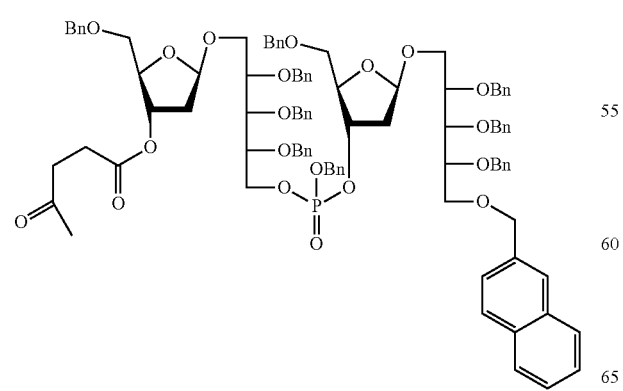

44

According to general procedure E), the 3-hydroxyl compound 40 and the 5-hydroxyl compound 42 were converted to dimer 44 (160 mg, 78%). HRMS (ESI$^+$) Calcd for $C_{99}H_{107}O_{20}PNa^+$[M+Na]$^+$1669.6991, found 1669.6981.

Example C-7. Compound 45

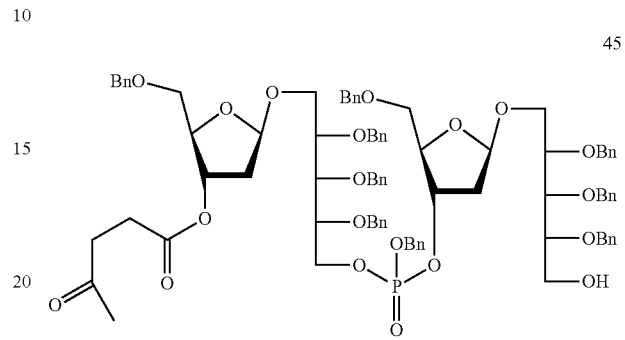

45

According to general procedure D), the dimer 44 was converted to 5-hydroxyl dimer 45 (53 mg, 73%). HRMS (ESI$^+$) Calcd for $C_{99}H_{107}O_{20}PNa^+$[M+Na]$^+$1529.6365, found 1529.6397.

Example C-8. Compound 46

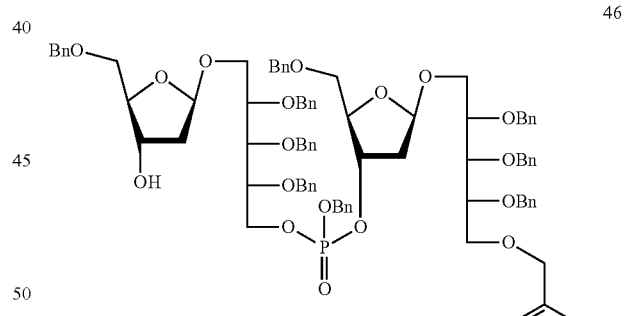

46

According to general procedure G), the dimer 44 was converted to 3-hydroxyl dimer 46 (85 mg, 91%). HRMS (ESI$^+$) Calcd for $C_{94}H_{101}O_{18}PNa^+$[M+Na]$^+$1571.6623, found 1571.6656.

Example C-9. Compound 49
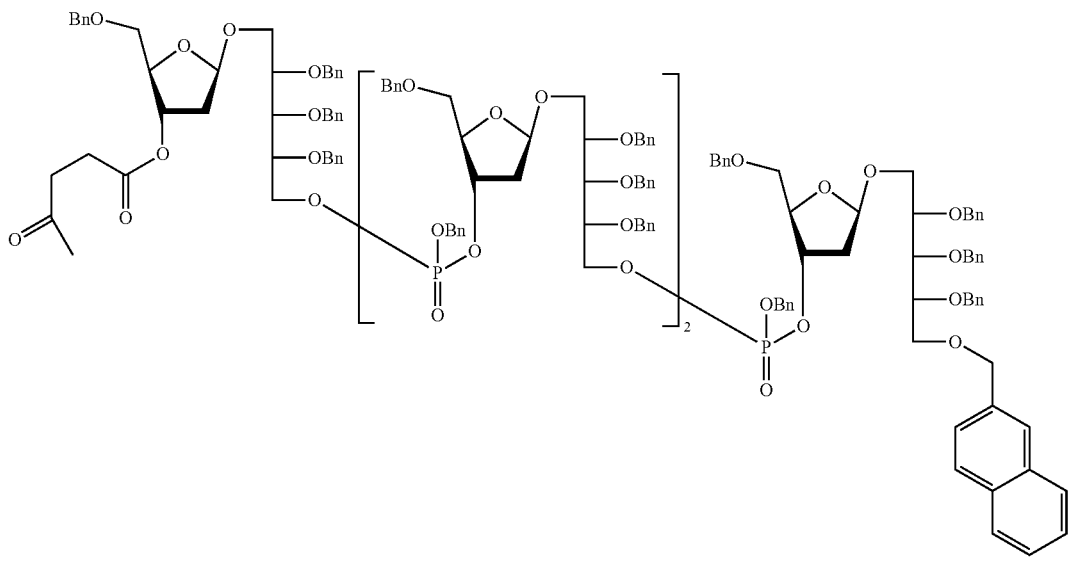
According to general procedure E), the 3-hydroxyl dimer 46 and the 5-hydroxyl dimer 45 were converted to tetramer 49 (96 mg, 83%). HRMS (ESI$^+$) Calcd for $C_{189}H_{205}O_{40}P_3Na^+$ [M+Na]$^+$ 3230.3118, found 3230.3111.
Example C-10. Compound 50
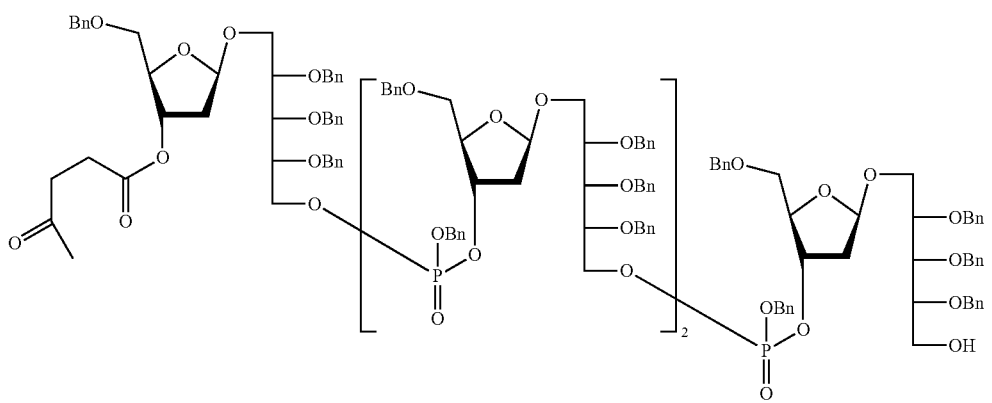
According to general procedure D), the NAP protected tetramer 49 was converted to the 5-hydroxyl tetramer 50 (50 mg, 56%). HRMS (ESI$^+$) Calcd for $C_{178}H_{197}O_{40}P_3Na^+$ [M+Na]$^+$ 3090.2492, found 3090.2405.

Example C-11. Compound 51
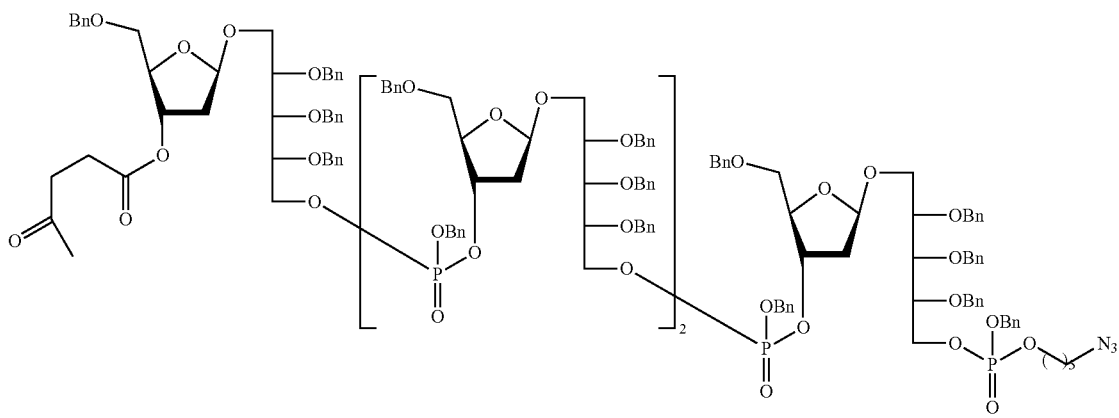
51
According to general procedure E), the tetramer 50 was coupled to the linker 5-azido-pentanol to give tetramer 51 (41 mg, 76%). HRMS (ESI$^+$) Calcd for $C_{190}H_{213}N_3O_{43}P_4Na^+[M+Na]^+$ 3371.3421, found 3371.3321.
Example C-12. Compound 52
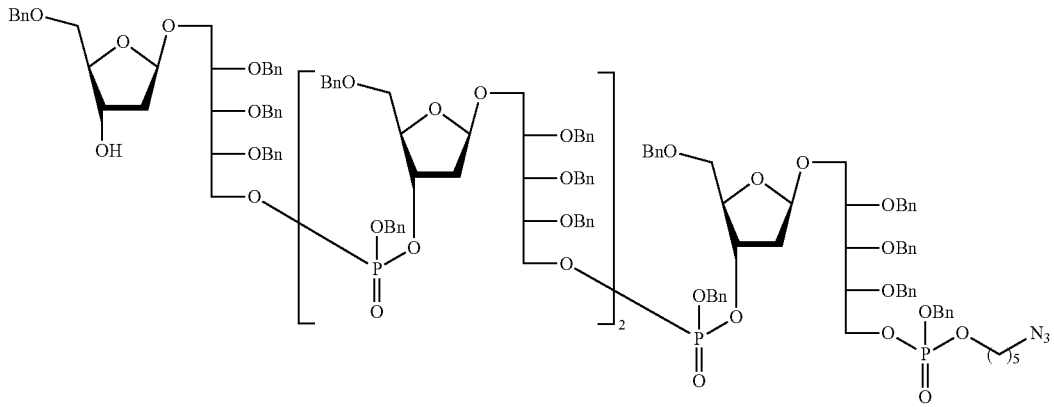
52
According to general procedure G), the tetramer 51 was converted to 3-hydroxyl tetramer 52 (36 mg, 92%). HRMS (ESI$^+$) Calcd for $C_{185}H_{207}N_3O_{41}P_4Na^+[M+Na]^+$ 3273.3053, found 3273.3079.
Example C-13. Compound 53
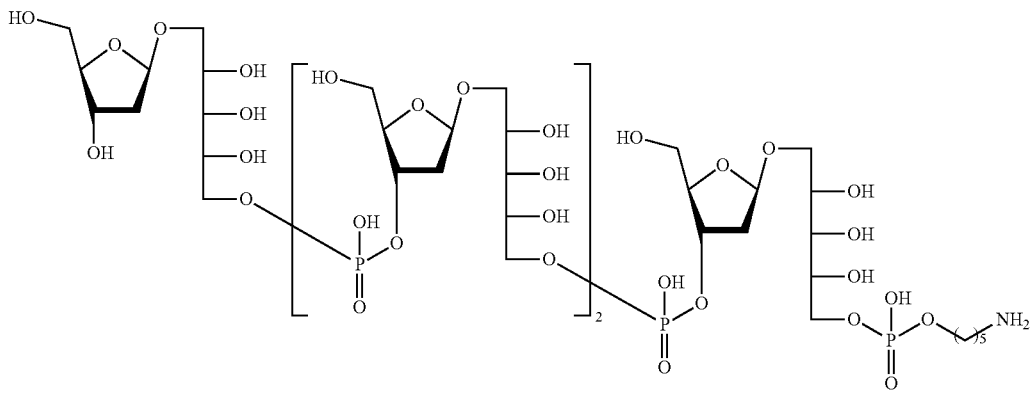
53

According to general procedure H), the tetramer 52 was converted to the deprotected tetramer 53 (6 mg, 70%). HRMS (ESI⁺) Calcd for $C_{45}H_{89}NO_{41}H_4Na^+[M+Na/2]^+$ 723.1879, found 723.1996.

Example D. 2'-N,N,-Dimethylaminocarbonylpolyribosylribitolphosphate

Example D-1. Compound 54

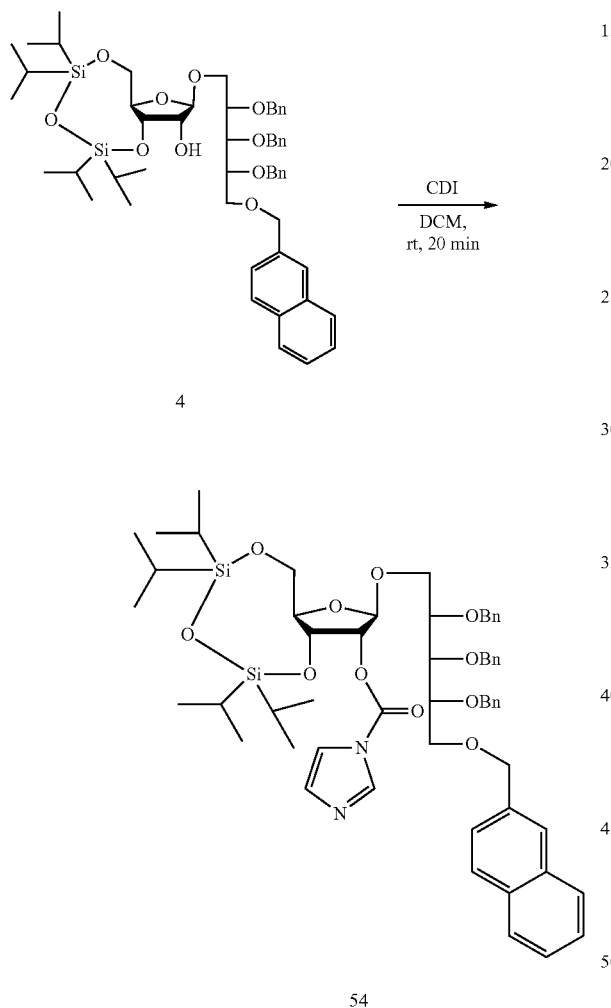

54

To a solution of alcohol 4 (2.153 g, 2.299 mmol) in DCM (10 mL) at room temperature under argon atmosphere was added 1,1'-carbonyldiimidazole (145 mg, 4.598 mmol). The reaction mixture was stirred for 20 min (when CDI was completely dissolved) and monitored by TLC until complete consumption of the starting material. The solvent was evaporated in vacuum to give the crude product. The crude product was purified by automated flash chromatography using EtOAc in n-hexane (0-100%) as the eluent. Concentration of solvent from test tubes containing the product 54 (based on TLC) in vacuum resulted in the colourless oil (2.35 g, 99%). HRMS (ESI⁺) Calcd for $C_{58}H_{75}N_2O_{11}Si_2^+$ [M+H]⁺ 1031.4909, found 1031.4936.

Example D-2. Compound 55

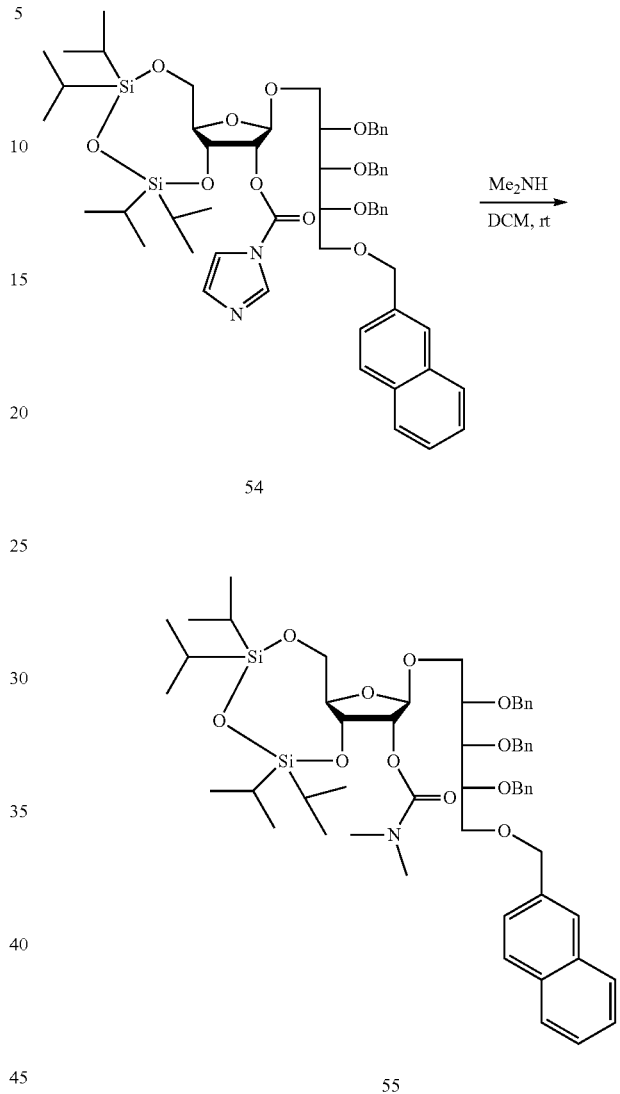

55

Monomer 54 (2.396 g, 2.32 mmol) was dissolved in ACN (20 mL) at room temperature under argon atmosphere and Me₂NH was added (1.89 g, 23.2 mmol). The reaction mixture was stirring at room temperature for 65 h and monitored by TLC. The solution was filtered off through a pad of celite and washed with DCM (50 mL). The solvent was evaporated in vacuum. The resulting solid was solubilized in DCM (100 mL) and the organic solution was washed with brine (100 mL) and dried with Na₂SO₄ (~2 g). The organic solvent was evaporated in vacuum to give to crude product. The crude product was purified by automated flash chromatography using EtOAc in n-hexane (0-100%) as the eluent. Concentration of solvent from test tubes containing the product 55 (based on TLC) in vacuum resulted in the colourless oil (2 g, 85%). HRMS (ESI⁺) Calcd for $C_{57}H_{77}NO_{11}Si_2Na^+[M+Na]^+$ 1030.4933, found 1030.4958.

Example D-3. Compound 56
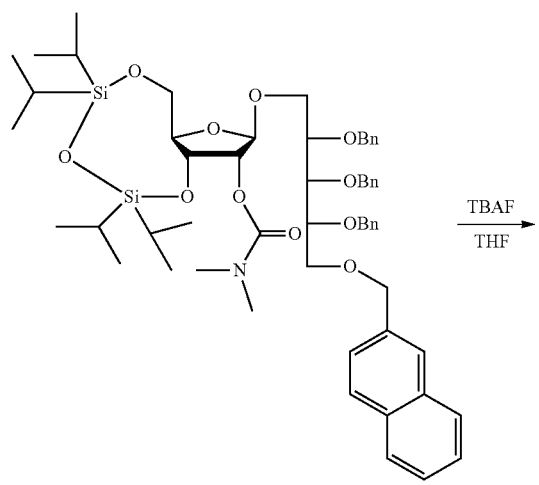
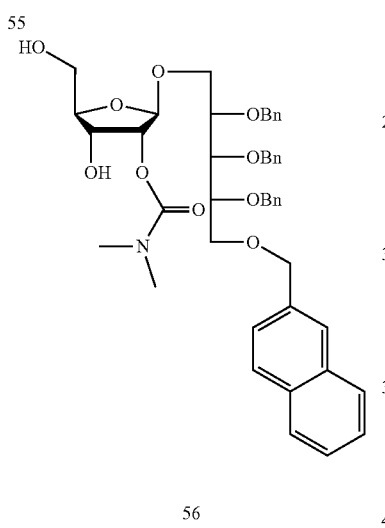
According to general procedure A) the silylated compound 55 was converted to diol product 56 (1.1 g, 73%). HRMS (ESI⁺) Calcd for $C_{45}H_{51}NO_{10}Na^+[M+Na]^+$ 788.3411, found 788.3431.
Example D-4. Compound 57
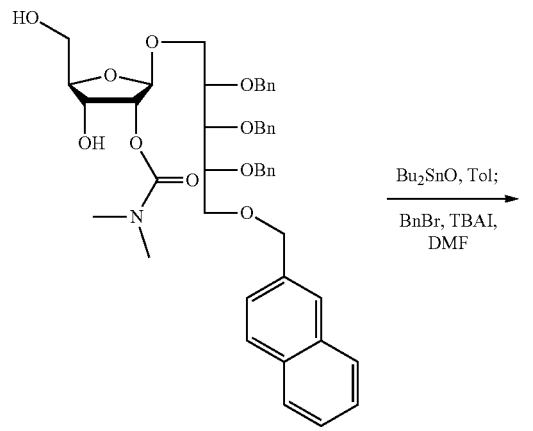
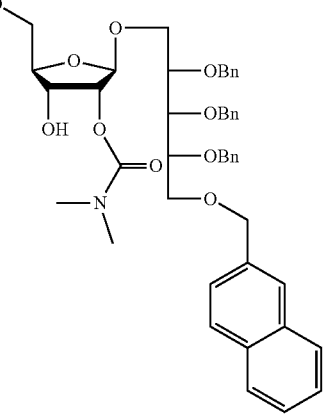
According to general procedure B) the diol 56 was converted to the benzylated product 57 (91 mg, 16%). HRMS (ESI⁺) Calcd for $C_{52}H_{57}NO_{10}Na^+[M+Na]^+$ 878.3880, found 878.3930.
Example D-5. Compound 58
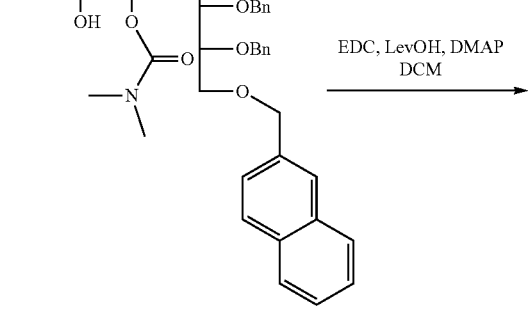
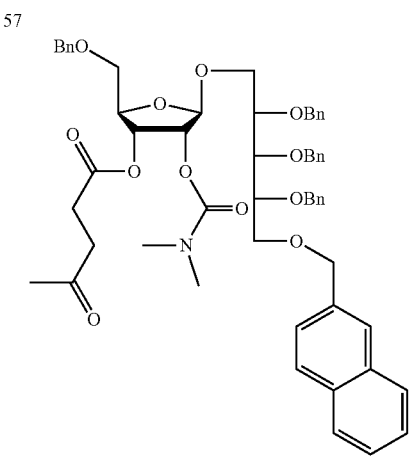

According to general procedure C), the 3-hydroxyl intermediate 57 was converted to the Lev protected compound 58 (46 mg, 92%). HRMS (ESI$^+$) Calcd for $C_{57}H_{63}NO_{12}Na^+$ [M+Na]$^+$976.4248, found 976.4318.

Example D-6. Compound 59

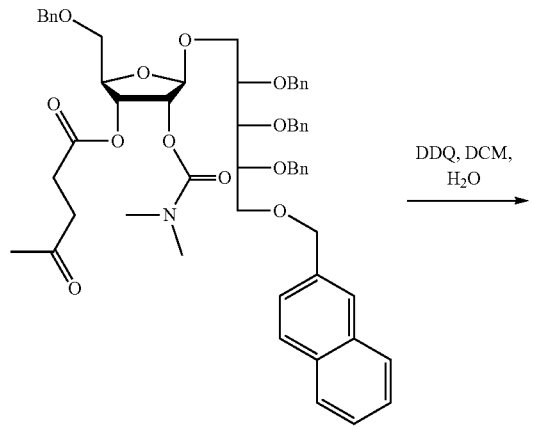

58

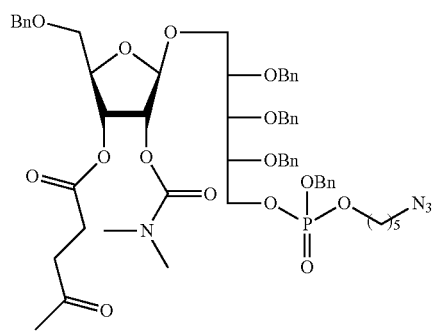

59

According to general procedure D), the monomer 58 was converted to 5-hydroxyl monomer 59 (23 mg, 60%). HRMS (ESI$^+$) Calcd for $C_{46}H_{55}NO_{12}Na^+$[M+Na]$^+$836.3622, found 836.3682.

Example D-7. Compound 60

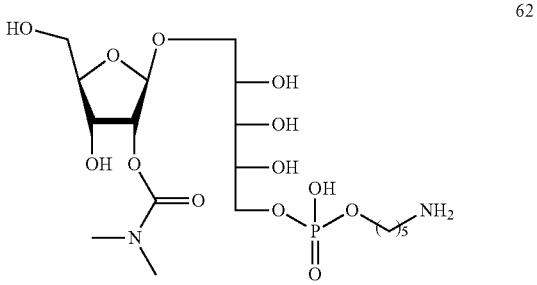

According to general procedure E), the monomer 59 was coupled to the linker 5-azido-pentanol to give monomer 60 (19 mg, 70%). HRMS (ESI$^+$) Calcd for $C_{58}H_{71}N_4O_{15}PNa^+$ [M+Na]$^+$1117.4551, found 1117.4628.

Example D-8. Compound 61

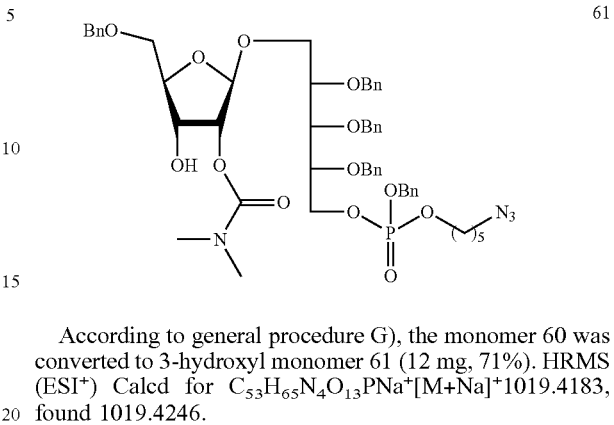

According to general procedure G), the monomer 60 was converted to 3-hydroxyl monomer 61 (12 mg, 71%). HRMS (ESI$^+$) Calcd for $C_{53}H_{65}N_4O_{13}PNa^+$[M+Na]$^+$1019.4183, found 1019.4246.

Example D-9. Compound 62

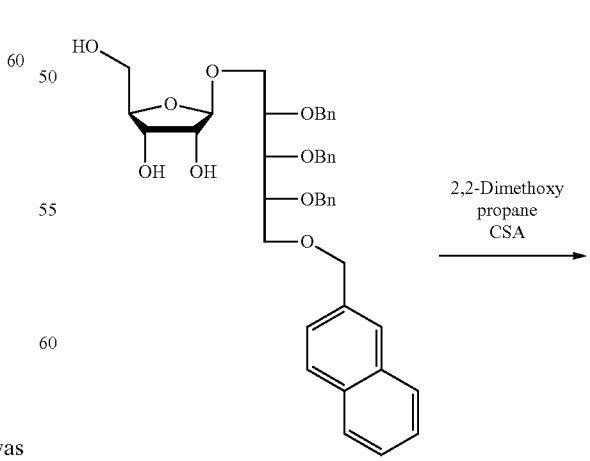

According to general procedure H), the monomer 61 was converted to the deprotected monomer 62 (3 mg, 60%). HRMS (ESI$^+$) Calcd for $C_{18}H_{38}N_2O_{13}PNa^+$[M+H]$^+$ 521.2112, found 521.2125.

Example E. 2'-Fluoropolyribosylribitolphosphate

Example E-1. Compound 63

-continued

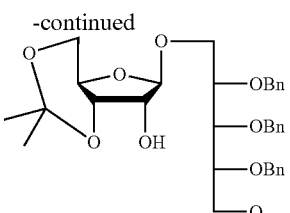

63

To compound 4 in acetone was added 2,2-dimethoxypropane (1.2 equiv.) followed by camphorsulfonic acid (0.5 equiv). After 6 h of stirring, the reaction mixture was concentrated under reduced pressure which on column chromatographic purification gave the pure compound 63.

Example E-2. Compound 64

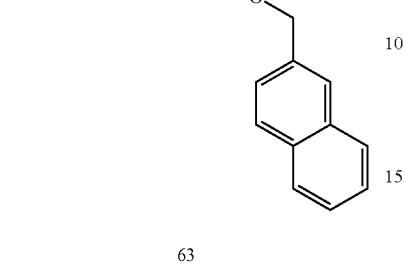

63

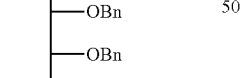

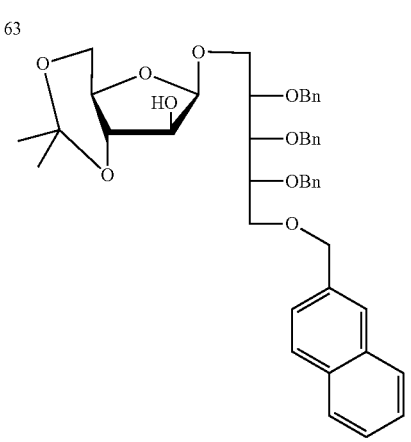

64

Compound 63 was treated at 0° C. with triflic anhydride and pyridine in DCM. After two hours, tetrabutylammonium nitrite and sodium nitrite were added and the mixture was stirred at r.t. for additional 5 hours. The product was extracted into hexane (200 mL). The extract was washed with aqueous sodium hydroxide (2N), brine, dried ($Na_2SO_4$) and concentrated under reduced pressure to give a brown oil. Purification by flash chromatography (eluting with hexane:ether) gave 64.

Example E-3. Compound 65

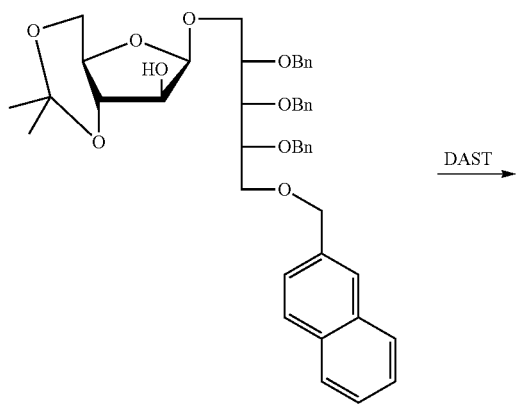

64

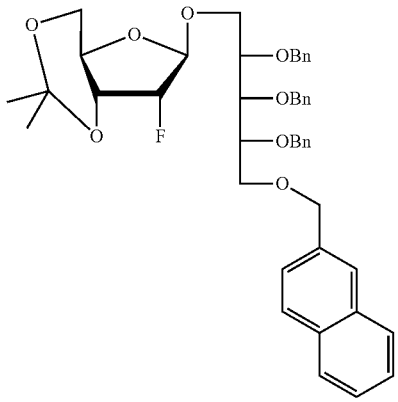

65

DAST (diethylamino sulfur trifluoride) (1.2 equiv.) was added dropwise to a stirred solution of 64 in dichloromethane at −78° C. The mixture was allowed to warm to room temperature overnight with the cooling bath in place. After 20 h, the solution was poured slowly into a vigorously stirred mixture of ice and excess saturated aqueous sodium bicarbonate. When effervescence had ceased, the product was extracted into hexane (200 mL). The extract was washed with aqueous sodium hydroxide (2N), brine, dried ($Na_2SO_4$) and concentrated under reduced pressure to give a brown oil. Purification by flash chromatography (eluting with hexane:ether) gave 65.

Example E-4. Compound 66

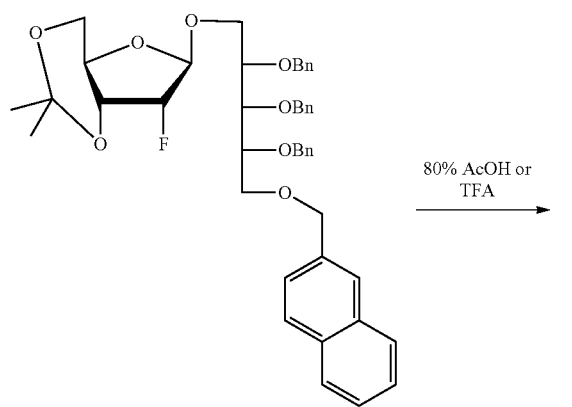

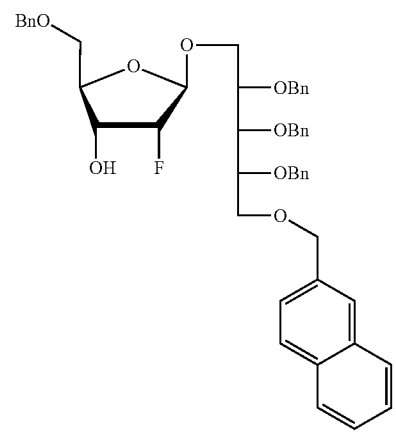

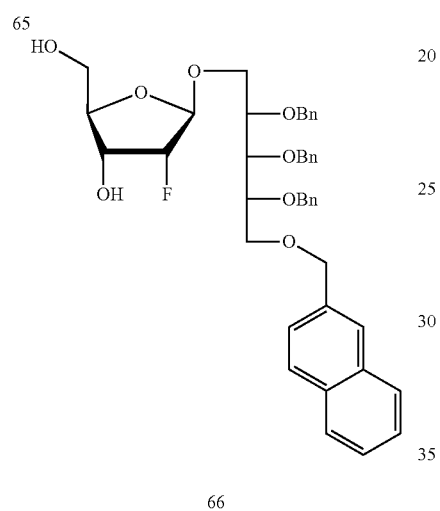

Compound 65 was taken in 80% acetic acid and stirred for 2 h at 80° C. After completion of reaction (TLC), the acidic solution was concentrated under reduced pressure to give a crude product which was purified by column chromatography to yield compound 66.

Example E-5. Compound 67

According to general procedure B) the diol 66 was converted to the benzylated product 67.

Example E-6. Compound 68

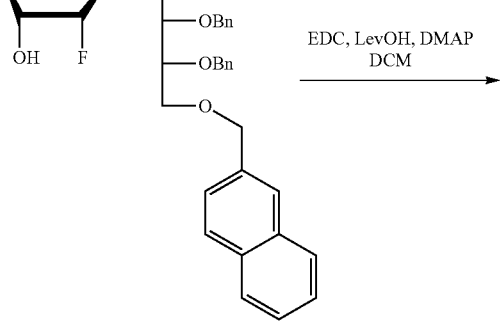

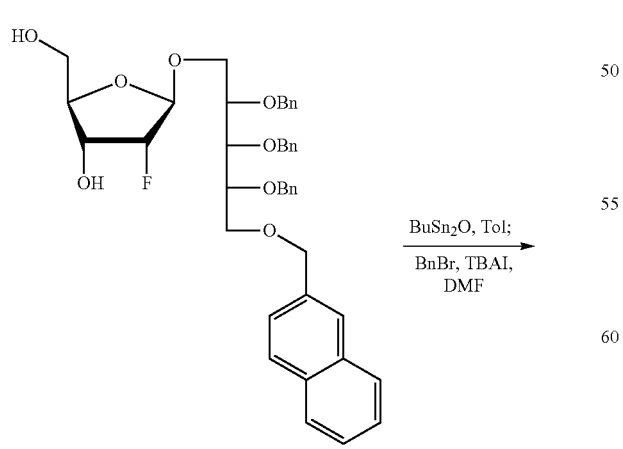

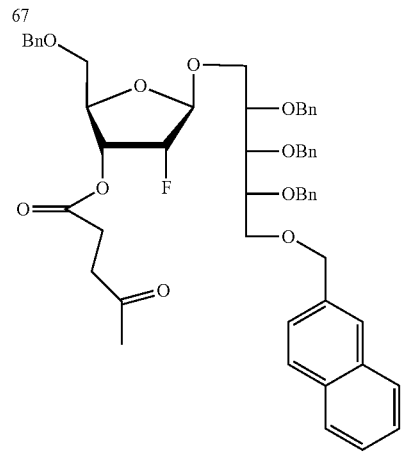

According to general procedure C), the 3-hydroxyl intermediate 67 was converted to the Lev protected compound 68.

Example E-7. Compound 69

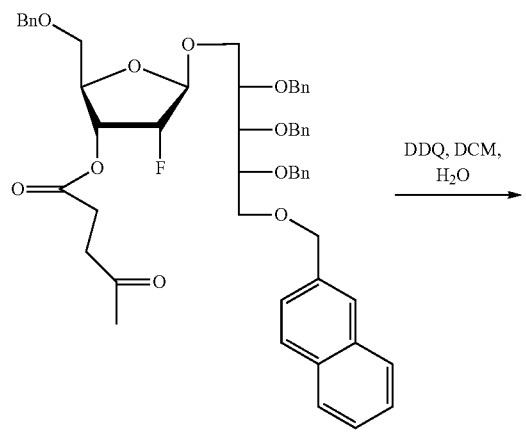

68

According to general procedure D), the NAP protected intermediate 68 was converted to the 5-hydroxyl compound 69.

Example E-8. Compound 71

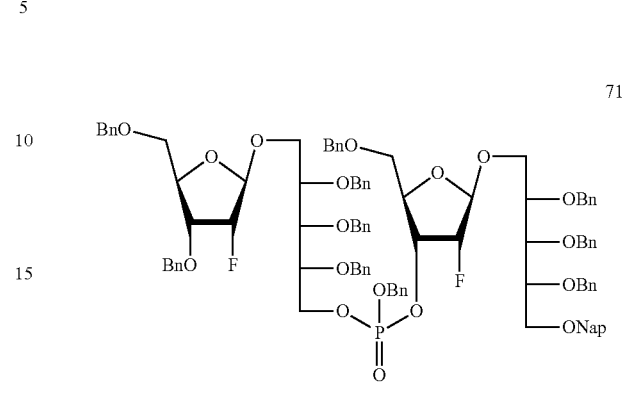

71

According to general procedure E), the 3-hydroxyl compound 67 and the 5-hydroxyl compound 69 were converted to dimer 71.

Example E-9. Compound 72

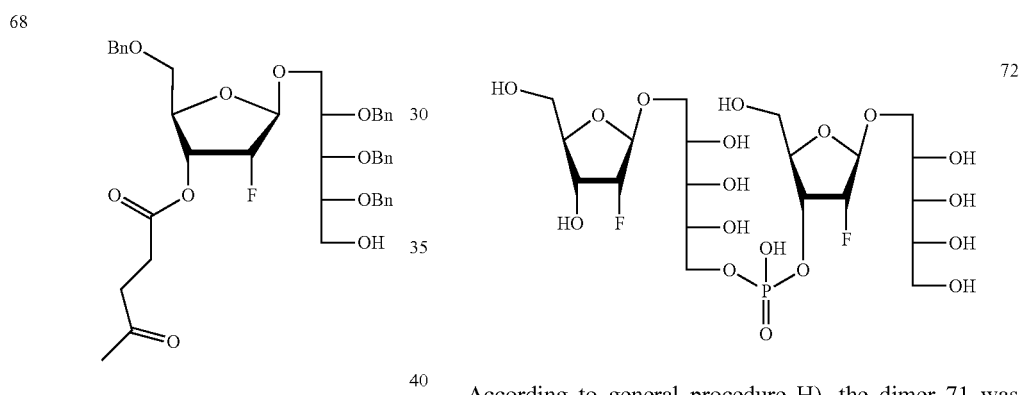

72

According to general procedure H), the dimer 71 was converted to the deprotected dimer 72.

Example E-10. Compound 73

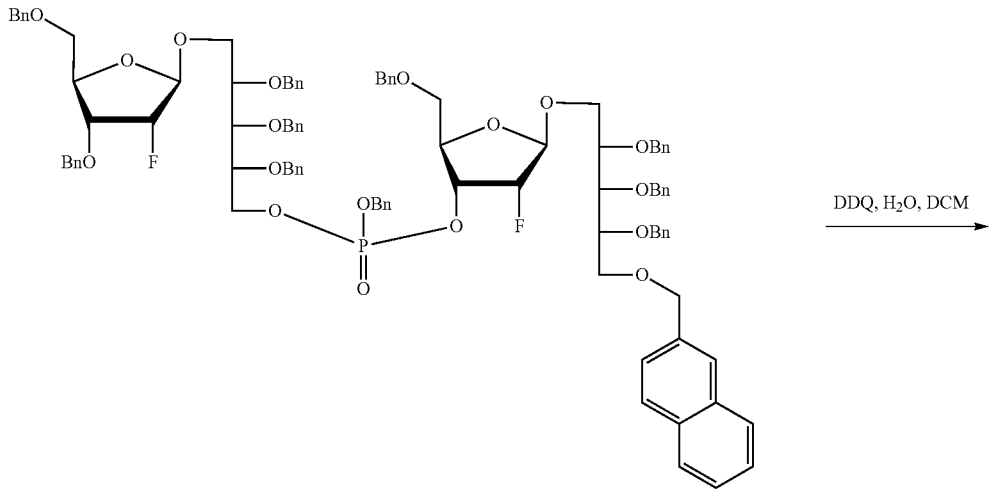

71

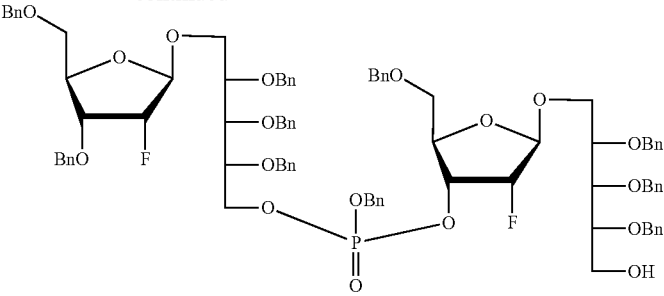
73
According to general procedure D), the NAP protected dimer 71 was converted to the 5-hydroxyl compound 73.
Example E-11. Compound 74
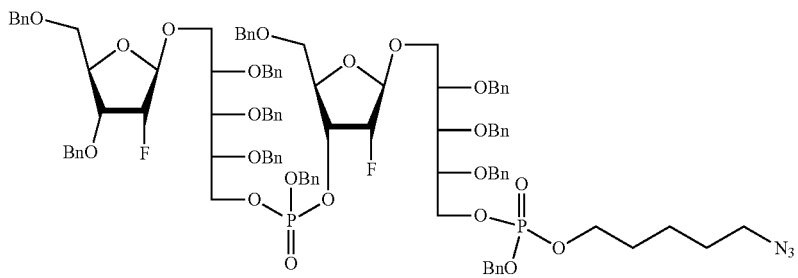
74
According to general procedure E), the dimer 73 was coupled to the linker 5-azido-pentanol to give dimer 74.
Example E-12. Compound 75
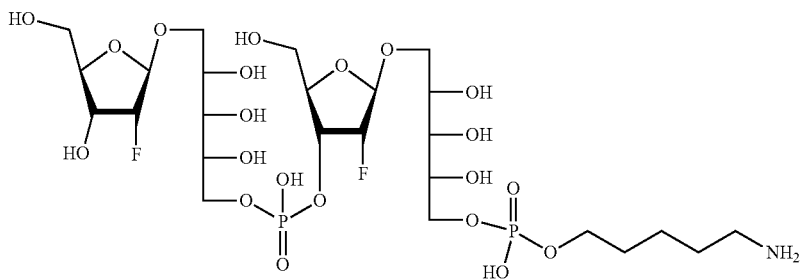
75
According to general procedure H), the dimer 74 was converted to the deprotected dimer 75.

Example F. 2'-Substituted Polyribosylribitolphosphates

Example F-1. Compound 76

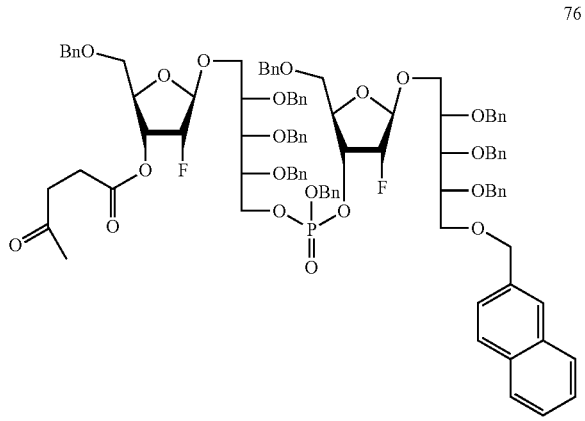

Example F-2. Compound 77

According to general procedure E), the 3-hydroxyl compound 67 and the 5-hydroxyl compound 69 were converted to dimer 76.

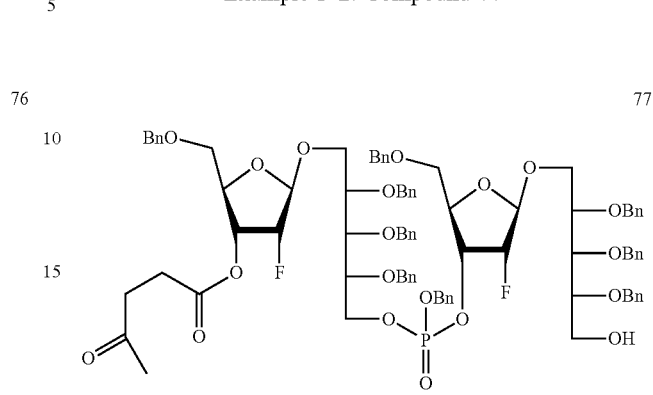

According to general procedure D), the NAP protected intermediate 76 was converted to the 5-hydroxyl compound 77.

Example F-3. Compound 79

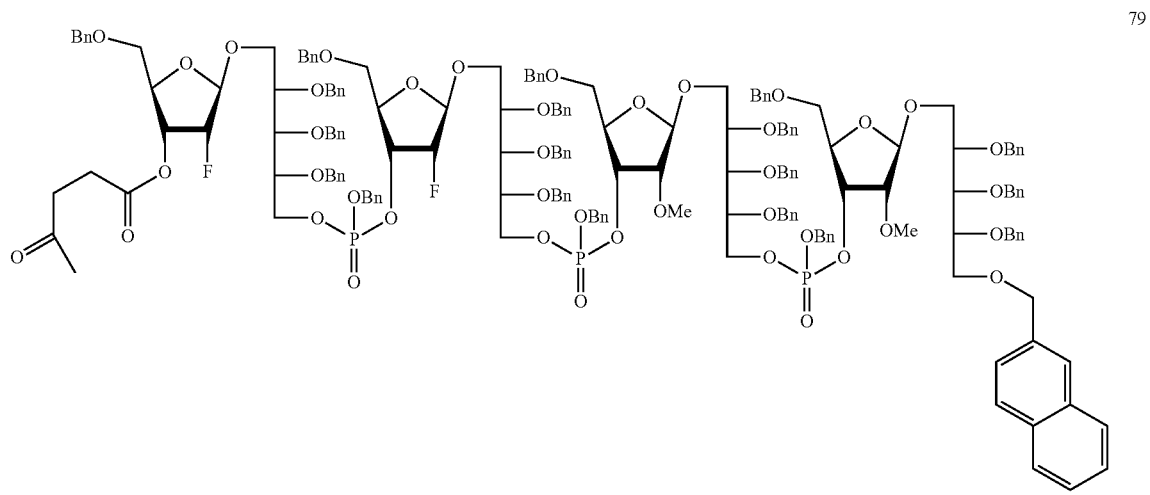

According to general procedure E), the 3-hydroxyl dimer 22 and the 5-hydroxyl dimer 77 were converted to tetramer 79.

Example F-4. Compound 80

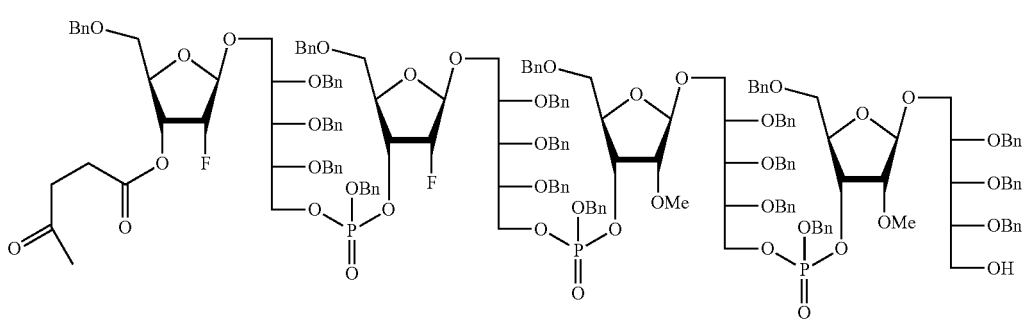

According to general procedure D), the NAP protected tetramer 79 was converted to the 5-hydroxyl tetramer 80.

Example F-5. Compound 81

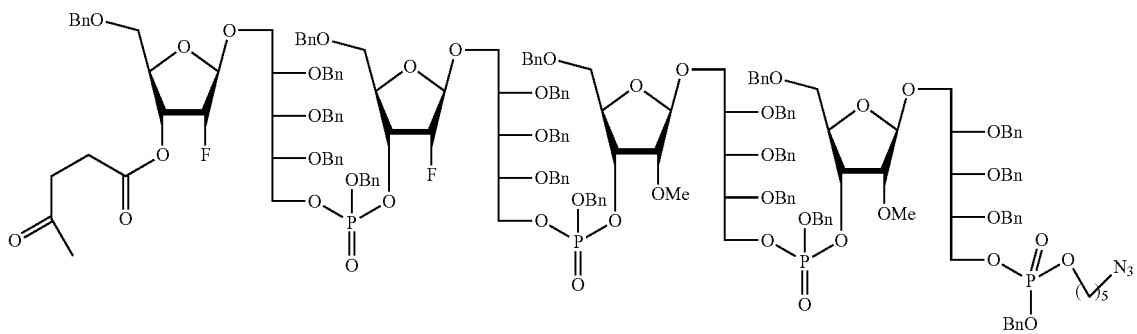

81

According to general procedure E), the tetramer 80 was coupled to the linker 5-azido-pentanol to give tetramer 81.

Example F-6. Compound 82

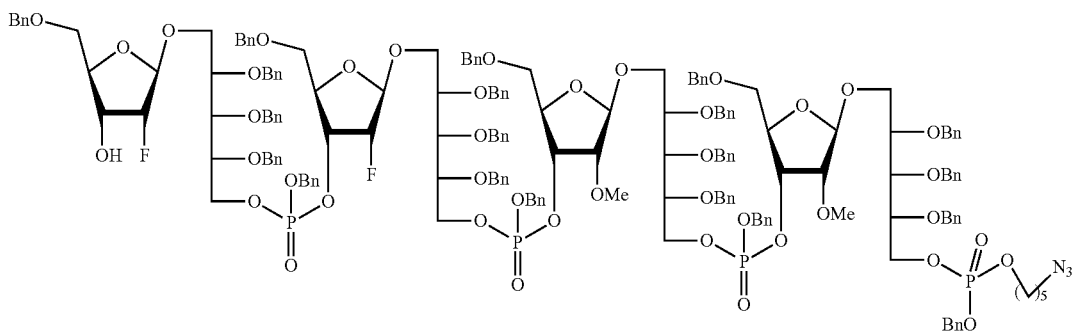

82

According to general procedure G), the tetramer 81 was converted to 3-hydroxyl tetramer 82.

Example F-7. Compound 83

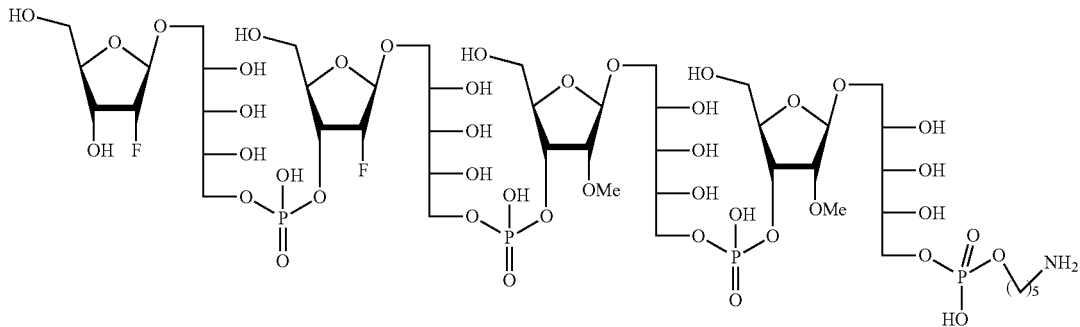

83

According to general procedure H), the tetramer 82 was converted to the deprotected tetramer 83.

Example F-8. Compound 85

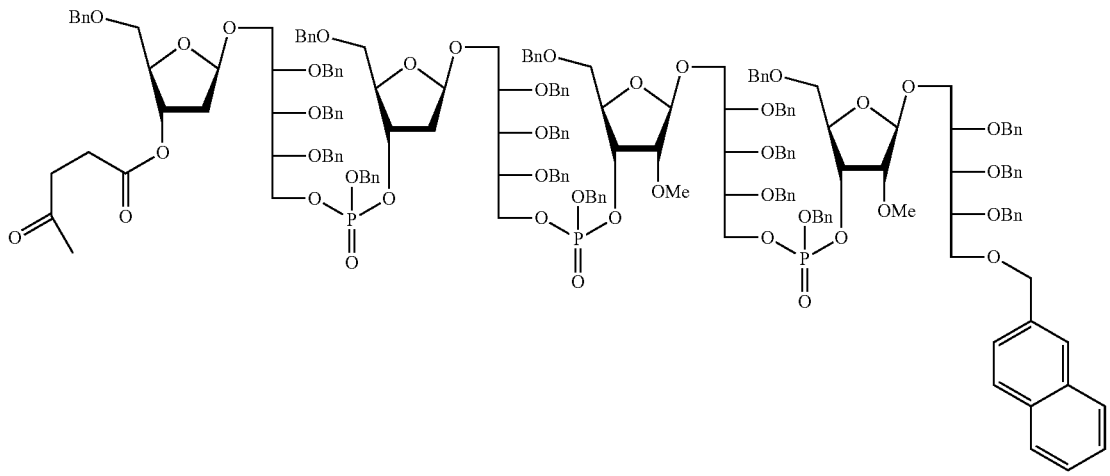

According to general procedure E), the 3-hydroxyl dimer 22 and the 5-hydroxyl dimer 45 were converted to tetramer 85.

Example F-9. Compound 86

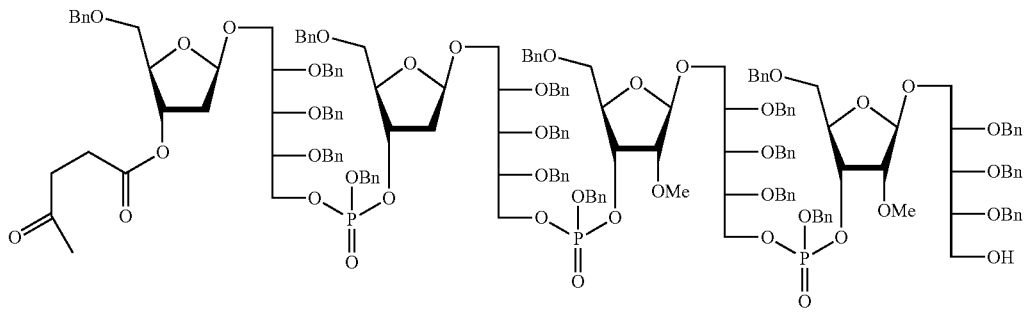

According to general procedure D), the NAP protected tetramer 85 was converted to the 5-hydroxyl tetramer 86.

Example F-10. Compound 87

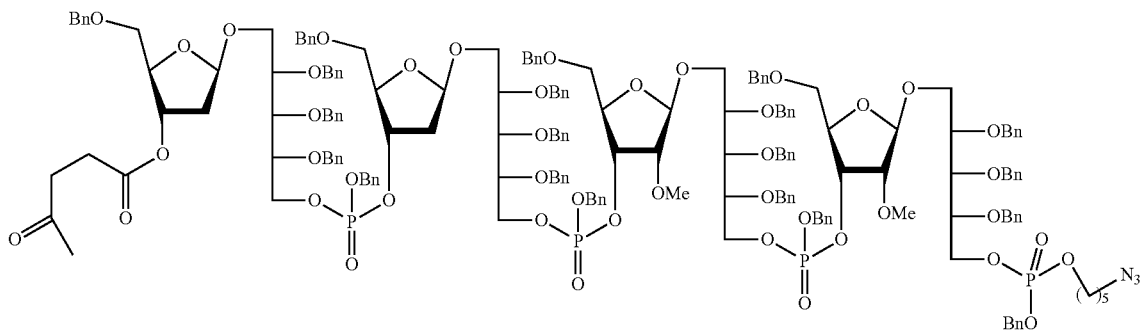

According to general procedure E), the tetramer 86 was coupled to the linker 5-azido-pentanol to give tetramer 87.

Example F-11. Compound 88

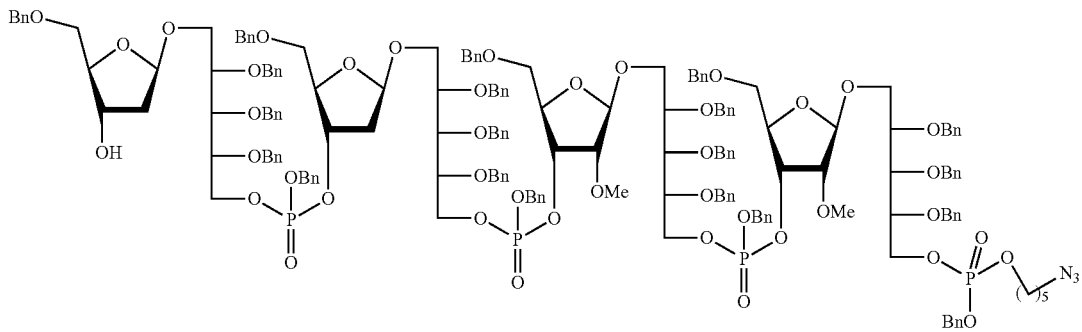

88

According to general procedure G), the tetramer 87 was converted to 3-hydroxyl tetramer 88.

Example F-12. Compound 89

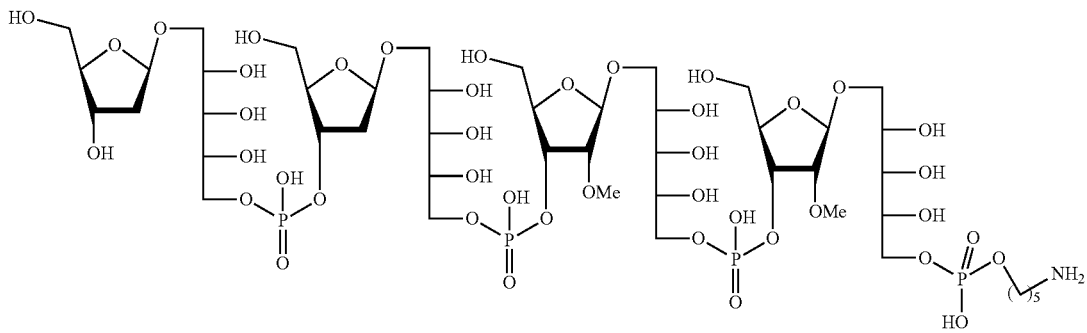

89

According to general procedure H), the tetramer 88 was converted to the deprotected tetramer 89.

Example G. Synthesis of a Stabilized Saccharide-CRM197—Cysteine Conjugate

Example G-1. Compound 90

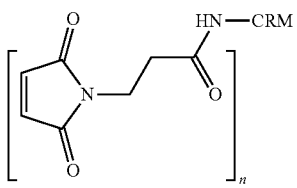

Making $CRM_{197}$ Ready for the Conjugation:

$CRM_{197}$ (3.0 mg, 0.0517 µmol) from the stock solution was transferred to the Amicon filter (0.5 mL, MWCO 30 KDa) and centrifuged for 3 min at 10000 RPM. 300 µL of the 1×PBS was added to the remaining protein in Amicon filter and centrifuged again for 3 min at 10000 RPM. Then 400 µL of 1×PBS buffer (pH 7.4) was added to Amicon filter and centrifuged for 3 min at 10000 RPM. Then the filter containing protein was reversed inside of a new Amicon micro centrifuge tube (1.5 mL) and centrifuged for 1 min at 1000 RPM to collect the protein in micro centrifuge tubes (volume ~=100-120 µL).

Conjugation Procedure:

$CRM_{197}$ in 1×PBS buffer (~100 µL) was diluted with 1.3 mL of 1×PBS buffer in the reaction vial at r.t. equipped with a stir bar.

3-(Maleimido)propionic acid N-hydroxysuccinimide ester (0.688 mg, 2.58 µmol) was transferred to a Type I glass-2 mL reaction vial, dissolved with 20 µL of DMSO, added it to the reaction vial containing CRM197 in 1×PBS buffer. Stirred the reaction at rt for 4 h. RM was clear colorless solution.

Washing Steps:

The reaction mixture was transferred to the Amicon filter (0.5 mL, MWCO 30 KDa) and centrifuged for 3 min at 10000 RPM and repeated the process till whole reaction mixture was transferred and centrifuged. Then added 400 µL of 1×PBS buffer to the reaction vial and rinsed and transferred it to the Amicon filter. This washing was repeated four more times with 400 µL of the PBS buffer solution. Finally, Amicon filter containing CRM197-maleimide was reversed inside of a new Amicon micro centrifuge tube (1.5 mL) and centrifuged for 1 min at 1000 RPM to collect ~130 µL CRM197-maleimide in micro centrifuge tubes. Added 950 µL of PBS solution (pH 7.4) to it and stored the vial at 2-8° C. (total volume=~1.08 mL). The CRM197-Maleimide conjugate was analyzed by MALDI, SDS-page, Western blot, SEC-HPLC and protein estimation by BCA. The CRM197-Maleimide conjugate was analyzed by MALDI and found between 21-24. BCA estimation also showed the good recovery of the protein. SDS page showed the CRM-maleimide conjugate 90 was higher molecular weight than $CRM_{197}$ and stable. Western blot shows that CRM anti-goat antibodies are recognizing the CRM-conjugate 90 whereas the Hib Anti-rabbit antibodies did not recognize the CRM-maleimide conjugate 90 which was without sugar. Sample was stored at 2-8° C. till further use.

Example G-2. Compound 94
Saccharide-CRM197—Cysteine Conjugate

Figure 3:
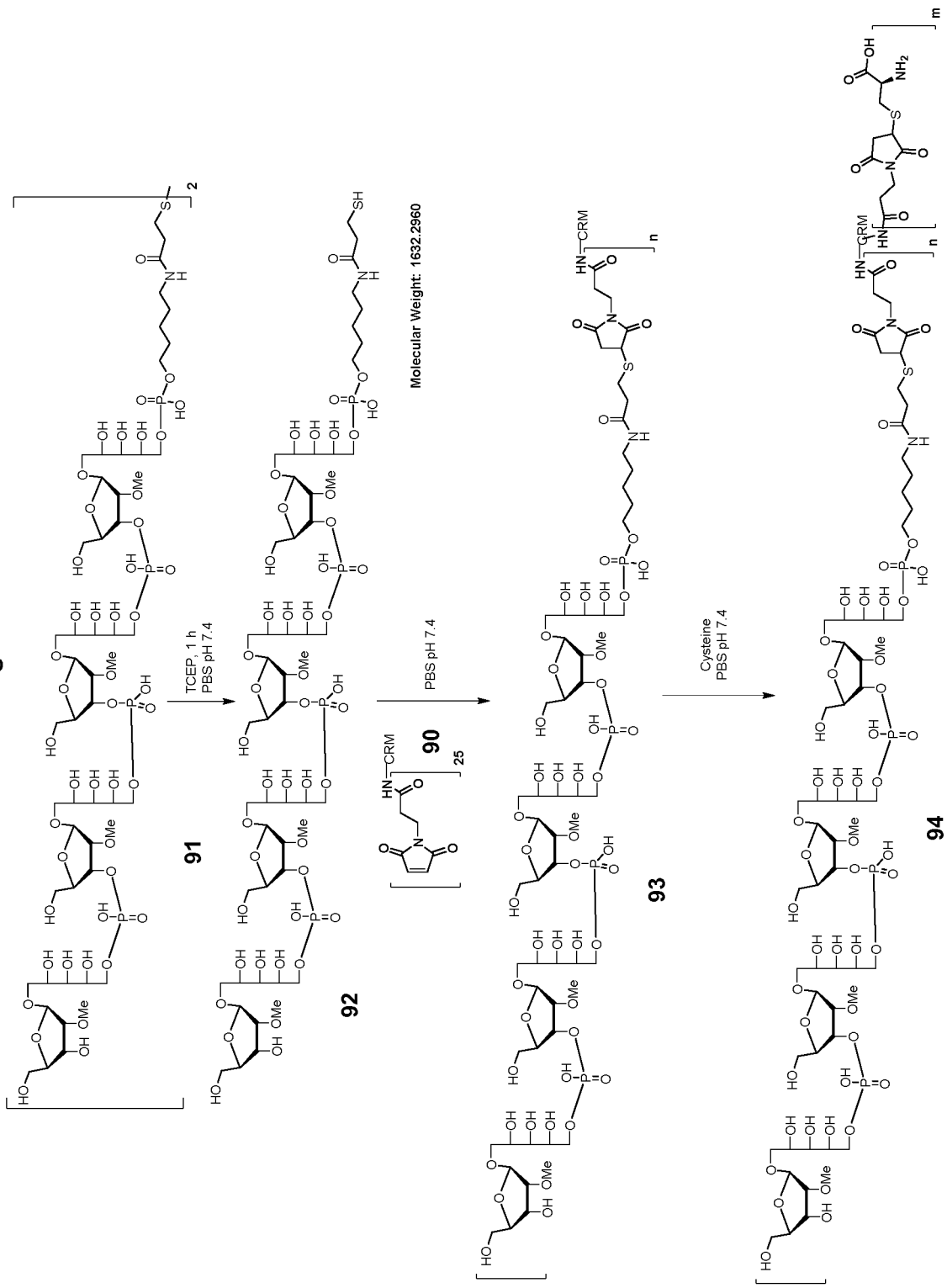
FIG. 3: Synthetic scheme of 2'-methoxyribosylribitol-phosphate tetramer 29 conjugated to $CRM_{197}$ and cysteine.

The synthetic route for compound 94 is outlined in FIG. 3.

DTT Method:

Compound 29 (5 mg, 0.003 mmol) was dissolved in pH 7.4 PBS buffer (5 mL) and DSP (dithiobis(succinimidyl propionate)) (20 mg, 0.049 mmol) in DMSO (2.5 mL) was added at room temperature overnight. After that, dithiothreitol (DTT) (4 mg, 0.025 mmol) was added and the solution stirred at 40° C. for further 2 h. Compound 91 was purified through Sephadex G-25 column chromatography (4.5 mg, 88%). HRMS (ESI$^+$) Calcd for $C_{51}H_{99}NO_{46}P_4S$ [M+2Na+2K−4H]$^-$ 1736.2793, found 1736.279.

Making Saccharide-Thiol Ready for the Conjugation: TCEP Method:

100 μL of TCEP suspension was taken in an 1.5 ml vial and added 300 μL of 1×PBS solution (pH 7.4) was added. Centrifuged, and the supernatant solution was removed. And the washing with PBS repeated once more. And finally the residue was taken in 100 μL of PBS solution and added to the Sugar-disulfide 91 (1.38 mg, 0.292 μmol) in PBS buffer (0.15 mL) in a 2 mL type I glass vial. Shaken gently using orbital shaker for 1 h at rt. The RM was transferred to vial, and glass reaction vial was rinsed with 200 μL of PBS solution and transferred to the vial. Centrifuged, collected the supernatant (~325 μL) of PBS solution in a 2 mL type I glass vial. Added 200 μL of PBS solution to the residue and mixed well, centrifuged, the supernatant was collected and transferred to the 2 mL type I glass vial again. So, total volume of the reduced thiol 78 solution was ~525 μL. ~25 μL were kept for analysis.

Conjugation Procedure:

$CRM_{197}$-maleimide 90 in 1×PBS buffer (~850 μL) was taken in a reaction vial at rt equipped with a stir bar. The saccharide-thiol 92 in PBS solution (~500 μL) in 1×PBS buffer was added to the $CRM_{197}$-maleimide 90 solution dropwise. The vial was rinsed with 50 μL PBS solution and the solution was transferred to the reaction mixture at rt. RM was clear solution and stirred at r.t. for 20 h. [An aliquot of ~40 μL of the reaction mixture was taken out for analysis purposes]. Then cysteine (0.14 mg) in phosphate buffer (pH 7.4, 30 μL) was added to the RM containing 93 and stirred for an hour at rt.

Washing Steps:

The reaction mixture containing 94 was transferred to the Amicon filter (0.5 mL, MWCO 30 KDa) and centrifuged for 3 min at 10000 RPM and repeated the process till whole reaction mixture was transferred and centrifuged. Then 400 μL of 1×PBS buffer were added to the reaction vial and rinsed and the solution was transferred to the Amicon filter. This washing was repeated four more times with 400 μL of the PBS buffer solution. Finally, the filter containing $CRM_{197}$-maleimide-saccharide-cysteine 94 was reversed inside of a new Amicon micro centrifuge tube (1.5 mL) and centrifuged for 1 min at 1000 RPM to collect ~150 μL CRM197-maleimide-sugar-Cysteine in micro centrifuge tube. Added 200 μL of PBS solution (pH 7.4) to the Amicon filter and rinsed well and transferred the solution to the micro centrifuge tube and diluted the solution with 750 μL of PBS solution (pH 7.4) and stored the vial at 2-8° C. (total volume=~1100 μL). An aliquot of 40 μL of the conjugate 94 was washed with milliQ water using Amicon filter and analyzed using MALDI (sinapinic acid matrix) and loading between 3.4-4.2 was obtained. The conjugate 94 was further successfully analyzed using SDS-Page, western blot and SEC-HPLC. Protein estimation using BCA method showed that good recovery of the protein in the conjugate.

Example H. Stability Tests

Example H-1. Stability of Hib Capsular Polysaccharide in Basic Medium

Stability study of the inventive saccharides is critical for the development of stable liquid Hib glycoconjugate vaccines. As a control we examined first the stability and cleavage of Hib polyribosylribitolphosphate capsular polysaccharide (CPS). Accordingly, Hib CPS was fragmented using standard procedures as described in *Vaccine*, 2000, 18, 1982-1993: 1 mg Hib CPS in 0.43 mL of 0.1 M NaOH, 20 h. Fragments obtained after purification (filtered through 30 kDa Amicon filters followed by desalting) were analyzed by $^1$H NMR, HPLC and HRMS.

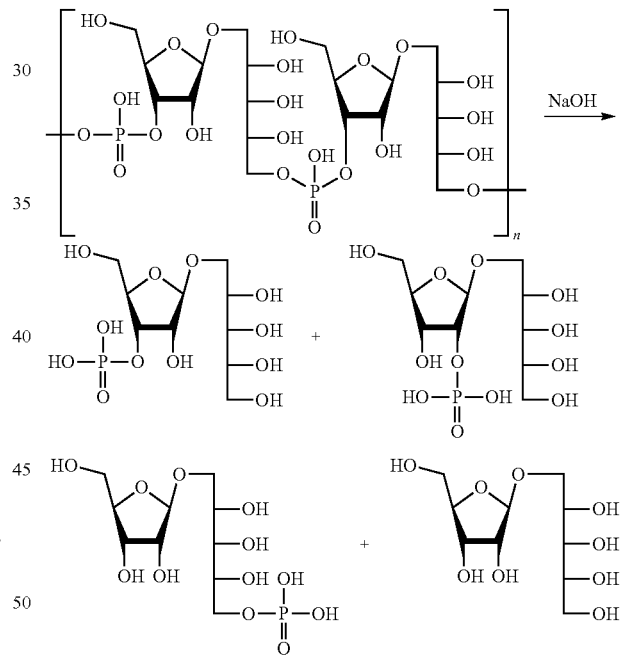

Figure 4:
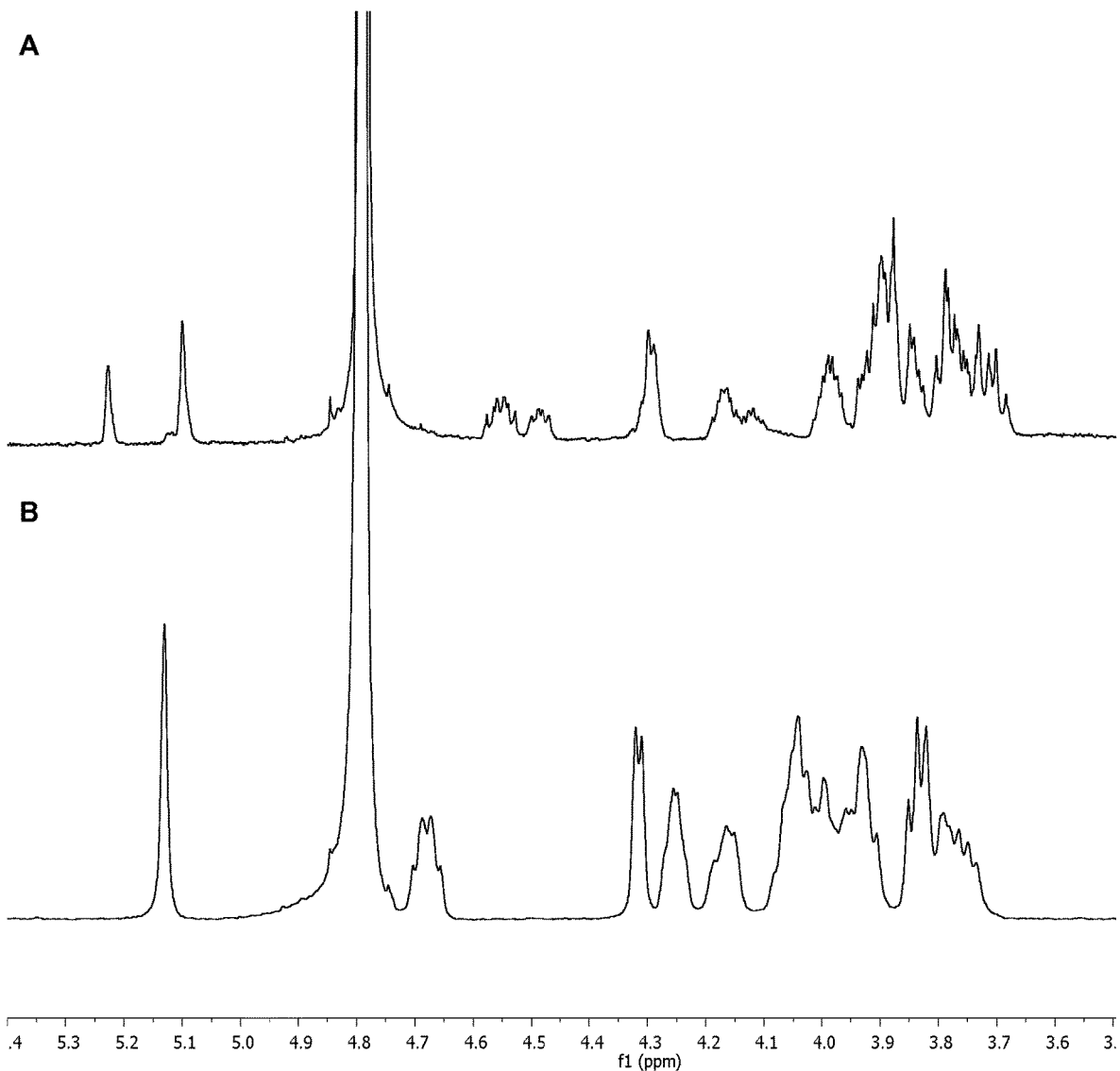
FIG. 4: $^1$H NMR spectra of (A) fragmented Hib CPS after treatment with 0.1 M sodium hydroxide solution for 20 hours and (B) untreated Hib CPS as reference. The comparison shows that Hib CPS hydrolyzes completely within 20 hours under basic conditions.

FIG. 4A shows the $^1$H NMR spectrum of fragmented Hib CPS and FIG. 4B shows the $^1$H NMR spectrum of untreated Hib CPS. FIG. 5A shows the HPLC chromatogram of fragmented Hib CPS and FIG. 5B shows the ESI mass spectrum of treated Hib CPS. This set of initial experiments demonstrated that the Hib CPS was cleaved to its smallest 2 and 3-0 phosphate fragments in basic medium.

Figure 6:
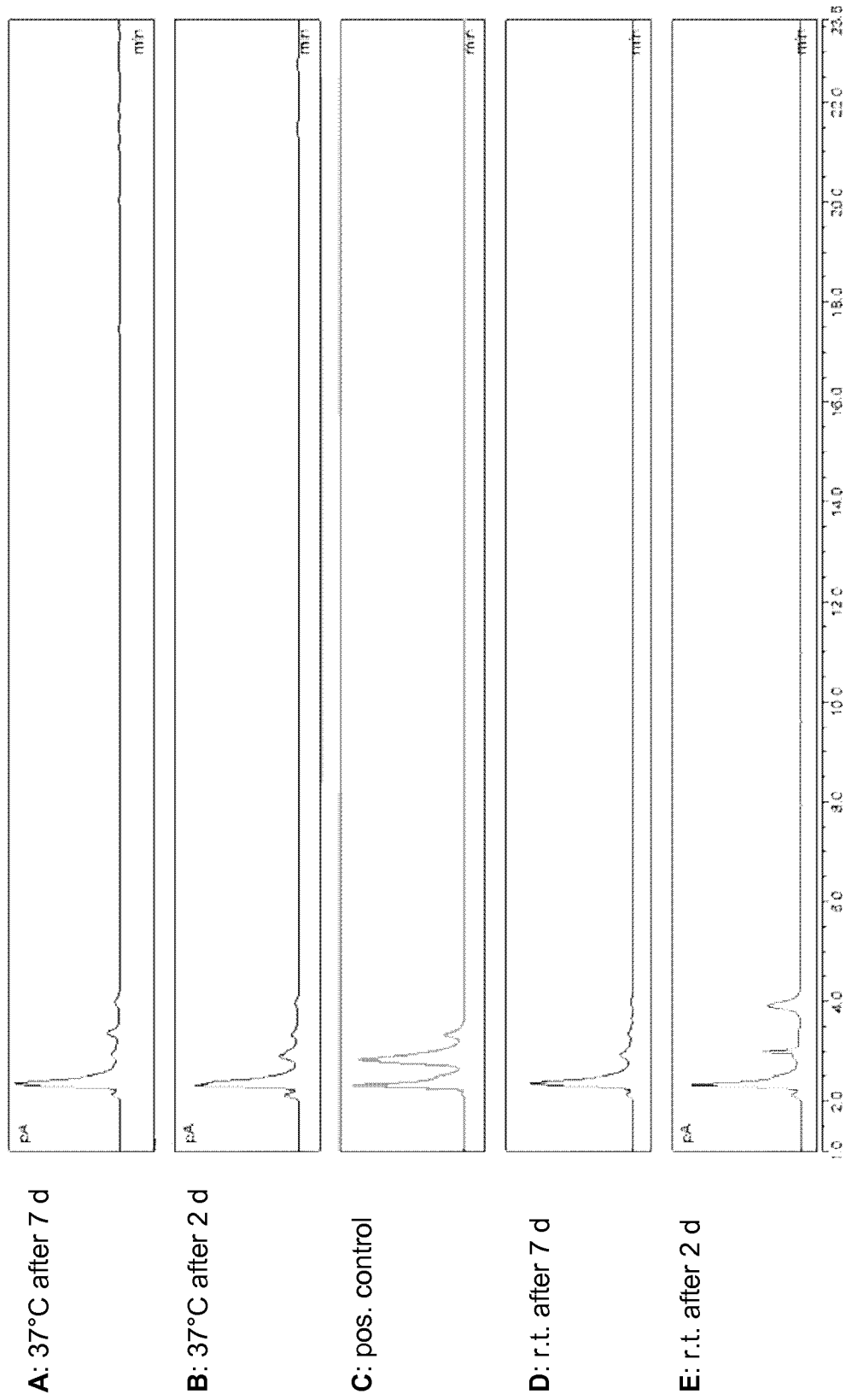
FIG. 6: HPLC chromatogram of Hib CPS after treatment with Alhydrogel® (A) for 7 days and (B) for 2 days at 37° C. as well as (D) for 7 days and (E) for 2 days at room temperature. HPLC chromatogram of untreated Hib CPS is shown in (C).
Figure 7:
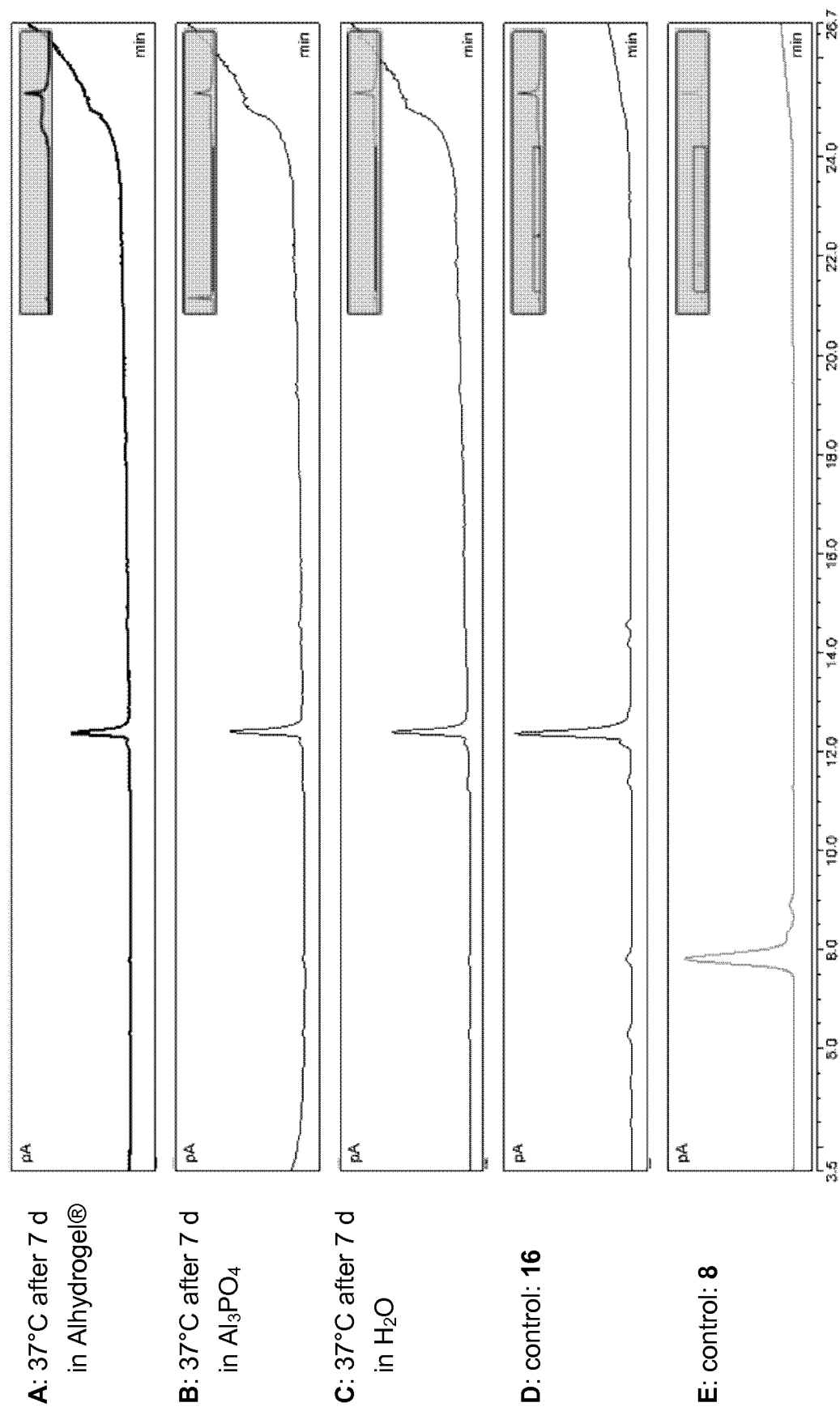
FIG. 7: HPLC chromatogram of compound 16 after treatment with (A) Alhydrogel®, (B) with aluminum phosphate, (C) with water for 7 days at 37° C. HPLC chromatograms of untreated compounds 16 and 8 are shown in (D) and (E).
Figure 8:
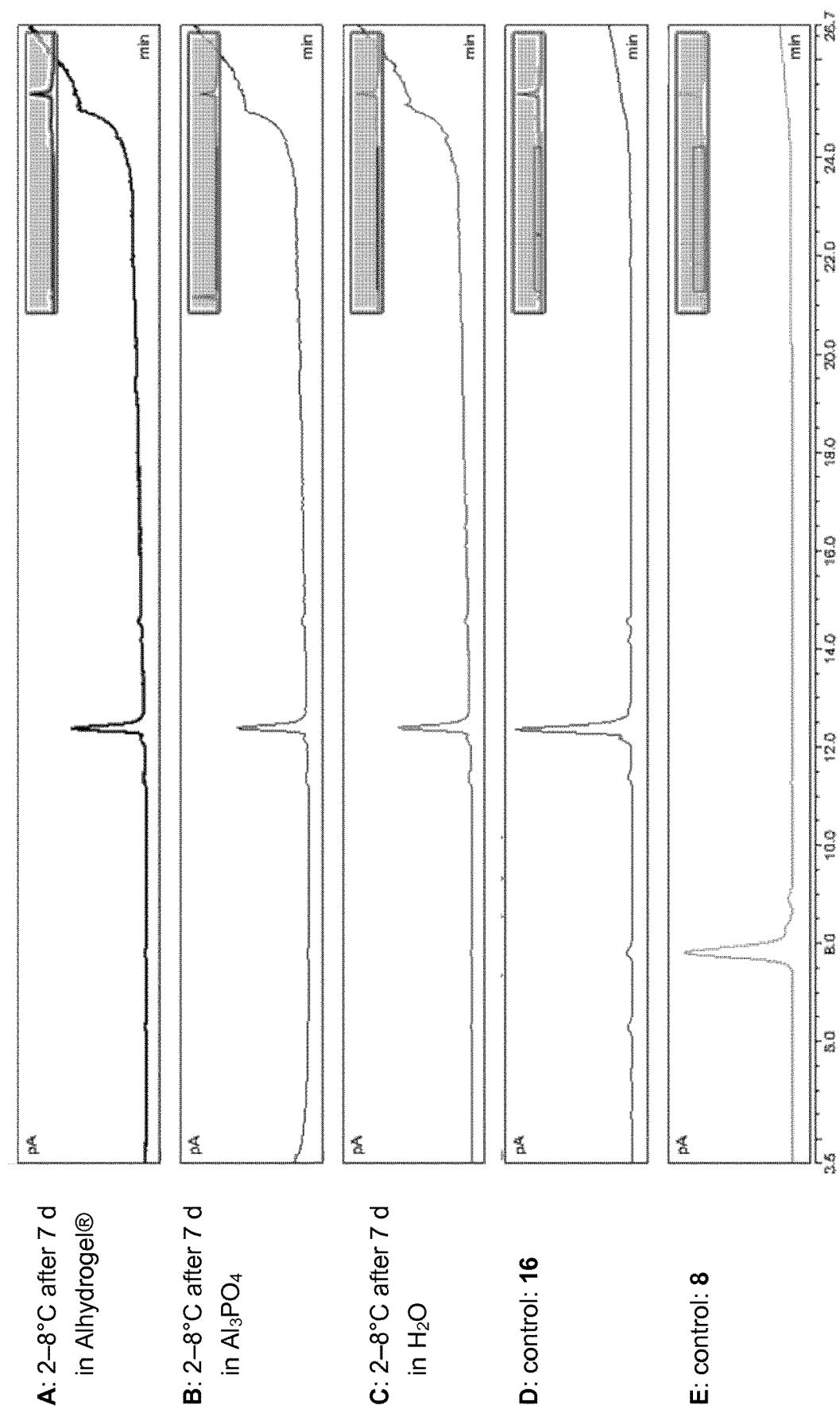
FIG. 8: HPLC chromatogram of compound 16 after treatment with (A) Alhydrogel®, (B) with aluminum phosphate, (C) with water for 7 days at 2-8° C. HPLC chromatograms of untreated compounds 16 and 8 are shown in (D) and (E).
Figure 9:
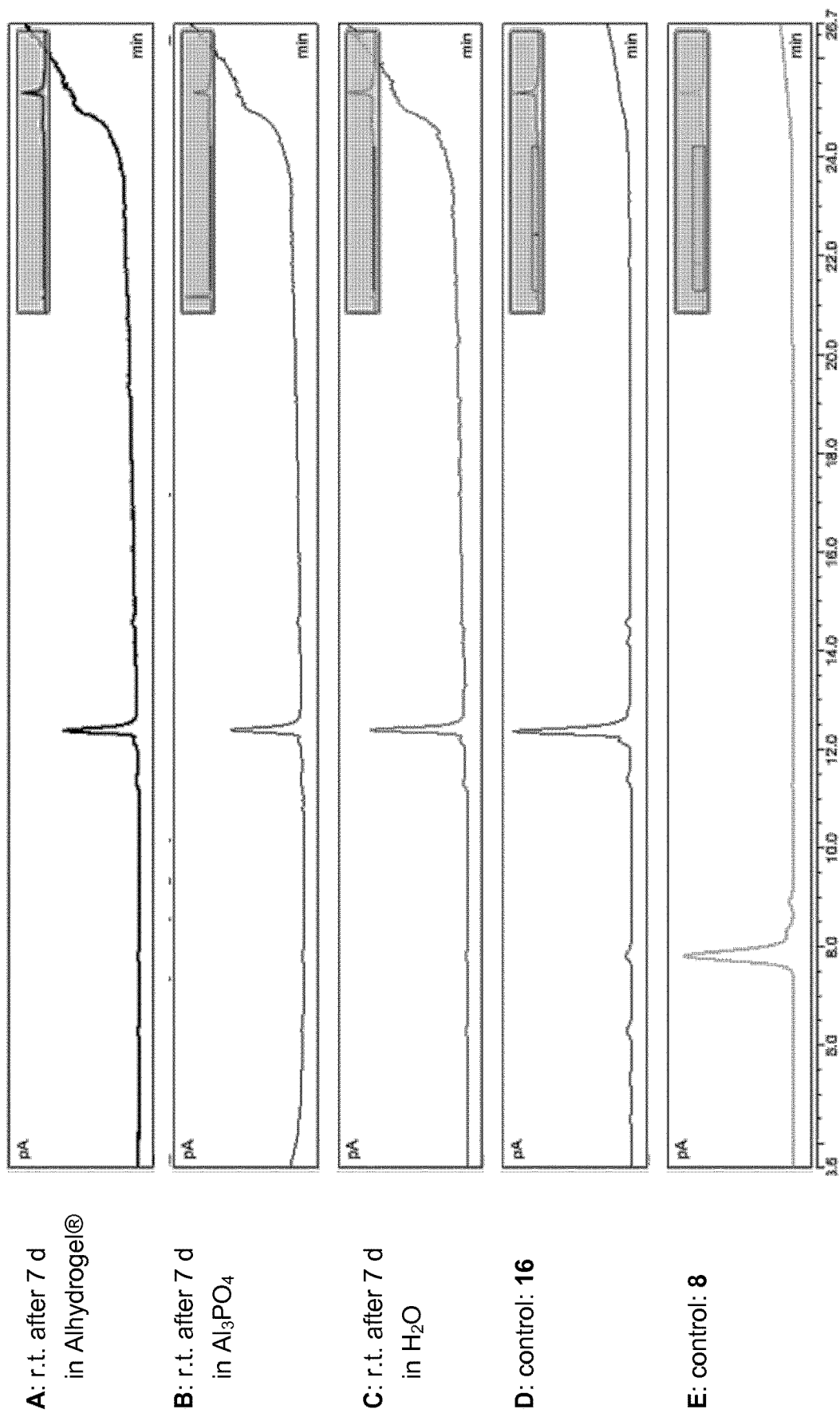
FIG. 9: HPLC chromatogram of compound 16 after treatment with (A) Alhydrogel®, (B) with aluminum phosphate, (C) with water for 7 days at room temperature. HPLC chromatograms of untreated compounds 16 and 8 are shown in (D) and (E).
Figure 10:
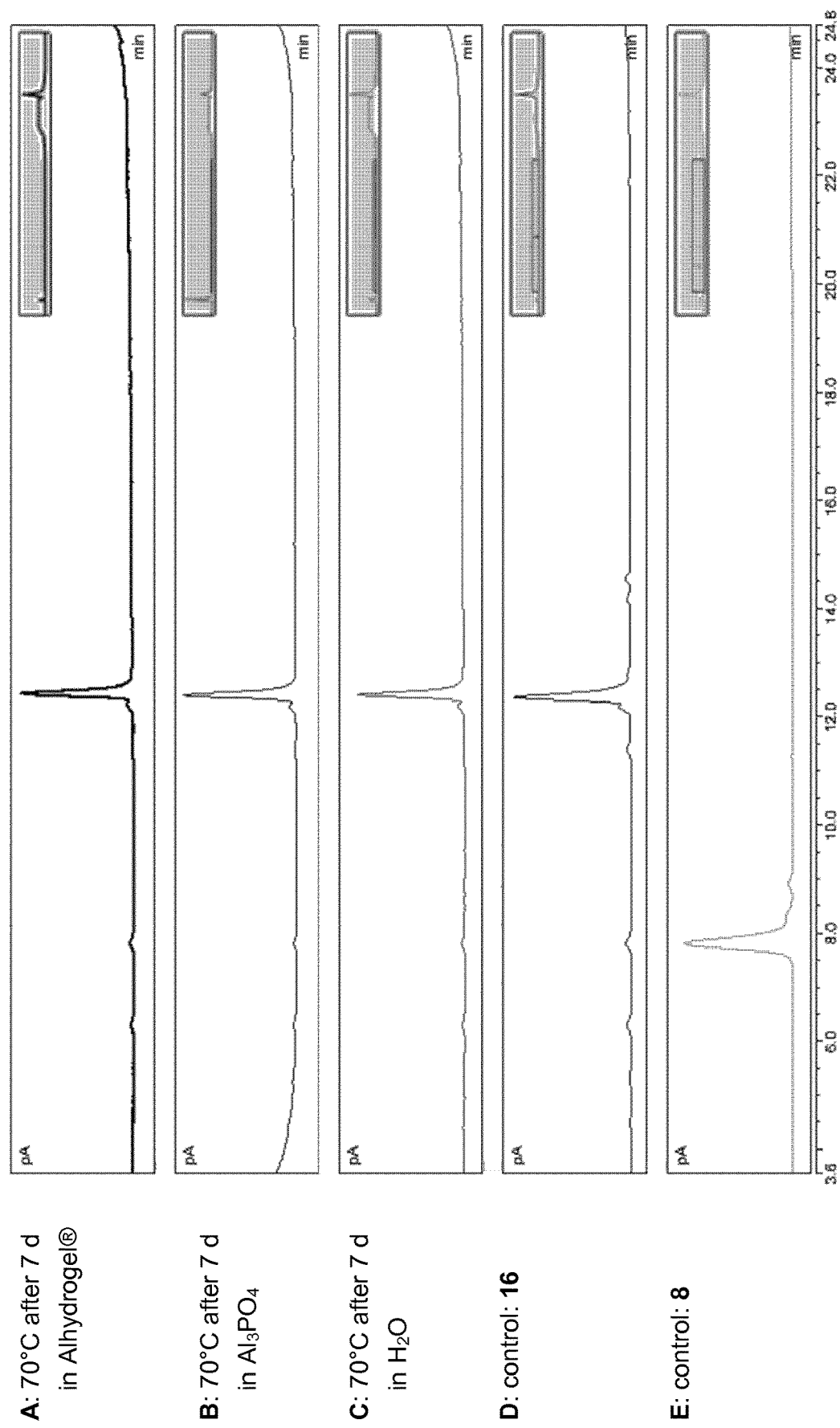
FIG. 10: HPLC chromatogram of compound 16 after treatment with (A) Alhydrogel®, (B) with aluminum phosphate, (C) with water for 7 days at 70° C. HPLC chromatograms of untreated compounds 16 and 8 are shown in (D) and (E).

Example H-2. Stability of Hib Capsular Polysaccharide in Aluminum Hydroxide Suspension Having established the stability data of the control Hib CPS, then the stability of Hib CPS in aluminum hydroxide was investigated, where it is known to be unstable in a vaccine formulation {0.5 mg Hib CPS, 3 mL Alhydrogel® (Brentag) and 22 mL milli-Q water} at various temperatures {37° C. (A1) and rt (A3)}. At 37° C. cleavage to smallest fragments were observed after 2 days and at rt this pattern was observed after day 7 (FIG. 6). From this experiment it was confirmed that, Hib CPS decomposes to 2 and 3-O phosphate fragments in 2 to 7 days depending on temperature in Aluminum hydroxide the most common adjuvant used in commercial vaccines.

Example H-3. Stability of Compound 16

Stability studies of synthesized 2'-methoxyribosylribitol-phosphate dimer 16 were conducted in presence of various adjuvants. As a first step stability of 16 was studied using Al(OH)$_3$, AlPO$_4$ and water at various temperatures {37° C. (A1), 2-8° C. (A2), rt (A3) and 70° C. (A4)}.

The amount of Al(OH)$_3$ and AlPO$_4$ used for this study was similar to the amount present in commercial Hib vaccines. Analysis of samples at different temperatures using HPLC after a week is shown in FIGS. 7-10. Compounds 16 and 8 were used as reference since decomposition of dimer 16 should lead to monomer 8. Every 24 h 40 µL of solution was aliquoted from each vial and centrifuged for 4 min at 5000 rpm. Supernatant (25 µL) was taken for HPLC analysis. Even after 7 days, no decomposition was observed. From this study it was clear that 2'-methoxyribosylribitol dimer 16 was stable at 37° C. (A1), 2-8° C. (A2), r.t. (A3) and at 70° C.

The stability of dimer 16 was further investigated under aqueous basic conditions as applied in Example H-1. From the HPLC chromatogram in FIG. 13D it was concluded that dimer 16 got cleaved completely after 4 days, while the natural Hib CPS got already cleaved completely within 20 hours. This demonstrates that the 2'-methoxyribosylribitol-phosphate oligomers are very stable even under extreme basic conditions compared to natural Hib CPS.

Example H-4. Stability of Compound 29

Stability studies of synthesized 2'-methoxyribosylribitol-phosphate tetramer bearing a linker 29 were conducted in presence of various adjuvants. As a first step stability of 29 was studied using Al(OH)$_3$, phosphate buffer (PBS) and water at various temperatures {2-8° C. (A2), and r.t. (A3)}.

Figure 11:
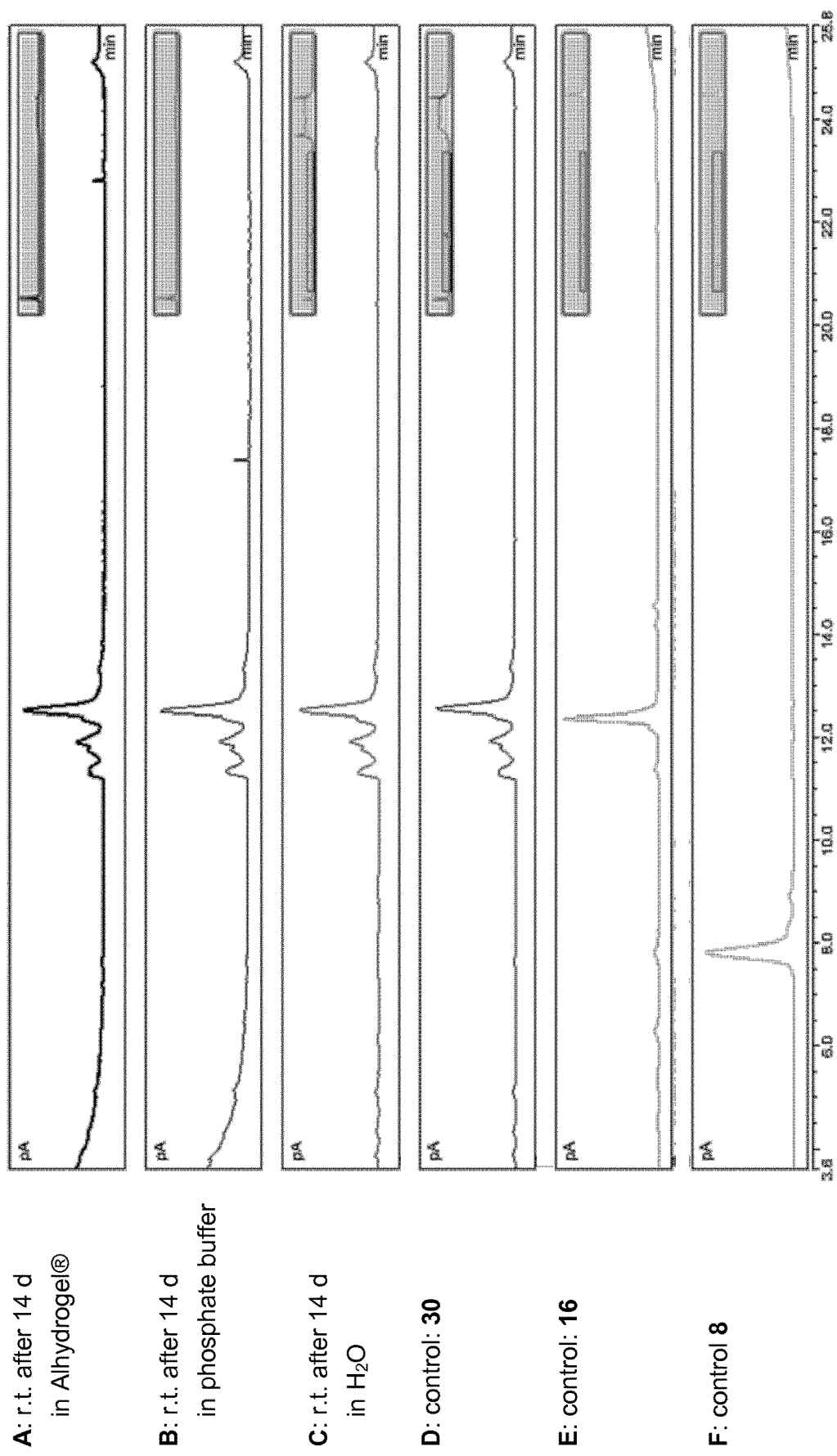
FIG. 11: HPLC chromatogram of compound 30 after treatment with (A) Alhydrogel®, (B) with phosphate buffer, (C) with water for 14 days at room temperature. HPLC chromatograms of untreated compounds 30, 16 and 8 are shown in (D), (E) and (F).
Figure 12:
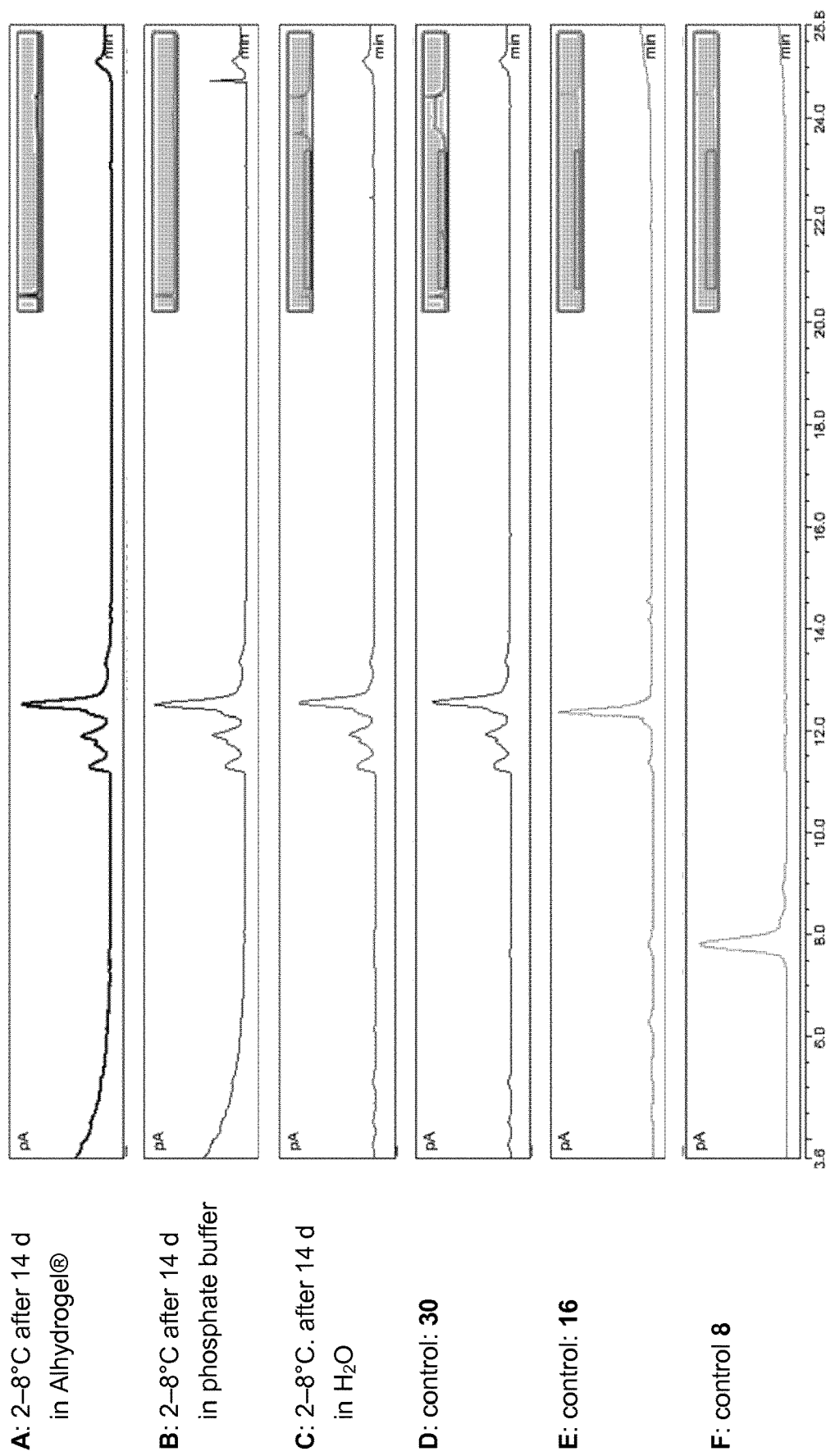
FIG. 12: HPLC chromatogram of compound 30 after treatment with (A) Alhydrogel®, (B) with phosphate buffer, (C) with water for 14 days at 2-8° C. HPLC chromatograms of untreated compounds 30, 16 and 8 are shown in (D), (E) and (F).
Figure 14A:
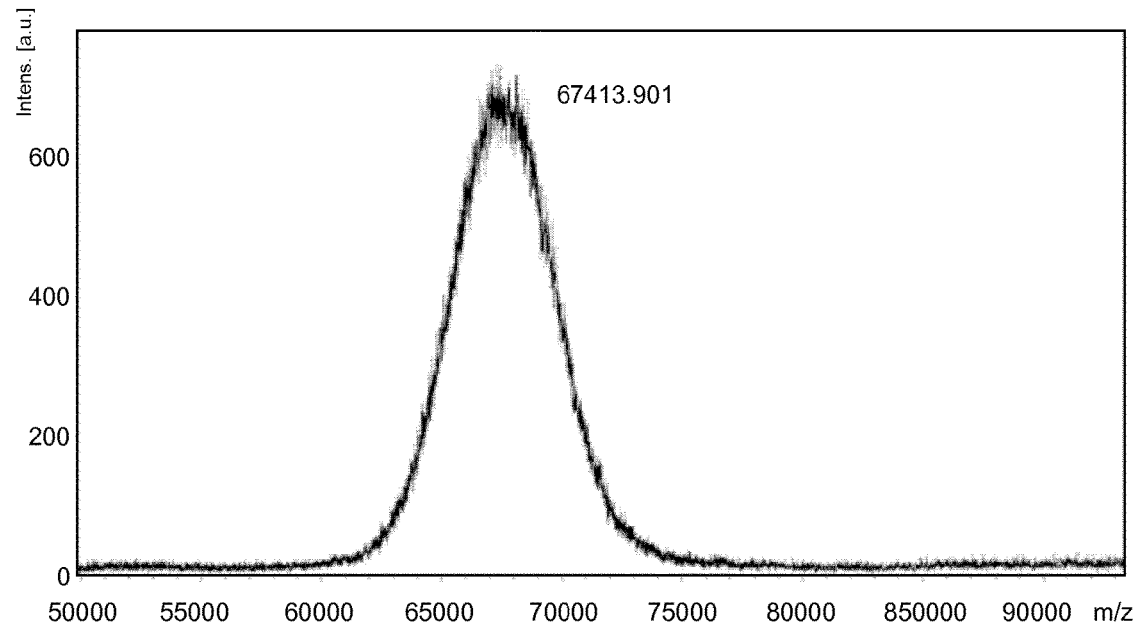
FIG. 14: MALDI mass spectra of (A) compound 30 conjugated to $CRM_{197}$ and (B) compound 94.
Figure 14B:
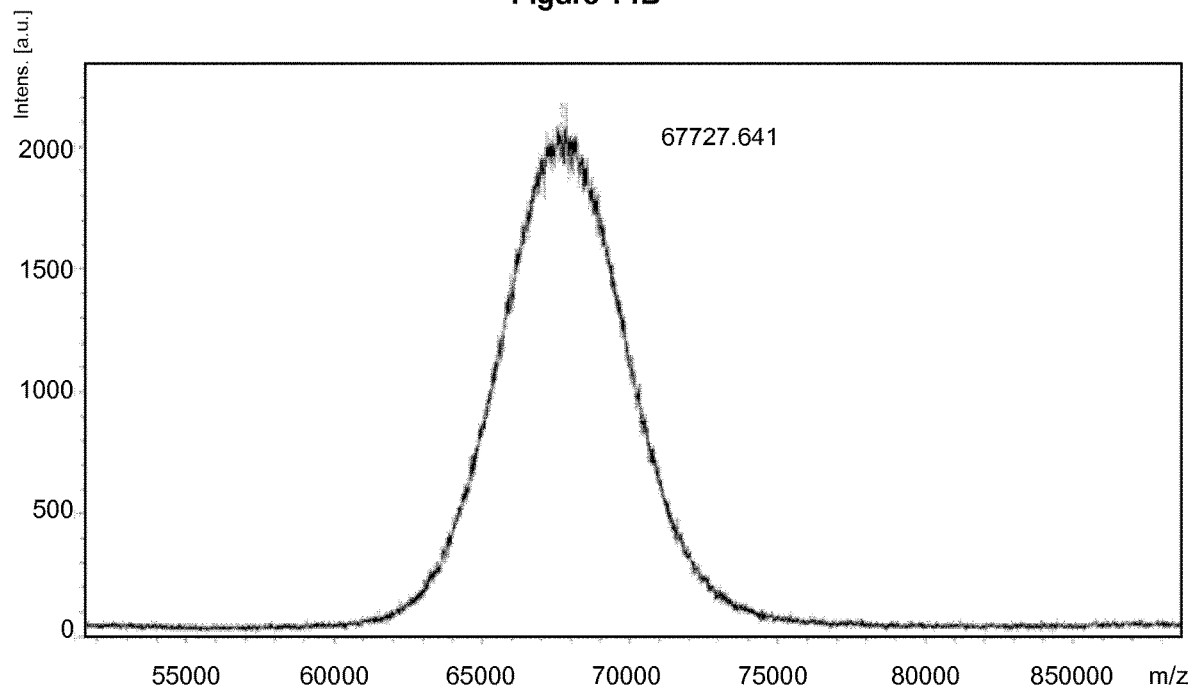
Figure 15:
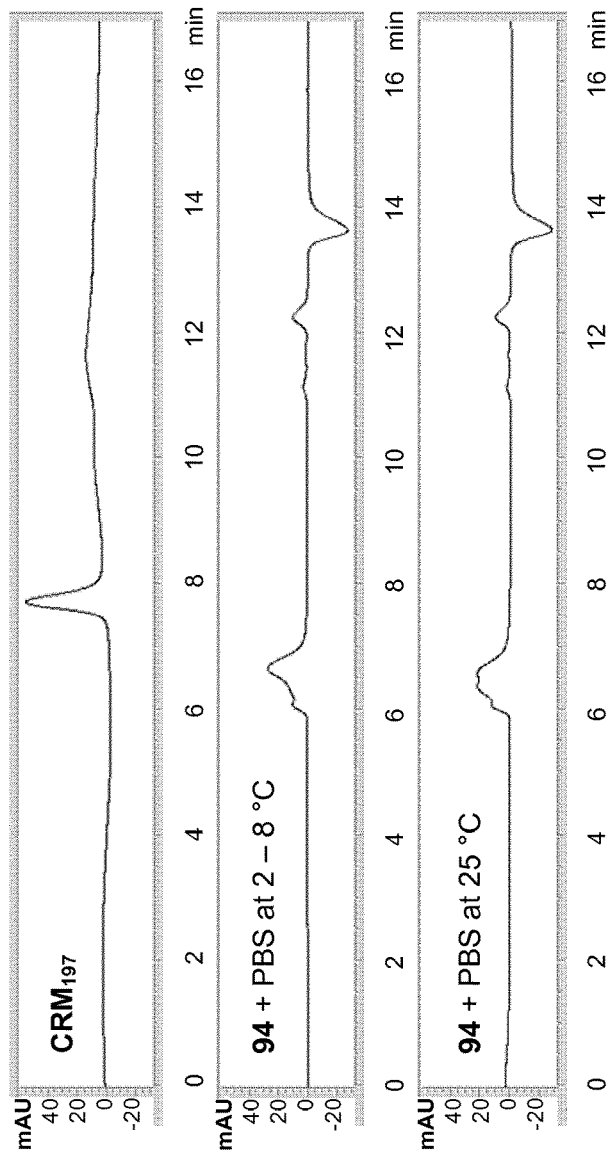
FIG. 15: HPLC-SEC chromatograms of compound 94 in presence of phosphate buffer.
Figure 16:
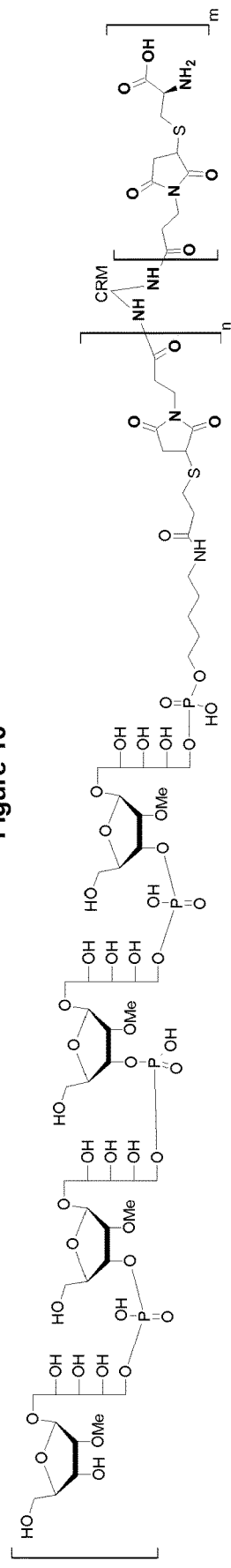
FIG. 16: shows the structure of conjugate 94.

The amount of Al(OH)$_3$ used for this study was similar to the amount present in commercial Hib vaccines. Analysis of samples at different temperatures using HPLC after a week is shown in FIGS. 11 and 12. Compounds 29, 16 and 8 were used as reference since decomposition of tetramer 29 should lead to dimer 16 and monomer 8. Every 24 h 40 µL of solution was aliquoted from each vial and centrifuged for 4 min at 5000 rpm. Supernatant (25 µL) was taken for HPLC analysis. Even after 7 days, no decomposition was observed. From this study it was clear that 2'-methoxyribosylribitol-phosphate tetramer 29 is stable in presence of Al(OH)$_3$, in phosphate buffer (PBS) and in water at 2-8° C. (A2) and r.t. (A3).

The stability of tetramer 29 was further investigated under aqueous basic conditions as applied in Example H-1. From the HPLC chromatogram in FIG. 13A it was concluded that tetramer 29 got cleaved completely after 4 days, while the natural Hib CPS got already cleaved completely within 20 hours. This demonstrates that the 2'-methoxyribosylribitol-phosphate oligomers are very stable even under extreme basic conditions compared to natural Hib CPS.

Example H-5. Stability of Conjugate 94 in Presence of Phosphate Buffer

~5 µg of compound 94 in two vials were each diluted to 500 µL of PBS pH 7.4; one vial was stored at 25° C. and another at 2-8° C. The samples were analyzed by bicinchoninic acid assay (BCA) and HPLC-SEC (column: TSK-gel G2000SWxl, buffer: 50 mM Tris, 20 mM NaCl, pH 7.2) after one day and after 15 days. The data showed that still after 15 days the conjugate 94 was present and stable at both temperature conditions 25° C. and 2-8° c.

Example H-6. Stability of Compound 94 in Presence of Aluminum Hydroxide

Two vials containing ~5 µg of compound 94 and Alhydrogel® (0.125 mg/dose) were each filled up to 500 µL of PBS pH 7.4; one vial was stored at 25° C. and another at 2-8° C. The samples were analyzed by bicinchoninic acid assay (BCA), HPLC-SEC column: TSKgel G2000SWxl, buffer: 50 mM Tris, 20 mM NaCl, pH 7.2), SDS-page and western blot after one day and after one week. The data showed that ~75% of the conjugate 94 were adsorbed onto Alhydrogel® and the adsorbed conjugate was stable at both temperature conditions. No degradation products were observed during this course of time.

TABLE 1

BCA assay of conjugate 94 in presence of phosphate buffer and aluminum hydroxide.

| | protein concentration at t = 0 in µg/mL | temperature in ° C. | final protein concentration in µg/mL |
|---|---|---|---|
| 94 + PBS | 155 | 2-8 | 119 after 15 d |
| 94 + PBS | 155 | 25 | 107 after 15 d |
| 94 + Alhydrogel ® | 113 | 2-8 | 32 after 1 d |
| 94 + Alhydrogel ® | 113 | 25 | 36 after 1 d |
| 94 + Alhydrogel ® | 113 | 2-8 | 34 after 7 d |
| 94 + Alhydrogel ® | 113 | 25 | 39 after 7 d |

Example I. Glycan Array Analysis

Example I-1. Immunization in Rabbits

Immunization experiments were performed on rabbits (Chong et al. Infect. Immun., 1997, p. 4918-4925; Fernández-Santana et al. Science, 2004, 305 (5683), p. 522-525.). Rabbits were housed and handled according to international animal regulations (EU Directive 2010/63/EU) and sanctioned by governmental authorities (Landesamt für Landwirtschaft, Lebensmittelsicherheit and Fischerei Mecklenburg-Vorpommern).

Four groups with four rabbits per each group were immunized in a prime-boost regime with unadjuvanted conjugate 94 containing 5 µg saccharide 29 or conjugate 94 (containing 5 µg Hib saccharide 29) adjuvanted with Alhydrogel. The negative control group received PBS/Alhydrogel only. The positive control group received the approved vaccine ActHIB® (5 µg PRP, corresponding to half the human dose), a conjugate of native PRP to tetanus toxoid (TT). Preimmune serum and antiserum of bleeding day 21 (following two immunizations) were taken and analyzed on a glycan array. The ActHIB-specific serum was obtained after three administrations in contrast to two immunisations of the HIB analogues of the present invention.

Example I-2. Glycan Array Analysis

Saccharides in PBS were printed on N-Hydroxy succinimide activated glass slides (CodeLink slides, Surmodics) using an S3 microarray spotter (Scienion). Slides were incubated overnight in a humidity saturated chamber, quenched for 2 h with 100 mM ethanolamine, 50 mM sodium phosphate, pH 7.5, washed with water and dried.

For incubation, slides were blocked for 1 h with 3% (w/v) BSA-PBS, washed with PBS and water, and dried by centrifugation. A 64 well incubation grid was attached. Sera were diluted in 3% BSA-PBS, 0.1% (v/v) Tween-20, incubated at 37° C. for 15 min, and centrifuged for 2 min at 3220 rpm. Serum dilutions were applied to the slide and incubated for 1 h at room temperature. Wells were washed three times with PBS+0.1% Tween-20 (PBS-T). Secondary antibodies (anti-rabbit IgG FITC, anti-rabbit IgM AlexaFluor 647, anti-human IgG-Fc AlexaFluor 488 and IgM AlexaFluor 594) were incubated on the slides for 30 min at r.t. Wells were washed twice with PBS-T, the incubation grid was removed, and the slide washed with PBS and water. After drying by centrifugation, the slide was scanned using a GenePix 4300A (Molecular Devices) microarray reader.

The primary immune response was assessed by glycan array screening of serum samples retrieved at day 0, day 21 and day 35. 2'-Methoxyribosylribitolphosphate dimer 19, 2'-methoxyribosylribitolphosphate dimer 24, 2'-Methoxyribosylribitolphosphate tetramer 29, 2'-deoxyribosylribitolphosphate tetramer 53 and 2'-dimethyl-aminocarbonylribosylribitolphosphate 62 as well as natural Hib PRP were printed on NHS ester-activated microarray slides. After immunization with conjugate 94 adjuvanted with Alhydrogel and without adjuvant, antibodies of the IgG and IgM subtypes against the Hib PRP derivatives 19, 24, 29, 53 and 62 as well as against the natural Hib PRP polysaccharide in all immunized rabbits were detected.

Figure 17A:
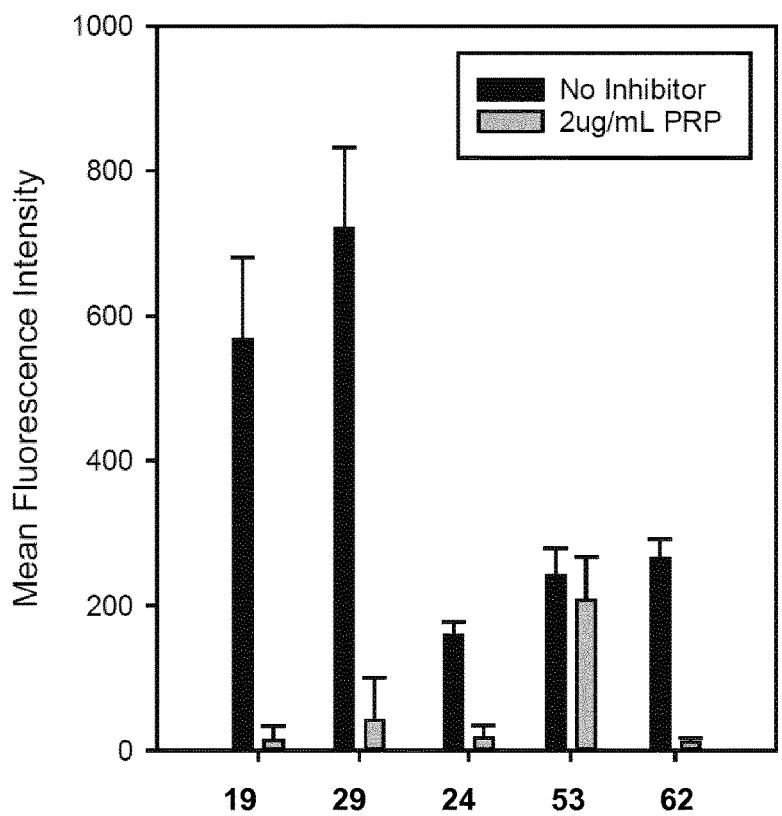
FIG. 17: Glycan array analysis: (A) Binding of compounds 19, 24, 29, 53 and 62 to antibodies (Hib human reference serum) in the presence of Hib PRP inhibitor (grey bars) or no inhibitor (black bars) after 21 days; (B) Binding of compounds 19, 24, 29, 53 and 62 to antibodies (rabbit typing serum) in the presence of Hib PRP inhibitor (grey bars) or no inhibitor (black bars) after 21 days; Binding of compounds 19, 24, 29, 53, 62 and natural Hib PRP as reference to antibodies raised by immunization with compound 94 (C) and compound 94 with Alhydrogel (D) after 35 days. Error bars represent the standard deviation of the quadruplicate samples.
Figure 17B:
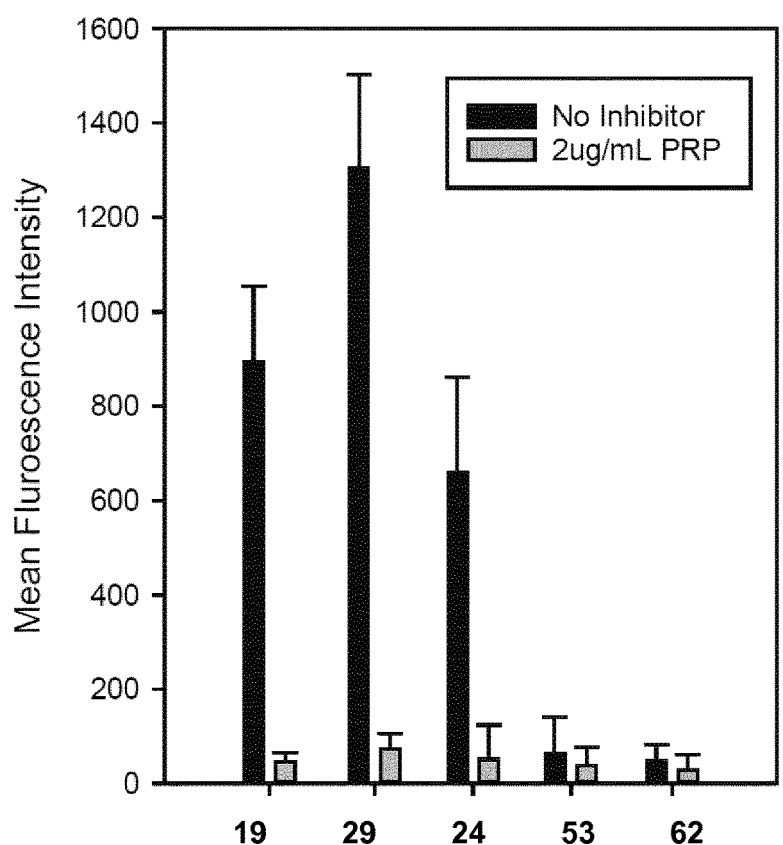
Figure 17C:
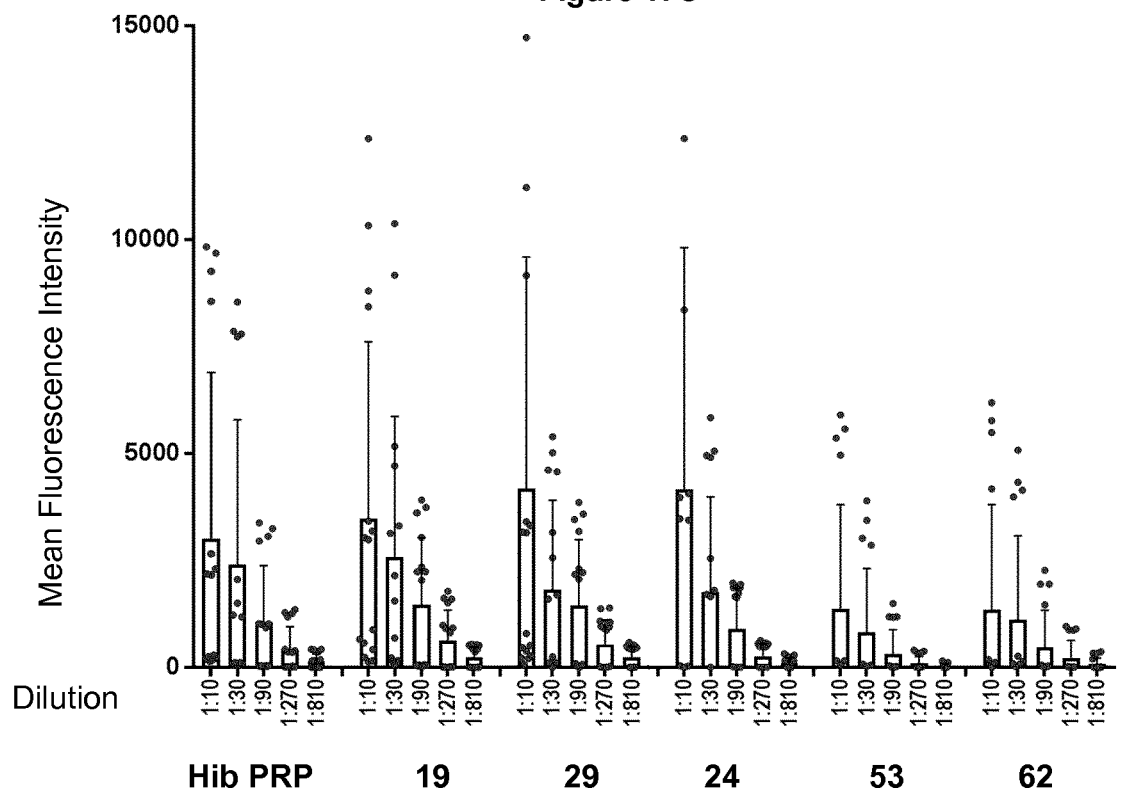
Figure 17D:
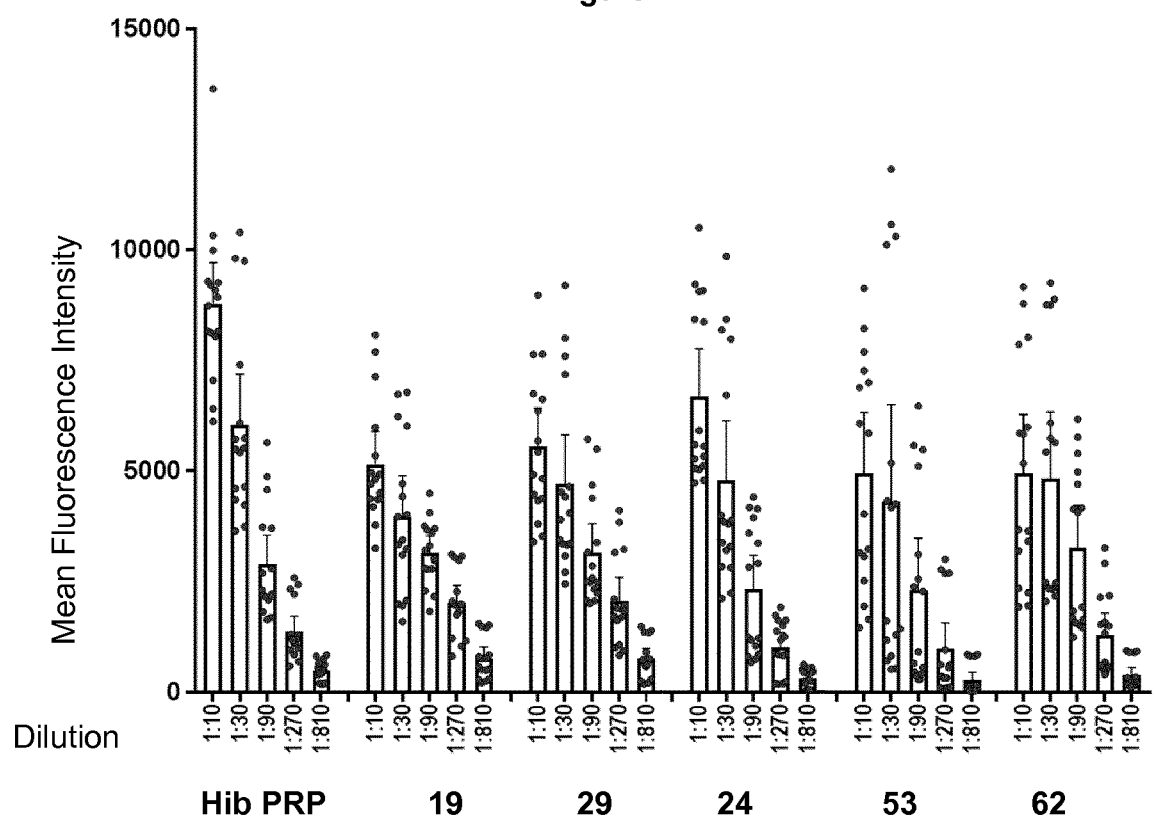

The glycan array screening also showed that anti-Hib antibodies present in human reference serum (FIG. 17A) and in rabbit typing serum (FIG. 17B) bind to the Hib PRP derivatives 19, 24, 29, 53 and 62. The presence of natural Hib PRP inhibits the binding of the Hib PRP derivatives 19, 24, 29 and 62, but not of the 2'-deoxyribosylribitolphosphate 53.

Serum IgG antibodies were detectable 21 days after the first immunization with the conjugate 94 adjuvanted with Alhydrogel and 35 days after the first immunization with undajuvanted conjugate 94. Antibodies cross-reacting with the natural Hib PRP polysaccharide indicates the potential of these antibodies to bind to *Haemophilus influenzae* bacteria and to confer protection against *Haemophilus influenzae* infection.

Example J. ELISA Studies

ELISA plates (high-binding, EIA/RIA Plate, 96 well, flat bottom with low evaporation lid, company: Costar® 3361)
commercial rabbit anti-Hib-PRP IgG ELISA assembly kit (Alpha Diagnostic Intl. Inc, #980-130-PRG; Lot: 170531K5, Expiry: June 2018)
antigen: Phosphoribosylphosphate (PRP) capsular polysaccharide from *Haemophilus influenza* b (NIBSC, Code: 12/306)
test sera: supplied by BioGenes GmbH.
detection antibody: goat anti rabbit IgG peroxidase conjugate (Sigma, #A4914).
Phosphate Buffered Saline (PBS): Made in-house from stock (Biochrom GmbH, Cat: L182-10)
blocking solution: 1% FCS (v/v) in PBS.
antibody diluent: PBS+1% BSA (w/v).
wash buffer: PBS+0.1% Tween 20 (PBS-T)
developing solution: 1 Step™ Ultra TMB-ELISA developer. (ThermoScientific, Cat #: 34028)
stop solution- 2M Sulphuric acid ($H_2 504$) (Made in-house)
plate reader: Anthos ht 2.
  software: WinRead 2.36 for absorbance measurements and GraphPad Prism 7 for data plotting and analysis.

Example J-1. Immunization Schedule and Sera Collection

All immunization experiments were performed at BioGenes GmbH Berlin. The experimental groups included i) PBS with Alhydrogel (negative control), ii) compound 94 without Alhydrogel, iii) compound 94 with Alhydrogel, and iv) the commercial vaccine HiberiX® (positive control). Briefly, rabbits (n=4) were immunized in a prime boost regime with the constructs for the respective experimental groups as mentioned in Table 1. The mice were immunized following a prime-boost regime and sera were collected on day 0 (pre-immune), day-14, day-21, and day-35.

TABLE 2

Immunization schedule and antigen dose information of rabbits (n = 4).

| Group | Rabbits | amount antigen [μg/dose] | amount Alhydrogel [mg/dose] | Excipient | Immunization schedule [days] | Sera collection [days] |
|---|---|---|---|---|---|---|
| 94 | 4 | 0.5 | 0 | 1X PBS pH 7.4 | d0, d14, d28 | d0, d14, d21, d28, d35 |
| 94 with Alhydrogel | 4 | 0.5 | 0.32 | 1X PBS pH 7.4 | d0, d14, d28 | d0, d14, d21, d28, d35 |
| PBS with Alhydrogel | 4 | 0 | 0.32 | 1X PBS pH 7.4 | d0, d14, d28 | d0, d14, d21, d28, d35 |
| HiberiX ® | 4 | 5 | — | | d0, d14, d28 | d0, d14, d21, d28, d35 |

Sera Collection and Handling:

The sera from different experimental groups and respective time points were stored at −20° C. Sera from the individual rabbits (20 μl) of specific experimental groups were pooled and stored at −20° C. Individual rabbit sera (20 μl) were aliquoted as a separate stock and stored at −20° C. till further use.

Example J-2. Enzyme Linked Immunosorbent Assay (ELISA) of Sera Using in-House Antigen Coated Plates Coating of Plates with Antigen:

The antigen, Hib PRP capsular polysaccharide (stock concentration 1 mg/mL) was diluted to a working antigen concentration of 10 μg/mL in PBS pH 7.4. 100 μL was added in each well (1 μg antigen/well) and incubated overnight at 4° C.

Washing:

After overnight adsorption of the antigen, the plates were washed 3× with PBS-T (200 μL/well) and the excess fluid per well was removed by inverting the plate and tapping on a clean dry tissue towel.

Blocking:

The plates were blocked using 300 μL of blocking solution (PBS+1% FCS) for 2 h at RT.

Washing:

After blocking, the plates were washed 3× with PBS-T (200 μL/well) and the excess fluid per well was removed by inverting the plate and by tapping on a clean dry tissue towel.

Dilution of Sera and Incubations:

Pooled (n=4 rabbits/group) pre-immune and test sera of the different experimental groups and individual rabbit test sera (n=4) were diluted to their respective dilutions, in the antibody diluent (PBS-+1% BSA). 100 μL of the diluted sera samples of the different experimental groups (100 were added in duplicates to the corresponding wells and incubated on a shaker set at 250 rpm for 1 h at RT. 100 μL/well of the antibody diluent (PBS+1% BSA) formed the experimental blank. After incubation with sera, the plates were washed 5× with PBS-T (200 μL/well) and the excess fluid per well was removed by inverting the plate and by tapping on a clean dry tissue towel.

Incubation (Detection Antibody):

The detection antibody, goat anti-rabbit IgG peroxidase was diluted 1:10,000 in the antibody diluent (PBS+1% BSA) and 100 μL was added to the well and incubated on a shaker at 250 rpm for 1 h at RT. After the incubation with detection antibody, the plates were washed 5× with PBS-T (200 μL/well) and the excess fluid per well was removed by inverting the plate and by tapping on a clean dry tissue towel.

Developing:

To each well, 100 μL of the ready to use TMB substrate (normalized to RT form 4° C.) was added and incubated in dark for 15 min. The blue color of the enzymatic reaction was stopped by adding 100 μL/well of 2M $H_2SO_4$ solution resulting in a yellow colored solution. The absorption of the yellow colored solution was measured at 450 nm with a correction wavelength of 630 nm using a plate reader. The absorption values were analyzed by plotting a graph using the Graphpad Prism software.

Figure 18:
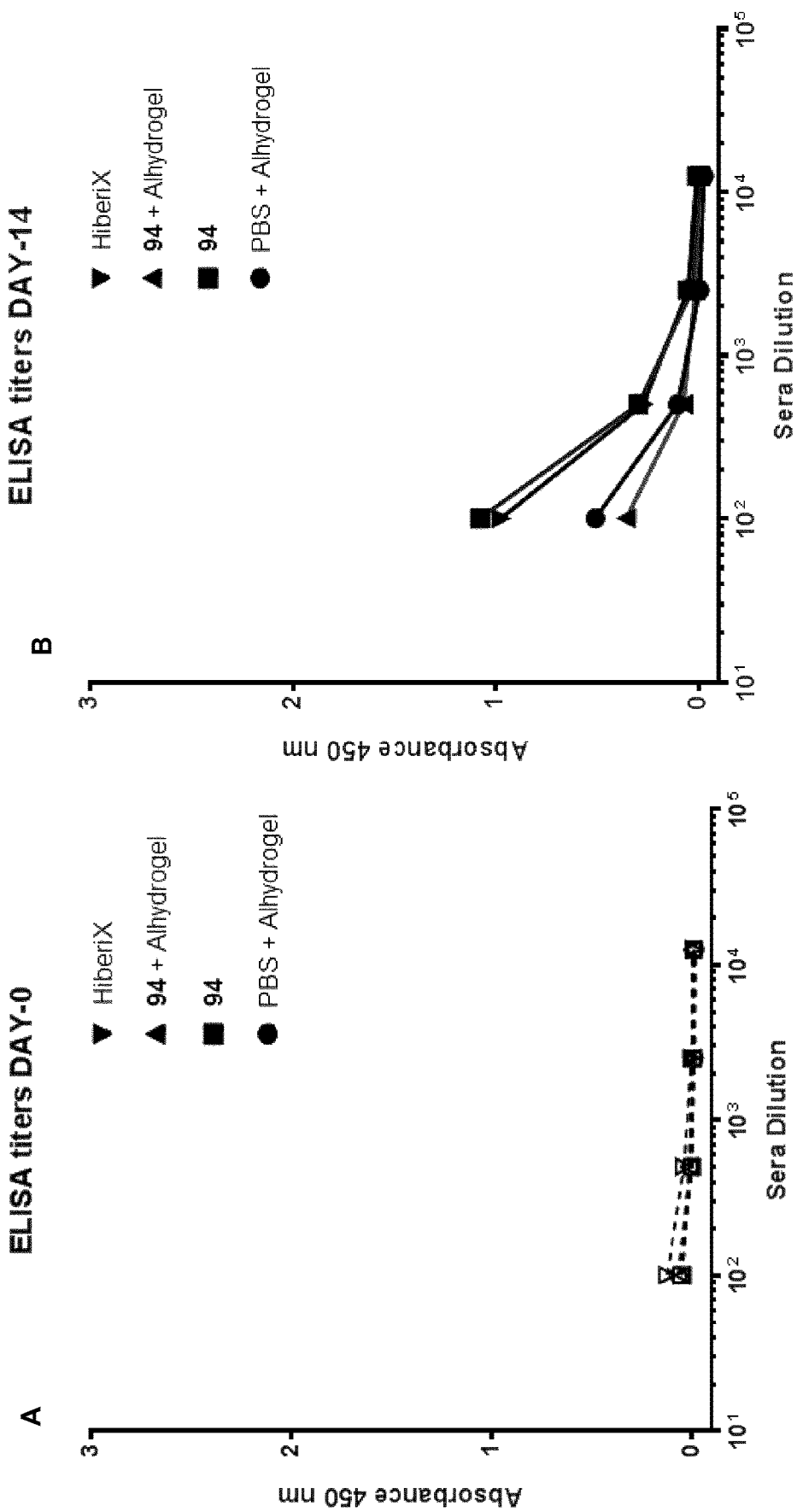
FIG. 18: ELISA study: Binding of IgG antibodies from rabbits (n=4) immunized with unadjuvanted conjugate 94 (■), with conjugate 94 adjuvanted with Alhydrogel (▲), with PBS/Alhydrogel (●) and with HiberiX® (▼) to plates coated with native Hib PRP antigen after 0 days (A—negative control), 14 days (B), 21 days (C) and 35 days (D). Sera were diluted 5-fold with 1% BSA-PBS. Diluted sera (100 µL) were added per well of the microtiter plate which was coated with 1 µg of Hib-PRP polysaccharide, detected with a HRP conjugated goat anti-rabbit secondary antibody diluted to 1:10000 and developed using TMB. Absorbance was measured at 450 nm and the data were plotted using the graphpad prism software.
Figure 18:
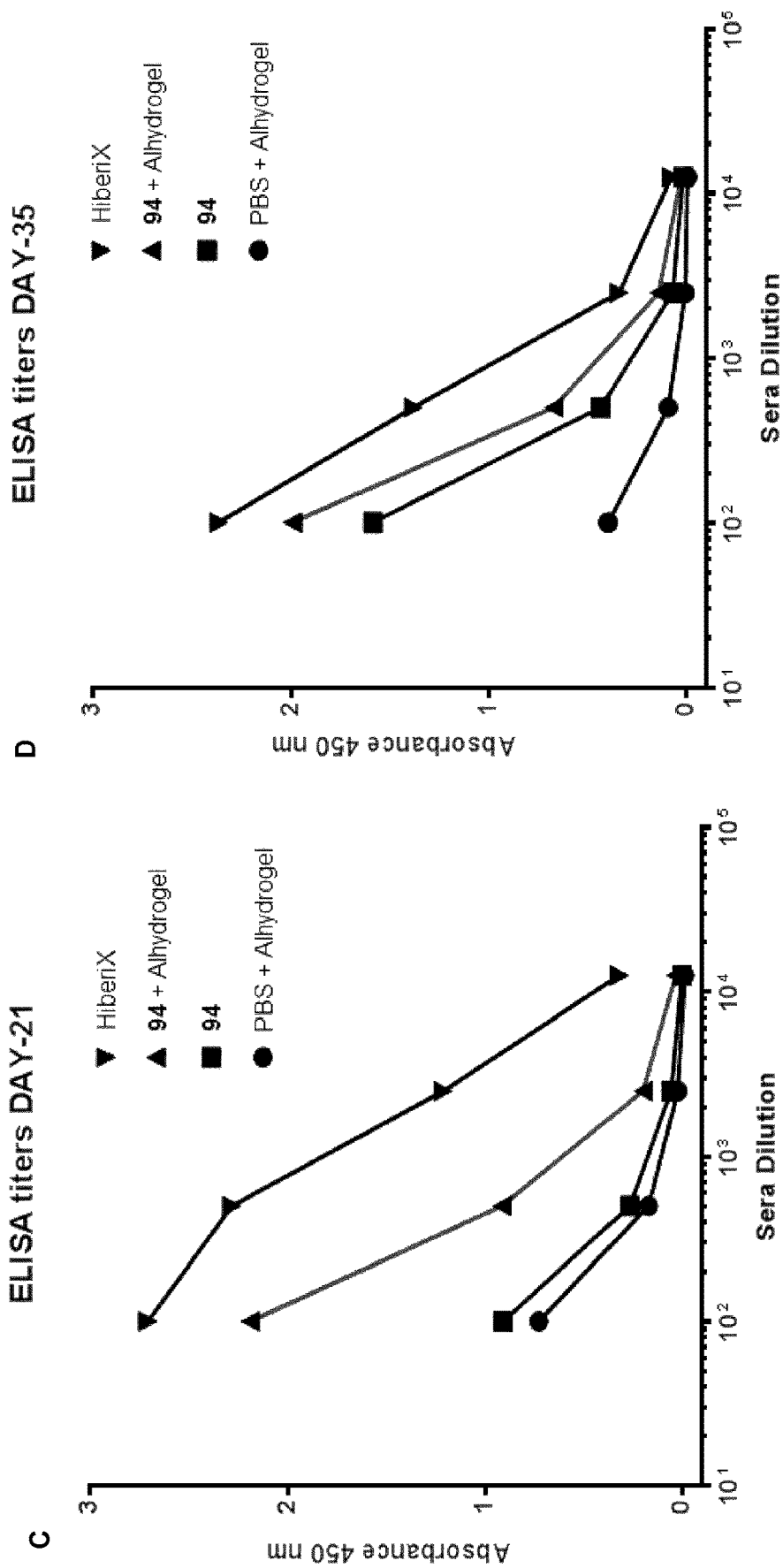

Results:

As seen in FIG. 18A, the pre-immune sera of all the experimental groups across all the dilutions did not show any significant response and the readings were equal to 0. In the post-immune/test sera, the day-14 HiberiX group (inverted triangles) showed an immune response considerably higher than the PBS control group (filled circles) that increased up to titers of 1:2500 in the day-21 and day-35 groups (FIGS. 18B-D). In the experimental groups immunized with adjuvanted compound 94 (triangles), the antibody titers were lower than that of the PBS group on day-14 which substantially increased to that of the HiberiX group at a titer of 1:25000 but 1-fold lower. Although the experimental group immunized with the unadjuvanted compound 94 (squares) showed immune titers comparable to the HiberiX group at day-14, no boosting response was observed at the day-21 time point where the adjuvanted group showed a boosting response. However, after the second boost, the unadjuvanted compound 94 showed an immune titer comparable to the adjuvanted group, but lower than that of the Hiberix group.

Example J-3. Enzyme Linked Immunosorbent Assay (ELISA) of Sera Using Commercial ADi Plates The rabbit anti-Hib-PRP IgG ELISA kit (ADi) detects Hib-PRP specific IgG antibodies in the sera of vaccinated animals. The kit includes a 96 well microtiter plate pre-coated with the antigen Hib-PRP polysaccharide, supplied with the wash buffers and the peroxide conjugated detection antibody. The kit also includes a set of calibrators (0.5, 1.0, 2.5, and 5.0 U/mL) and a positive control/reference sera. The calibrators provided a control of the internal assay parameters and differentiates false positives in a sera dilution of 1:50 and above. The 0.5 U/mL value becomes the lowest detectable titer below which values of tests would be a false positive. The assay was performed in a normal ELISA format by following the instructions from the manufacturer. Briefly, the sera to be tested was diluted to an appropriate dilution range of 1:100 and above in the diluent provided in the kit. 100 μL of the diluted sera along with the calibrator, positive, and negative control was added to pre-determined wells and incubated for 1 h at room temperature. The wells were then washed 4 times with the kit wash buffer and 100 μL of the detection antibody is added and further incubated for 30 min followed by 5 washes. The wells were developed by adding 100 μL of the TMB substrate and incubating for 15 min followed by stopping the reaction using 100 μL stop solution resulting in a yellow colored solution. The absorption of the yellow colored solution was measured at 450 nm with a correction wavelength of 630 nm using a microplate reader. The absorption values were analyzed by plotting a graph using the Graphpad Prism software.

Results:

The Hib-PRP polysaccharide (antigen) is very sensitive to hydrolysis due to pH differences and other physiochemical factors which might lead to lower detection of antigen in an ELISA. To corroborate the immune titers observed in FIGS. 18B-D and to rule out the anomalies arising due to in-house coating of the antigen, the rabbit sera were screened on a commercial diagnostic plate (Advanced Diagnostics-adi) pre-coated with the Hib-PRP polysaccharide. As described in Example J-2, the rabbit immunized sera from the different experimental groups and time-points were diluted 5-fold (1:100, 500, 2500, and 12500) and analyzed for polysaccharide specific IgG antibodies. As seen in FIG. 19A, the pre-immune sera of all the experimental groups across all the dilutions did not show any significant response and the readings were below the threshold value. The threshold refers to the absorption value got for the 0.5 U/mL calibrator run on the same plate, values below which can be assigned as negatives or false positives.

In the post-immune/test sera, the day-14 HiberiX group (inverted triangles), compound 94 with (triangles) and without (squares) Alhydrogel showed an immune titer lower than the threshold value even at the highest dilution of 1:100 (FIG. 19B). However, the PBS control group (filled circles) showed a higher signal than the threshold value at the highest dilution of 1:100 only in the day-14 time point but was lower than the threshold in all other time points of day-21, and −35. This was a similar trend observed in the in-house coated antigen plates (FIG. 18B-D). The adjuvanted compound 94 (triangles) and the HiberiX group (inverted triangles) in the day-21 and -35 time points showed a saturation up to dilutions of 1:500 and 1:2500, respectively. The effect of the adjuvant and boosting response was clearly visible in the compound 94 with Alhydrogel group as the titers significantly increase from 1:2500 in the day-21 time point to 1:12500 in the day-35 time point. Clearly at day-35, the group immunized with adjuvanted compound 94 showed comparable response to HiberiX but 1-fold lower. However, in the group immunized with unadjuvanted compound 94, there were no IgG titers detectable till day-21, but significantly increased up to 1:2500 post second boost. This trend was similar to that observed in ELISA performed using the in-house antigen coated plates (FIG. 18C, D).

These data demonstrate the immunogenicity of the conjugate 94. Isotype switching indicates T cell-dependent antibody responses. Serum IgG antibodies were detectable 21 days after the first immunization with the conjugate 94 adjuvanted with Alhydrogel and 35 days after the first immunization with the unadjuvanted conjugate 94. Antibodies cross-reacting with the natural Hib PRP polysaccharide indicates the potential of these antibodies to bind to *Haemophilus influenzae* bacteria and to confer protection against *Haemophilus influenzae* infection

The invention claimed is:
1. A saccharide of the formula (IV-1)

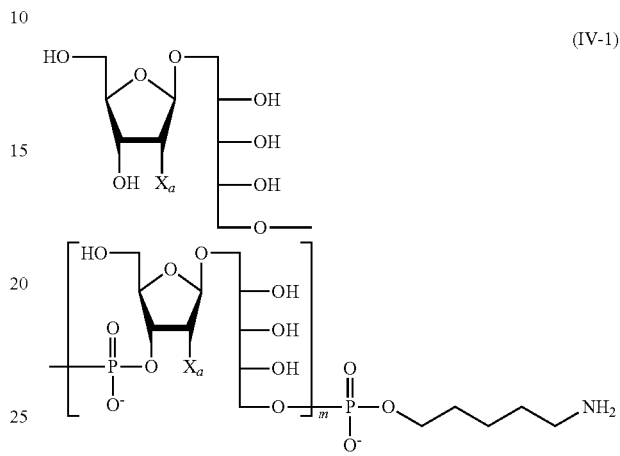

wherein
m is an integer selected from 1 to 9; and
$X_a$ is H, F, —OCO—N(CH$_3$)$_2$, or —OCH$_3$.
2. A saccharide selected from the group consisting of:

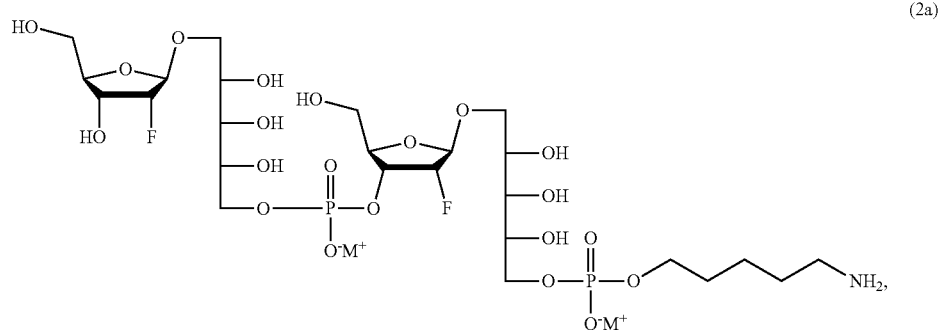

(2a)

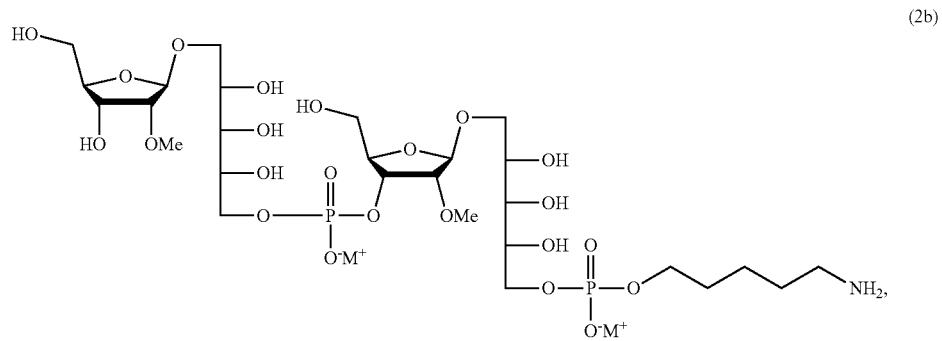

(2b)

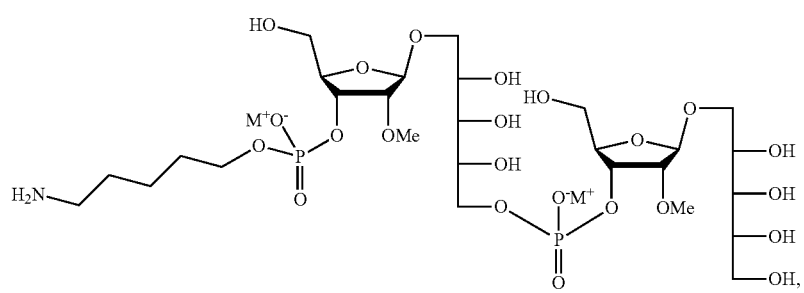
(2b')
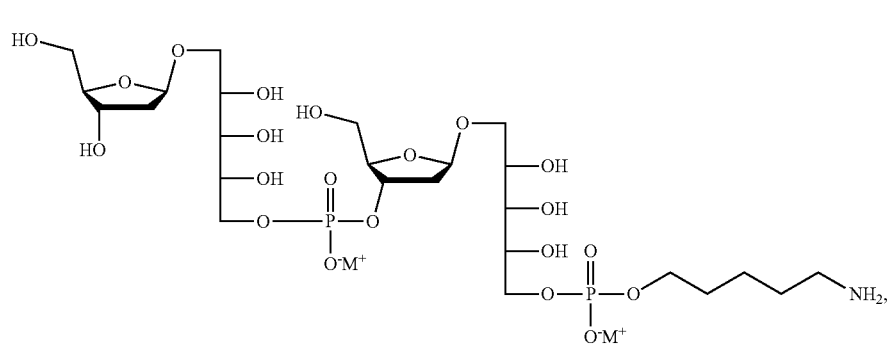
(2c)
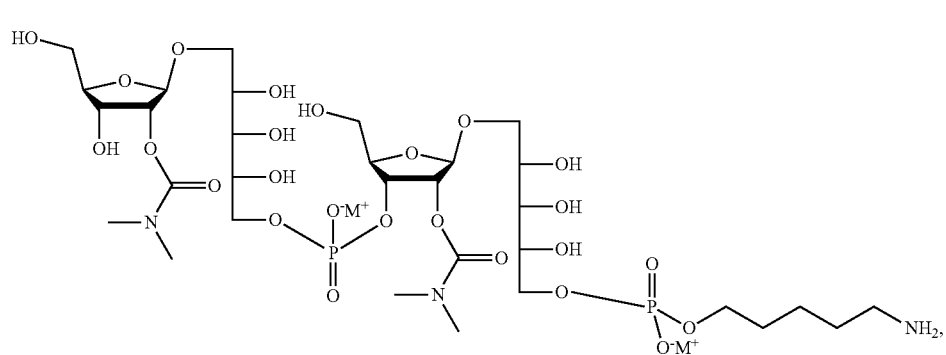
(2f)
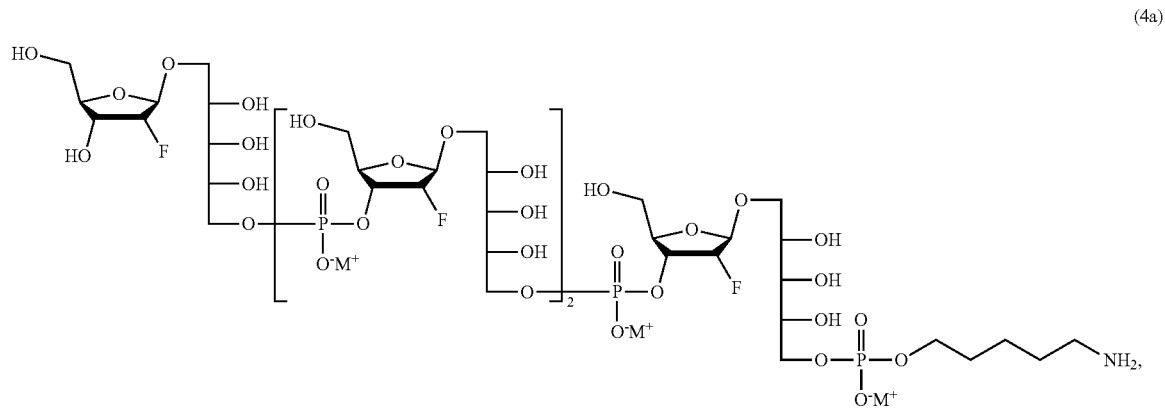
(4a)

-continued
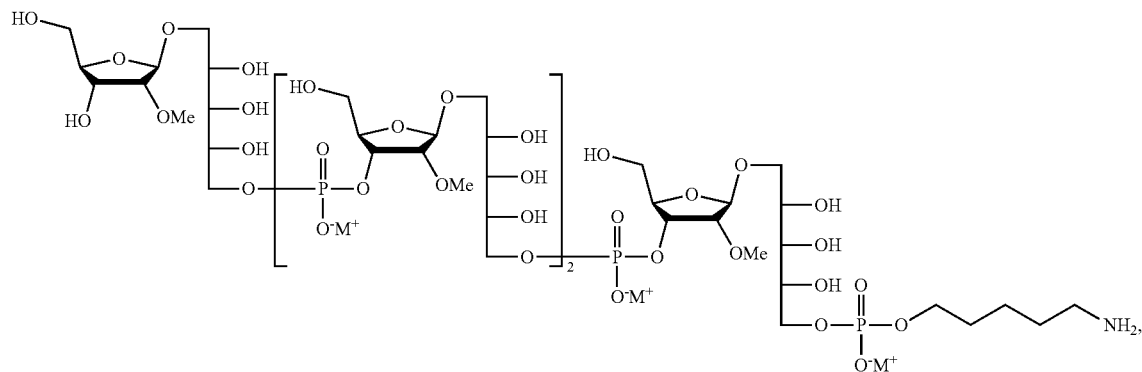
(4b)
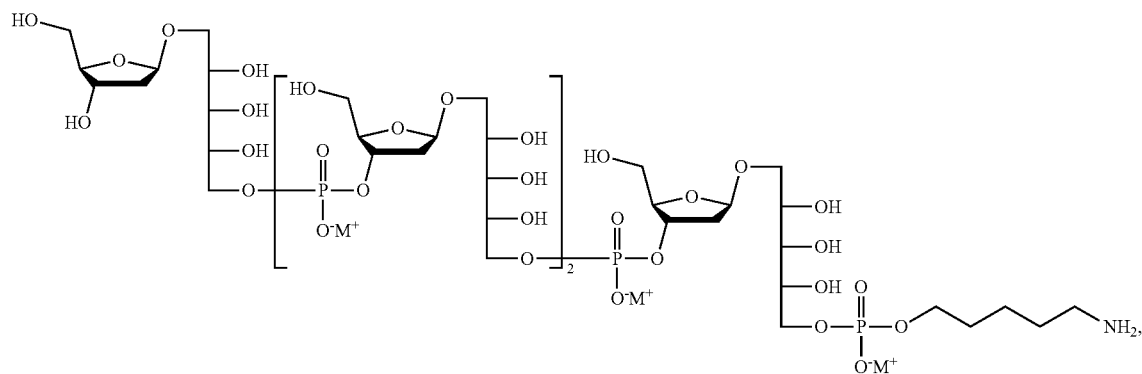
(4c)
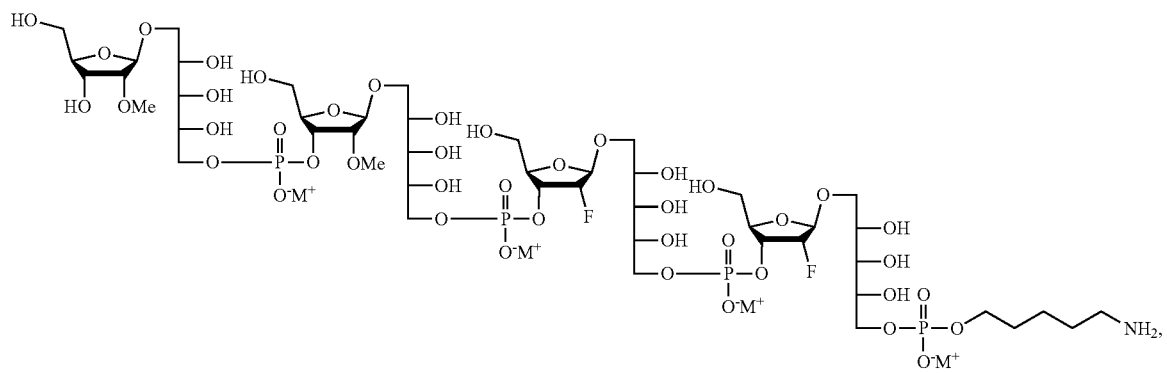
(4d)
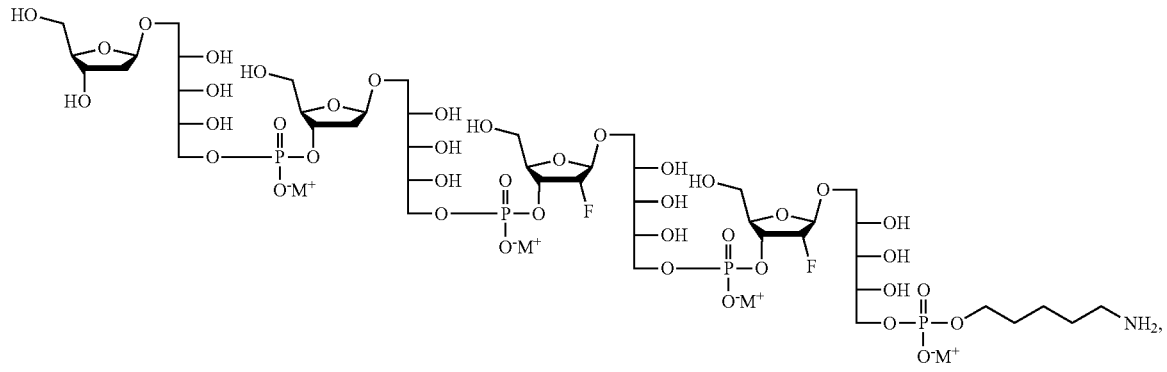
(4e)

-continued
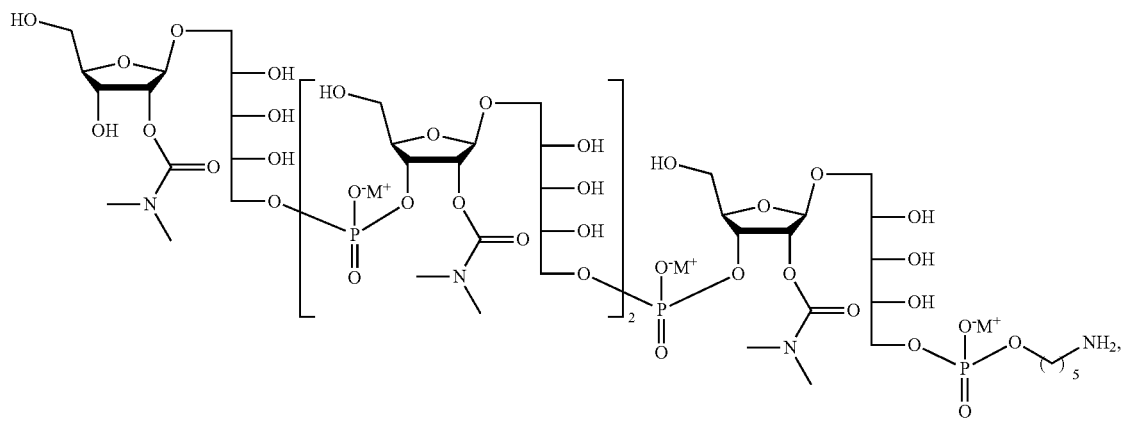
(4f)
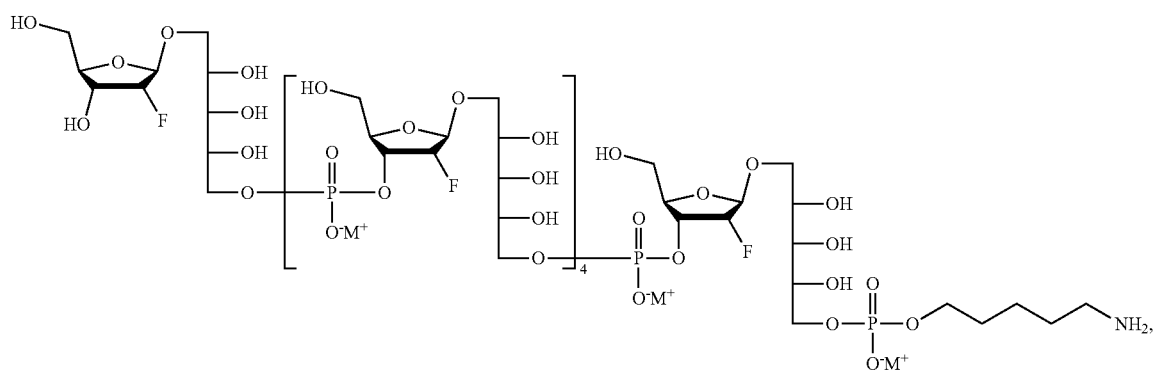
(6a)
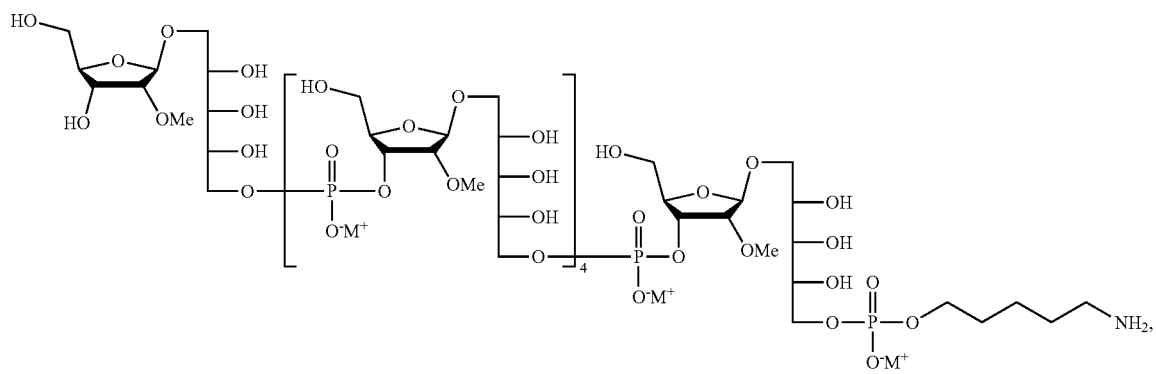
(6b)
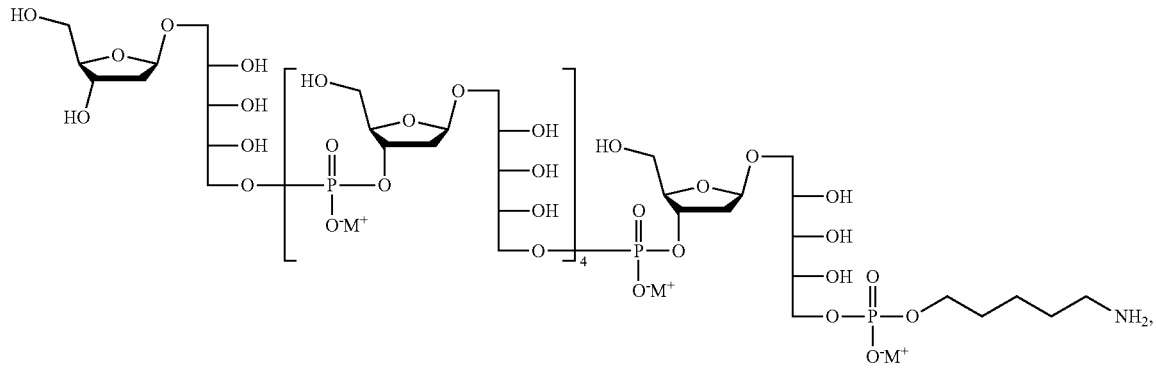
(6c)

-continued
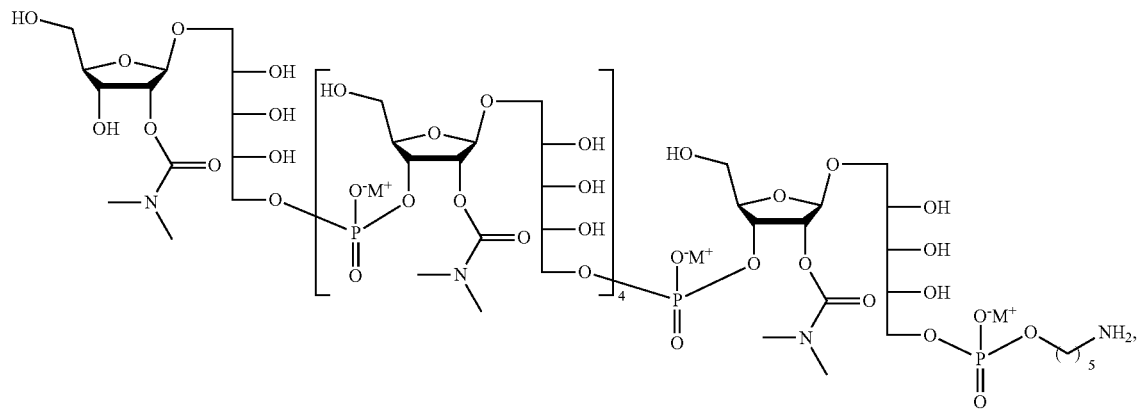
(6f)
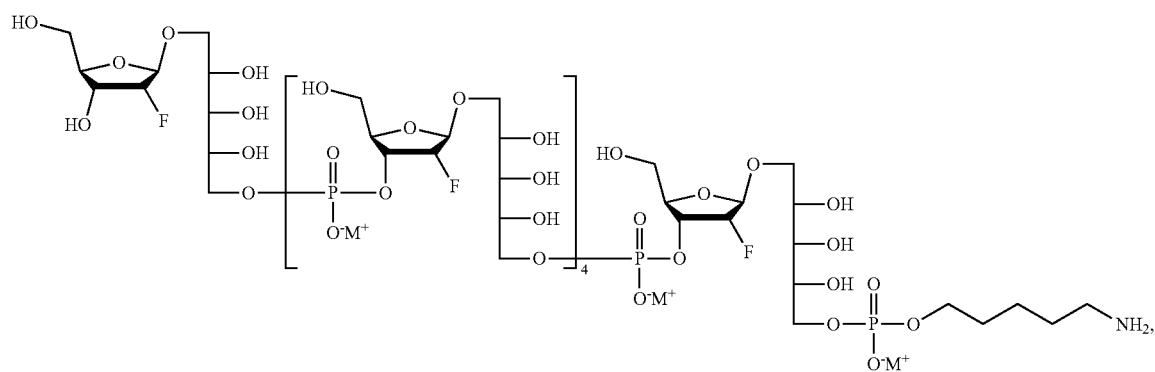
(8a)
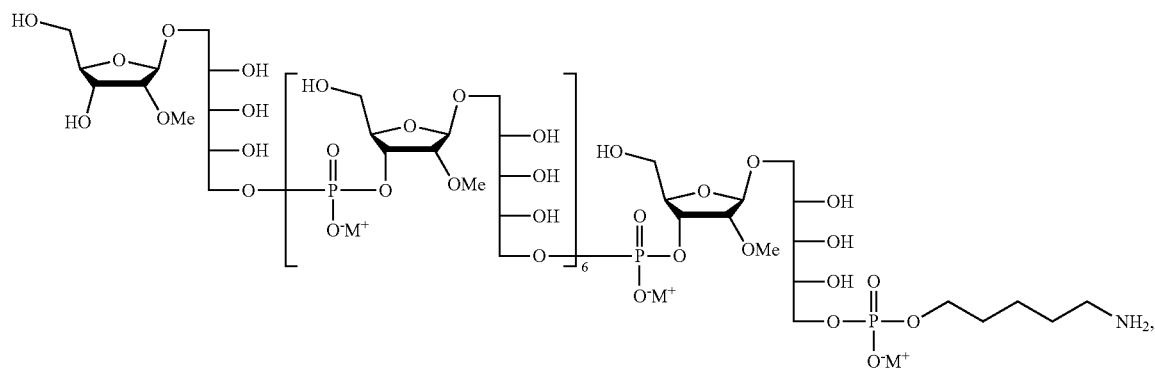
(8b)
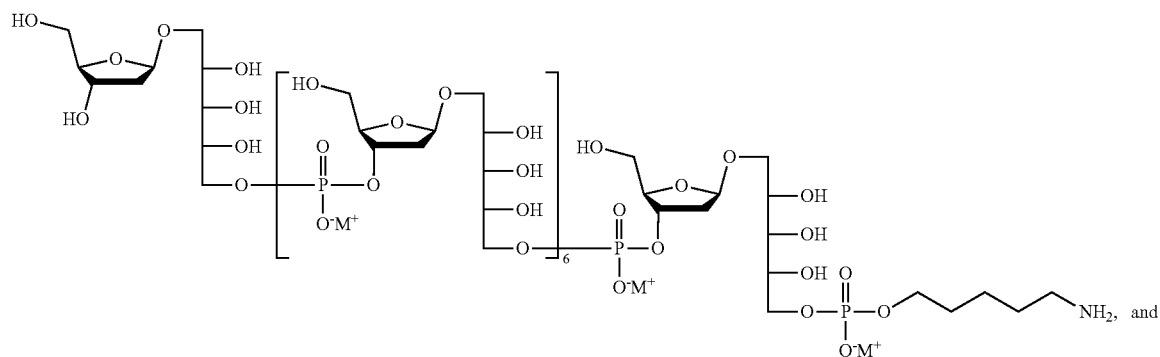
(8c)

(8f)

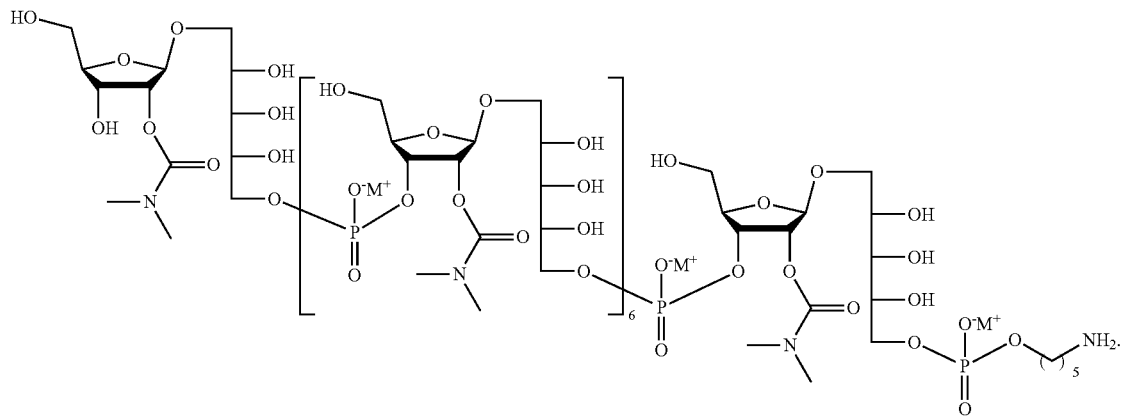

3. The saccharide according to claim 1, conjugated with an immunogenic carrier through the nitrogen atom of the —O—(CH$_2$)$_5$—NH$_2$ group.

4. A pharmaceutical composition comprising an effective amount of a saccharide of claim 1.

5. A vaccine composition comprising a saccharide according to claim 1 together with at least one pharmaceutically acceptable adjuvant, carrier, cryoprotectant, lyoprotectant, excipient and/or diluent.

6. The vaccine composition according to claim 5 further comprising at least one of diphtheria antigen, tetanus antigen, pertussis antigen, hepatitis B antigen, inactivated polio vaccine and inactivated rotavirus vaccine.

7. The saccharide according of claim 2, conjugated with an immunogenic carrier through the nitrogen atom of the —O—(CH$_2$)$_5$—NH$_2$ group.

8. A pharmaceutical composition comprising an effective amount of a saccharide of claim 2.

* * * * *